(12) United States Patent
Amadio et al.

(10) Patent No.: US 12,296,102 B2
(45) Date of Patent: May 13, 2025

(54) MEDICAL TUBES AND METHODS OF MANUFACTURE

(71) Applicant: Fisher & Paykel Healthcare Limited, Auckland (NZ)

(72) Inventors: Christopher Jaye Norman Amadio, Auckland (NZ); Elmo Benson Stoks, Auckland (NZ); Charles Christopher North, Auckland (NZ); Mahran Maumoon Sujau, Auckland (NZ); Joshua Daniel Stroobant, Cambridge (GB); Gavin Walsh Millar, Auckland (NZ); Matthew Liam Buswell, Auckland (NZ); Ibrahim AL-Tiay, Auckland (NZ); David Leon McCauley, Auckland (NZ); Andre Van Schalkwyk, Auckland (NZ); Katja Munkelt, Hermsdorf (DE); Matthew Robert Wilson, Auckland (NZ); Helgard Oosthuysen, Auckland (NZ); Sanjay Parag Patel, Auckland (NZ); Dominique Richard D'Andrea, Auckland (NZ); Grant Martin Dover, Auckland (NZ); Dean Antony Barker, Auckland (NZ); Jonathan David Harwood, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 167 days.

(21) Appl. No.: 17/236,335

(22) Filed: Apr. 21, 2021

(65) Prior Publication Data
US 2021/0353895 A1 Nov. 18, 2021

Related U.S. Application Data

(63) Continuation of application No. 14/649,801, filed as application No. PCT/NZ2013/000222 on Dec. 4, 2013, now Pat. No. 11,058,844.
(Continued)

(51) Int. Cl.
*A61M 16/08* (2006.01)
*A61M 16/00* (2006.01)
(Continued)

(52) U.S. Cl.
CPC ........ *A61M 16/0875* (2013.01); *A61M 39/08* (2013.01); *A61M 16/0066* (2013.01);
(Continued)

(58) Field of Classification Search
CPC .............. A61M 16/0666; A61M 16/08; A61M 16/0816; A61M 16/0875; A61M 16/1095;
(Continued)

(56) References Cited

U.S. PATENT DOCUMENTS

| 485,127 A | 10/1892 | Lynch |
|---|---|---|
| 2,073,335 A | 3/1937 | Connell |

(Continued)

FOREIGN PATENT DOCUMENTS

| AU | 1448473 | 9/1976 |
|---|---|---|
| AU | 727989 | 6/2000 |

(Continued)

OTHER PUBLICATIONS

US 10,426,912 B2, 10/2019, Buswell et al. (withdrawn)
(Continued)

*Primary Examiner* — Colin W Stuart
*Assistant Examiner* — Douglas Y Sul
(74) *Attorney, Agent, or Firm* — VIA LLP

(57) ABSTRACT

The disclosure relates to medical tubes and methods of manufacturing medical tubes. The tube may be a composite
(Continued)

structure made of two or more distinct components that are spirally wound to form an elongate tube. For example, one of the components may be a spirally wound elongate hollow body, and the other component may be an elongate structural component also spirally wound between turns of the spirally wound hollow body. The tube need not be made from distinct components, however. For instance, an elongate hollow body formed (e.g., extruded) from a single material may be spirally wound to form an elongate tube. The elongate hollow body itself may in transverse cross-section have a thin wall portion and a relatively thicker or more rigid reinforcement portion. The tubes can be incorporated into a variety of medical circuits or may be employed for other medical uses.

24 Claims, 84 Drawing Sheets

Related U.S. Application Data

(60) Provisional application No. 61/877,784, filed on Sep. 13, 2013, provisional application No. 61/877,566, filed on Sep. 13, 2013, provisional application No. 61/877,622, filed on Sep. 13, 2013, provisional application No. 61/877,736, filed on Sep. 13, 2013, provisional application No. 61/733,360, filed on Dec. 4, 2012, provisional application No. 61/733,359, filed on Dec. 4, 2012.

(51) Int. Cl.
*A61M 16/06* (2006.01)
*A61M 16/10* (2006.01)
*A61M 16/16* (2006.01)
*A61M 39/08* (2006.01)
*A61M 39/10* (2006.01)
B29C 53/78 (2006.01)

(52) U.S. Cl.
CPC ..... *A61M 16/0666* (2013.01); *A61M 16/0683* (2013.01); *A61M 16/0816* (2013.01); *A61M 16/1095* (2014.02); *A61M 16/16* (2013.01); *A61M 2039/1022* (2013.01); *A61M 2205/3372* (2013.01); *A61M 2207/00* (2013.01); *B29C 53/785* (2013.01)

(58) Field of Classification Search
CPC ................ A61M 16/066; A61M 16/16; A61M 16/0683; A61M 2207/00; A61M 2039/1022; A61M 2205/3372; G01F 1/6842; G01K 13/02; G01K 13/024
See application file for complete search history.

(56) References Cited

U.S. PATENT DOCUMENTS

| | | |
|---|---|---|
| 2,516,864 A | 8/1950 | Gilmore et al. |
| 2,602,608 A | 7/1952 | Darling |
| 2,788,936 A | 4/1957 | Kemnitz |
| 2,874,722 A | 2/1959 | Hamblin |
| 2,895,001 A | 7/1959 | Mark, IV |
| 2,970,475 A * | 2/1961 | Werner ............... G01K 13/028 374/138 |
| 3,117,596 A | 1/1964 | Khan |
| 3,163,707 A | 12/1964 | Darling |
| 3,188,866 A * | 6/1965 | Mayer ............... G01K 1/08 374/E1.011 |
| 3,283,580 A | 11/1966 | Jacob et al. |
| 3,394,954 A | 7/1968 | Sams |
| 3,495,628 A | 2/1970 | Boender |
| 3,582,968 A | 6/1971 | Buiting |
| 3,584,193 A | 6/1971 | Badertscher |
| 3,638,926 A | 2/1972 | Melville et al. |
| 3,695,267 A | 10/1972 | Hirtz et al. |
| 3,766,914 A | 10/1973 | Jacobs |
| 3,914,349 A | 10/1975 | Stipanuk |
| 3,926,223 A | 12/1975 | Petzetakis |
| 3,963,856 A | 6/1976 | Carlson et al. |
| 3,990,727 A | 11/1976 | Gallagher |
| 4,013,122 A | 3/1977 | Long |
| 4,013,742 A | 3/1977 | Lang |
| 4,033,808 A | 7/1977 | Petzetakis |
| 4,038,519 A | 7/1977 | Foucras |
| 4,038,980 A | 8/1977 | Fodor |
| 4,051,205 A | 9/1977 | Grant |
| 4,060,576 A | 11/1977 | Grant |
| 4,098,853 A | 7/1978 | Brown et al. |
| 4,110,419 A | 8/1978 | Miller |
| 4,111,197 A | 9/1978 | Warncke et al. |
| 4,160,466 A | 7/1979 | Jousson |
| 4,172,105 A | 10/1979 | Miller et al. |
| 4,301,200 A | 11/1981 | Langenfeld |
| 4,333,451 A | 6/1982 | Paluch |
| 4,428,403 A | 1/1984 | Lee et al. |
| 4,430,994 A | 2/1984 | Clawson et al. |
| 4,487,232 A | 12/1984 | Kanao |
| 4,490,575 A | 12/1984 | Kutnyak |
| 4,500,480 A | 2/1985 | Cambio, Jr. |
| 4,529,867 A | 7/1985 | Velnosky et al. |
| 4,531,551 A | 7/1985 | Eichelberger et al. |
| 4,553,023 A | 11/1985 | Jameson et al. |
| 4,574,188 A | 3/1986 | Midgley et al. |
| 4,597,917 A | 7/1986 | Lunsford |
| 4,621,632 A | 11/1986 | Bartels et al. |
| 4,640,804 A | 2/1987 | Mizoguchi |
| 4,676,237 A | 6/1987 | Wood et al. |
| 4,684,786 A | 8/1987 | Mann et al. |
| 4,686,354 A | 8/1987 | Makin |
| 4,695,955 A | 9/1987 | Faisandier |
| 4,708,831 A | 11/1987 | Elsworth et al. |
| 4,710,887 A | 12/1987 | Ho |
| 4,719,945 A | 1/1988 | Richards et al. |
| 4,722,334 A | 2/1988 | Blackmer et al. |
| 4,753,758 A | 6/1988 | Miller |
| 4,773,448 A | 9/1988 | Francis |
| 4,780,247 A | 10/1988 | Yasuda |
| 4,825,863 A | 5/1989 | Dittmar et al. |
| 4,829,781 A | 5/1989 | Hitzler |
| 4,829,997 A | 5/1989 | Douwens et al. |
| 4,829,998 A | 5/1989 | Jackson |
| 4,844,512 A | 7/1989 | Gahwiler |
| 4,861,523 A | 8/1989 | Beran |
| 4,903,736 A | 2/1990 | Baston et al. |
| 4,911,157 A | 3/1990 | Miller |
| 4,911,357 A | 3/1990 | Kitamura |
| 4,921,642 A | 5/1990 | LaTorraca |
| 4,941,469 A | 7/1990 | Adahan |
| 4,953,986 A * | 9/1990 | Olson ................ G01K 13/00 374/135 |
| 4,967,744 A | 11/1990 | Chua |
| 5,031,612 A | 7/1991 | Clementi |
| 5,062,145 A | 10/1991 | Zwaan et al. |
| 5,092,326 A | 3/1992 | Winn et al. |
| 5,101,820 A | 4/1992 | Christopher |
| 5,127,442 A | 7/1992 | Blomqvist |
| 5,148,801 A | 9/1992 | Douwens et al. |
| 5,164,652 A | 11/1992 | Johnson et al. |
| 5,213,376 A | 5/1993 | Szabo |
| 5,224,923 A | 7/1993 | Moffett et al. |
| 5,230,331 A | 7/1993 | Rusz et al. |
| 5,231,979 A | 8/1993 | Rose et al. |
| 5,252,691 A | 10/1993 | Watanabe et al. |
| 5,336,156 A | 8/1994 | Miller et al. |
| 5,346,128 A | 9/1994 | Wacker |
| 5,347,211 A | 9/1994 | Jakubowski |
| 5,357,948 A | 10/1994 | Ellentropp |
| 5,367,604 A | 11/1994 | Murray |
| 5,388,443 A | 2/1995 | Manaka |

(56) References Cited

U.S. PATENT DOCUMENTS

| | | |
|---|---|---|
| 5,392,770 A | 2/1995 | Clawson et al. |
| 5,404,729 A | 4/1995 | Matsuoka et al. |
| 5,405,269 A | 4/1995 | Stupecky |
| 5,428,752 A | 6/1995 | Goren et al. |
| 5,449,234 A | 9/1995 | Gipp et al. |
| 5,450,859 A | 9/1995 | Litovitz |
| 5,454,061 A | 9/1995 | Carlson |
| 5,482,031 A | 1/1996 | Lambert |
| 5,512,732 A | 4/1996 | Yagnik et al. |
| 5,516,466 A | 5/1996 | Schlesch et al. |
| 5,529,060 A | 6/1996 | Salmon et al. |
| 5,537,996 A | 7/1996 | McPhee |
| 5,551,731 A | 9/1996 | Gray et al. |
| 5,558,084 A | 9/1996 | Daniell et al. |
| 5,564,415 A | 10/1996 | Dobson et al. |
| 5,588,423 A | 12/1996 | Smith |
| 5,591,292 A | 1/1997 | Blomqvist |
| 5,600,752 A | 2/1997 | Lopatinsky |
| 5,630,806 A | 5/1997 | Inagaki |
| 5,637,168 A | 6/1997 | Carlson |
| 5,640,951 A * | 6/1997 | Huddart ............. F16L 11/24 128/911 |
| 5,673,687 A | 10/1997 | Dobson et al. |
| 5,759,149 A | 6/1998 | Goldberg et al. |
| 5,769,071 A | 6/1998 | Turnbull |
| 5,778,872 A | 7/1998 | Fukunaga et al. |
| 5,803,770 A | 9/1998 | Swendson et al. |
| 5,848,223 A | 12/1998 | Carlson |
| 5,906,201 A | 5/1999 | Nilson |
| 5,943,473 A | 8/1999 | Levine |
| 5,988,164 A | 11/1999 | Paluch |
| 5,991,507 A | 11/1999 | Bencsits |
| 6,010,118 A | 1/2000 | Milewicz |
| 6,024,694 A | 2/2000 | Goldberg et al. |
| 6,038,457 A | 3/2000 | Barkat |
| 6,050,260 A | 4/2000 | Daniell et al. |
| 6,078,730 A | 6/2000 | Huddart et al. |
| 6,095,505 A | 8/2000 | Miller |
| 6,105,649 A | 8/2000 | Levingston et al. |
| 6,109,782 A | 8/2000 | Fukura et al. |
| 6,120,496 A | 9/2000 | Whayne |
| 6,125,847 A | 10/2000 | Lin |
| 6,138,674 A | 10/2000 | Gull et al. |
| 6,142,974 A | 11/2000 | Kistner et al. |
| 6,158,431 A | 12/2000 | Poole |
| 6,167,883 B1 | 1/2001 | Beran et al. |
| 6,189,870 B1 | 2/2001 | Withall |
| 6,190,480 B1 | 2/2001 | Carlson |
| 6,219,490 B1 | 4/2001 | Gibertoni et al. |
| 6,272,933 B1 | 8/2001 | Gradon et al. |
| 6,311,958 B1 | 11/2001 | Stanek |
| 6,347,646 B2 | 2/2002 | Fukui et al. |
| 6,349,722 B1 | 2/2002 | Gradon et al. |
| 6,367,472 B1 | 4/2002 | Koch |
| 6,367,510 B1 | 4/2002 | Carlson |
| 6,374,864 B1 | 4/2002 | Philip |
| 6,384,755 B1 | 5/2002 | Hayden |
| 6,394,084 B1 | 5/2002 | Nitta |
| 6,394,145 B1 | 5/2002 | Bailly |
| 6,397,841 B1 | 6/2002 | Kenyon et al. |
| 6,397,846 B1 | 6/2002 | Skog et al. |
| 6,398,197 B1 | 6/2002 | Dickinson et al. |
| 6,463,925 B2 | 10/2002 | Nuckols et al. |
| 6,474,335 B1 | 11/2002 | Lammers |
| 6,537,405 B1 | 3/2003 | Henderson et al. |
| 6,540,734 B1 | 4/2003 | Chiu et al. |
| 6,543,412 B2 | 4/2003 | Amou et al. |
| 6,564,011 B1 | 5/2003 | Janoff et al. |
| 6,584,972 B2 | 7/2003 | McPhee |
| 6,594,366 B1 | 7/2003 | Adams |
| 6,598,604 B1 | 7/2003 | Seakins |
| 6,668,828 B1 | 12/2003 | Figley et al. |
| 6,691,707 B1 | 2/2004 | Gunaratnam et al. |
| 6,694,974 B1 | 2/2004 | George-Gradon et al. |
| 6,698,457 B2 | 3/2004 | Hayashi et al. |
| 6,718,974 B1 | 4/2004 | Moberg |
| 6,827,109 B2 | 12/2004 | Mccaughtry |
| 6,918,389 B2 | 7/2005 | Seakins et al. |
| 6,932,119 B2 | 8/2005 | Carlson |
| 6,953,354 B2 | 10/2005 | Edirisuriya et al. |
| 7,043,979 B2 | 5/2006 | Smith et al. |
| 7,086,422 B2 | 8/2006 | Kressierer/Huber et al. |
| 7,096,864 B1 | 8/2006 | Mayer et al. |
| 7,120,354 B2 | 10/2006 | Mackie et al. |
| 7,140,367 B2 | 11/2006 | White et al. |
| 7,156,127 B2 | 1/2007 | Moulton et al. |
| 7,157,035 B2 | 1/2007 | Edirisuriya et al. |
| 7,291,240 B2 | 11/2007 | Smith et al. |
| 7,468,116 B2 | 12/2008 | Smith et al. |
| 7,559,324 B2 | 7/2009 | Smith et al. |
| 7,588,029 B2 | 9/2009 | Smith et al. |
| 7,588,186 B2 | 9/2009 | Steffen et al. |
| 7,637,288 B2 | 12/2009 | Huber et al. |
| 7,647,926 B2 | 1/2010 | Gerder et al. |
| 7,766,050 B2 | 8/2010 | Patel |
| 7,814,907 B2 | 10/2010 | Bremner et al. |
| 7,870,857 B2 | 1/2011 | Dhuper et al. |
| 7,938,113 B2 | 5/2011 | Weinstein et al. |
| 7,965,930 B2 | 6/2011 | Carlson et al. |
| 7,983,542 B2 | 7/2011 | Mcghin et al. |
| 7,997,267 B2 | 8/2011 | Ging et al. |
| 8,091,547 B2 | 1/2012 | Thudor et al. |
| 8,122,882 B2 | 2/2012 | Mcghin et al. |
| 8,186,345 B2 | 5/2012 | Payton et al. |
| 8,235,041 B2 | 8/2012 | Seakins et al. |
| 8,253,076 B2 | 8/2012 | Andel et al. |
| 8,333,194 B2 | 12/2012 | Lewis et al. |
| 8,333,199 B2 | 12/2012 | Landis et al. |
| 8,360,059 B2 | 1/2013 | Koulechov et al. |
| 8,453,641 B2 | 6/2013 | Payton et al. |
| 8,459,259 B2 | 6/2013 | Klasek et al. |
| 8,469,025 B2 | 6/2013 | Mayer et al. |
| 8,511,305 B2 | 8/2013 | Liu et al. |
| 8,511,651 B2 | 8/2013 | Fridberg et al. |
| 8,522,782 B2 | 9/2013 | Lewis et al. |
| 8,563,863 B2 | 10/2013 | Carlson |
| 8,563,864 B2 | 10/2013 | Carlson |
| 8,631,789 B2 | 1/2014 | Virr et al. |
| 8,701,966 B2 | 4/2014 | Nikkhoo et al. |
| 8,709,187 B2 | 4/2014 | Smith et al. |
| 8,733,349 B2 | 5/2014 | Bath et al. |
| 8,844,522 B2 | 9/2014 | Huby et al. |
| 9,119,933 B2 | 9/2015 | Bedford et al. |
| 9,440,040 B2 | 9/2016 | Klasek et al. |
| 9,517,321 B2 | 12/2016 | Buechi et al. |
| 9,555,210 B2 | 1/2017 | Seakins et al. |
| 9,572,949 B2 | 2/2017 | Vos et al. |
| 9,855,398 B2 | 1/2018 | Klasek et al. |
| 10,080,866 B2 | 9/2018 | Stoks et al. |
| 10,589,050 B2 | 3/2020 | Buswell et al. |
| 10,960,167 B2 | 3/2021 | Liu et al. |
| 11,058,844 B2 | 7/2021 | Amadio |
| 11,129,954 B2 | 9/2021 | Buswell et al. |
| 11,311,695 B2 | 4/2022 | Petrochenko et al. |
| 11,318,270 B2 | 5/2022 | Stoks |
| 11,338,104 B2 | 5/2022 | Klasek et al. |
| 2001/0017134 A1 | 8/2001 | Bahr |
| 2001/0050080 A1 | 12/2001 | Seakins et al. |
| 2002/0017302 A1 | 2/2002 | Fukunaga et al. |
| 2002/0038392 A1 | 3/2002 | De La Huerga |
| 2002/0120236 A1 | 8/2002 | Diaz et al. |
| 2002/0124847 A1 | 9/2002 | Smith et al. |
| 2002/0173717 A1 | 11/2002 | Rohling et al. |
| 2002/0186966 A1 | 12/2002 | Zimmer et al. |
| 2003/0059213 A1 | 3/2003 | Mackie et al. |
| 2003/0079790 A1 | 5/2003 | Atkinson et al. |
| 2003/0183294 A1 | 10/2003 | Carlson |
| 2003/0236015 A1 | 12/2003 | Edirisuriya et al. |
| 2004/0074493 A1 | 4/2004 | Seakins et al. |
| 2004/0074495 A1 | 4/2004 | Wickham et al. |
| 2004/0079371 A1 | 4/2004 | Gray |
| 2004/0081784 A1 | 4/2004 | Smith et al. |
| 2004/0099268 A1 | 5/2004 | Smith et al. |
| 2004/0101026 A1 | 5/2004 | Nitta et al. |

(56) References Cited

U.S. PATENT DOCUMENTS

| | | |
|---|---|---|
| 2004/0149284 A1 | 8/2004 | Smith et al. |
| 2004/0182392 A1 | 9/2004 | Gerder et al. |
| 2004/0244585 A1 | 12/2004 | Meckes et al. |
| 2004/0244858 A1 | 12/2004 | Jeong |
| 2005/0059957 A1 | 6/2005 | Byerly et al. |
| 2005/0152733 A1 | 7/2005 | Marchan |
| 2006/0118113 A1 | 6/2006 | Bremner et al. |
| 2006/0165829 A1 | 7/2006 | Smith et al. |
| 2006/0283447 A1 | 12/2006 | Dhuper et al. |
| 2007/0012317 A1 | 1/2007 | Flagler et al. |
| 2007/0047733 A1 | 3/2007 | Bremer et al. |
| 2007/0051368 A1 | 3/2007 | Seakins et al. |
| 2007/0079982 A1 | 4/2007 | Laurent et al. |
| 2007/0107737 A1 | 5/2007 | Landis et al. |
| 2007/0144519 A1 | 6/2007 | Henry et al. |
| 2007/0169776 A1 | 7/2007 | Kepler et al. |
| 2007/0277828 A1 | 12/2007 | Ho et al. |
| 2008/0028560 A1 | 2/2008 | Policiccio et al. |
| 2008/0028850 A1* | 2/2008 | Payton .............. A61M 16/1075 73/204.19 |
| 2008/0078259 A1 | 4/2008 | Duff |
| 2008/0105257 A1* | 5/2008 | Klasek .............. A61M 16/0875 128/203.26 |
| 2008/0105258 A1 | 5/2008 | Deane et al. |
| 2008/0173305 A1 | 7/2008 | Frater |
| 2008/0202512 A1 | 8/2008 | Kressierer/Huber et al. |
| 2008/0251073 A1 | 10/2008 | Jassell et al. |
| 2008/0264413 A1 | 10/2008 | Doherty et al. |
| 2009/0017651 A1 | 1/2009 | Nagata et al. |
| 2009/0050150 A1 | 2/2009 | Rossen et al. |
| 2009/0078259 A1 | 3/2009 | Kooij et al. |
| 2009/0078440 A1 | 3/2009 | Carlson et al. |
| 2009/0107493 A1 | 4/2009 | Liu et al. |
| 2009/0107496 A1 | 4/2009 | McGhin et al. |
| 2009/0110379 A1 | 4/2009 | McGhin et al. |
| 2009/0126817 A1 | 5/2009 | Gray |
| 2009/0149696 A1 | 6/2009 | Chilton, III |
| 2009/0320840 A1 | 12/2009 | Klasek et al. |
| 2010/0083965 A1 | 4/2010 | Virr et al. |
| 2010/0116272 A1* | 5/2010 | Row ............... A61M 16/0816 128/204.17 |
| 2010/0147301 A1 | 6/2010 | Kwok |
| 2010/0218763 A1 | 9/2010 | Payton et al. |
| 2010/0224276 A1 | 9/2010 | Forrester et al. |
| 2011/0022748 A1 | 1/2011 | Edwards et al. |
| 2011/0023874 A1* | 2/2011 | Bath ............... A61M 16/0816 128/203.14 |
| 2011/0046494 A1 | 2/2011 | Balji et al. |
| 2011/0073109 A1 | 3/2011 | Mayer et al. |
| 2011/0108031 A1 | 5/2011 | Korneff et al. |
| 2011/0155132 A1 | 6/2011 | Virr et al. |
| 2011/0168287 A1 | 7/2011 | Carlson |
| 2011/0186048 A1 | 8/2011 | Casse |
| 2012/0000703 A1 | 1/2012 | Kim et al. |
| 2012/0125333 A1 | 5/2012 | Bedford |
| 2012/0146251 A1 | 6/2012 | Heine |
| 2012/0160024 A1* | 6/2012 | Matsumoto .......... G01F 15/185 73/204.11 |
| 2012/0255758 A1 | 10/2012 | Lee |
| 2013/0104888 A1 | 5/2013 | Landis et al. |
| 2013/0104901 A1 | 5/2013 | Landis et al. |
| 2013/0174839 A1 | 7/2013 | Ging et al. |
| 2013/0239966 A1 | 9/2013 | Klasek et al. |
| 2013/0255677 A1 | 10/2013 | Varga |
| 2013/0280055 A1 | 10/2013 | Daly et al. |
| 2013/0333701 A1 | 12/2013 | Herron |
| 2013/0340752 A1 | 12/2013 | Landis et al. |
| 2014/0037276 A1 | 2/2014 | Carlson |
| 2014/0130802 A1 | 5/2014 | Virr et al. |
| 2014/0191457 A1 | 7/2014 | Sharma et al. |
| 2014/0202460 A1 | 7/2014 | Bath et al. |
| 2014/0202462 A1 | 7/2014 | Stoks |
| 2014/0216459 A1 | 8/2014 | Vos et al. |
| 2014/0236083 A1 | 8/2014 | Sims |
| 2014/0238397 A1 | 8/2014 | Buechi et al. |
| 2014/0246021 A1 | 9/2014 | Buechi et al. |
| 2014/0311487 A1 | 10/2014 | Buechi et al. |
| 2014/0318536 A1 | 10/2014 | Landis et al. |
| 2014/0366876 A1 | 12/2014 | Huby et al. |
| 2015/0090260 A1 | 4/2015 | Seakins et al. |
| 2015/0108670 A1 | 4/2015 | Magee |
| 2015/0177037 A1* | 6/2015 | Wagner .............. G01N 27/048 73/204.22 |
| 2015/0306333 A1 | 10/2015 | Amadio et al. |
| 2016/0008560 A1 | 1/2016 | Kwok |
| 2016/0199612 A1 | 7/2016 | Foote et al. |
| 2016/0256657 A1 | 9/2016 | Klasek et al. |
| 2016/0271356 A1 | 9/2016 | Robertson et al. |
| 2016/0354573 A1 | 12/2016 | Buswell et al. |
| 2017/0095637 A1 | 4/2017 | Seakins |
| 2017/0100556 A1 | 4/2017 | Munkelt et al. |
| 2018/0214657 A1 | 8/2018 | Forrester |
| 2018/0214659 A1 | 8/2018 | Forrester |
| 2018/0280651 A1 | 10/2018 | Liu et al. |
| 2019/0001091 A1 | 1/2019 | Bath et al. |
| 2019/0076620 A1 | 3/2019 | Stoks et al. |
| 2020/0016361 A1 | 1/2020 | Buswell et al. |
| 2020/0338295 A1 | 10/2020 | Munkelt et al. |
| 2021/0069448 A1 | 3/2021 | Andresen et al. |
| 2021/0205564 A1 | 7/2021 | Virr et al. |
| 2021/0260330 A1 | 8/2021 | Liu et al. |
| 2022/0008678 A1 | 1/2022 | Virr et al. |
| 2022/0023578 A1 | 1/2022 | Klasek et al. |
| 2022/0040437 A1 | 2/2022 | Buswell et al. |
| 2022/0211966 A1 | 7/2022 | Stoks et al. |
| 2022/0273902 A1 | 9/2022 | Petrochenko et al. |

FOREIGN PATENT DOCUMENTS

| | | |
|---|---|---|
| AU | 756477 | 6/2000 |
| AU | 780911 | 1/2002 |
| AU | 2003278649 A1 | 6/2004 |
| AU | 2007317198 A1 | 5/2008 |
| AU | 2008237548 | 5/2009 |
| AU | 2008237550 | 5/2009 |
| CA | 2674249 C | 4/2014 |
| CN | 2243015 Y | 12/1996 |
| CN | 1204266 | 1/1999 |
| CN | 1549910 | 11/2004 |
| CN | 1899641 | 1/2007 |
| CN | 2926729 Y | 7/2007 |
| CN | 101018582 A | 8/2007 |
| CN | 101541367 A | 9/2007 |
| CN | 201672170 U | 12/2010 |
| DE | 36 29 353 | 1/1988 |
| DE | 4020522 A1 | 1/1992 |
| DE | 40 34 611 | 5/1992 |
| DE | 4102223 A1 | 7/1992 |
| DE | 9200567 U1 | 7/1992 |
| DE | 33 11 811 | 10/1994 |
| DE | 94 09 231.1 | 12/1994 |
| DE | 19647548 A1 | 5/1998 |
| DE | 19958296 C1 | 9/2001 |
| DE | 20202906 U1 | 5/2002 |
| DE | 10312881 B3 | 5/2004 |
| DE | 20 2004 006 484 U1 | 9/2005 |
| DE | 202005008152 | 10/2006 |
| DE | 202005008156 U1 | 11/2006 |
| DE | 202006007397 U1 | 9/2007 |
| DE | 102006056781 A1 | 6/2008 |
| DE | 102007003454 A1 | 7/2008 |
| DE | 102007003455 | 8/2008 |
| DE | 202007018764 U1 | 6/2009 |
| DE | 102011055439 A1 | 5/2013 |
| EP | 0111248 A2 | 6/1984 |
| EP | 0201985 | 11/1986 |
| EP | 0232864 A2 | 8/1987 |
| EP | 0258928 | 9/1988 |
| EP | 0342802 | 11/1989 |
| EP | 0481 459 | 4/1992 |
| EP | 0556561 | 8/1993 |
| EP | 616 166 | 9/1994 |
| EP | 0621050 A2 | 10/1994 |

(56) References Cited

FOREIGN PATENT DOCUMENTS

| | | |
|---|---|---|
| EP | 0672430 A2 | 9/1995 |
| EP | 0 885 623 | 12/1998 |
| EP | 0956068 | 11/1999 |
| EP | 1078645 | 2/2001 |
| EP | 1127583 | 8/2001 |
| EP | 1 138 341 | 10/2001 |
| EP | 1145678 | 10/2001 |
| EP | 1147004 B1 | 2/2003 |
| EP | 1352670 A1 | 10/2003 |
| EP | 1380276 A1 | 1/2004 |
| EP | 1396277 A2 | 3/2004 |
| EP | 1 457 223 | 9/2004 |
| EP | 1535722 A2 | 6/2005 |
| EP | 1579984 A2 | 9/2005 |
| EP | 1 634 614 | 3/2006 |
| EP | 1741462 B1 | 11/2007 |
| EP | 2055336 | 5/2009 |
| EP | 2055338 | 5/2009 |
| EP | 2055339 | 5/2009 |
| EP | 2055340 | 5/2009 |
| EP | 2075026 A1 | 7/2009 |
| EP | 2079505 | 7/2009 |
| EP | 2269680 A1 | 1/2011 |
| EP | 2133611 B1 | 9/2011 |
| EP | 2269680 B1 | 9/2012 |
| EP | 2514478 | 7/2013 |
| EP | 2689174 | 1/2014 |
| EP | 2337604 | 3/2014 |
| EP | 2747816 B1 | 1/2018 |
| GB | 836599 | 6/1960 |
| GB | 897292 A | 5/1962 |
| GB | 1 167 551 | 10/1969 |
| GB | 2056611 | 3/1981 |
| GB | 2173274 A | 2/1989 |
| GB | 2 277 689 | 11/1994 |
| JP | 48-031555 U | 3/1973 |
| JP | S56-109189 U | 8/1981 |
| JP | 57-10781 U | 1/1982 |
| JP | 57-0104781 U | 6/1982 |
| JP | S59-113392 | 6/1984 |
| JP | 04-328211 | 11/1992 |
| JP | 05-317428 | 12/1993 |
| JP | 08-061731 | 3/1996 |
| JP | H08-109984 A | 4/1996 |
| JP | H09-234247 | 9/1997 |
| JP | H09-276408 | 10/1997 |
| JP | 10-149996 A | 6/1998 |
| JP | H11-033119 A | 2/1999 |
| JP | H11-286058 | 10/1999 |
| JP | 2000-252450 A | 9/2000 |
| JP | 2001-129091 | 5/2001 |
| JP | 2001-511507 A | 8/2001 |
| JP | 2003-139276 A | 5/2003 |
| JP | 2004-148817 | 5/2004 |
| JP | 2005-161012 | 6/2005 |
| JP | 2005-331101 | 12/2005 |
| JP | 5-403996 | 5/2009 |
| JP | 2009-106746 | 5/2009 |
| JP | 4422293 B2 | 2/2010 |
| JP | 2010-194130 | 9/2010 |
| JP | 2010-256993 | 11/2010 |
| JP | 2011-118836 | 6/2011 |
| JP | 2012-134934 | 7/2012 |
| NZ | 579384 | 5/2011 |
| NZ | 587113 | 12/2011 |
| NZ | 589766 | 5/2012 |
| NZ | 575837 | 7/2012 |
| NZ | 583968 | 10/2012 |
| NZ | 597827 | 6/2013 |
| NZ | 590924 | 8/2013 |
| NZ | 600986 | 8/2013 |
| NZ | 597179 | 9/2013 |
| NZ | 605324 | 6/2014 |
| NZ | 605326 | 7/2014 |
| NZ | 607629 | 7/2014 |
| NZ | 610299 | 11/2014 |
| NZ | 701541 | 5/2015 |
| NZ | 625795 | 6/2015 |
| NZ | 620739 | 8/2015 |
| NZ | 625605 | 4/2016 |
| NZ | 710351 | 1/2017 |
| NZ | 631008 | 7/2017 |
| NZ | 730968 | 1/2019 |
| NZ | 765241 | 2/2022 |
| RU | 48212 | 9/2005 |
| SU | 379270 | 4/1973 |
| TW | 200722123 | 6/2007 |
| WO | 87000423 | 1/1987 |
| WO | WO 92/21163 A1 | 11/1992 |
| WO | WO 1996/020748 A1 | 7/1996 |
| WO | WO 97/18001 A1 | 5/1997 |
| WO | WO 98/26826 | 6/1998 |
| WO | WO 01/10489 | 2/2001 |
| WO | WO 01/095965 | 12/2001 |
| WO | WO 02/017030 | 2/2002 |
| WO | WO 02/32486 | 4/2002 |
| WO | WO 2003/022342 A1 | 3/2003 |
| WO | WO 2003/026721 A2 | 4/2003 |
| WO | WO 03/055554 | 7/2003 |
| WO | WO 04/001873 | 12/2003 |
| WO | WO 04/011072 | 2/2004 |
| WO | WO 2004/024429 A1 | 3/2004 |
| WO | WO 2004/039444 A1 | 5/2004 |
| WO | WO 04/112873 | 12/2004 |
| WO | WO 2004/105847 | 12/2004 |
| WO | WO 2004/105848 A1 | 12/2004 |
| WO | WO 2005/021076 A2 | 3/2005 |
| WO | 2006019323 A1 | 2/2006 |
| WO | WO 06/094576 | 9/2006 |
| WO | WO 2006/092001 A1 | 9/2006 |
| WO | WO 2006/095151 | 9/2006 |
| WO | WO 07/048414 | 5/2007 |
| WO | WO 2007/051230 A1 | 5/2007 |
| WO | WO 2008/055307 A1 | 5/2008 |
| WO | WO 2008/055308 A1 | 5/2008 |
| WO | WO 2008/060046 A1 | 5/2008 |
| WO | WO 2008/060295 | 5/2008 |
| WO | WO 2008/076230 | 6/2008 |
| WO | WO 2009/015410 A1 | 2/2009 |
| WO | WO 2009/022004 A2 | 2/2009 |
| WO | WO 2010/084183 A2 | 7/2010 |
| WO | WO 10/098022 | 9/2010 |
| WO | WO 2011/051837 A1 | 5/2011 |
| WO | WO 2011/051870 A1 | 5/2011 |
| WO | WO 2011/136665 A1 | 11/2011 |
| WO | WO 2011/162622 A1 | 12/2011 |
| WO | WO 2012/053910 A1 | 4/2012 |
| WO | WO 11/030251 | 7/2012 |
| WO | WO 12/154064 | 11/2012 |
| WO | WO 2012/164407 A1 | 12/2012 |
| WO | WO 13/022356 | 2/2013 |
| WO | WO 2013/026901 A1 | 2/2013 |
| WO | WO 2013/045575 | 4/2013 |
| WO | WO 2013/072119 A1 | 5/2013 |
| WO | WO 2013/127474 | 9/2013 |
| WO | WO 2013/137753 A1 | 9/2013 |
| WO | WO 2013/147623 A1 | 10/2013 |
| WO | WO 2013/165263 A1 | 11/2013 |
| WO | WO 2014/025266 | 2/2014 |
| WO | WO 2014/077706 A1 | 5/2014 |
| WO | WO 2014/088430 A1 | 6/2014 |
| WO | WO 2014/205513 | 12/2014 |
| WO | WO 2015/038013 A1 | 3/2015 |
| WO | WO 2015/142192 | 9/2015 |
| WO | WO 2017/043981 A1 | 3/2017 |
| WO | WO 2018/116187 | 6/2018 |
| WO | WO 04/043256 | 5/2024 |

OTHER PUBLICATIONS

MR810 Respiratory Humidifier Technical Manual, Revision C.
Fisher & Paykel Healthcare, Annual Report 2003.

(56) References Cited

OTHER PUBLICATIONS

Fisher & Paykel Healthcare, FY04 Full Year Overview & Update, May 24, 2004.
Fisher & Paykel Healthcare, Full Year Analyst Briefing, Jun. 5, 2002.
MR850 Respiratory Humidifier Instruction Sheet, Rev. G, Feb. 2004.
Fisher & Paykel Healthcare, 900HC506 Heated Wall Tube Part Brochure, Jul. 10, 2001, in 1 page.
Fisher & Paykel Healthcare, 900HC506/505 Product Specification, Jul. 10, 2001, in 3 pages.
Freescale Semiconductors, Inc., White Paper: Thermal Analysis of Semiconductor Systems, 2008, p. 1-24. (Year: 2008).
Merriam-Webster, Definition of "Lateral", Downloaded to pdf on Apr. 7, 2023. https://www.merriam-webster.com/dictionary/lateral ( Year: 2023).
A R Wilkes, "Humidification: its importance and delivery," BJA CEPD Reviews, vol. 1, Issue 2, Apr. 2001, pp. 40-43.
ISO, "Respiratory Tract Humidifiers for Medical Use—Particular Requirements for Respiratory Humidification Systems," https://www.iso.org/obp/ui#iso:std:iso:8185:ed-3:v2:en, Jul. 1, 2007, in 58 pages.
NIV Masks & Heated Wire Circuits Brochure, 2018, 16 pages.
Zhang et al., Thermal Design and Thermal Analysis of Printed Circuit Board, Modern Electronic Technology, vol. 30, No. 18, pp. 180-192, 2007.

\* cited by examiner

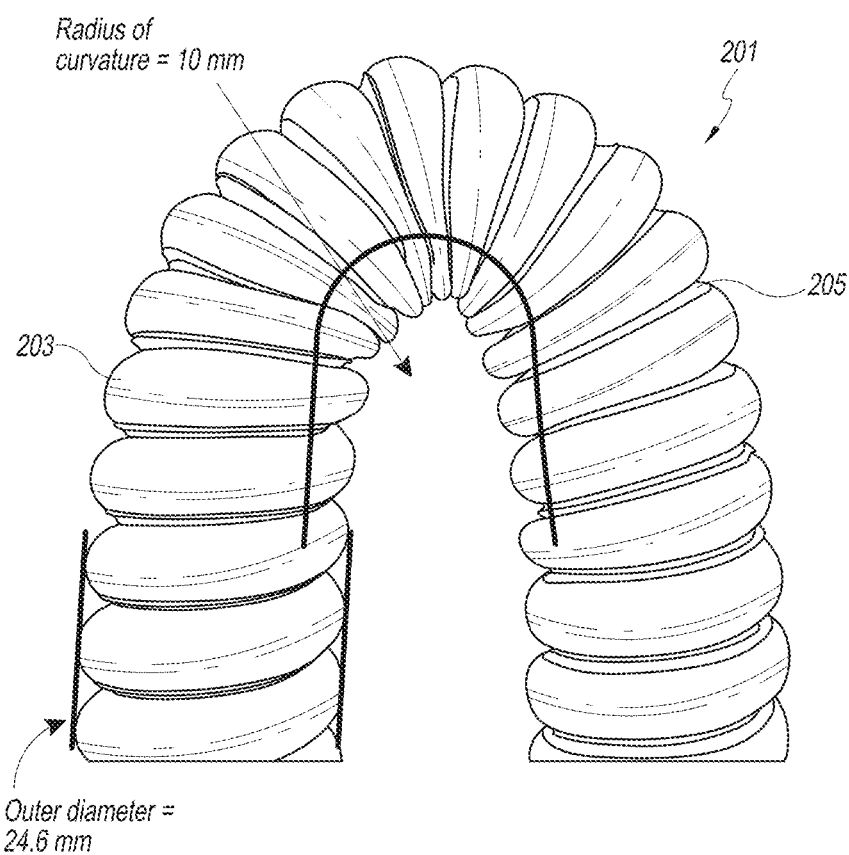
FIG. IIA
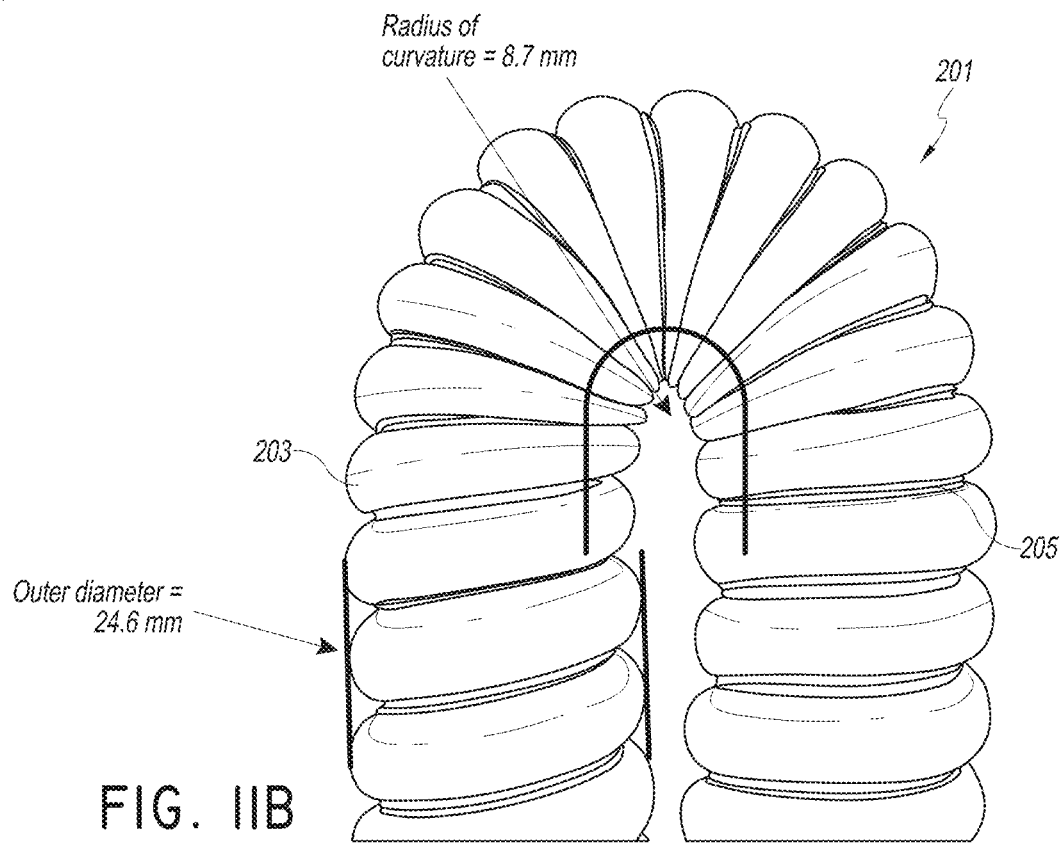
FIG. IIB

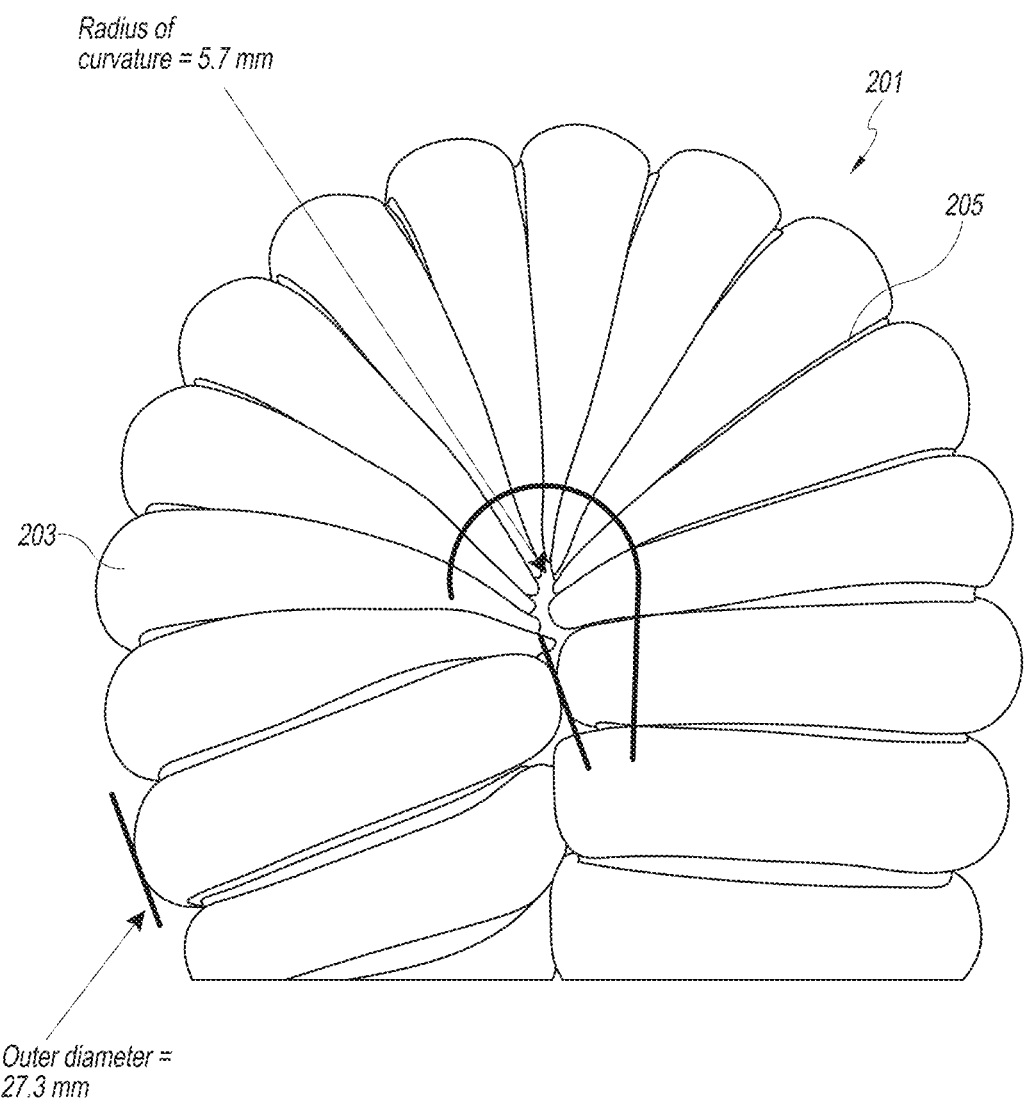
FIG. IIC

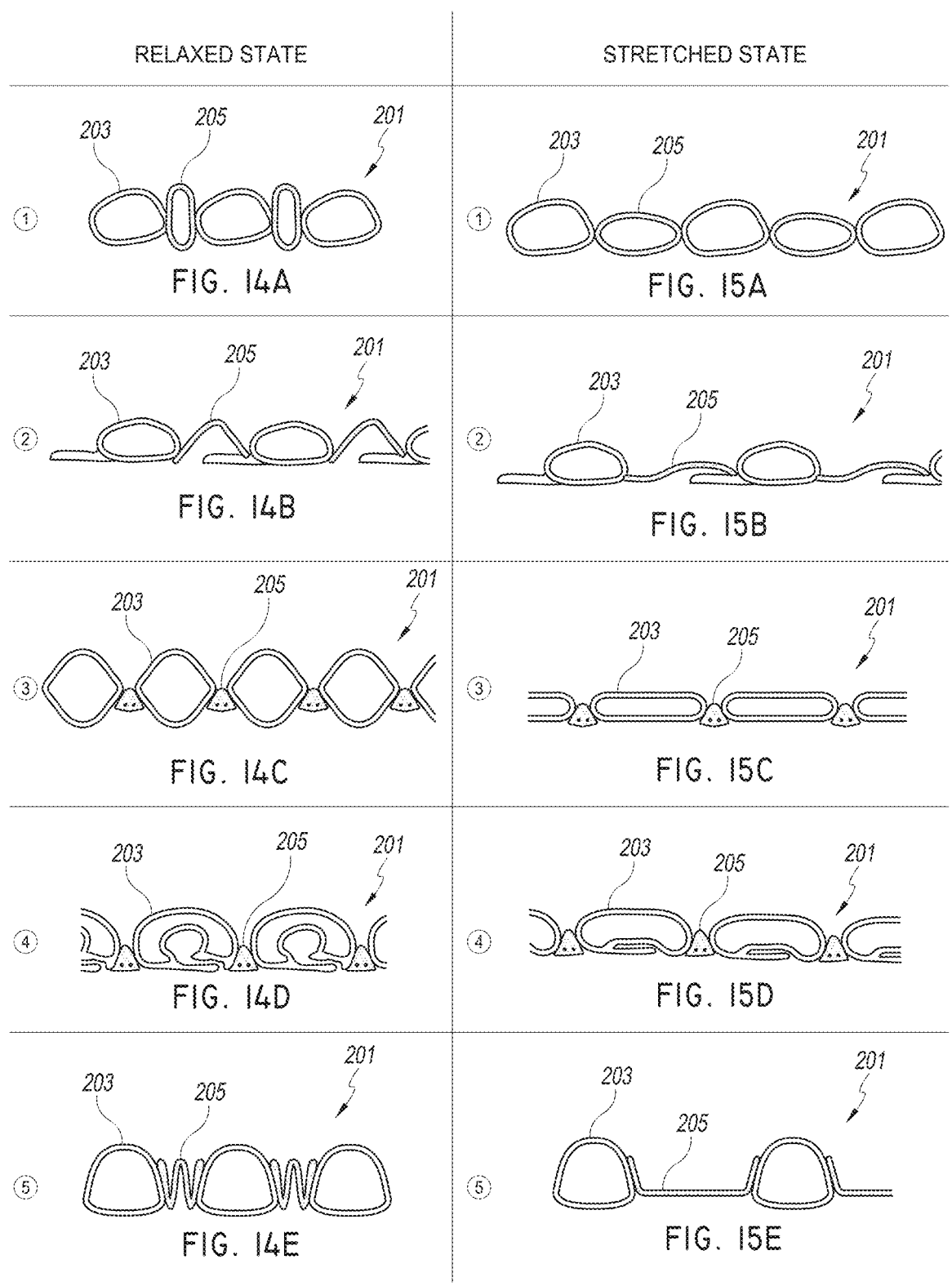

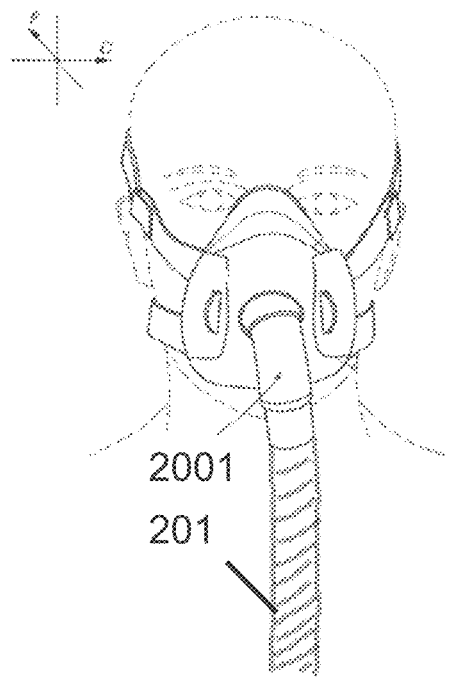
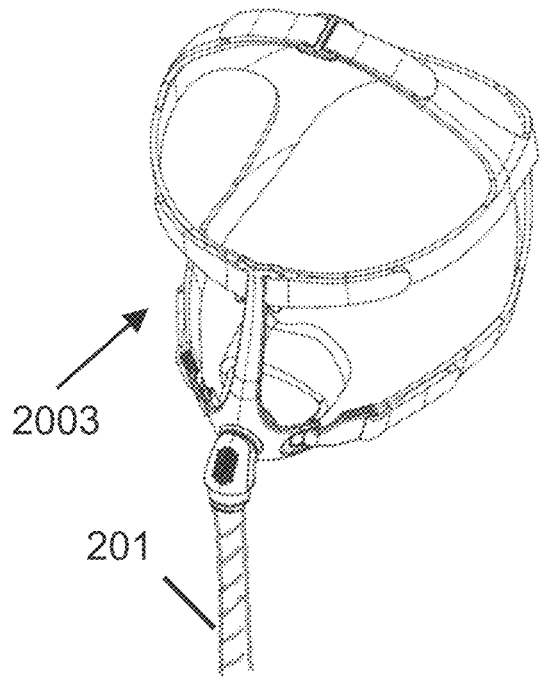
FIG. 20A    FIG. 20B
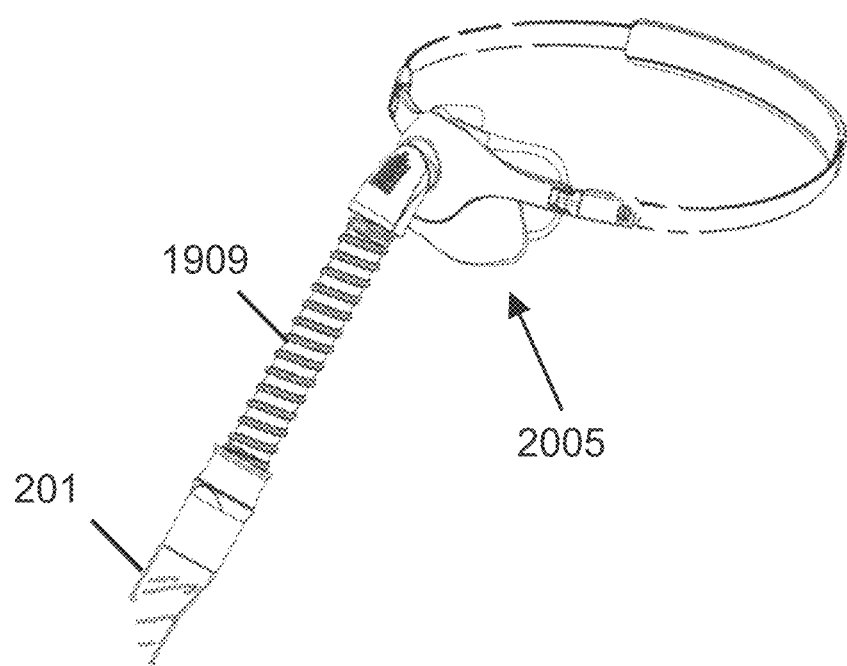
FIG. 20C

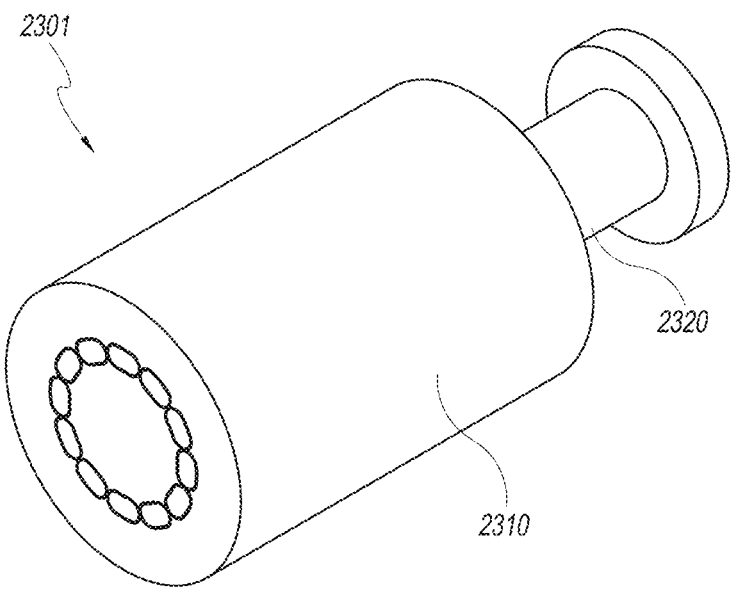
FIG. 23C
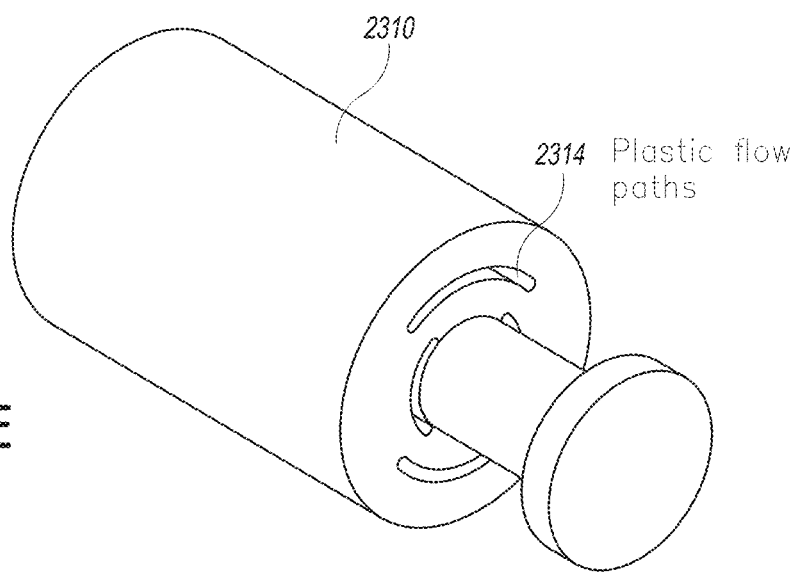
FIG. 23D
FIG. 23E

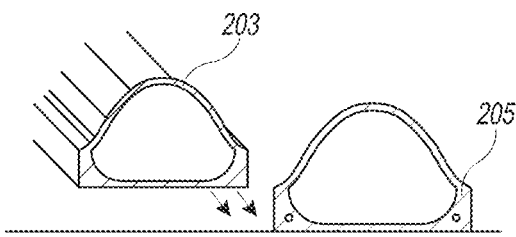
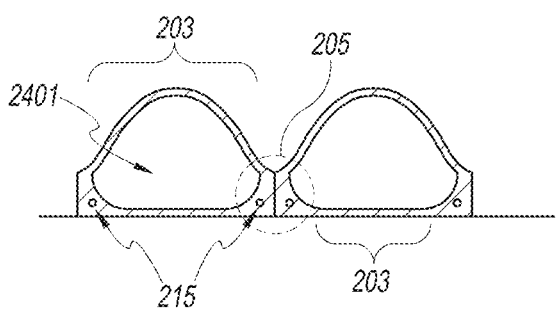
FIG. 24A FIG. 24B
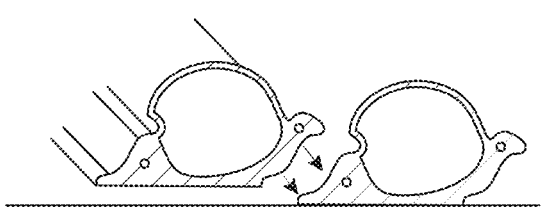
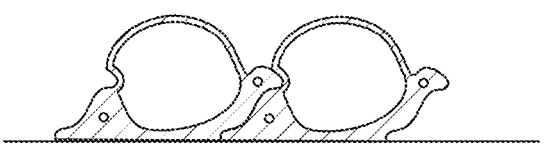
FIG. 24C FIG. 24D
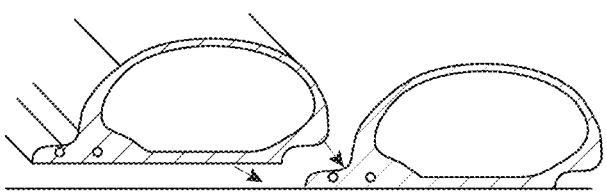
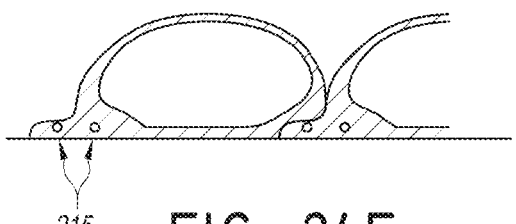
FIG. 24E FIG. 24F

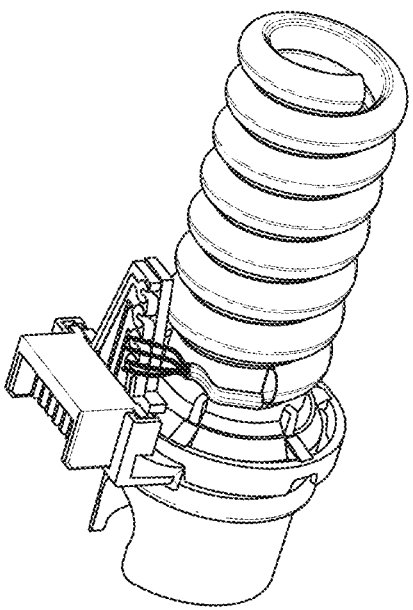
FIG. 25H
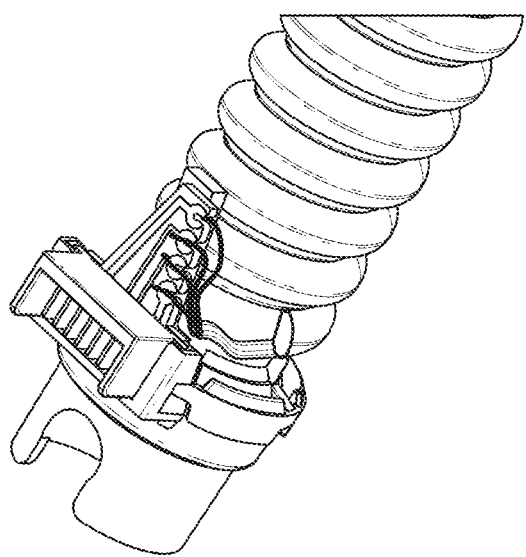
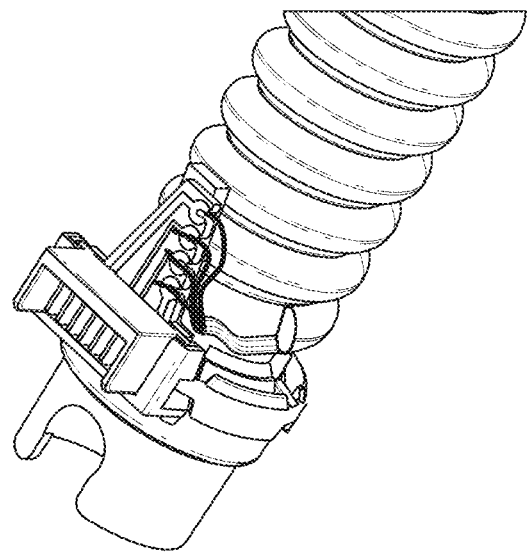
FIG. 25I
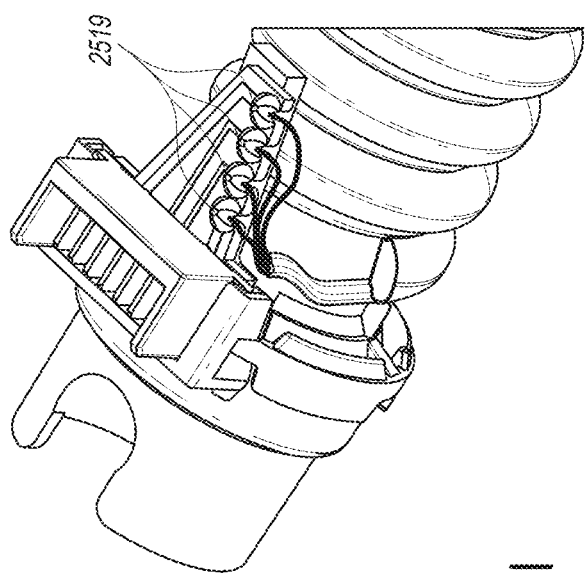

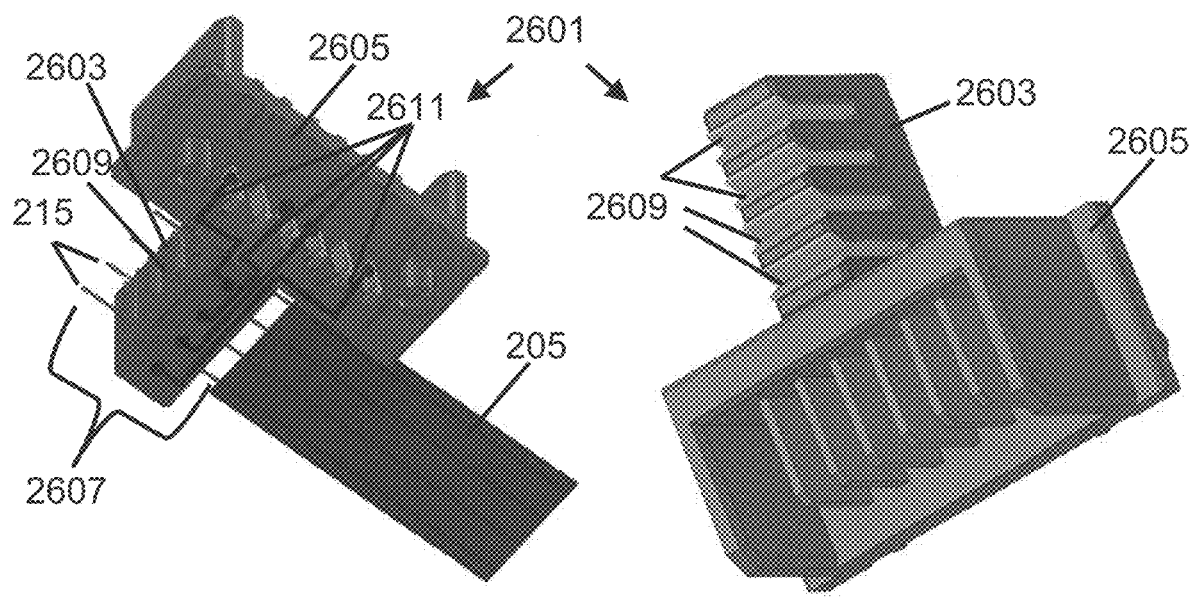
*FIG. 26A*  *FIG. 26B*
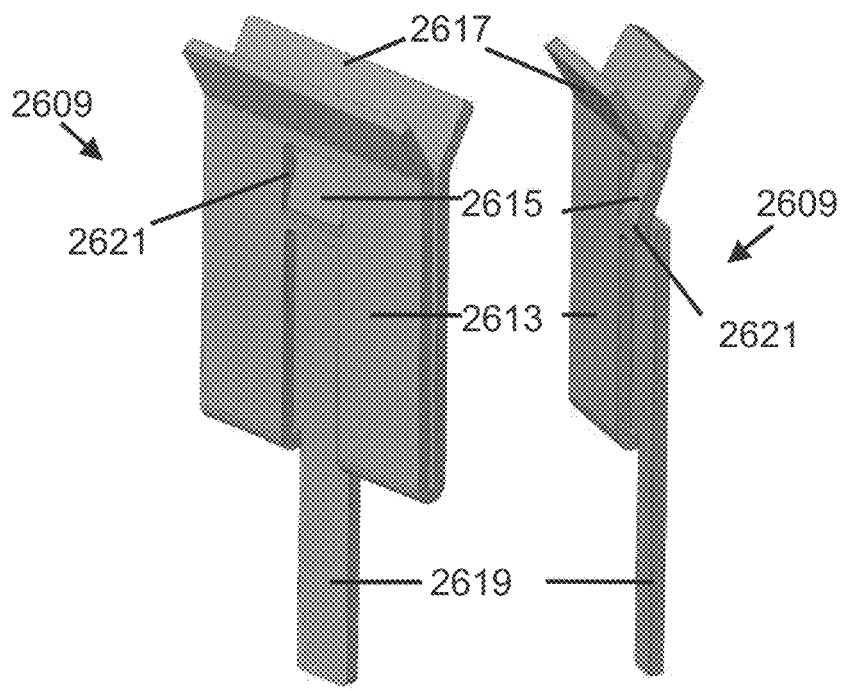
*FIG. 26C*  *FIG. 26D*

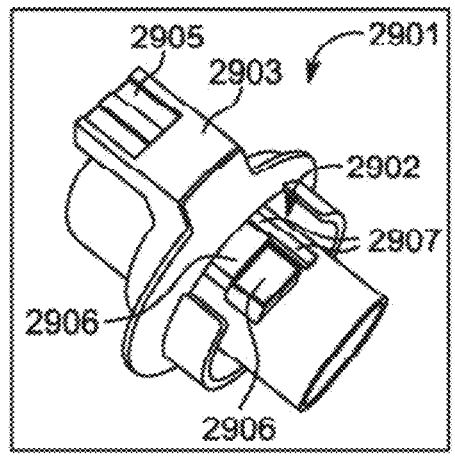
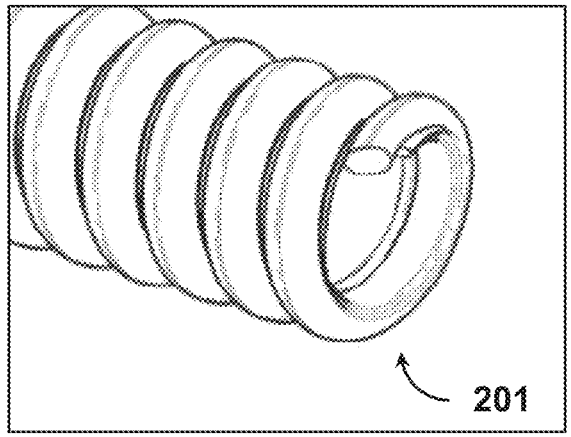
FIG. 29A  FIG. 29B
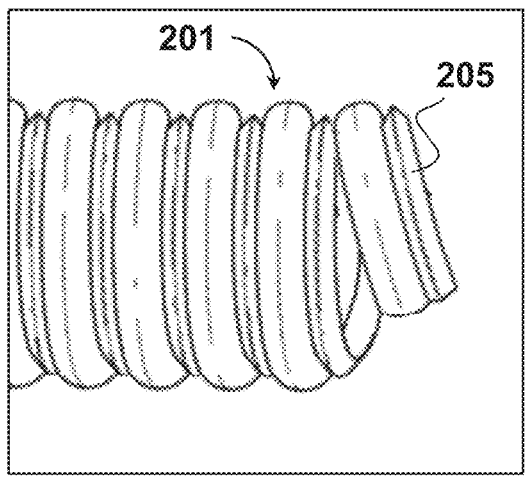
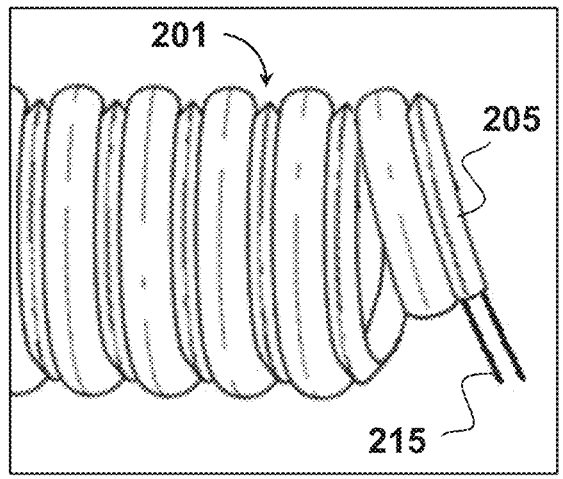
FIG. 29C  FIG. 29D

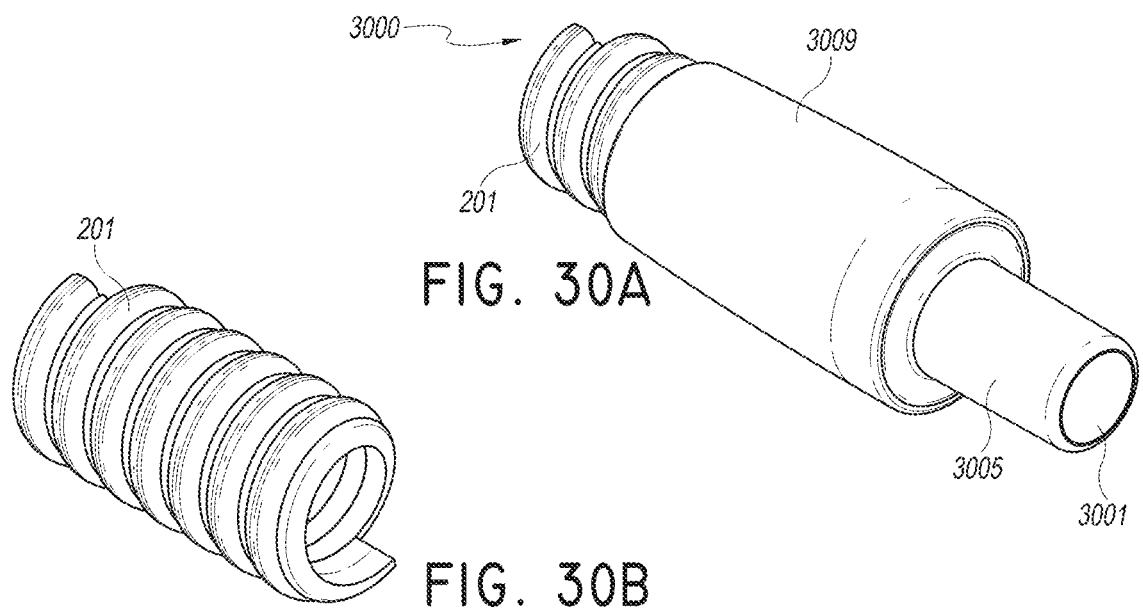
FIG. 30A
FIG. 30B
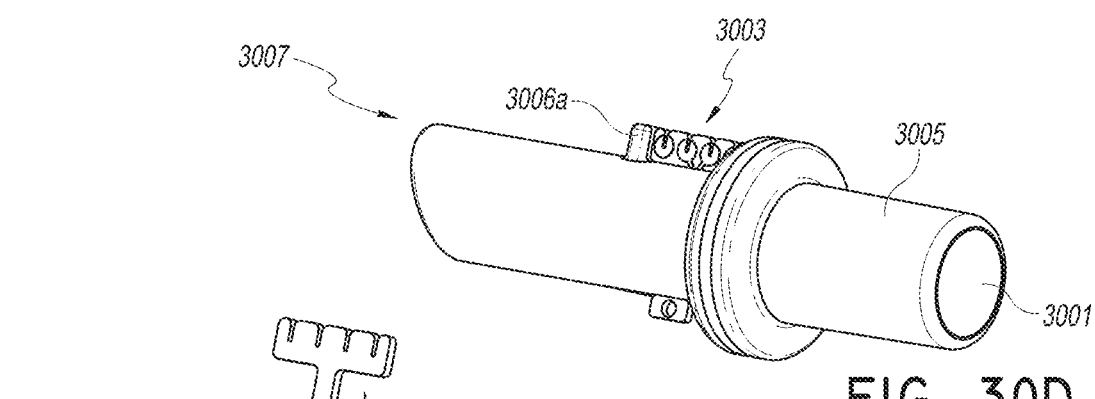
FIG. 30D
FIG. 30C
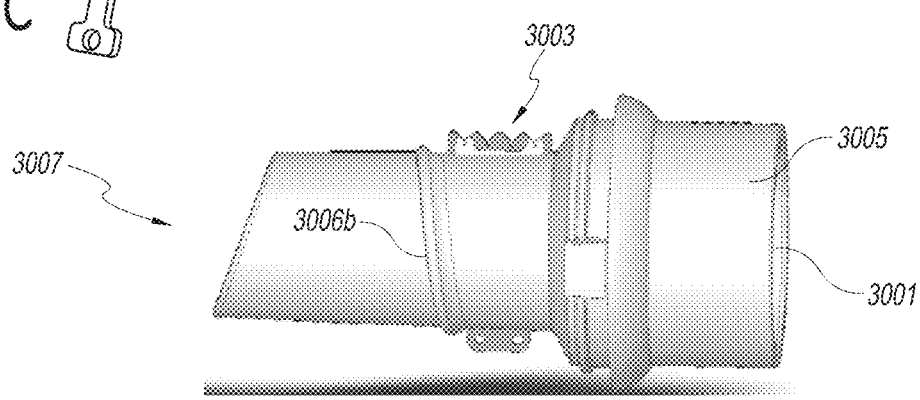
FIG. 30E

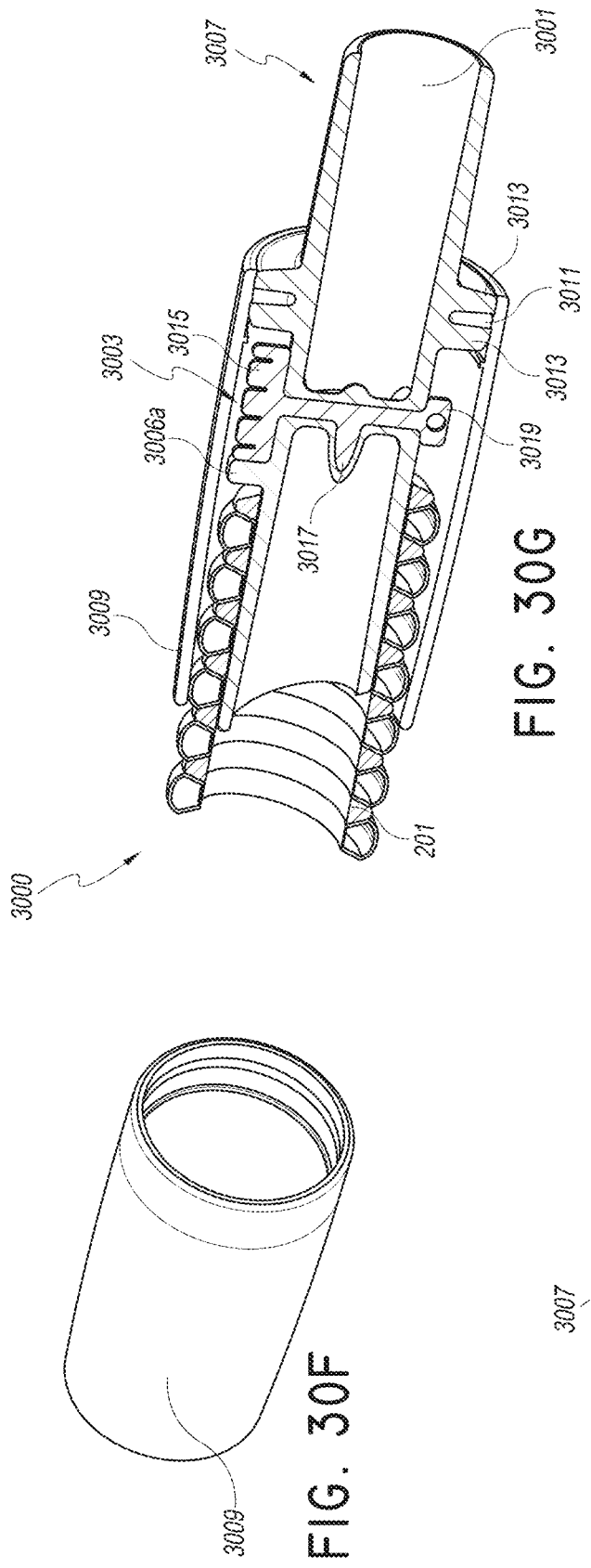

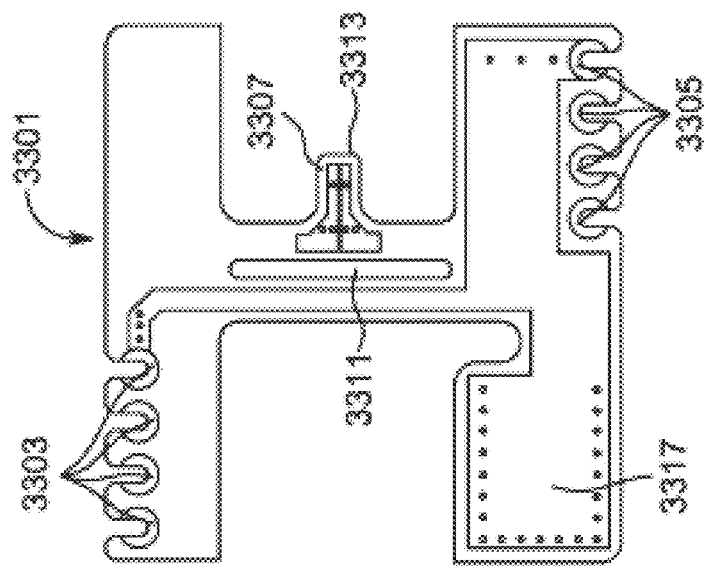
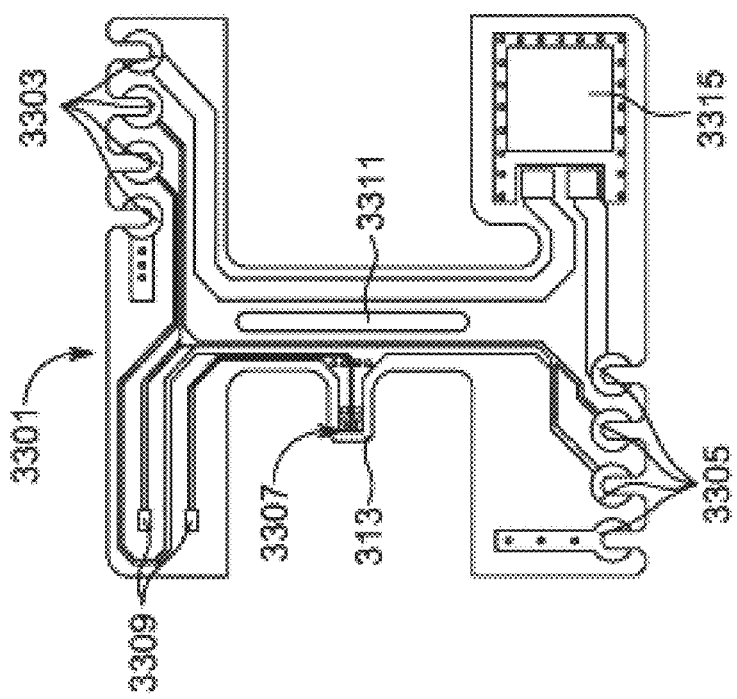
FIG. 33B
FIG. 33A

MEDICAL TUBES AND METHODS OF MANUFACTURE

INCORPORATION BY REFERENCE

This application is a divisional of U.S. patent application Ser. No. 14/649,801, filed Jun. 4, 2015, which is the U.S. national phase of International Application No. PCT/NZ2013/000222, filed Dec. 4, 2013, which claims the benefit of priority under 35 U.S.C. § 119 (e) to U.S. Provisional Application No. 61/733,359, entitled MEDICAL TUBES AND METHODS OF MANUFACTURE, filed on Dec. 4, 2012; U.S. Provisional Application No. 61/733,360, entitled MEDICAL TUBES AND METHODS OF MANUFACTURE, filed on Dec. 4, 2012; U.S. Provisional Application No. 61/877,622, entitled MEDICAL TUBES AND METHODS OF MANUFACTURE, filed on Sep. 13, 2013; U.S. Provisional Application No. 61/877,566, entitled HUMIDIFICATION SYSTEM, filed on Sep. 13, 2013; U.S. Provisional Application No. 61/877,784, entitled CONNECTIONS FOR HUMIDIFICATION SYSTEM, filed on Sep. 13, 2013; and U.S. Provisional Application No. 61/877,736, entitled ZONE HEATING FOR RESPIRATORY CIRCUITS, filed on Sep. 13, 2013, each of which is incorporated herein by reference in its entirety.

In addition, PCT Application No. PCT/IB2012/001786, entitled MEDICAL TUBES AND METHODS OF MANUFACTURE, filed May 30, 2012, is also incorporated herein by reference in its entirety.

BACKGROUND

Field

This disclosure relates generally to tubes suitable for medical use, and in particular to tubes for use in medical circuits suitable for providing gases to and/or removing gases from a patient, such as in positive airway pressure (PAP), respirator, anaesthesia, ventilator, and insufflation systems.

Description of the Related Art

In medical circuits, various components transport warm and/or humidified gases to and from patients. For example, in some breathing circuits such as PAP or assisted breathing circuits, gases inhaled by a patient are delivered from a heater-humidifier through an inspiratory tube. As another example, tubes can deliver humidified gas (commonly $CO_2$) into the abdominal cavity in insufflation circuits. This can help prevent "drying out" of the patient's internal organs, and can decrease the amount of time needed for recovery from surgery. Unheated tubing allows significant heat loss to ambient cooling. This cooling may result in unwanted condensation or "rainout" along the length of the tubing transporting warm, humidified air. A need remains for tubing that insulates against heat loss and, for example, allows for improved temperature and/or humidity control in medical circuits. Accordingly, it is an object of the invention to overcome or ameliorate one or more of the disadvantages of the prior art or to at least provide the public with a useful choice.

SUMMARY

Medical tubes and methods of manufacturing medical tubes are disclosed herein in various embodiments. In some embodiments, the tube may be a composite structure made of two or more distinct components that are spirally wound to form an elongate tube. For example, one of the components may be a spirally wound elongate hollow body, and the other component may be an elongate structural component also spirally wound between turns of the spirally wound hollow body In other embodiments, the tube need not be made from distinct components. For instance, an elongate hollow body formed (e.g., extruded) from a single material may be spirally wound to form an elongate tube. The elongate hollow body itself may in transverse cross-section have a thin wall portion and a relatively thicker or more rigid reinforcement portion. The tubes can be incorporated into a variety of medical circuits or may be employed for other medical uses.

In at least one embodiment, a composite tube can comprise a first elongate member comprising a hollow body spirally wound to form at least in part an elongate tube having a longitudinal axis, a lumen extending along the longitudinal axis, and a hollow wall surrounding the lumen. A second elongate member may be spirally wound and joined between adjacent turns of the first elongate member, the second elongate member forming at least a portion of the lumen of the elongate tube. The name "first elongate member" and "second elongate member" do not necessarily connote an order, such as the order in which the components are assembled. As described herein, the first elongate member and the second elongate member can also be portions of a single tube-shaped element.

In various embodiments, the foregoing component has one, some, or all of the following properties, as well as properties described elsewhere in this disclosure.

The first elongate member can be a tube. The first elongate member can form in longitudinal cross-section a plurality of bubbles with a flattened surface at the lumen. Adjacent bubbles can be separated by a gap above the second elongate member, or may not be directly connected to each other. The bubbles can have perforations. The second elongate member can have a longitudinal cross-section that is wider proximal the lumen and narrower at a radial distance from the lumen. Specifically, the second elongate member can have a longitudinal cross-section that is generally triangular, generally T-shaped, or generally Y-shaped. One or more conductive filaments can be embedded or encapsulated in the second elongate member. The one or more conductive filaments can be heating filaments (or more specifically, resistance heating filaments) and/or sensing filaments. The tube can comprise pairs of conductive filaments, such as two or four conductive filaments. Pairs of conductive filaments can be formed into a connecting loop at one end of the composite tube. The one or more conductive filaments can be spaced from the lumen wall. In at least one embodiment, the second elongate member can have a longitudinal cross-section that is generally triangular, generally T-shaped, or generally Y-shaped, and one or more conductive filaments can be embedded or encapsulated in the second elongate member on opposite sides of the triangle, T-shape, or Y-shape.

The foregoing component according to any or all of the preceding embodiments can be incorporated into a medical circuit component, an inspiratory tube, an expiratory tube, a PAP component, an insufflation circuit, an exploratory component, or a surgical component, among other applications.

A method of manufacturing a composite tube is also disclosed. The resulting tube can have one, some, or all of the properties described above or anywhere in this disclosure. In at least one embodiment, the method comprises providing a first elongate member comprising a hollow body and a second elongate member configured to provide structural support for the first elongate member. The second elongate member is spirally wrapped around a mandrel with opposite side edge portions of the second elongate member being spaced apart on adjacent wraps, thereby forming a second-elongate-member spiral. The first elongate member is spirally wrapped around the second-elongate-member spiral, such that portions of the first elongate member overlap adjacent wraps of the second-elongate-member spiral and a portion of the first elongate member is disposed adjacent the mandrel in the space between the wraps of the second-elongate-member spiral, thereby forming a first-elongate-member spiral.

In various embodiments, the foregoing method can comprise one, some, or all of the following. The method can comprise supplying air at a pressure greater than atmospheric pressure to an end of the first elongate member. The method can comprise cooling the second-elongate-member spiral and the first-elongate-member spiral, thereby forming a composite tube having a lumen extending along a longitudinal axis and a hollow space surrounding the lumen. The method can comprise forming the first elongate member. The method can comprise extruding the first elongate member with a first extruder. The method can comprise forming the second elongate member. The method can comprise extruding the second elongate member with a second extruder. The second extruder can be configured to encapsulate one or more conductive filaments in the second elongate member. Forming the second elongate member can comprise embedding conductive filaments in the second elongate member. The conductive filaments can be non-reactive with the second elongate member. The conductive filaments can comprise alloys of aluminum or copper or other conductive materials. The method can comprise forming pairs of conductive filaments into a connecting loop at one end of the composite tube. The first extruder can be distinct from the second extruder.

A medical tube is also disclosed. In at least one embodiment, the tube comprises an elongate hollow body spirally wound to form an elongate tube having a longitudinal axis, a lumen extending along the longitudinal axis, and a hollow wall surrounding the lumen, wherein the elongate hollow body has in transverse cross-section a wall defining at least a portion of the hollow body. The tube can further comprise a reinforcement portion extending along a length of the elongate hollow body being spirally positioned between adjacent turns of the elongate hollow body, wherein the reinforcement portion forms a portion of the lumen of the elongate tube. The reinforcement portion can be relatively thicker or more rigid than the wall of the elongate hollow body.

In various embodiments, the foregoing tube has one, some, or all of the following properties, as well as properties described elsewhere in this disclosure. The reinforcement portion can be formed from the same piece of material as the elongate hollow body. The elongate hollow body in transverse cross-section can comprise two reinforcement portions on opposite sides of the elongate hollow body, wherein spiral winding of the elongate hollow body joins adjacent reinforcement portions to each other such that opposite edges of the reinforcement portions touch on adjacent turns of the elongate hollow body. Opposite side edges of the reinforcement portions can overlap on adjacent turns of the elongate hollow body. The reinforcement portion can be made of a separate piece of material than the elongate hollow body. The hollow body can form in longitudinal cross-section a plurality of bubbles with a flattened surface at the lumen. The bubbles can have perforations. The medical tube can also comprise one or more conductive filaments embedded or encapsulated within the reinforcement portion. The conductive filament can be a heating filament and/or or sensing filament. The medical tube can comprise two conductive filaments, wherein one conductive filament is embedded or encapsulated in each of the reinforcement portions. The medical tube can comprise two conductive filaments positioned on only one side of the elongate hollow body. Pairs of conductive filaments can be formed into a connecting loop at one end of the elongate tube. The one or more filaments can be spaced from the lumen wall.

The foregoing tube according to any or all of the preceding embodiments can be incorporated into a medical circuit component, an inspiratory tube, an expiratory tube, a PAP component, an insufflation circuit, an exploratory component, or a surgical component, among other applications.

A method of manufacturing a medical tube is also disclosed. In at least one embodiment, the method comprises spirally winding an elongate hollow body around a mandrel to form an elongate tube having a longitudinal axis, a lumen extending along the longitudinal axis, and a hollow wall surrounding the lumen, wherein the elongate hollow body has in transverse cross-section a wall defining at least a portion of the hollow body and two reinforcement portions on opposite sides of the elongate body forming a portion of the wall of the lumen, the two reinforcement portions being relatively thicker or more rigid than the wall defining at least a portion of the hollow body. The method can further comprise joining adjacent reinforcement portions to each other such that opposite edges of the reinforcement portions touch on adjacent turns of the elongate hollow body.

In various embodiments, the foregoing method can comprise one, some, or all of the following or any other properties described elsewhere in this disclosure. Joining adjacent reinforcement portions to each other can cause edges of the reinforcement portions to overlap. The method can further comprise supplying air at a pressure greater than atmospheric pressure to an end of the elongate hollow body. The method can further comprise cooling the elongate hollow body to join the adjacent reinforcement portions to each other. The method can further comprise extruding the elongate hollow body. The method can further comprise embedding conductive filaments in the reinforcement portions. The method can further comprise forming pairs of conductive filaments into a connecting loop at one end of the elongate tube.

A breathing tube is also disclosed. In at least one embodiment, the tube comprises a first elongate member comprising a hollow body spirally wound to form at least in part an elongate tube having a longitudinal axis, a lumen extending along the longitudinal axis, and a hollow wall surrounding the lumen, the wall having an inner portion proximal the lumen and an outer portion facing away from the lumen, wherein the inner portion of the wall has a smaller thickness than the outer portion of the wall.

In various embodiments, the foregoing breathing tube can comprise one, some, or all of the following properties or any other properties described elsewhere in this disclosure. The breathing tube can further comprising a second elongate member spirally wound and joined between adjacent turns of the first elongate member, the second elongate member forming at least a portion of the lumen of the elongate tube. The thickness of the outer portion of the wall can be in the range of about 0.14 mm and about 0.44 mm. The thickness of the outer portion of the wall can be about 0.24 mm. The thickness of the inner portion of the wall can be in the range of about 0.05 mm and about 0.30 mm. The thickness of the inner portion of the wall can be about 0.10 mm.

A breathing tube is also disclosed. In at least one embodiment, the tube comprises a first elongate member comprising a hollow body spirally wound to form at least in part an elongate tube having a longitudinal axis, a lumen extending along the longitudinal axis, and a hollow wall surrounding the lumen, the hollow body forming in longitudinal cross section a plurality of bubbles, a bubble having a maximum width along the longitudinal axis and a maximum height perpendicular to the longitudinal axis between the outward-facing apex of the wall and the lumen, wherein the ratio of the maximum height to the maximum width is at least about 0.16.

In various embodiments, the foregoing breathing tube can comprise one, some, or all of the following properties or any other properties described elsewhere in this disclosure. The breathing tube can further comprise a second elongate member spirally wound and joined between adjacent turns of the first elongate member, the second elongate member forming at least a portion of the lumen of the elongate tube. The maximum height can be in the range of about 1.2 mm and about 8.2 mm. The maximum height can be about 8.2 mm. The maximum width can be in the range of about 3.5 mm and about 7.5 mm. The maximum width can be about 5.5 mm. The ratio of the maximum height to the maximum width can be greater than 1.0.

A breathing tube is also disclosed. In at least one embodiment, the tube comprises a first elongate member comprising a hollow body spirally wound to form at least in part an elongate tube having a longitudinal axis, a lumen extending along the longitudinal axis, and a hollow wall surrounding the lumen, the hollow body forming in longitudinal cross section a plurality of bubbles, wherein a vertical distance between corresponding points on adjacent bubbles defines a pitch, wherein the ratio of pitch to the maximum outer diameter of the composite tube is less than about 0.35.

In various embodiments, the foregoing breathing tube can comprise one, some, or all of the following properties or any other properties described elsewhere in this disclosure. The breathing tube can further comprising a second elongate member spirally wound and joined between adjacent turns of the first elongate member, the second elongate member forming at least a portion of the lumen of the elongate tube. The pitch can be in the range of about 1.2 mm and about 8.1 mm. The pitch can be about 5.1 mm. The maximum outer diameter can be in the range of about 19.5 mm and 25.5 mm. The maximum outer diameter can be about 22.5 mm.

A composite tube is also disclosed. In at least one embodiment, the tube comprises a first elongate member comprising a hollow body spirally wound to form at least in part an elongate tube having a longitudinal axis, a lumen extending along the longitudinal axis, and a hollow wall surrounding the lumen, the hollow body forming in longitudinal cross section a plurality of bubbles, a bubble having a maximum height, perpendicular to the longitudinal axis, between the outward-facing apex of the wall and the lumen that defines the maximum height of the first elongate member; and a second elongate member spirally wound and joined between adjacent turns of the first elongate member, the second elongate member forming at least a portion of the lumen of the elongate tube, the second elongate member having a maximum height, perpendicular to the longitudinal axis, between the outward-facing apex of the second elongate member and the lumen, wherein the ratio of the difference between the maximum height of the first elongate member and the maximum height of the second elongate member to the maximum outer diameter of the composite tube is less than about 0.049:1.

In various embodiments, the foregoing composite tube can comprise one, some, or all of the following properties or any other properties described elsewhere in this disclosure. The wall can have an inner portion proximal the lumen and an outer portion facing away from the lumen and the inner portion of the wall has a smaller thickness than the outer portion of the wall.

A composite tube is also disclosed. In at least one embodiment, the tube comprises a first elongate member comprising a hollow body spirally wound to form at least in part an elongate tube having a longitudinal axis, a lumen extending along the longitudinal axis, and a hollow wall surrounding the lumen, the wall having an inner portion proximal the lumen and an outer portion facing away from the lumen; and a second elongate member spirally wound between adjacent turns of the first elongate member, the second elongate member forming at least a portion of the lumen of the elongate tube and the first elongate member being joined at connection points on adjacent turns of the second elongate member; wherein the composite tube's bend radius is limited by the length of the outer portion between the connection points.

In various embodiments, the foregoing composite tube can comprise one, some, or all of the following properties or any other properties described elsewhere in this disclosure. The wall has an inner portion proximal the lumen and an outer portion facing away from the lumen and the inner portion of the wall has a smaller thickness than the outer portion of the wall.

A breathing tube is also disclosed. In at least one embodiment, the tube comprises a first elongate member comprising a hollow body component, wherein the weight per length of the tube within at least a portion of the 300 mm nearest an end of the tube is less than about 0.08 g/mm.

In various embodiments, the foregoing breathing tube can comprise one, some, or all of the following properties or any other properties described elsewhere in this disclosure. The first elongate member can comprise a hollow body spirally wound to form at least in part an elongate tube having a longitudinal axis, a lumen extending along the longitudinal axis, and a hollow wall surrounding the lumen. The breathing tube can further comprise a second elongate member spirally wound and joined between adjacent turns of the first elongate member, the second elongate member forming at least a portion of the lumen of the elongate tube. The breathing tube can comprise one or more conductive filaments embedded or encapsulated within the second elongate member. At least one of the one or more conductive filaments can be a heating filament. At least one of the one or more conductive filaments can be a sensing filament. The tube mass in the 300 mm nearest an end of the tube can be less than about 24 g. The weight per length of the tube within at least a portion of the 300 mm nearest an end of the tube can be less than about 0.06 g/mm. The tube mass in the 300 mm nearest an end of the tube can be less than about 16 g. The thickness of the wall can be at most about 0.50 mm.

A breathing tube is also disclosed. In at least one embodiment, the tube comprises a first elongate member comprising a hollow body spirally wound to form at least in part an elongate tube having a longitudinal axis, a lumen extending along the longitudinal axis, and a hollow wall surrounding the lumen, the wall having an inner portion proximal the lumen and an outer portion facing away from the lumen, wherein, in at least a portion of the composite tube, when force is applied to the outer portion of the wall with a 2.5-mm probe until the outer portion of the wall contacts the inner portion, the outer portion deflects by a vertical distance that satisfies the equation: $D>0.5\times F_{2.5}$, where D represents the vertical distance in millimeters, and $F_{2.5}$ represents the force in Newtons applied by the 2.5-mm probe.

In various embodiments, the foregoing breathing tube can comprise one, some, or all of the following properties or any other properties described elsewhere in this disclosure. The breathing tube can further comprise a second elongate member spirally wound and joined between adjacent turns of the first elongate member, the second elongate member forming at least a portion of the lumen of the elongate tube. The outer portion can deflect more than about 1 mm when a force of about 1 N is applied with the 2.5-mm probe.

A conduit suitable for use with a tube for delivering humidified gases to a patient is also disclosed. In at least one embodiment, the conduit comprises a connector configured to connect to the tube, the connector comprising a lumen extending along a longitudinal axis and walls surrounding the lumen, the lumen defining a flow path for the humidified gases when in use; and a printed circuit board assembly comprising a printed circuit board and further comprising a dividing portion embedded in the walls of the connector and extending across the lumen of the connector along a diameter or chord line, such that the dividing portion generally bisects at least part of the flow path, at least part of the dividing portion being overmolded by an overmolding composition, a wiring portion adjacent the dividing portion and projecting outward from the wall of the connector in a direction away from the lumen of the connector, and a sensor portion disposed in the lumen of the connector and projecting from the dividing portion along the longitudinal axis, the sensor portion comprising at least one sensor, and the sensor portion being overmolded by the overmolding composition.

In various embodiments, the foregoing conduit can comprise one, some, or all of the following properties or any other properties described elsewhere in this disclosure. The printed circuit board assembly can further comprise a support portion adjacent the dividing portion and projecting outward from the connector in a direction away from the lumen and in a direction opposite the wiring portion. The wiring portion can be configured to electrically connect to one or more heater wires from the conduit. The at least one sensor can comprise a thermistor. The sensor portion can project upstream of the flow path. The at least one sensor can comprise a sensor adjacent an upstream leading edge of the sensor portion. The sensor portion can project downstream of the flow path. The at least one sensor can comprise a sensor adjacent a downstream leading edge of the sensor portion. The overmolding composition proximal the sensor portion can have a tapered shape extending along the longitudinal axis. The overmolding can be thinnest proximal a leading edge of the sensor portion. The sensor portion can have an airfoil shape extending along the longitudinal axis. The sensor portion can have a bullet or torpedo shape.

A respiratory conduit is also disclosed. In at least one embodiment, the conduit comprises a lumen extending along a longitudinal axis and a wall surrounding the lumen, the lumen defining a gas-flow path when in use; and an overmolded printed circuit board assembly secured to the wall, the printed circuit board assembly comprising a printed circuit board and further comprising a mount portion disposed in the lumen of the connector and projecting along the longitudinal axis, and a temperature sensor on a surface of the mount portion.

In various embodiments, the foregoing conduit can comprise one, some, or all of the following properties or any other properties described elsewhere in this disclosure. The temperature sensor can be a thermistor.

A respiratory conduit is also disclosed. In at least one embodiment, the conduit comprises a lumen extending along a longitudinal axis and walls surrounding the lumen, the lumen defining a gas-flow path when in use; and a component secured to the walls and extending across the lumen along a diameter or chord line, such that the component generally bisects at least part of the flow path, the component comprising a mount portion disposed in the lumen and projecting along the longitudinal axis, a temperature sensor on a surface of the mount portion, and electrical connection to the sensor.

In various embodiments, the foregoing conduit can comprise one, some, or all of the following properties or any other properties described elsewhere in this disclosure. The temperature sensor can be a thermistor. The component can be a printed circuit board. The electrical connection can span the component's length along the diameter or chord line.

A respiratory conduit is also disclosed. In at least one embodiment, the conduit comprises a lumen extending along a longitudinal axis and a wall surrounding the lumen, the lumen defining a gas-flow path when in use; and an overmolded printed circuit board assembly secured to the wall, the printed circuit board assembly comprising a printed circuit board and further comprising a mount portion disposed in the lumen and projecting along the longitudinal axis, and a temperature sensor on a surface of the mount portion, wherein the overmolding proximal the mount portion has a tapered shape.

In various embodiments, the foregoing conduit can comprise one, some, or all of the following properties or any other properties described elsewhere in this disclosure. The temperature sensor can be a thermistor.

A respiratory conduit is also disclosed. In at least one embodiment, the conduit comprises a lumen extending along a longitudinal axis and a wall surrounding the lumen, the lumen defining a gas-flow path when in use; and a component connected to the wall and comprising a mount portion disposed in the lumen and projecting along the longitudinal axis, the mount portion comprising a temperature sensor positioned longitudinally upstream from the connection to the wall.

In various embodiments, the foregoing breathing tube can comprise one, some, or all of the following properties or any other properties described elsewhere in this disclosure. The temperature sensor can be a thermistor. The temperature sensor can be proximal an upstream extreme of the mount portion. The mount portion can be overmolded. The overmolding can be thinnest proximal the temperature sensor. The mount can project longitudinally downstream. The mount can have an airfoil shape extending along the longitudinal axis. The mount can have a bullet or torpedo shape. A vertical distance between the mount and the wall can be at least 30% of the lumen's diameter.

A respiratory conduit segment is also disclosed. In at least one embodiment, the segment comprises a lumen extending along a longitudinal axis and a wall surrounding the lumen, the lumen defining a gas-flow path when in use; and a printed circuit board assembly comprising a printed circuit board and comprising a first portion extending across the lumen along a diameter or chord line, such that a portion of the printed circuit board assembly generally bisects at least part of the flow path, the first portion being overmolded by an overmolding composition, a second portion adjacent the first portion projecting outward from the wall in a direction away from the lumen, the second portion comprising one or more connection pads on the printed circuit board configured to receive one or more wires from a first assembly, a third portion adjacent the first portion projecting outward from the wall in a direction away from the lumen and in a direction opposite the second portion, the third portion comprising one or more connection pads on the printed circuit board configured to receive one or more wires from a second assembly that is distinct from the first assembly, and one or more conductive tracks on the printed circuit board electrically coupled to the one or more connection pads of the second portion and to the one or more connection pads of the third portion and configured to provide electrical connectivity between the first assembly and the second assembly.

In various embodiments, the foregoing segment can comprise one, some, or all of the following properties or any other properties described elsewhere in this disclosure. The first assembly can be a breathing tube. The second assembly can be a breathing tube. The printed circuit board assembly can further comprise a mount portion disposed in the lumen of the connector and projecting along the longitudinal axis, and a temperature sensor on a surface of the mount portion.

In various embodiments, a breathing tube comprises a first elongate member comprising a hollow body spirally wound to form at least in part an elongate tube having a longitudinal axis, a lumen extending along the longitudinal axis, and a hollow wall surrounding the lumen, the hollow body forming in longitudinal cross section a plurality of bubbles, a bubble having a maximum width along the longitudinal axis and a maximum height perpendicular to the longitudinal axis between the outward-facing apex of the wall and the lumen, wherein the ratio of the maximum height to the maximum width is at least about 0.16. A second elongate member may be spirally wound and joined between adjacent turns of the first elongate member, the second elongate member forming at least a portion of the lumen of the elongate tube. The maximum height may be in the range of about 0.7 mm and about 7.7 mm. The maximum height may be about 2.7 mm. The maximum width may be in the range of about 2.0 mm and about 6.0 mm. The maximum width may be about 4.0 mm. The maximum height to the maximum width may be greater than 1.0.

In various embodiments, a breathing tube comprises a first elongate member comprising a hollow body spirally wound to form at least in part an elongate tube having a longitudinal axis, a lumen extending along the longitudinal axis, and a hollow wall surrounding the lumen, the hollow body forming in longitudinal cross section a plurality of bubbles, wherein a vertical distance between corresponding points on adjacent bubbles defines a pitch, wherein the ratio of pitch to the maximum outer diameter of the composite tube is less than about 0.35. A second elongate member may be spirally wound and joined between adjacent turns of the first elongate member, the second elongate member forming at least a portion of the lumen of the elongate tube. The pitch may be in the range of about 1.2 mm and about 8.1 mm. The pitch may be about 5.1 mm. The maximum outer diameter may be in the range of about 19.5 mm and 25.5 mm. The maximum outer diameter may be about 22.5 mm.

In various embodiments, a composite tube comprises a first elongate member comprising a hollow body spirally wound to form at least in part an elongate tube having a longitudinal axis, a lumen extending along the longitudinal axis, and a hollow wall surrounding the lumen, the hollow body forming in longitudinal cross section a plurality of bubbles, a bubble having a maximum height, perpendicular to the longitudinal axis, between the outward-facing apex of the wall and the lumen that defines the maximum height of the first elongate member; and a second elongate member spirally wound and joined between adjacent turns of the first elongate member, the second elongate member forming at least a portion of the lumen of the elongate tube, the second elongate member having a maximum height, perpendicular to the longitudinal axis, between the outward-facing apex of the second elongate member and the lumen, wherein the ratio of the difference between the maximum height of the first elongate member and the maximum height of the second elongate member to the maximum outer diameter of the composite tube is less than about 0.049:1. The wall may have an inner portion proximal the lumen and an outer portion facing away from the lumen and the inner portion of the wall may have a smaller thickness than the outer portion of the wall.

In various embodiments, a composite tube comprises a first elongate member comprising a hollow body spirally wound to form at least in part an elongate tube having a longitudinal axis, a lumen extending along the longitudinal axis, and a hollow wall surrounding the lumen, the wall having an inner portion proximal the lumen and an outer portion facing away from the lumen; and a second elongate member spirally wound between adjacent turns of the first elongate member, the second elongate member forming at least a portion of the lumen of the elongate tube and the first elongate member being joined at connection points on adjacent turns of the second elongate member; wherein the composite tube's bend radius is limited by the length of the outer portion between the connection points. The wall may have an inner portion proximal the lumen and an outer portion facing away from the lumen and the inner portion of the wall may have a smaller thickness than the outer portion of the wall.

In various embodiments, a conduit suitable for use with a tube for delivering humidified gases to a patient is provided, the conduit comprising a connector configured to connect to the tube, the connector comprising a lumen extending along a longitudinal axis and walls surrounding the lumen, the lumen defining a flow path for the humidified gases when in use; and a printed circuit board assembly comprising a printed circuit board and further comprising a dividing portion embedded in the walls of the connector and extending across the lumen of the connector along a diameter or chord line, such that the dividing portion generally bisects at least part of the flow path, at least part of the dividing portion being overmolded by an overmolding composition, a wiring portion adjacent the dividing portion and projecting outward from the wall of the connector in a direction away from the lumen of the connector, and a sensor portion disposed in the lumen of the connector and projecting from the dividing portion along the longitudinal axis, the sensor portion comprising at least one sensor, and the sensor portion being overmolded by the overmolding composition. The printed circuit board assembly may further comprise a support portion adjacent the dividing portion and projecting outward from the connector in a direction away from the lumen and in a direction opposite the wiring portion. The wiring portion may be configured to electrically connect to one or more heater wires from the conduit. The at least one sensor may comprise a thermistor. The sensor portion may project upstream of the flow path. The at least one sensor may comprise a sensor adjacent an upstream leading edge of the sensor portion. The sensor portion may project downstream of the flow path. The at least one sensor may comprise a sensor adjacent a downstream leading edge of the sensor portion. The overmolding composition proximal the sensor portion may have a tapered shape extending along the longitudinal axis. The overmolding may be thinnest proximal a leading edge of the sensor portion. The sensor portion may have an airfoil shape extending along the longitudinal axis. The sensor portion may have a bullet or torpedo shape.

In various embodiments, a respiratory conduit comprises a lumen extending along a longitudinal axis and a wall surrounding the lumen, the lumen defining a gas-flow path when in use; and an overmolded printed circuit board assembly secured to the wall, the printed circuit board assembly comprising a printed circuit board and further comprising a mount portion disposed in the lumen and projecting along the longitudinal axis, and a temperature sensor on a surface of the mount portion, wherein the overmolding proximal the mount portion has a tapered shape. The temperature sensor may be a thermistor.

In various embodiments, a respiratory conduit comprises a lumen extending along a longitudinal axis and a wall surrounding the lumen, the lumen defining a gas-flow path when in use; and a component connected to the wall and comprising a mount portion disposed in the lumen and projecting along the longitudinal axis, the mount portion comprising a temperature sensor positioned longitudinally upstream from the connection to the wall. The temperature sensor may be a thermistor. The temperature sensor may be proximal an upstream extreme of the mount portion. The mount portion may be overmolded. The overmolding may be thinnest proximal the temperature sensor. The mount may project longitudinally downstream. The mount may have an airfoil shape extending along the longitudinal axis. The mount may have a bullet or torpedo shape. A vertical distance between the mount and the wall may be at least 30% of the lumen's diameter.

In various embodiments, a respiratory conduit segment comprises a lumen extending along a longitudinal axis and a wall surrounding the lumen, the lumen defining a gas-flow path when in use; and a printed circuit board assembly comprising a printed circuit board and comprising a first portion extending across the lumen along a diameter or chord line, such that a portion of the printed circuit board assembly generally bisects at least part of the flow path, the first portion being overmolded by an overmolding composition, a second portion adjacent the first portion projecting outward from the wall in a direction away from the lumen, the second portion comprising one or more connection pads on the printed circuit board configured to receive one or more wires from a first assembly, a third portion adjacent the first portion projecting outward from the wall in a direction away from the lumen and in a direction opposite the second portion, the third portion comprising one or more connection pads on the printed circuit board configured to receive one or more wires from a second assembly that is distinct from the first assembly, and one or more conductive tracks on the printed circuit board electrically coupled to the one or more connection pads of the second portion and to the one or more connection pads of the third portion and configured to provide electrical connectivity between the first assembly and the second assembly. The first assembly may be a breathing tube. The second assembly may be a breathing tube. The printed circuit board assembly may further comprise a mount portion disposed in the lumen of the connector and projecting along the longitudinal axis, and a temperature sensor on a surface of the mount portion.

In various embodiments, a composite tube comprises a first elongate member comprising a hollow body spirally wound to form at least in part an elongate tube having a longitudinal axis, a lumen extending along the longitudinal axis, and a hollow wall surrounding the lumen; a second elongate member spirally wound and joined between adjacent turns of the first elongate member, the second elongate member forming at least a portion of the lumen of the elongate tube; wherein at least a portion of the first elongate member is formed of a breathable material. In one example, the composite tube may be provided with a source of humidification fluid and/or be pre-charged with a volume of humidification fluid, and a heater provided to heat the fluid such that fluid vapour passes through the breathable material into or from the lumen. The heater may comprise one or more heating filaments disposed in the second elongate member.

For purposes of summarizing the invention, certain aspects, advantages and novel features of the invention have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

BRIEF DESCRIPTION OF THE DRAWINGS

Example embodiments that implement the various features of the disclosed systems and methods will now be described with reference to the drawings. The drawings and the associated descriptions are provided to illustrate embodiments and not to limit the scope of the disclosure.

FIGS. 9C and 9E show a front-perspective view of samples under testing in the jig. FIGS. 9D and 9F show a rear-perspective view of samples under testing in the jig.

FIGS. 11A-11D demonstrate radius of curvature properties of tubes.

FIGS. 14A-14E show variations of a tube, adapted to provide increased lateral stretch in the tube.

FIGS. 15A-15E show a stretched state of the tubes shown in FIGS. 13A-E, respectively.

FIG. 20A shows a composite tube in use with a full face mask.

FIG. 20B shows a composite tube in use with a nasal mask.

FIG. 20C shows a composite tube in use with a nasal/pillow mask.

FIGS. 23A-23H show an alternative method of forming a tube.

FIGS. 24A-24B show another example illustrating a single elongate hollow body being spirally wound to form a medical tube.

FIGS. 24C-24F show examples of other single elongate hollow bodies being spirally wound to form a medical tube.

FIGS. 25A-25L show a general flow chart and more detailed schematics and photographs relating to a method for attaching a connector to the end of the tube that is configured in use to connect to a humidifier.

FIGS. 26A-26E show a connector for attaching filaments to an electrical connector.

FIGS. 28A-28F and 29A-29L show connectors that can be used for medical circuits having electrical wires running therethrough and associated methods of assembly.

FIGS. 33A-33D illustrate an example PCB assembly.

Generally throughout the drawings, reference numbers are reused to indicate correspondence between referenced (or similar) elements. Nevertheless, corresponding referenced (or similar) elements may have different reference numbers in some circumstances. In addition, the first digit(s) of each reference number generally indicate the figure in which the element first appears.

DETAILED DESCRIPTION

Details regarding several illustrative embodiments for implementing the apparatuses and methods described herein are described below with reference to the figures. The invention is not limited to these described embodiments.

Breathing Circuit Comprising One Or More Medical Tubes

Figure 1:
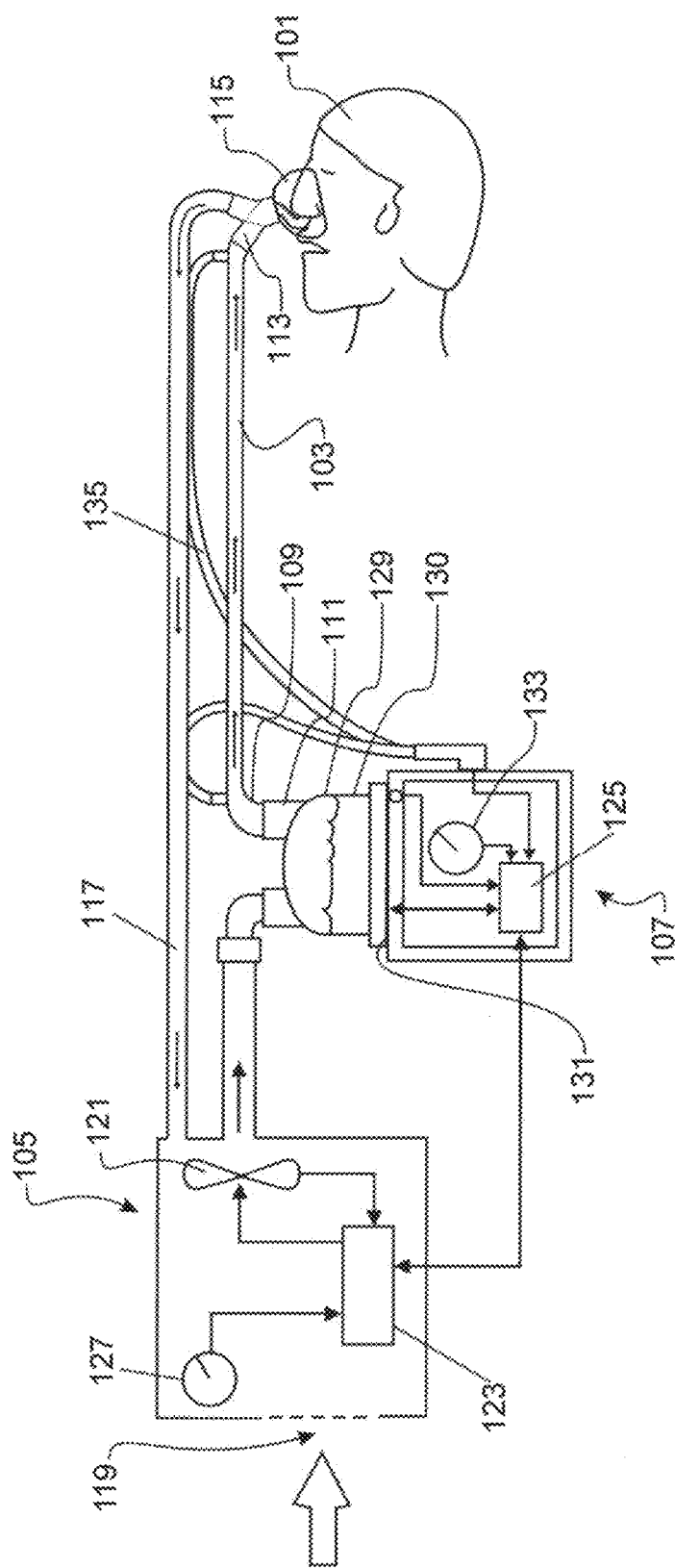
FIG. 1 shows a schematic illustration of a medical circuit incorporating one or more medical tubes.

For a more detailed understanding of the disclosure, reference is first made to FIG. 1, which shows a breathing circuit according to at least one embodiment, which includes one or more medical tubes. Tube is a broad term and is to be given its ordinary and customary meaning to a person of ordinary skill in the art (that is, it is not to be limited to a special or customized meaning) and includes, without limitation, cylindrical and non-cylindrical passageways. Certain embodiments may incorporate a composite tube, which may generally be defined as a tube comprising two or more portions, or, specifically, in some embodiments, two or more components, as described in greater detail below. Such a breathing circuit can be a continuous, variable, or bi-level positive airway pressure (PAP) system or other form of respiratory therapy.

Gases can be transported in the circuit of FIG. 1 as follows. Dry gases pass from a ventilator/blower 105 to a humidifier 107, which humidifies the dry gases. The humidifier 107 connects to the inlet 109 (the end for receiving humidified gases) of the inspiratory tube 103 via a port 111, thereby supplying humidified gases to the inspiratory tube 103. An inspiratory tube is a tube that is configured to deliver breathing gases to a patient, and may be made from a composite tube as described in further detail below. The gases flow through the inspiratory tube 103 to the outlet 113 (the end for expelling humidified gases), and then to the patient 101 through a patient interface 115 connected to the outlet 113.

An expiratory tube 117 optionally connects to the patient interface 115. An expiratory tube is a tube that is configured to move exhaled humidified gases away from a patient. Here, the expiratory tube 117 returns exhaled humidified gases from the patient interface 115 to the ventilator/blower 105.

In this example, dry gases enter the ventilator/blower 105 through a vent 119. A fan 121 can improve gas flow into the ventilator/blower by drawing air or other gases through vent 119. The fan 121 can be, for instance, a variable speed fan, where an electronic controller 123 controls the fan speed. In particular, the function of the electronic controller 123 can be controlled by an electronic master controller 125 in response to inputs from the master controller 125 and a user-set predetermined required value (preset value) of pressure or fan speed or gases flow rate via a dial 127.

The humidifier 107 comprises a humidification chamber 129 containing a volume of water 130 or other suitable humidifying liquid. Preferably, the humidification chamber 129 is removable from the humidifier 107 after use. Removability allows the humidification chamber 129 to be more readily sterilized or disposed. However, the humidification chamber 129 portion of the humidifier 107 can be a unitary construction. The body of the humidification chamber 129 can be formed from a non-conductive glass or plastics material. But the humidification chamber 129 can also include conductive components. For instance, the humidification chamber 129 can include a highly heat-conductive base (for example, an aluminum base) contacting or associated with a heater plate 131 on the humidifier 107.

The humidifier 107 can also include electronic controls. In this example, the humidifier 107 includes an electronic, analog or digital master controller 125. Preferably, the master controller 125 is a microprocessor-based controller executing computer software commands stored in associated memory. In response to the user-set humidity or temperature value input via a user interface 133, for example, and other inputs, the master controller 125 determines when (or to what level) to energize heater plate 131 to heat the water 130 within humidification chamber 129.

Any suitable patient interface 115 can be incorporated. Patient interface is a broad term and is to be given its ordinary and customary meaning to a person of ordinary skill in the art (that is, it is not to be limited to a special or customized meaning) and includes, without limitation, masks (such as tracheal mask, face masks and nasal masks), cannulas, and nasal pillows. A temperature probe 135 can connect to the inspiratory tube 103 near the patient interface 115, or to the patient interface 115. The temperature probe 135 monitors the temperature near or at the patient interface 115. A heating filament (not shown) associated with the temperature probe can be used to adjust the temperature of the patient interface 115 and/or inspiratory tube 103 to raise the temperature of the inspiratory tube 103 and/or patient interface 115 above the saturation temperature, thereby reducing the opportunity for unwanted condensation.

In FIG. 1, exhaled humidified gases are returned from the patient interface 115 to the ventilator/blower 105 via the expiratory tube 117. The expiratory tube 117 can also be a composite tube, as described in greater detail below. However, the expiratory tube 117 can also be a medical tube as previously known in the art. In either case, the expiratory tube 117 can have a temperature probe and/or heating filament, as described above with respect to the inspiratory tube 103, integrated with it to reduce the opportunity for condensation. Furthermore, the expiratory tube 117 need not return exhaled gases to the ventilator/blower 105. Alternatively, exhaled humidified gases can be passed directly to ambient surroundings or to other ancillary equipment, such as an air scrubber/filter (not shown). In certain embodiments, the expiratory tube is omitted altogether.

Composite Tubes

Figure 2A:
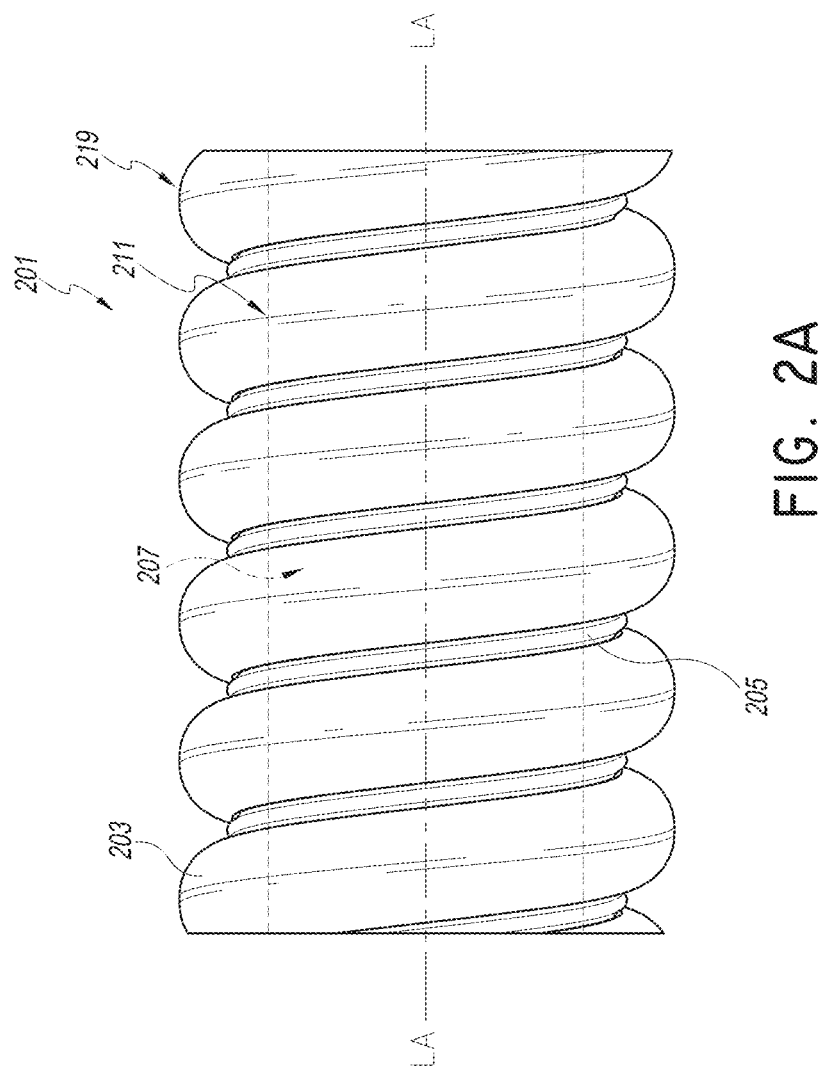
FIG. 2A shows a side-plan view of a section of an example composite tube.

FIG. 2A shows a side-plan view of a section of example composite tube 201. In general, the composite tube 201 comprises a first elongate member 203 and a second elongate member 205. Member is a broad term and is to be given its ordinary and customary meaning to a person of ordinary skill in the art (i.e., it is not to be limited to a special or customized meaning) and includes, without limitation, integral portions, integral components, and distinct components. Thus, although FIG. 2A illustrates an embodiment made of two distinct components, it will be appreciated that in other embodiments (such as described in below), the first elongate member 203 and second elongate member 205 can also represent regions in a tube formed from a single material. Thus, the first elongate member 203 can represent a hollow portion of a tube, while the second elongate member 205 represents a structural supporting or reinforcement portion of the tube which adds structural support to the hollow portion. The hollow portion and the structural supporting portion can have a spiral configuration, as described herein.

The composite tube 201 may be used to form the inspiratory tube 103 and/or the expiratory tube 117 in a breathing circuit, as described above, a coaxial tube as described below, or any other tubes as described elsewhere in this disclosure. In certain embodiments, the composite tube 201 is at least an inspiratory tube 103.

The following describes components and properties of example composite tubes 201 in greater detail. Sub-headings are used, such as "first elongate member" and "second elongate member." These sub-headings are not, and should not be construed as, limiting. For example, aspects of one or more embodiments described under the first-elongate-member subheading can also apply to one or more embodiments described under the second-elongate-member subheading, and the reverse is also true.

First Elongate Member

In FIG. 2A, the first elongate member 203 comprises a hollow body spirally wound to form, at least in part, an elongate tube having a longitudinal axis LA-LA and a lumen 207 (tube bore) extending along the longitudinal axis LA-LA. The first elongate member 203 has an inner portion 211 near the lumen 207. In certain embodiments, a surface of the inner portion 211 forms the lumen 207. The first elongate member 203 also has an outer portion 219 opposite the inner portion and facing away from the lumen 207 in the radial direction. As discussed in greater detail below, the first elongate member 203 can form in longitudinal cross-section a plurality of bubbles. In certain embodiments, the bubbles have a cross-sectional profile resembling the letter "D." The bubbles can be arced at the outward-facing surface. The bubbles can be flatter at the surface at the lumen 207. In at least one embodiment, the first elongate member 203 is a tube.

Preferably, the first elongate member 203 is flexible. Flexible refers to the ability to bend. Furthermore, the first elongate member 203 is preferably transparent or, at least, semi-transparent or semi-opaque. A degree of optical transparency allows a caregiver or user to inspect the lumen 207 for blockage or contaminants or to confirm the presence of moisture.

A variety of plastics, including medical grade plastics, are suitable for the body of the first elongate member 203. Examples of suitable materials include Polyolefin elastomers, Polyether block amides, Thermoplastic co-polyester elastomers, EPDM-Polypropylene mixtures, and Thermoplastic polyurethanes. In certain embodiments, the material is selected such that the material density of the resulting first elongate member 203 is less than or equal to 1 g/cm$^3$ (or about 1 g/cm$^3$).

The first elongate member 203 material is preferably soft. Softness reflects the amount the material "gives" or compresses upon application of a force. A soft material gives or compresses more than a firm material. Bubble deflection can be used to quantify the softness of the first elongate member 203 material. Bubble deflection is distance that the outer portion 219 of the first elongate member 203 vertically deflects (that is, displaces radially inward in the direction of the lumen 207) upon application of a force. Bubble deflection can be tested, for example, using a bubble deflection jig, such as the jig 301 shown in the photograph of FIG. 3.

Figure 3:
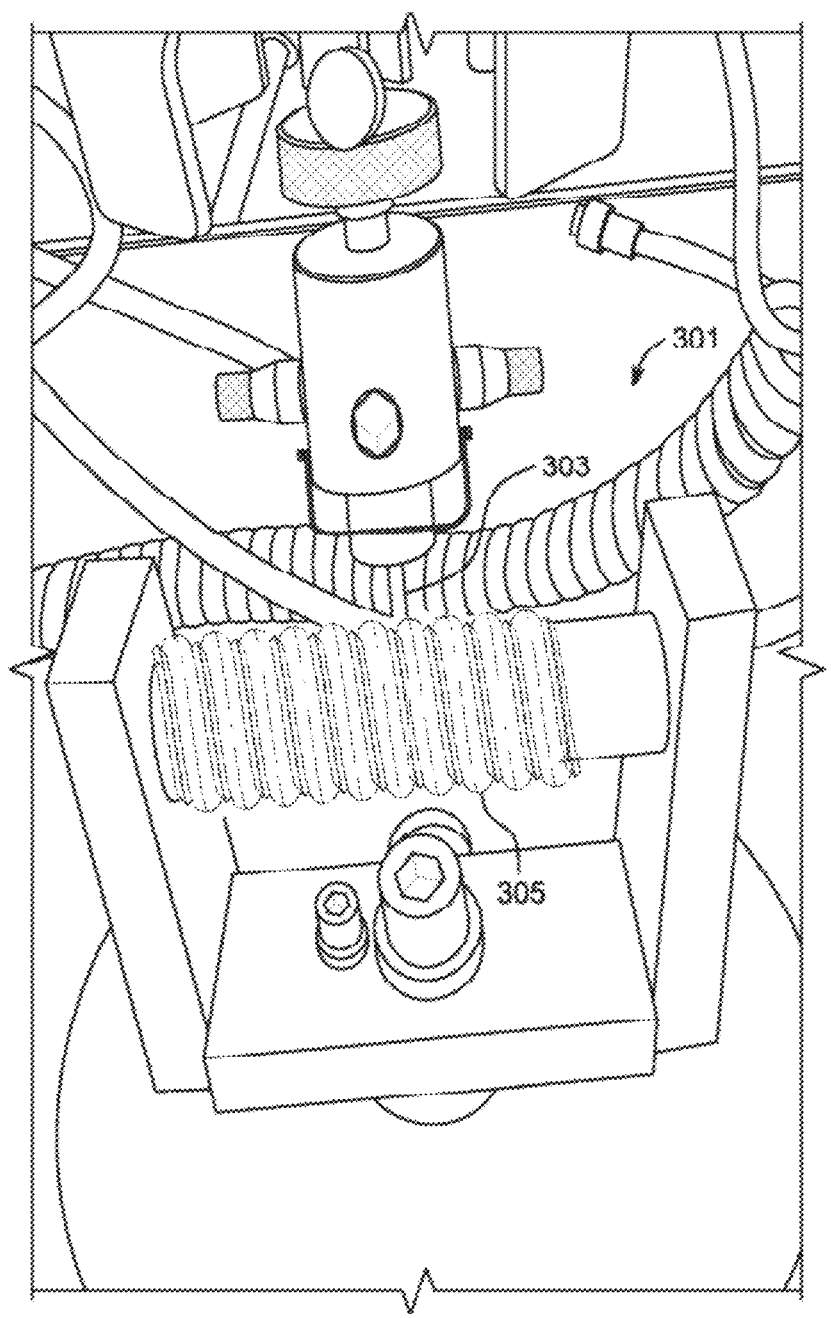
FIG. 3 shows a jig suitable for determining bubble deflection.

In one softness test, four samples of composite tubes having the properties shown in TABLE 1 (hereinafter "Type 1") and four samples of composite tubes having the properties shown in TABLE 2 (hereinafter "Type 2") were each tested on the jig 301 of FIG. 3.

TABLE 1

| Feature | Dimension (mm) | Range (±) |
|---|---|---|
| Lumen diameter | 17.2 | 5.0 |
| Pitch | 5.1 | 3.0 |
| Bubble width | 4.0 | 2.0 |
| Bead width | 2.3 | +3.0/−2.0 |
| Bubble height | 2.7 | +5.0/−2.0 |
| Bead height | 1.6 | 1.5 |
| Bubble thickness on top, farthest from lumen (outer wall thickness) | 0.24 | +0.20/−0.10 |
| Bubble thickness adjacent lumen (inner wall thickness) | 0.10 | +0.20/−0.05 |
| Outer diameter of tube | 22.5 | 3.0 |

TABLE 2

| Feature | Dimension (mm) | Range (±) |
|---|---|---|
| Lumen diameter | 18.25 | 0.25 |
| Pitch | 8.2 | 0.15 |
| Bubble width | 7.0 | 1 |
| Bead width | 2.30 | 0.15 |
| Bubble height | 4.0 | 0.05 |
| Bead height | 1.95 | 0.15 |
| Bubble thickness on top, farthest from lumen (outer wall thickness) | 0.42 | 0.04 |
| Bubble thickness adjacent lumen (inner wall thickness) | 0.22 | 0.04 |
| Outer diameter of tube | 26 | 0.5 |

Figure 4:
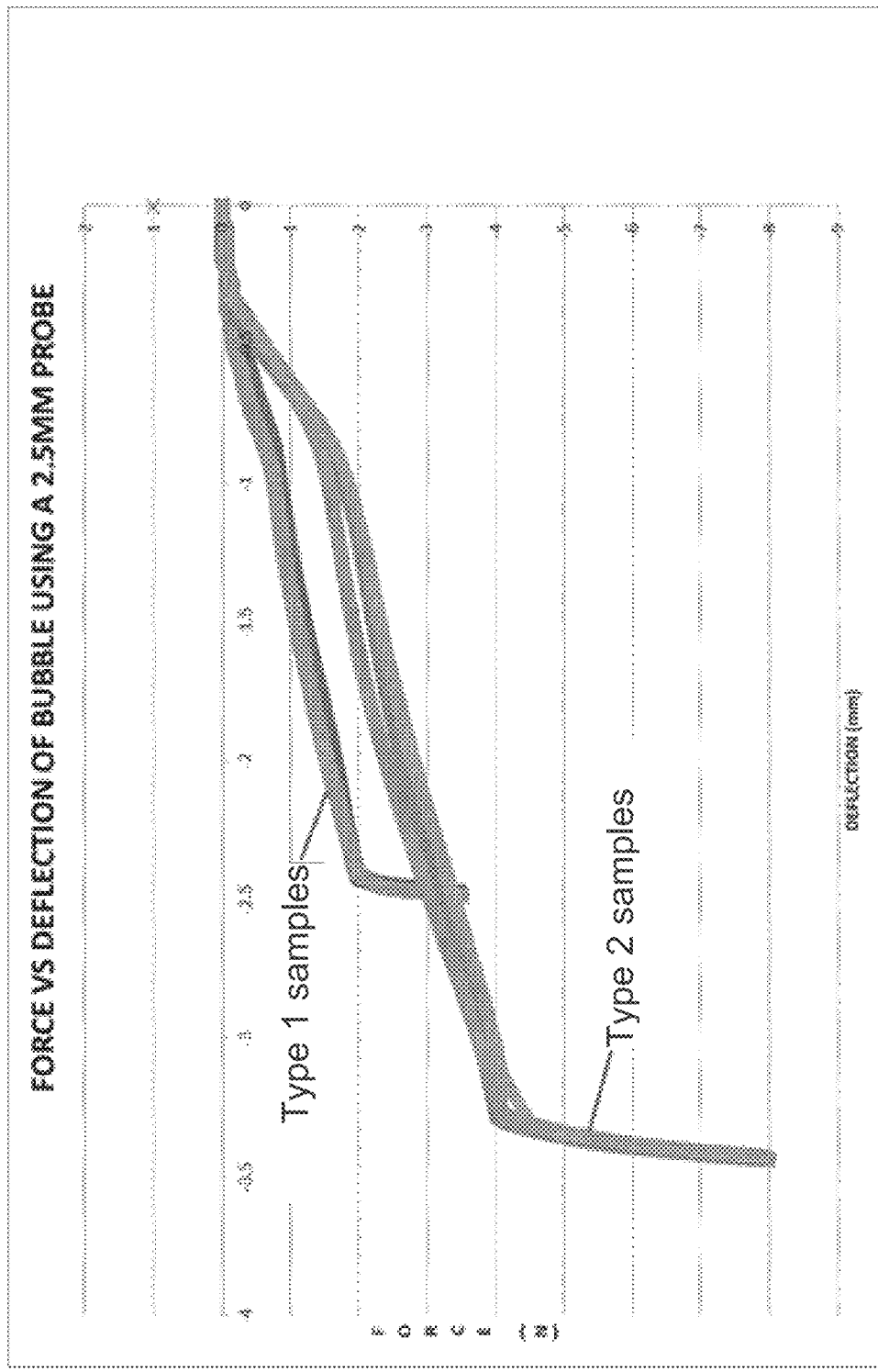
FIG. 4 shows a curve of force vs. bubble deflection.

A probe 303 with a 2.5-mm diameter applied a force to each sample 305 and bubble deflection was measured. The resulting curves are plotted in FIG. 4. Until their respective outer portion 219 contacted the inner portion 211, Type 1 samples generally required less force to achieve a similar bubble deflection as Type 2 samples. In certain embodiments, until the outer portion 219 contacts the inner wall 211, the bubble deflection can satisfy the equation: $D > 0.5 \times F_{2.5}$, where D represents the bubble deflection in millimeters and $F_{2.5}$ represents the force in Newtons applied by a 2.5-mm probe. For example, the first elongate member 203 can deflect more than 1 mm when a force of 1 N is applied with a 2.5-mm probe 303, until the outer portion 219 contacts the inner portion 211.

It should be appreciated that, although the configuration in TABLE 1 may be preferred in certain embodiments, other configurations and variations, may be used in other embodiments as may be desired.

Figure 2B:
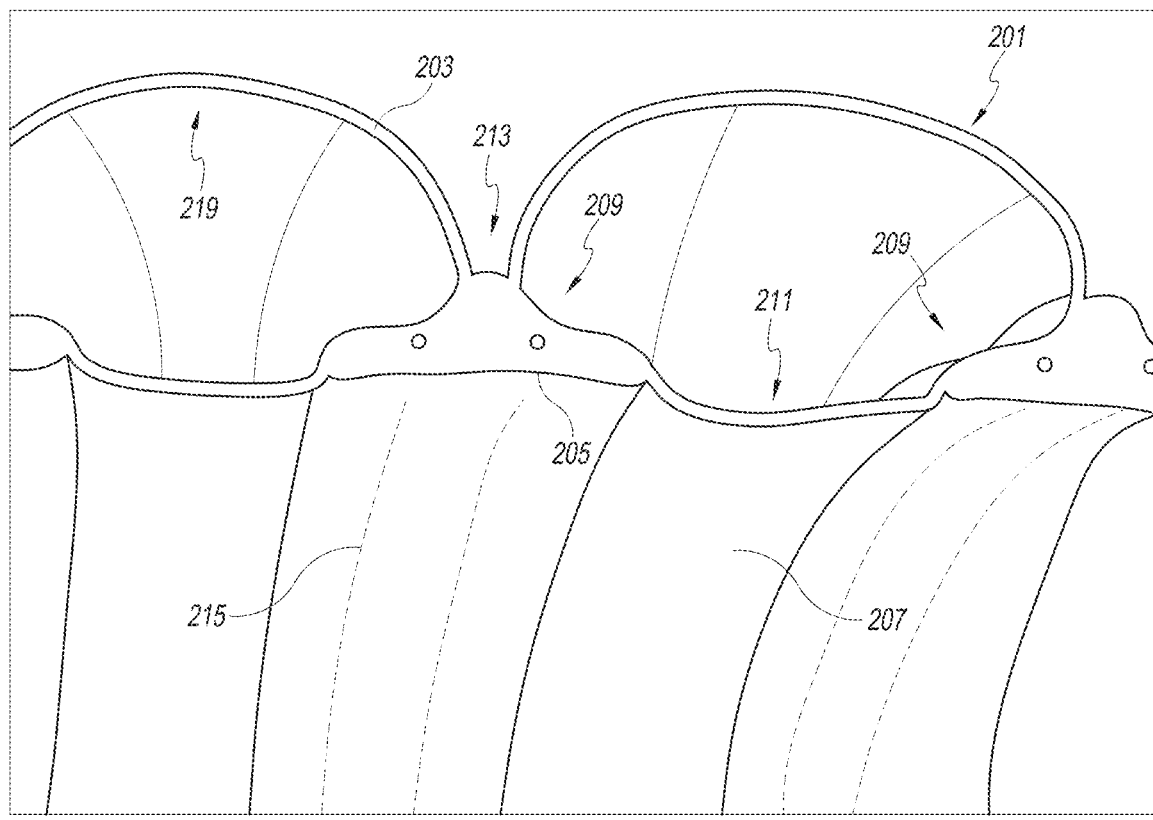
FIG. 2B shows a longitudinal cross-section of a top portion a tube similar to the example composite tube of FIG. 2A.

FIG. 2B shows a longitudinal cross-section of a top portion of the example composite tube 201 of FIG. 2A. FIG. 2B has the same orientation as FIG. 2A. This example further illustrates the hollow-body shape of the first elongate member 203. As seen in this example, the first elongate member 203 forms in longitudinal cross-section a plurality of hollow bubbles. Thus, in this description, the term "bubble" refers to cross-sectional shape of a wind or turn of the first elongate member 203. Portions 209 of the first elongate member 203 overlap adjacent wraps of the second elongate member 205. An inner portion 211 of the first elongate member 203 forms the wall of the lumen 207.

The hollow body structure of the first elongate member 203 contributes to the sound damping properties to the composite tube 201. In at least one embodiment, the outer diameter of the first elongate member 203 is larger than the outer diameter of the second elongate member 205. The bubble-shaped structure forms a cushion. Thus, the fluid (gas or liquid) filled bubble-shaped first elongate member 203 can muffle the noise made when the composite tube 201 is dragged over an object, such as the edge of a desk or bedside table. In this way, the composite tube 201 can be quieter compared with one-piece solid-body corrugated tubes.

The hollow body structure of the first elongate member 203 also contributes to the insulating properties to the composite tube 201. An insulating composite tube 201 is desirable because, as explained above, it prevents heat loss. This can allow the composite tube 201 to deliver gas from a heater-humidifier to a patient while maintaining the gas's conditioned state with minimal energy consumption.

It was discovered that having a gap 213 between adjacent turns of the first elongate member 203, that is, between adjacent bubbles, unexpectedly improved the overall insulating properties of the composite tube 201. Thus, in certain embodiments, adjacent bubbles are separated by a gap 213. Furthermore, certain embodiments include the realization that providing a gap 213 between adjacent bubbles increases the heat transfer resistivity (the R value) and, accordingly, decreases the heat transfer conductivity of the composite tube 201. This gap configuration was also found to improve the flexibility of the composite tube 201 by permitting shorter-radius bends. A triangular second elongate member 205 or a T-shaped second elongate member 205, as shown in FIG. 2B, can help maintain a gap 213 between adjacent bubbles. Nevertheless, in certain embodiments, adjacent bubbles are touching. For example, adjacent bubbles can be bonded together.

Figure 2C:
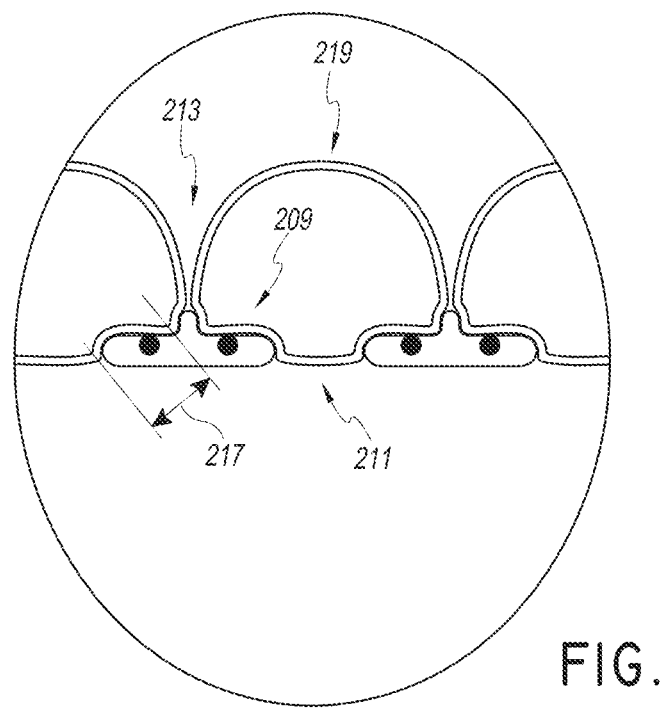
FIG. 2C shows another longitudinal cross-section illustrating a first elongate member in the composite tube.
Figure 2D:
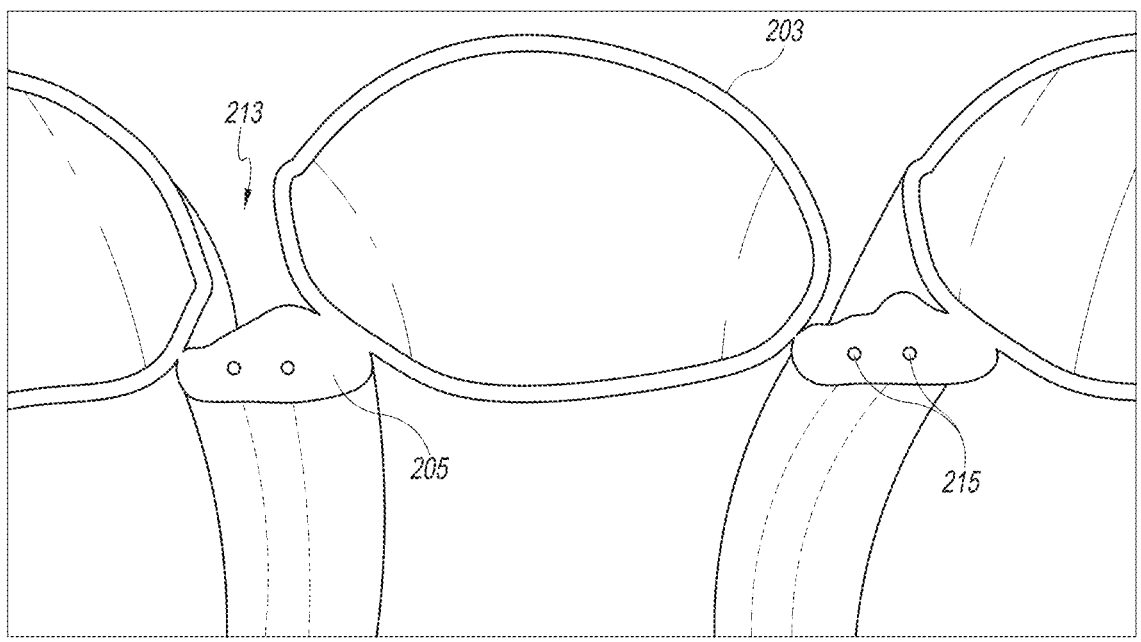
FIG. 2D shows another longitudinal cross-section of a top portion of a tube.
Figure 5A:
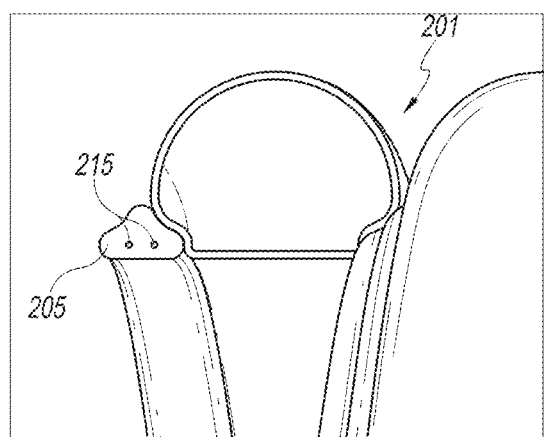
FIGS. 5A-5C show examples of first elongate member shapes configured to improve thermal efficiency.
Figure 5B:
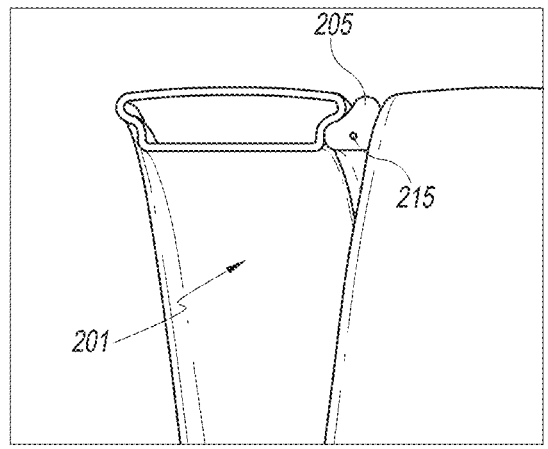
Figure 5C:
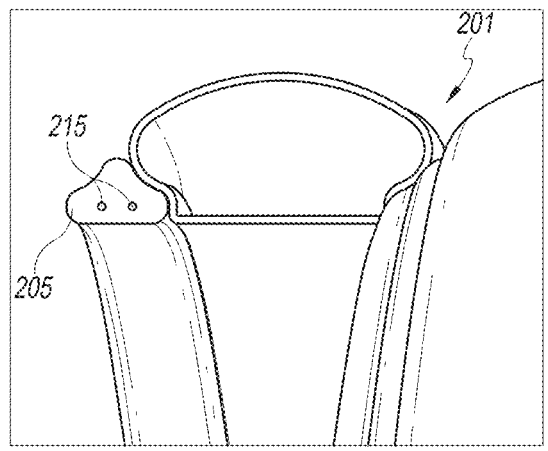

FIG. 2C shows a longitudinal cross-section of the bubbles in FIG. 2B. As shown, the portions 209 of the first elongate member 203 overlapping adjacent wraps of the second elongate member 205 are characterized by a degree of bond region 217. A larger bond region improves the tube's resistance to delamination at the interface of the first and second elongate members. Additionally or alternatively, the shape of the bead and/or the bubble can be adapted to increase the bond region 217. For example, FIG. 2D shows a relatively small bonding area on the left-hand side. FIG. 5B also demonstrates a smaller bonding region. In contrast, FIG. 2E has a much larger bonding region than that shown in FIG. 2D, because of the size and shape of the bead. FIGS. 5A and 5C also illustrate a larger bonding region. Each of these figures is discussed in more detail below. It should be appreciated that, although the configurations in FIGS. 2E, 3A, and 5C may be preferred in certain embodiments, other configurations, including those of FIGS. 2D, 5B, and other variations, may be used in other embodiments as may be desired.

FIG. 2D shows a longitudinal cross-section of a top portion of another composite tube. FIG. 2D has the same orientation as FIG. 2B. This example further illustrates the hollow-body shape of the first elongate member 203 and demonstrates how the first elongate member 203 forms in longitudinal cross-section a plurality of hollow bubbles. In this example, the bubbles are completely separated from each other by a gap 213. A generally triangular second elongate member 205 supports the first elongate member 203.

Figure 2E:
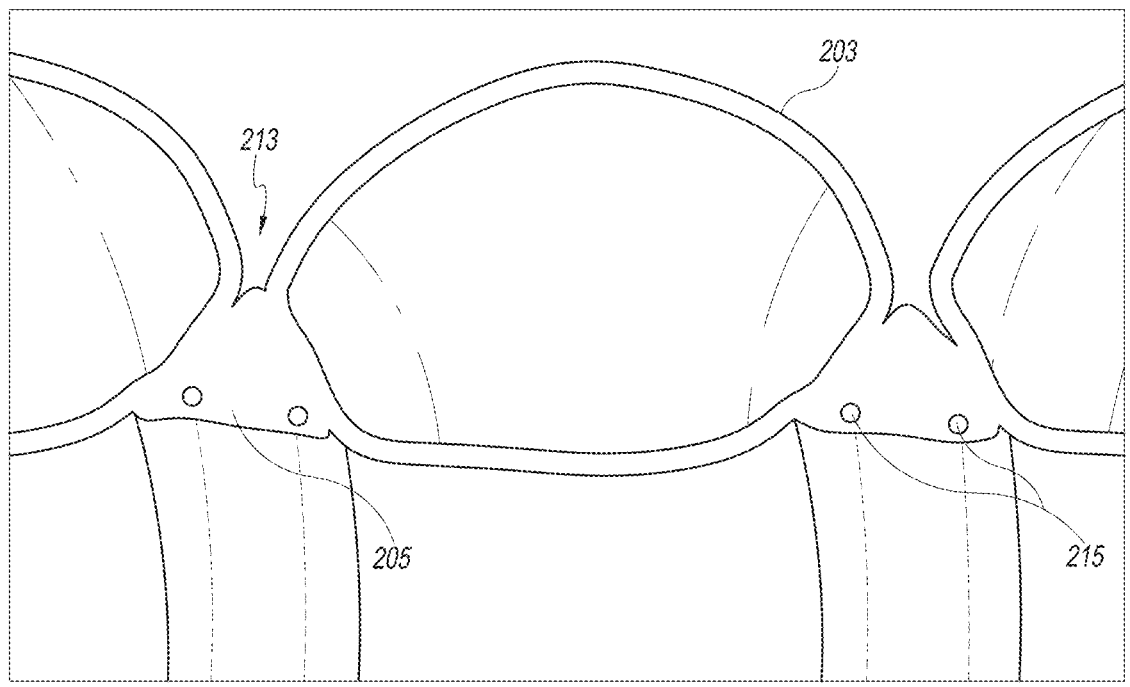
FIG. 2E shows another longitudinal cross-section of a top portion of a tube.
Figure 2F:
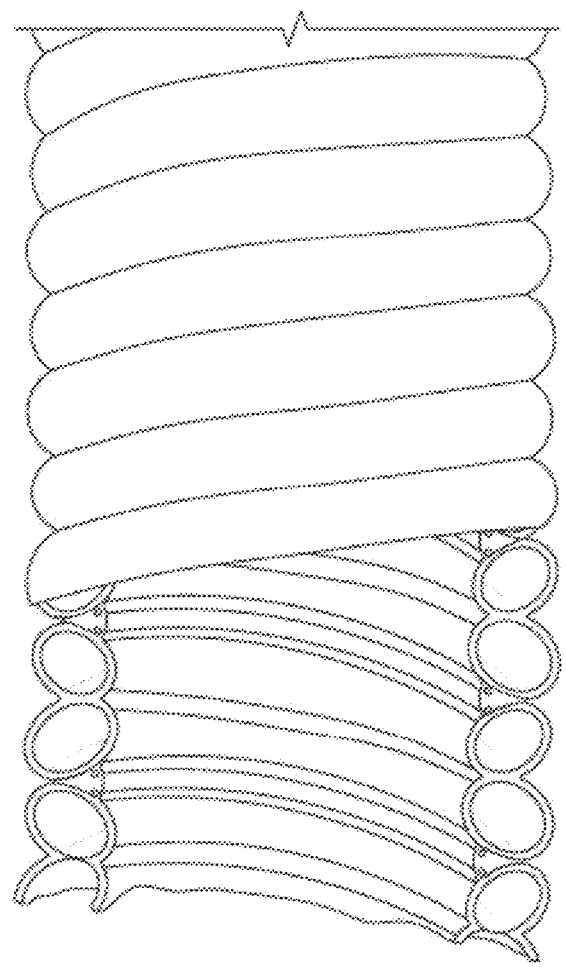
FIG. 2F shows a tube with a portion exposed in longitudinal cross-section.
Figure 2G:
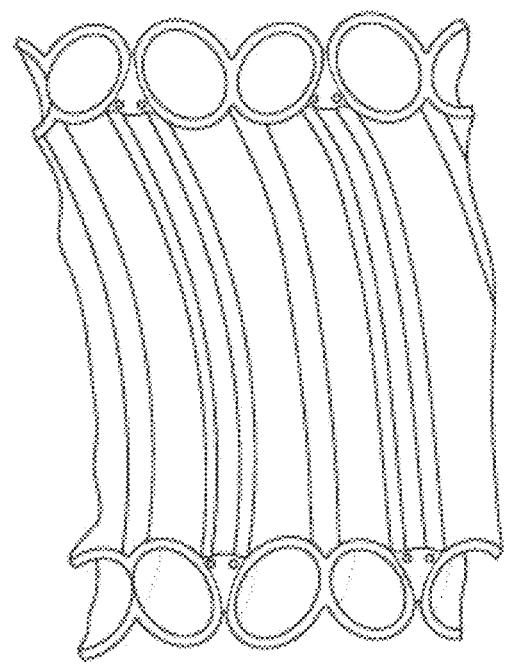
FIG. 2G shows a longitudinal cross-section of a portion of a tube similar to the example tube of FIG. 2F.
Figure 2H:
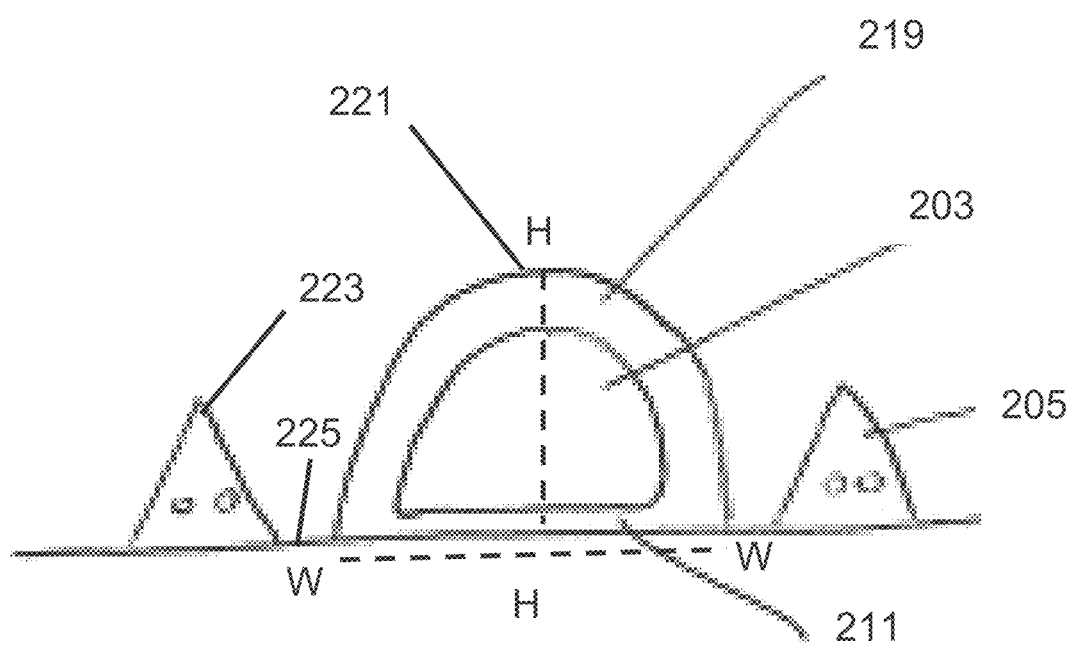
FIG. 2H shows a longitudinal cross-section of a top portion of a tube.

FIG. 2H shows a longitudinal cross-section of a top portion of another composite tube. FIG. 2H has the same orientation as FIG. 2B.

In the example of FIG. 2H, the cross-sectional thickness of the inner portion 211 of the first elongate member 203 forming the wall of the lumen is less than the thickness of the outer portion 219. Because the first elongate member 203 has a D-shaped bubble profile, the outer-facing portion of the first elongate member 203 has material slack between adjacent winds of the second elongate member, which facilitates movement and stretching as the composite tube 201 is bent into a ∩-shape. Because the configuration of FIG. 2H results in a thinner bubble near the lumen 207, such a configuration allows the inner portion 211 to compress or "bunch" more readily when the composite tube 201 is bent into a ∩-shape. Thus, certain embodiments include the realization that a configuration in which the cross-sectional thickness of the inner portion 211 is less than the cross-sectional thickness of the outer portion 219 can improve the flexibility of the composite tube 201 by permitting shorter radius bends. In addition, certain embodiments include the realization that overall tube flexibility can be improved by providing a first elongate member 203 with a variable cross-sectional wall thickness. Desirably, the thickness of the inner portion 211 is less than the thickness of the outer portion 219.

In at least one embodiment, the thickness of the inner portion 211 is at least 20% (or about 20%) less than the thickness of the outer portion 219. For example, in certain embodiments, the thickness of the inner portion 211 is at least 30% (or about 30%), at least 40% (or about 40%), at least 50% (or about 50%), or at least 60% (or about 60%) less than the thickness of the outer portion 219. In certain embodiments, the thickness of the inner portion 211 is 27% (or about 27%) less than the thickness of the outer portion 219. In certain embodiments, the thickness of the inner portion 211 is 32% (or about 32%) less than the thickness of the outer portion 219. In certain embodiments, the thickness of the inner portion 211 is 58% (or about 58%) less than the thickness of the outer portion 219. In certain embodiments, the thickness of the inner portion 211 is 64% (or about 64%) less than the thickness of the outer portion 219.

The thickness of the outer portion 219 can be in the range of 0.14 mm (or about 0.14 mm) and 0.44 mm (or about 0.44 mm), such as 0.22 mm (or about 0.22 mm) or 0.24 mm (or about 0.24 mm). The thickness of the inner portion 211 can be in the range of 0.05 mm (or about 0.05 mm) and 0.30 mm (or about 0.30 mm), and preferably 0.10 mm (or about 0.10 mm) or 0.16 mm (or about 0.16 mm).

Referring again to FIG. 2H, the height (designated as H-H) of a single longitudinal cross-sectional bubble of the first elongate member 203 can be greater than the width (designated as W-W) of a single longitudinal cross-sectional bubble of the first elongate member 203. Because a greater height increases the amount of material slack in the outer wall of the bubble of the first elongate member 203, such configuration can improve the flexibility of the composite tube 201 by permitting shorter radius bends. Accordingly, certain embodiments include the realization that overall tube flexibility can be improved by providing a first elongate member 203 with a longitudinal cross-sectional height that is greater than the longitudinal cross-sectional width. It should be appreciated that, although this example configuration may be preferred in certain embodiments, other configurations and variations, may be used in other embodiments as may be desired. For example, the height of a longitudinal cross-sectional bubble of the first elongate member 203 can be less than its width.

In at least one embodiment, the bubble height (H-H) can be in the range of 1.2 mm (or about 1.2 mm) and 8.2 mm (or about 8.2 mm), such as 1.2 mm (or about 1.2 mm), 1.7 mm (or about 1.7 mm), 1.8 mm (or about 1.8 mm), 2.7 mm (or about 2.7 mm), 2.8 mm (or about 2.8 mm), 3 mm (or about 3 mm), 3.2 mm (or about 3.2 mm), 3.5 mm (or about 3.5 mm), 3.8 mm (or about 3.8 mm), 4 mm (or about 4 mm), 4.5 mm (or about 4.5 mm), 7.7 mm (or about 7.7 mm), or 8.2 mm (or about 8.2 mm). In at least one embodiment, the bubble width (W-W) can be in the range of 1.7 mm (or about 1.7 mm) and 8 mm (or about 8 mm), such as 1.7 mm (or about 1.7 mm), 3.2 mm (or about 3.2 mm), 3.5 mm (or about 3.5 mm), 4.0 mm (or about 4.0 mm), 4.2 mm (or about 4.2 mm), 5.2 mm (or about 5.2 mm), 5.5 mm (or about 5.5 mm), 6 mm (or about 6 mm), 7 mm (or about 7 mm), 7.5 mm (or about 7.5 mm), or 8 mm (or about 8 mm).

The relationship between bubble height (H-H) and bubble width (W-W) can be expressed as a ratio. A ratio of bubble height (H-H) to bubble width (W-W) equal to 0 is least flexible. Flexibility increases as the ratio increases. In at least one embodiment, the ratio of bubble height (H-H) to bubble width (W-W) can be in the range of 0.15 (or about 0.15) and 1.5 mm (or about 1.5), such as 0.16 (or about 0.16), 0.34 (or about 3.4), 0.50 (or about 0.50), 0.56 (or about 0.56), 0.57 (or about 0.57), 0.58 (or about 0.58), 0.67 (or about 0.67), 0.68 (or about 0.68), 0.73 (or about 0.73), 0.85 (or about 0.85), 1.1 (or about 1.1), and 1.3 (or about 1.3).

It can be desirable for the outer profile of the corrugated tube to be relatively smooth. Relative smoothness, as used in this description, relates to the ridges between the first elongate member 203 and second elongate member 205 along the length of the composite tube 201. A relatively smoother corrugated tube has flatter, more closely spaced, or otherwise less pronounced ridges. A relatively smoother profile can advantageously reduce noise when the corrugated tube is dragged across an object, such as a desk or table edge.

An example parameter for quantifying relative smoothness is the vertical difference between an outer radial apex 221 of first elongate member 203 and an outer radial apex 223 of the second elongate member 205 of a composite tube 201 (as shown, for example, in FIG. 2H). As the distance between the outer radial apex 221 and the outer radial apex 223 decreases, the composite tube 201 feels relatively smoother. In at least one embodiment, the vertical distance is in the range of 1 mm (or about 1 mm) and 4.6 mm (or about 4.6 mm), such as 1.0 mm (or about 1.0 mm), 1.1 mm (or about 1.1 mm), 1.3 mm (or about 1.3 mm), 1.4 mm (or about 1.4 mm), 1.6 mm (or about 1.6 mm), 1.9 mm (or about 1.9 mm), 2.0 mm (or about 2.0 mm), 2.3 mm (or about 2.3 mm), 2.4 mm (or about 2.4 mm), 3.0 mm (or about 3.0 mm), 3.3 mm (or about 3.3 mm), or 4.6 mm (or about 4.6 mm). It is also possible to quantify relative smoothness as the vertical distance between an outer radial apex 221 of the first elongate member 203 and an outer radial nadir 225 of the second elongate member 205 of the composite tube 201. For example, the vertical distance can be 1.5 mm (or about 1.5 mm).

Another example parameter for quantifying relative smoothness is the ratio of the vertical difference between a radial apex 221 of first elongate member 203 and a radial apex 223 (or a radial nadir 225) of the second elongate member 205 of a composite tube 201 to the maximum outer diameter of the composite tube 201 (that is, from outer radial apex 221 to outer radial apex 221 on the opposite side of the tube 201). As the maximum outer diameter increases, the vertical difference between the outer radial apex 221 and the outer radial apex 223 or nadir 225 has less effect on relative smoothness. In at least one embodiment, the ratio is in the range of 0.04 to 0.18, such as 0.04, 0.05, 0.07, 0.08, 0.09, 0.10, 0.11, 0.12, 0.16, 0.17, or 0.18 or thereabout.

As another example, the distance between corresponding points from one turn to the next (that is, the pitch) can be selected to quantify relative smoothness. In certain embodiments, the pitch can be in the range of 2.1 mm (or about 2.1 mm) and 9.5 mm (or about 9.5 mm), such as 2.1 mm (or about 2.1 mm), 3.8 mm (or about 3.8 mm), 4.8 mm (or about 4.8 mm), 5.1 mm (or about 5.1 mm), 5.5 mm (or about 5.5 mm), 5.8 mm (or about 5.8 mm), 6.4 mm (or about 6.4 mm), 7.5 mm (or about 7.5 mm), 8.1 mm (or about 8.1 mm), or 9.5 mm (or about 9.5 mm).

The ratio of the pitch of the composite tube 201 to the vertical difference between a radial apex 221 of the first elongate member 203 and a radial apex 223 of the second elongate member 205 of the composite tube 201 to can be selected to quantify relative smoothness. In certain embodiments, the ratio is in the range of 1.3 (or about 1.3) and 4.8 (or about 4.8), such as 1.31 (or about 1.31), 1.76 (or about 1.76), 2.39 (or about 2.39), 2.42 (or about 2.42), 2.53 (or about 2.53), 2.71 (or about 2.71), 2.75 (or about 2.75), 3.26 (or about 3.26), 3.75 (or about 3.75), 4.13 (or about 4.13), 4.64 (or about 4.64), or 4.75 (or about 4.75).

The ratio of pitch to maximum outer diameter can also be selected to improve relative smoothness. In certain embodiments, the ratio of pitch to the outer diameter of the tube can be in the range of 0.10 (or about 0.10) and 0.35 (or about 0.32), such as 0.11 (or about 0.11), 0.23 (or about 0.23), 0.28 (or about 0.28), 0.29 (or about 0.29), 0.30 (or about 0.30), 0.31 (or about 0.31), or 0.32 (or about 0.32).

As discussed above, the hollow portion of the first elongate member 203 can be filled with a fluid, that is, a liquid or gas. The first elongate member 203 can be substantially sealed so as to prevent the quantity of fluid escaping. The first elongate member 203 can also be open at one or both ends to allow a continuous flow of liquid or gas.

The gas can be air, which is desirable because of its low thermal conductivity ($2.62 \times 10^{-2}$ W/m·K at 300K). A gas that is more viscous than air may also be used advantageously, as a higher viscosity reduces heat transfer under conditions of natural convection. Thus, gases such as argon ($17.72 \times 10^{-3}$ W/m·K at 300K), krypton ($9.43 \times 10^{-3}$ W/m·K at 300K), and xenon ($5.65 \times 10^{-3}$ W/m·K at 300K) can increase insulating performance. Each of these gases is non-toxic, chemically inert, fire-inhibiting, and commercially available. The hollow portion of the first elongated member 203 can be sealed at both ends of the tube, causing the gas within to be substantially stagnant. Alternatively, the hollow portion can be a secondary pneumatic connection, such as a pressure sample line for conveying pressure feedback from the patient-end of the tube to a controller.

Examples of liquids can include water or other biocompatible liquids with a high thermal capacity. For instance, nanofluids can be used. An example nanofluid with suitable thermal capacity comprises water and nanoparticles of substances such as aluminum.

In use, the fluid in the hollow portion of the first elongate member 203 can be configured to be used to measure one or more properties of the tube 201, the first elongate member 203, the second elongate member 205, and/or the gas in the tube 201 lumen 207. In at least one embodiment, the pressure of gas passing along the tube lumen ("lumen gas") can be measured. A reference measurement of the pressure of the fluid in the hollow portion of the first elongate member 203 ("hollow fluid") is made before the lumen gas begins to circulate. As the lumen gas begins to pass through the tube 201, the pressure of the lumen gas will tend to cause a proportional rise in the pressure of the hollow fluid within the first elongate member 203. By comparing a measurement taken in use with the reference measurement, the pressure of the lumen gas within the tube 201 can be determined. In another embodiment, a hollow fluid is chosen that changes one or more properties based on the operational heat range of the lumen gas within the tube 201. In this manner, by measuring the property of the hollow fluid, the temperature of the lumen gas can be determined. For example, a hollow fluid which expands with temperature can be used. In use, the temperature of the hollow fluid will tend towards the temperature of the lumen gas flow. By then measuring the pressure of the hollow fluid, the temperature of the lumen gas can be determined. This may have particular benefit when the temperature of the lumen gas flow is difficult or undesirable to measure directly.

In at least one embodiment, the extrudate used to form the first elongate member 203 further comprises a mineral filler. The extrusion process is described in greater detail below. Talc or hydrous magnesium silicate is suitable mineral filler. In addition to talc, other suitable mineral fillers include calcium carbonate, calcium magnesium carbonate such as dolomite, barium sulfate, wollastonite, kaolin, and mica, each of which can be added alone or in combination. Suitable mineral fillers can also have particle sizes less than 10 μm (or about 10 mm), or less than 2.5 μm (or about 2.5 mm).

It was discovered that the addition of mineral filler to the plastic extrudate reduces the stickiness of the resultant first elongate member 203. Stickiness refers to the tactile gumminess or clinginess of the first elongate member 203 material. A stickier material feels gummier than a less sticky material. A stickier material can also tend to cling to more unwanted matter, such as dirt or hair, than a less sticky material. The addition of mineral filler was discovered to reduce the noise the tube makes when it is moved, flexed, and so forth by reducing the extent to which adjacent bubbles stick (and unstick) to each other when bunched (and unbunched) around the vicinity of a bend.

It was also discovered that the addition of mineral filler to the extrudate can further reduce the noise made when the first elongate member 203 is dragged over an object, such as the edge of a desk or bedside table. The mineral filler may help reflect sound within the surrounding polymer so that the sound does not pass straight through. The improved sound reflection also may give the polymer phase more opportunity to absorb the sound energy, the mineral filler thereby providing intrinsic sound damping. The mineral filler may also reduce the hardness of the plastic extrudate and thereby improve sound damping properties.

In certain embodiments, the mineral filler is in the range of 1.5 to 10 (or about 1.5 to about 10) weight percent of the total extrudate. In certain embodiments, the mineral filler is in the range of 1.5 to 5 (or about 1.5 to about 5) weight percent of the total extrudate. In certain embodiments, the mineral filler is in the range of 10 (or about 10) weight percent or less of the total extrudate. In certain embodiments, the mineral filler is in the range of 5 (or about 5) weight percent or less of the total extrudate. In certain embodiments, the mineral filler is in the range of 1.5 (or about 1.5) weight percent or more of the total extrudate.

In FIG. 2F, the first elongate member 203 forms in longitudinal cross-section a plurality of hollow bubbles. In this example, there are a plurality of bubbles, and more specifically, two adjacent wraps of the first elongate member 203, between wraps of the second elongate member 205. This configuration is shown in greater detail in FIG. 2G. As described and shown elsewhere in this disclosure, certain configurations can implement greater than two, for example, three, wraps of the first elongate member 203 between wraps of the second elongate member 205.

Embodiments comprising a plurality of adjacent wraps of the first elongate member 203 between wraps of the second elongate member 205 can be advantageous because of improvements in overall tube flexibility. As described below, the substantially solid second elongate member 205 is generally less flexible than the hollow first elongate member 203. Accordingly, certain embodiments include the realization that overall tube flexibility can be improved by increasing the number of bubbles of first elongate member 203 between wraps of the second elongate member 205.

Another advantage of embodiments comprising a plurality of adjacent wraps of the first elongate member 203 between wraps of the second elongate member 205 is improved recovery from crushing. It was observed that, after crushing, samples having multiple bubbles between wraps of the first elongate member 203 recovered their shape more quickly than samples having a single bubble between wraps of the first elongate member 203.

Yet another advantage of embodiments comprising a plurality of adjacent wraps of the first elongate member 203 between wraps of the second elongate member 205 is improved resistance to crushing. Crush resistance is a mechanical property that plays an important role in the resilience of the tube while in service. The hospital environment can be harsh, as the tube can be subjected to crushing by a patient's arm or leg, bed frames, and other equipment. Example crush resistance properties are discussed in greater detail below.

Yet another advantage to the multiple-bubble configuration is that the configuration imparts the ability to hold or transport additional fluids. As explained above, the hollow portion of the first elongate member 203 can be filled with a gas. The multiple discrete bubbles or hollow portions can be filled with multiple discrete gases. For example, one hollow portion can hold or transport a first gas and a second hollow portion can be used as a secondary pneumatic connection, such as a pressure sample line for conveying pressure feedback from the patient-end of the tube to a controller. As another example, multiple discrete bubbles or hollow portions can be filled with a combination of liquids, or a combination of liquids and gases. A first bubble can hold or transport a gas, and a second bubble can hold or transport a liquid, for instance. Suitable liquids and gases are described above.

It should be appreciated that, although the configurations in FIGS. 2F and 2G may be preferred in certain embodiments, other configurations, may be utilized in other embodiments as may be desired.

Second Elongate Member

Referring again to FIGS. 2A and 2B, the second elongate member 205 is also spirally wound and joined to the first elongate member 203 between turns of the first elongate member 203. The second elongate member 205 can form at least a portion of the lumen 207 of the elongate tube. The second elongate member 205 acts as structural support for the first elongate member 203.

CPAP machines ordinarily weigh in the range of 2 and 4 kg (or about 2 and 4 kg). Thus, the break strength of the composite tube 201 (the horizontal tensile load or force required to cause separation of the first elongate member 203 and the second elongate member 205) desirably is high enough to prevent separation if a user attempts to use the composite tube 201 to lift a CPAP machine connected to the composite tube 201. Thus, the break strength is preferably greater than 20 N (or about 20 N) and, more preferably, greater than 30 N (or about 30 N). In certain embodiments, the break strength is in the range of 75 and 80 N (or about 75 and 80 N). The yield strength (the maximum stress that can be developed without causing plastic deformation) can be in the range of 55 and 65 N (or about 55 and 65 N). In certain embodiments, the composite tube 201 will not stretch (horizontally deflect) more than 0.5 mm (or about 0.5 mm) when a lateral force of 2 N is applied.

In at least one embodiment, the second elongate member 205 is wider at the base (proximal the lumen 207) and narrower at the top. For example, the second elongate member can be generally triangular in shape, generally T-shaped, or generally Y-shaped. However, any shape that meets the contours of the corresponding first elongate member 203 is suitable.

Preferably, the second elongate member 205 is flexible, to facilitate bending of the tube. Desirably, the second elongate member 205 is less flexible than the first elongate member 203. This improves the ability of the second elongate member 205 to structurally support the first elongate member 203. For example, the modulus of the second elongate member 205 is preferably 30-50 MPa (or about 30-50 MPa). The modulus of the first elongate member 203 is less than the modulus of the second elongate member 205. The second elongate member 205 can be solid or mostly solid.

Figure 6A:
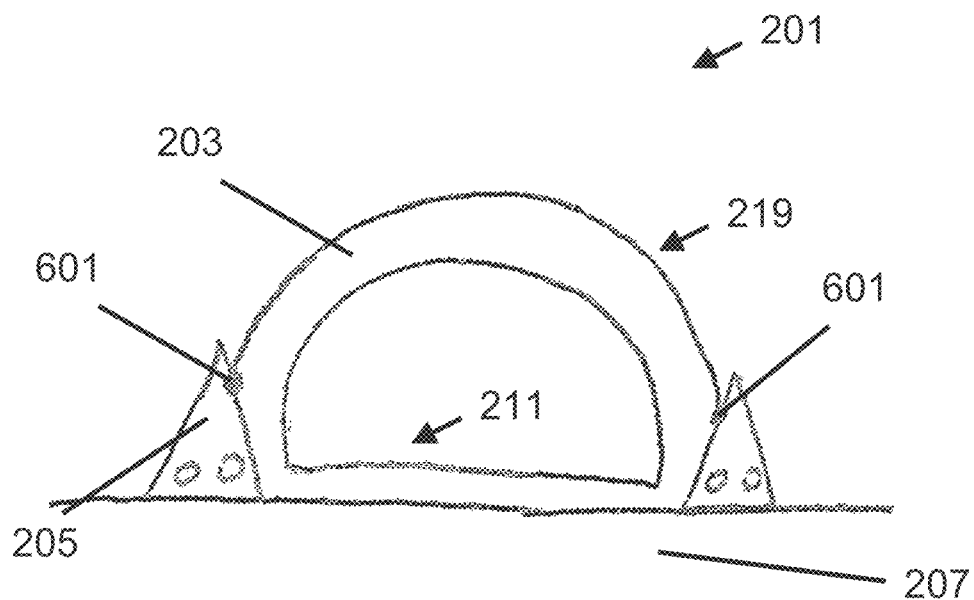
FIG. 6A shows a longitudinal cross section of a portion of a composite tube in a neutral position.
Figure 6B:
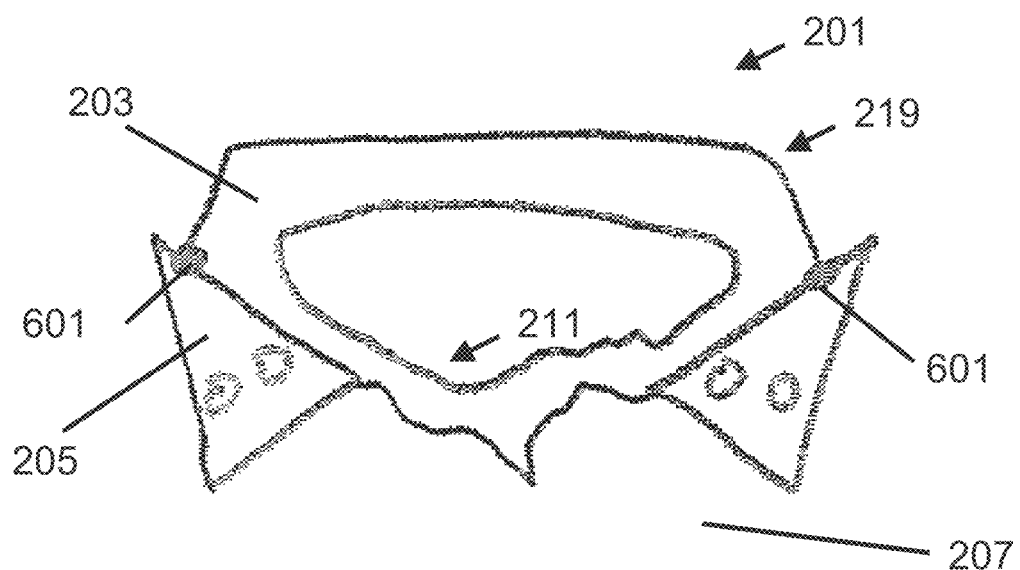
FIG. 6B shows the portion of the composite tube of FIG. 6A in a bent position, in which the composite tube has been bent to a ∩-shape.
Figure 6C:
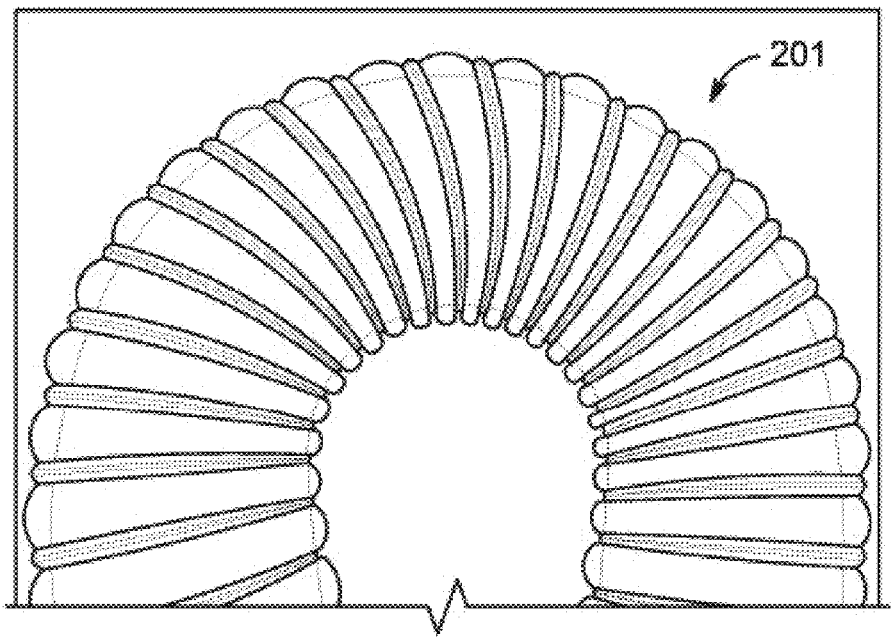
FIG. 6C shows a composite tube that has been bent to a ∩-shape.
Figure 6D:
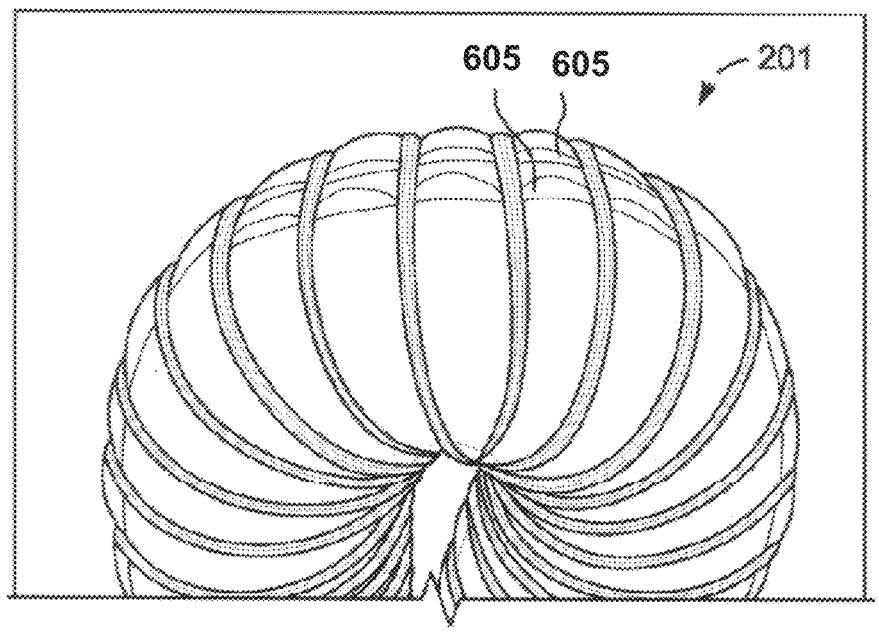
FIG. 6D shows a composite tube that has been bent beyond the minimum radius of curvature.

FIG. 6A shows a longitudinal cross section of a composite tube 201 in a neutral position. FIG. 6A focuses on one wind or bubble of the first elongate member 203 and two winds of the second elongate member 205. The first elongate member 203 and second elongate member 205 have a radially-outermost connection point 601. In this example, the inner portion 211 of the first elongate member 203 is thinner than the outer portion 219 of the first elongate member 203. Also in this example, the second elongate member 205 has a triangular cross section. The lumen 207 is situated under the base of the first elongate member 203 and second elongate member 205. FIG. 6B shows the composite tube 201 of FIG. 6A in a bent position, in which the composite tube 201 has been bent to a ∩-shape (as shown in FIG. 6C). FIG. 6B again focuses on one wind or bubble of the first elongate member 203 and two winds of the second elongate member 205. More specifically, FIG. 6B focuses on the wind or bubble of the first elongate member 203 at the top of the ∩-shape, that is, at the location of maximum bend. The radius of curvature of the composite tube 201 is constrained by the length of the section of the outer portion 219 between adjacent outermost connection points 601. If the composite tube 201 is bent beyond the minimum radius of curvature, the outer wall forms dimples 605, as shown in FIG. 6D.

A variety of polymers and plastics, including medical grade plastics, are suitable for the body of the second elongate member 205. Examples of suitable materials include Polyolefin elastomers, Polyether block amides, Thermoplastic co-polyester elastomers, EPDM-Polypropylene mixtures and Thermoplastic polyurethanes. In certain embodiments, the first elongate member 203 and the second elongate member 205 may be made from the same material. The second elongate member 205 may also be made of a different color material from the first elongate member 203, and may be transparent, translucent or opaque. For example, in one embodiment the first elongate member 203 may be made from a clear plastic, and the second elongate member 205 may be made from an opaque blue, black, or other color plastic.

This spirally-wound structure comprising a flexible, hollow body and an integral support can provide crush resistance, while leaving the tube wall flexible enough to permit short-radius bends without kinking, occluding or collapsing. Preferably, the tube can be bent around a 25 mm diameter metal cylinder without kinking, occluding, or collapsing, as defined in the test for increase in flow resistance with bending according to ISO 5367:2000(E).

This structure also can provide a smooth lumen 207 surface, which helps keep the tube free from deposits and improves gas flow. The hollow body has been found to improve the insulating properties of a tube, while allowing the tube to remain light weight.

In some embodiments, the second elongate member 205 can be made of a material that wicks water. For example, an absorbent sponge-like material can be used. In such embodiments, the second elongate member 205 can be connected to a water source, such as a water bag. In use, water would be conveyed along at least a portion of the length of the second elongate member 205 (preferably, substantially the whole length). As gas passes along the second elongate member 205, water vapor will tend to be picked up by the gases in the lumen 207, thereby humidifying the gas flow.

In some embodiments, the one or more heating filaments 215 embedded in the second elongate member 205, as shown in FIG. 2B, can be controlled to alter the rate of evaporation and thereby alter the level of humidification provided to the gas flow. Although FIG. 2B specifically shows heating filaments 215, it should be understood that the second elongate member 205 can encapsulate or house other conductive material(s), such as one or more filaments, and specifically sensors (not shown). Such conductive materials can be disposed in the second elongate member 205 for heating or sensing the gas flow. Heating filaments 215 can minimize the cold surfaces onto which condensate from moisture-laden air can form. Heating filaments 215 can also be used to alter the temperature profile of gases in the lumen 207 of composite tube 201.

In the example of FIG. 2B, two heating filaments 215 are encapsulated in the second elongate member 205, one on either side of the vertical portion of the "T." The heating filaments 215 comprise conductive material, such as alloys of Aluminum (Al) and/or Copper (Cu), or conductive polymer. Preferably, the material forming the second elongate member 205 is selected to be non-reactive with the metal in the heating filaments 215 when the heating filaments 215 reach their operating temperature. The filaments 215 may be spaced away from lumen 207 so that the filaments are not exposed to the lumen 207. At one end of the composite tube, pairs of filaments can be formed into a connecting loop.

In at least one embodiment, a plurality of filaments are disposed in the second elongate member 205. The filaments can be electrically connected together to share a common rail. For example, a first filament, such as a heating filament, can be disposed on a first side of the second elongate member 205. A second filament, such as a sensing filament, can be disposed on a second side of the second elongate member 205. A third filament, such as a ground filament, can be disposed between the first and second filaments. The first, second, and/or third filaments can be connected together at one end of the second elongate member 205.

FIG. 2E shows a longitudinal cross-section of a top portion of another composite tube. FIG. 2E has the same orientation as FIG. 2B. In the example of FIG. 2E, the heating filaments 215 are spaced farther apart from each other than the filaments 215 in FIG. 2B. It was discovered that increasing the space between heating filaments can improve heating efficiency, and certain embodiments include this realization. Heating efficiency refers to the ratio of the amount of heat input to the tube to the amount of energy output or recoverable from the tube. Generally speaking, the greater the energy (or heat) that is dissipated to ambient atmosphere from the tube, the lower the heating efficiency. For improved heating performance, the heating filaments 215 can be equally (or about equally) spaced along the bore of the tube. Alternatively, the filaments 215 can be positioned at extremities of the second elongate member 205, which may provide simpler manufacturing.

Figure 7A:
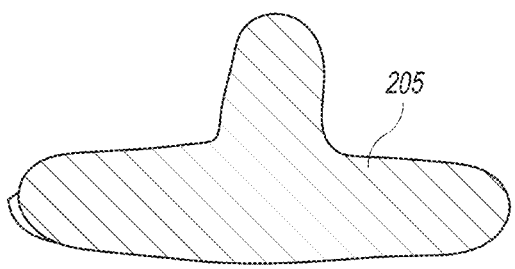
FIG. 7A shows a transverse cross-section of a second elongate member in the composite tube.

Reference is next made to FIGS. 7A through 7G which demonstrate example configurations for the second elongate member 205. FIG. 7A shows a cross-section of a second elongate member 205 having a shape similar to the T-shape shown in FIG. 2B. In this example embodiment, the second elongate member 205 does not have heating filaments. Other shapes for the second elongate member 205 may also be utilized, including variations of the T-shape as described below and triangular shapes.

Figure 7B:
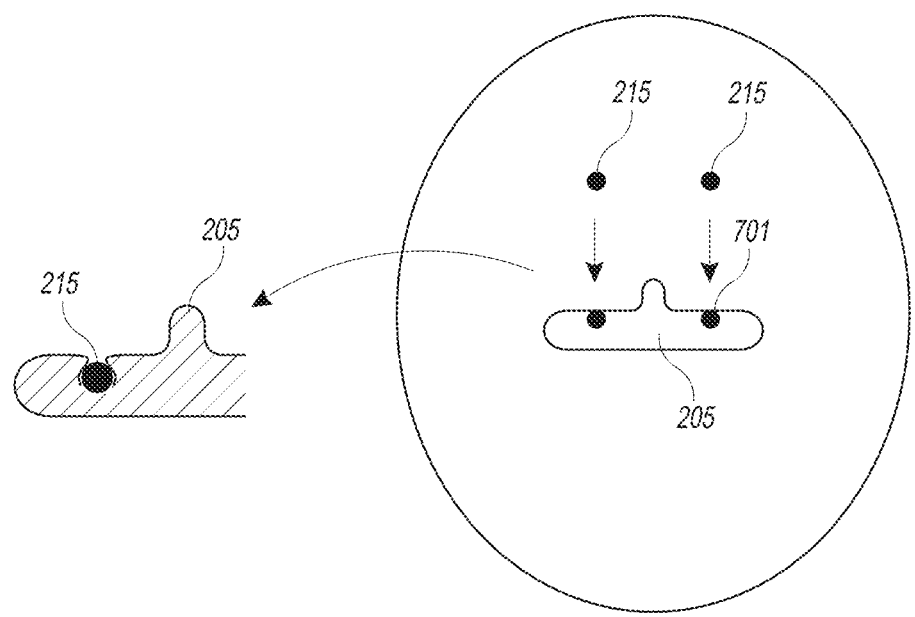
FIG. 7B shows another transverse cross-section of a second elongate member.

FIG. 7B shows another example second elongate member 205 having a T-shape cross-section. In this example, heating filaments 215 are embedded in cuts 701 in the second elongate member 205 on either side of the vertical portion of the "T." In some embodiments, the cuts 701 can be formed in the second elongate member 205 during extrusion. The cuts 701 can alternatively be formed in the second elongate member 205 after extrusion. For example, a cutting tool can form the cuts in the second elongate member 205. Preferably, the cuts are formed by the heating filaments 215 as they are pressed or pulled (mechanically fixed) into the second elongate member 205 shortly after extrusion, while the second elongate member 205 is relatively soft. Alternatively, one or more heating filaments can be mounted (e.g., adhered, bonded, or partially embedded) on the base of the elongate member, such that the filament(s) are exposed to the tube lumen. In such embodiments, it can be desirable to contain the filament(s) in insulation to reduce the risk of fire when a flammable gas such as oxygen is passed through the tube lumen.

Figure 7C:
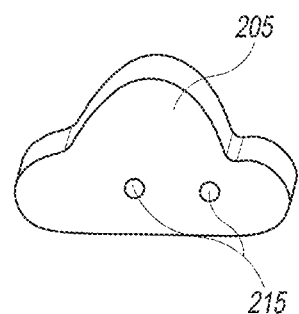
FIG. 7C shows another example second elongate member.

FIG. 7C shows yet another example second elongate member 205 in cross-section. The second elongate member 205 has a generally triangular shape. In this example, heating filaments 215 are embedded on opposite sides of the triangle.

Figure 7D:
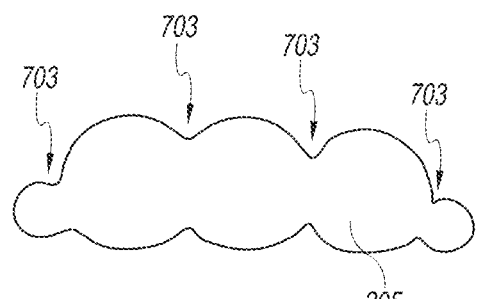
FIG. 7D shows another example second elongate member.

FIG. 7D shows yet another example second elongate member 205 in cross-section. The second elongate member 205 comprises four grooves 703. The grooves 703 are indentations or furrows in the cross-sectional profile. In some embodiments, the grooves 703 can facilitate the formation of cuts (not shown) for embedding filaments (not shown). In some embodiments, the grooves 703 facilitate the positioning of filaments (not shown), which are pressed or pulled into, and thereby embedded in, the second elongate member 205. In this example, the four initiation grooves 703 facilitate placement of up to four filaments, for example, four heating filaments, four sensing filaments, two heating filaments and two sensing filaments, three heating filaments and one sensing filament, or one heating filament and three sensing filaments. In some embodiments, heating filaments can be located on the outside of the second elongate member 205. Sensing filaments can be located on the inside.

Figure 7E:
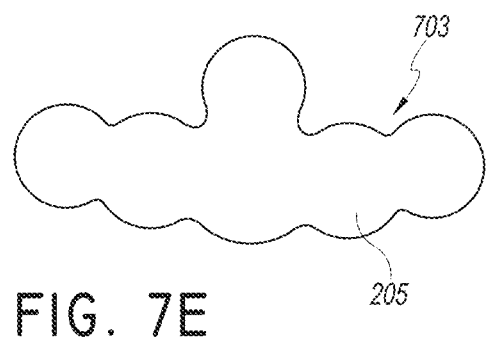
FIG. 7E shows another example second elongate member.

FIG. 7E shows still another example second elongate member 205 in cross-section. The second elongate member 205 has a T-shape profile and a plurality of grooves 303 for placing heating filaments.

Figure 7F:
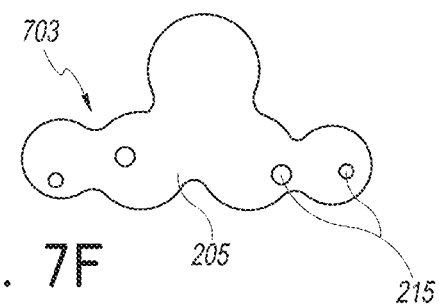
FIG. 7F shows another example second elongate member.

FIG. 7F shows yet another example second elongate member 205 in cross-section. Four filaments 215 are encapsulated in the second elongate member 205, two on either side of the vertical portion of the "T." As explained in more detail below, the filaments are encapsulated in the second elongate member 205 because the second elongate member 205 was extruded around the filaments. No cuts were formed to embed the heating filaments 215. In this example, the second elongate member 205 also comprises a plurality of grooves 703. Because the heating filaments 215 are encapsulated in the second elongate member 205, the grooves 703 are not used to facilitate formation of cuts for embedding heating filaments. In this example, the grooves 703 can facilitate separation of the embedded heating filaments, which makes stripping of individual cores easier when, for example, terminating the heating filaments.

Figure 7G:
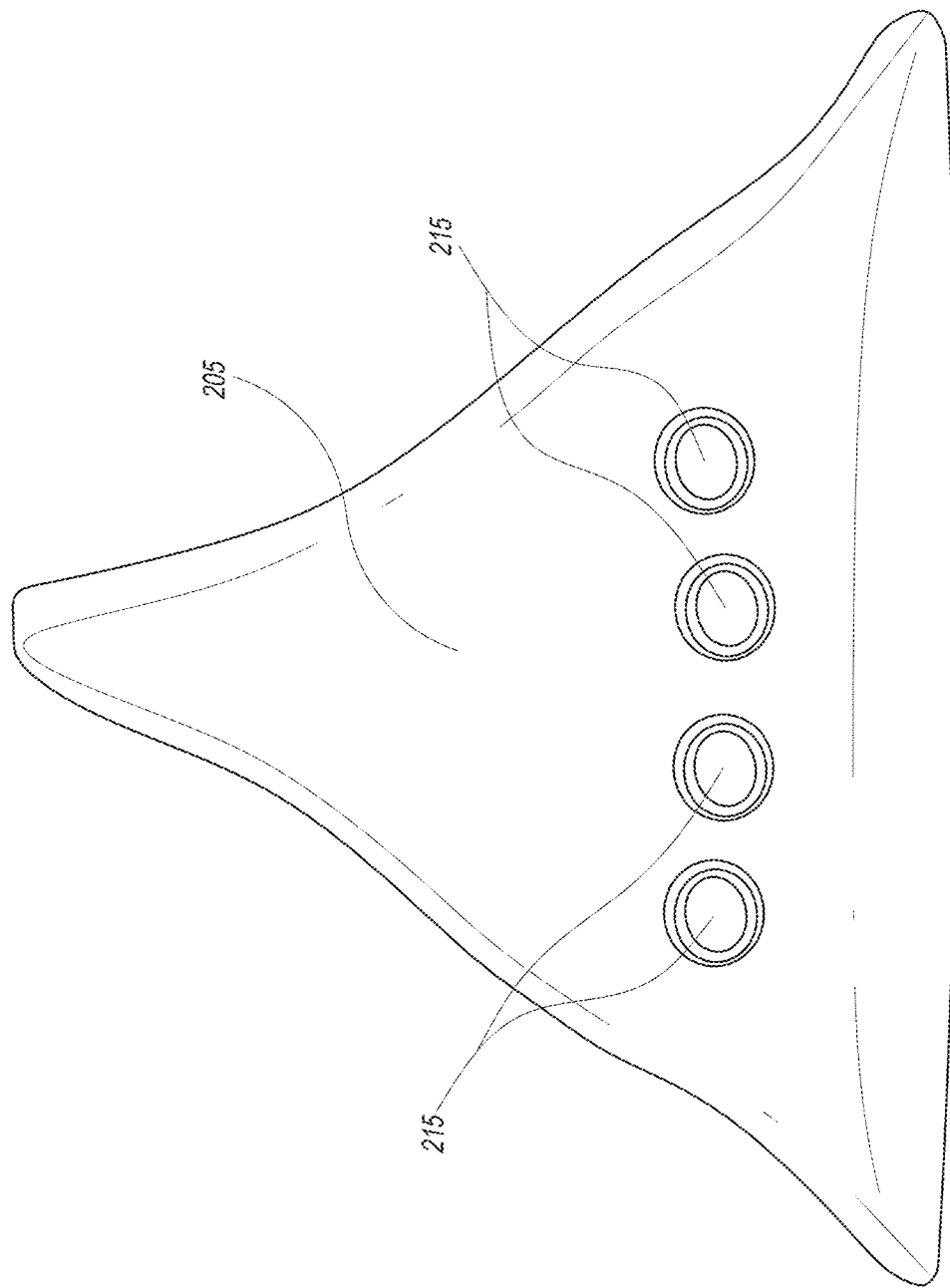
FIG. 7G shows another example second elongate member.

FIG. 7G shows yet another example second elongate member 205 in cross-section. The second elongate member 205 has a generally triangular shape. In this example, the shape of the second elongate member 205 is similar to that of FIG. 7C, but four filaments 215 are encapsulated in the second elongate member 205, all of which are central in the bottom third of the second elongate member 205 and disposed along a generally horizontal axis.

As explained above, it can be desirable to increase the distance between filaments to improve heating efficiency. In some embodiments, however, when heating filaments 215 are incorporated into the composite tube 201, the filaments 215 can be positioned relatively central in the second elongate member 205. A centralized position promotes robustness of the composite tubing for reuse, due in part to the position reducing the likelihood of the filament breaking upon repeating flexing of the composite tube 201. Centralizing the filaments 215 can also reduce the risk of an ignition hazard because the filaments 215 are coated in layers of insulation and removed from the gas path.

As explained above, some of the examples illustrate suitable placements of filaments 215 in the second elongate member 205. In the foregoing examples comprising more than one filament 215, the filaments 215 are generally aligned along a horizontal axis. Alternative configurations are also suitable. For example, two filaments can be aligned along a vertical axis or along a diagonal axis. Four filaments can be aligned along a vertical axis or a diagonal axis. Four filaments can be aligned in a cross-shaped configuration, with one filament disposed at the top of the second elongate member, one filament disposed at the bottom of the second elongate member (near the tube lumen), and two filaments disposed on opposite arms of a "T," "Y," or triangle base.

Dimensions

TABLES 3 and 4 show some example dimensions of medical tubes described herein, as well as some ranges for these dimensions. The dimensions refer to a transverse cross-section of a tube. In these tables, lumen diameter represents the inner diameter of a tube. Pitch represents the distance between two repeating points measured axially along the tube, namely, the distance between the tip of the vertical portions of adjacent "T"s of the second elongate member. Bubble width represents the width (maximum outer diameter) of a bubble. Bubble height represents the height of a bubble from the tube lumen. Bead height represents the maximum height of the second elongate member from the tube lumen (e.g., the height of the vertical portion of the "T"). Bead width represents the maximum width of the second elongate member (e.g., the width of the horizontal portion of the "T"). Bubble thickness represents the thickness of the bubble wall.

TABLE 3

| Feature | Infant | | Adult | |
| --- | --- | --- | --- | --- |
| | Dimension (mm) | Range (±) | Dimension (mm) | Range (±) |
| Lumen diameter | 11 | 1 | 18 | 5 |
| Pitch | 4.8 | 1 | 7.5 | 2 |
| Bubble width | 4.2 | 1 | 7 | 1 |
| Bead width | 2.15 | 1 | 2.4 | 1 |
| Bubble height | 2.8 | 1 | 3.5 | 0.5 |
| Bead height | 0.9 | 0.5 | 1.5 | 0.5 |
| Bubble thickness | 0.4 | 0.35 | 0.2 | 0.15 |

TABLE 4

| Feature | Infant | | Adult | |
| --- | --- | --- | --- | --- |
| | Dimension (mm) | Range (±) | Dimension (mm) | Range (±) |
| Lumen diameter | 11 | 1 | 18 | 5 |
| Pitch | 4.8 | 1 | 7.5 | 2 |
| Bubble width | 4.2 | 1 | 7 | 1 |
| Bead width | 2.15 | 1 | 3.4 | 1 |
| Bubble height | 2.8 | 1 | 4.0 | 0.5 |
| Bead height | 0.9 | 0.5 | 1.7 | 0.5 |
| Bubble thickness | 0.4 | 0.35 | 0.2 | 0.15 |

In another example embodiment, a medical tube has the approximate dimensions shown in TABLE 5.

TABLE 5

| Feature | Dimension (mm) |
|---|---|
| Pitch | 6.4 |
| Bubble width | 5.5 |
| Bubble height | 3.2 |
| Bubble thickness on top, farthest from lumen (outer wall thickness) | 0.22 |
| Bubble thickness adjacent lumen (inner wall thickness) | 0.16 |

In another example embodiment, a medical tube has the approximate dimensions shown in TABLE 6.

TABLE 6

| Feature | Dimension (mm) | Range (±) |
|---|---|---|
| Lumen diameter | 17.2 | 5.0 |
| Pitch | 5.1 | 3.0 |
| Bubble width | 4.0 | 2.0 |
| Bead width | 2.3 | +3.0/−2.0 |
| Bubble height | 2.7 | +5.0/−2.0 |
| Bead height | 1.6 | 1.5 |
| Bubble thickness on top, farthest from lumen (outer wall thickness) | 0.24 | +0.20/−0.10 |
| Bubble thickness adjacent lumen (inner wall thickness) | 0.10 | +0.20/−0.05 |
| Outer diameter of tube | 22.5 | 3.0 |

Preferably, the low ends of the ranges of TABLE 6 correspond to each other, and the high ends of the ranges of Table 6 correspond to each other.

The embodiments of TABLES 5 and 6 can be particularly advantageous for obstructive sleep apnea applications.

TABLES 7, 8, and 9 provide example ratios between the dimensions of tube features for the tubes described in TABLES 3, 4, and 6 respectively.

TABLE 7

| Ratios | Infant | Adult |
|---|---|---|
| Lumen diameter:Pitch | 2.3:1 | 2.4:1 |
| Pitch:Bubble width | 1.1:1 | 1.1:1 |
| Pitch:Bead width | 2.2:1 | 3.1:1 |
| Bubble width:Bead width | 2.0:1 | 2.9:1 |
| Lumen diameter:Bubble height | 3.9:1 | 5.1:1 |
| Lumen diameter:Bead height | 12.2:1 | 12.0:1 |
| Bubble height:Bead height | 3.1:1 | 2.3:1 |
| Lumen diameter:Bubble thickness | 27.5:1 | 90.0:1 |

TABLE 8

| Ratios | Infant | Adult |
|---|---|---|
| Lumen diameter:Pitch | 2.3:1 | 2.4:1 |
| Pitch:Bubble width | 1.1:1 | 1.1:1 |
| Pitch:Bead width | 2.2:1 | 2.2:1 |
| Bubble width:Bead width | 2.0:1 | 2.1:1 |
| Lumen diameter:Bubble height | 3.9:1 | 4.5:1 |
| Lumen diameter:Bead height | 12.2:1 | 10.6:1 |
| Bubble height:Bead height | 3.1:1 | 2.4:1 |
| Lumen diameter:Bubble thickness | 27.5:1 | 90.0:1 |

TABLE 9

| Ratios | Value |
|---|---|
| Lumen diameter:Pitch | 3.4:1 |
| Pitch:Bubble width | 0.93:1 |

TABLE 9-continued

| Ratios | Value |
|---|---|
| Pitch:Bead width | 2.2:1 |
| Bubble width:Bead width | 1.7:1 |
| Lumen diameter:Bubble height | 5.4:1 |
| Lumen diameter:Bead height | 10.8:1 |
| Bubble height:Bead height | 1.7:1 |
| Lumen diameter:Bubble thickness on top, farthest from lumen | 71.7:1 |
| Lumen diameter:Bubble thickness adjacent lumen | 172:1 |

Variable Pitch and/or Variable Diameter

The foregoing description discloses various constant pitch and constant diameter configurations. Certain embodiments can incorporate variable pitch and/or variable diameter, however.

A variable pitch can be desirable because it can better allow heat delivered to the gas flow to be varied along the length of the tube. The ability to control where the heat is delivered in a tube can be used to control or reduce rainout within the tube. For example, an end-of-tube temperature set point may be achieved for a given condition, yet be insufficient to prevent rainout within the tube, particularly at or near the inlet of the tube where the gas temperature may be close to the dew point temperature (high relative humidity). Certain embodiments include the realization that redistributing the heat source to concentrate it near the entrance of the tube can help to ensure a greater axial concentration of heat in this region, Q(z) [W/m], where z is the axial displacement of the tube, beginning at the unit end.

Figure 8A:
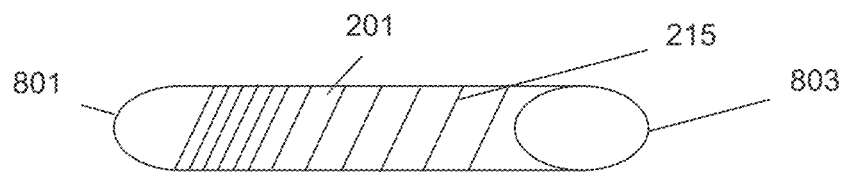
FIG. 8A shows a schematic of a composite tube with a variable pitch.
Figure 8B:
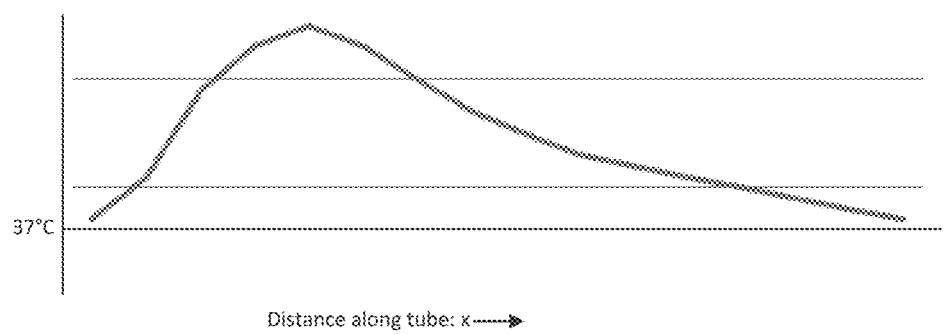
FIG. 8B is a graph depicting an example temperature profile in a variable-pitch composite tube.

FIG. 8A shows an example composite tube 201 with variable pitch. In this example, the tube 201 has a smaller pitch proximal the unit end 801. Thus, the heating filaments 215 in this region will be more densely spaced, enabling greater heating at that part of the tube 201 as well as greater and more accurate temperature control. The tube 201 has a larger pitch at the patient end 803. The greater spacing between heating filaments 215 can allow the gases to decrease in temperature as they approach the patient. This can prevent the patient from receiving gases that are too hot and can reduce rainout formation. FIG. 8B shows the temperature profile of the composite tube of FIG. 8A. Other temperature profiles are also possible and can be customized to achieve specific desired effects.

The geometry of the tube 201 also affects the mechanical properties of the tube. By increasing the size of the bubble of the first elongate member, the flexibility of the tube 201 will be increase. Conversely, a smaller bubble size will produce a more rigid region of the tube 201. By altering flexibility and rigidity, the mechanical properties of the tube 201 can be customized. By varying the diameter of the tube 201, it is possible to have a smaller diameter near a patient interface which will increase patient comfort, improve the aesthetics, and reduce the invasiveness of the interface.

Additional Properties

TABLES 10-13 show some example properties of a composite tube (labeled "A"), described herein, having a heating filament integrated inside the second elongate member. For comparison, properties of a Fisher & Paykel model RT100 disposable corrugated tube (labeled "B") having a heating filament helically wound inside the bore of the tube are also presented.

Measurement of resistance to flow (RTF) was carried out according to Annex A of ISO 5367:2000(E). The results are summarized in TABLE 10. As seen below, the RTF for the composite tube is lower than the RTF for the model RT100 tube.

TABLE 10

| Flow rate (L/min) | RTF (cm H$_2$O) | | | |
|---|---|---|---|---|
| | 3 | 20 | 40 | 60 |
| A | 0 | 0.05 | 0.18 | 0.38 |
| B | 0 | 0.28 | 0.93 | 1.99 |

Condensate or "rainout" within the tube refers to the weight of condensate collected per day at 20 L/min gas flow rate and room temperature of 18° C. Humidified air is flowed through the tube continuously from a chamber. The tube weights are recorded before and after each day of testing. Three consecutive tests are carried out with the tube being dried in between each test. The results are shown below in TABLE 11. The results showed that rainout is significantly lower in the composite tube than in the model RT100 tube.

TABLE 11

| | Tube | | | | | |
|---|---|---|---|---|---|---|
| | A (Day 1) | A (Day 2) | A (Day 3) | B (Day 1) | B (Day 2) | B (day 3) |
| Weight before (g) | 136.20 | 136.70 | 136.70 | 111.00 | 111.10 | 111.10 |
| Weight after (g) | 139.90 | 140.00 | 139.20 | 190.20 | 178.80 | 167.10 |
| Condensate weight (g) | 3.7 | 3.3 | 2.5 | 79.20 | 67.70 | 56.00 |

The power requirement refers to the power consumed during the condensate test. In this test, the ambient air was held at 18° C. Humidification chambers (see, e.g., the humidification chamber 129 in FIG. 1) were powered by MR850 heater bases. The heating filaments in the tubes were powered independently from a DC power supply. Different flow rates were set and the chamber was left to settle to 37° C. at the chamber output. Then, the DC voltage to the circuits was altered to produce a temperature of 40° C. at the circuit output. The voltage required to maintain the output temperature was recorded and the resulting power calculated. The results are shown in TABLE 12. The results show that composite Tube A uses significantly more power than Tube B. This is because Tube B uses a helical heating filament in the tube bore to heat the gas from 37° C. to 40° C. The composite tube does not tend to heat gas as quickly because the heating filament is in the wall of the tube (embedded in the second elongate member). Instead, the composite tube is designed to maintain the gas temperature and prevent rainout by maintaining the tube bore at a temperature above the dew point of the humidified gas.

TABLE 12

| Flow rate (L/min) | 40 | 30 | 20 |
|---|---|---|---|
| Tube A, power required (W) | 46.8 | 38.5 | 37.8 |
| Tube B, power required (W) | 28.0 | 27.5 | 26.8 |

Figure 9A:
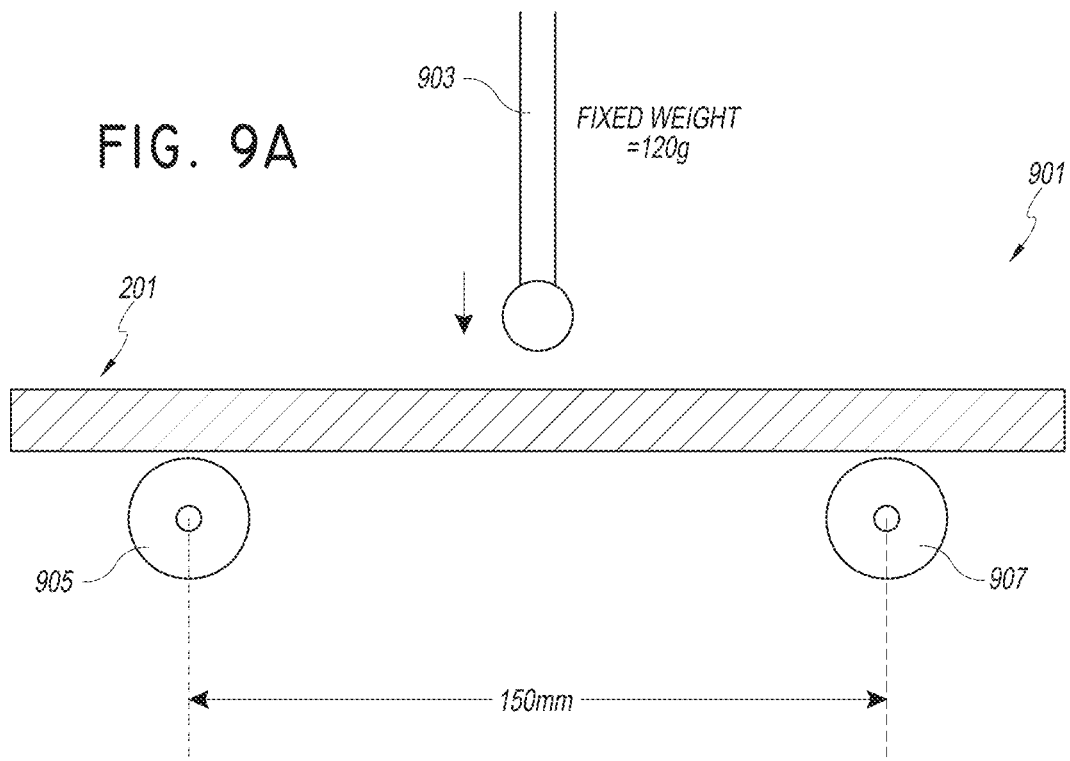
FIG. 9A shows a front-plan cross-sectional schematic of a flexibility jig.
Figure 9B:
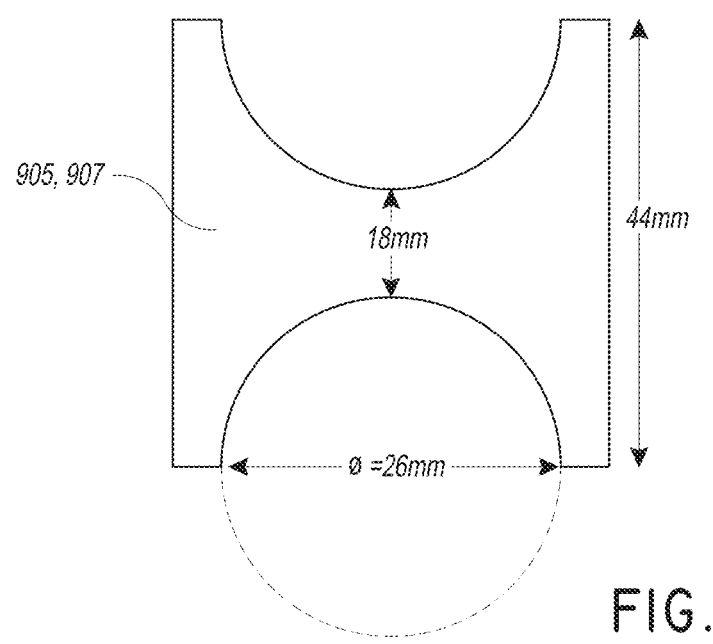
FIG. 9B shows a detailed front-plan cross-sectional schematic of rollers on the flexibility jig of FIG. 9A.

Vertical deflection can be used to quantify flexibility of a composite tube. Vertical deflection can be tested, for example, using a three-point bend test. A first 300 mm-length sample of Tube A and a second 300 mm-length sample of Tube B were each tested on a flexibility jig. A front-plan cross-sectional schematic of the flexibility jig is shown in FIG. 9A. The jig 901 used a 25-mm rod 903 with a fixed mass of 120 g to apply a force to each tube 201, which was positioned between two rollers 905 and 907. The rollers were spaced 150 mm apart. The force exerted by the rod 903 was about 1.2 N (0.12 kg×9.81 m/s$^2$). A detailed front-plan cross-sectional schematic of rollers 905 and 907 is shown in FIG. 9B. Both rollers 905 and 907 had the same dimensions, which are shown in FIG. 9B. An Instron 5560 Test System instrument was used to measure load and extension. Each tube sample was tested three times; measuring the extension of the tube against the applied load, to obtain average respective stiffness constants. The average stiffness constants for Tube A and Tube B are reproduced in TABLE 13.

TABLE 13

| Tube | Stiffness (N/mm) |
|---|---|
| A | 0.028 |
| B | 0.088 |

Tube weight can be very important, particularly for CPAP applications. If a patient experiences less weight near the patient's face, the patient will be more comfortable during sleep. A lighter composite tube 201 will not pull the patient's head in a particular direction as much as a heavier tube. To ensure patient comfort, it is possible to specify that the total mass or weight in a region near the patient end of the composite tube 201 must be less than a specified value. In certain embodiments, the tube mass in the 300 mm nearest the patient end is less than 24 g (or about 24 g). Desirably, the tube mass in the 300 mm nearest the patient end is less than 16 g (or about 16 g). In certain embodiments, the tube mass in the 300 mm nearest the patient end is less than 15 g (or about 15 g). It is also possible to specify that the total mass of the composite tube be less than a specified value. In certain embodiments, the tube mass is less than 130 g (or about 130 g). Desirably, the tube mass is less than 120 g (or about 120 g). In certain embodiments, the tube mass is less than 100 g (or about 100 g).

The following discussion now describes additional properties relating to a composite tube 201 with two bubbles between wraps of the second elongate member 205, as discussed above.

A first 300 mm-length sample of tube comprising two bubbles between wraps of the second elongate member 205 and a second 300 mm-length sample of tube comprising one bubble between wraps of the second elongate member 205 were each tested on the flexibility jig 901 discussed above. The vertical deflection was measured using the position of the fixed weight with respect to a vertical support 909 of the flexibility jig, shown in the photographs of FIGS. 9C through 9F.

Figure 9C:
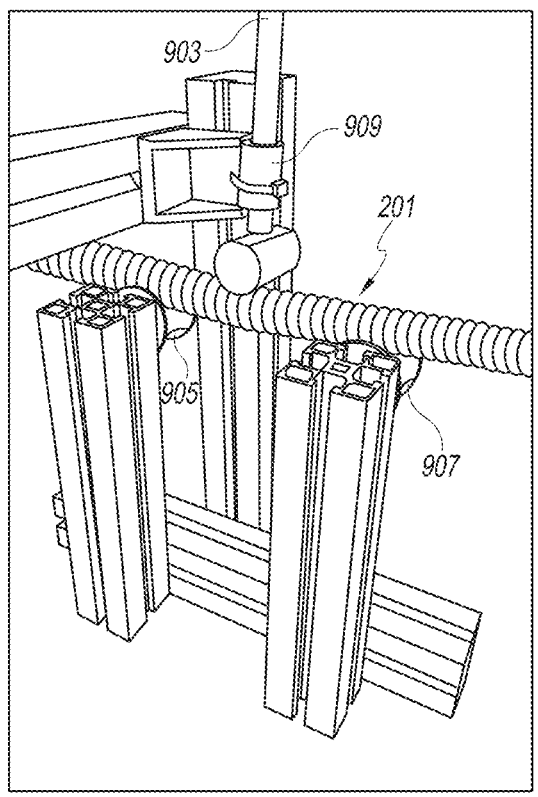
FIGS. 9C-9F show a flexibility jig in use.
Figure 9D:
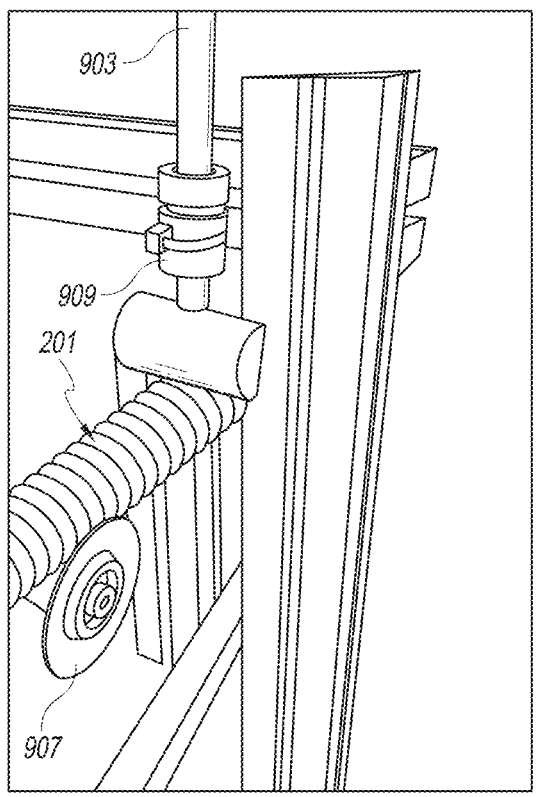
Figure 9E:
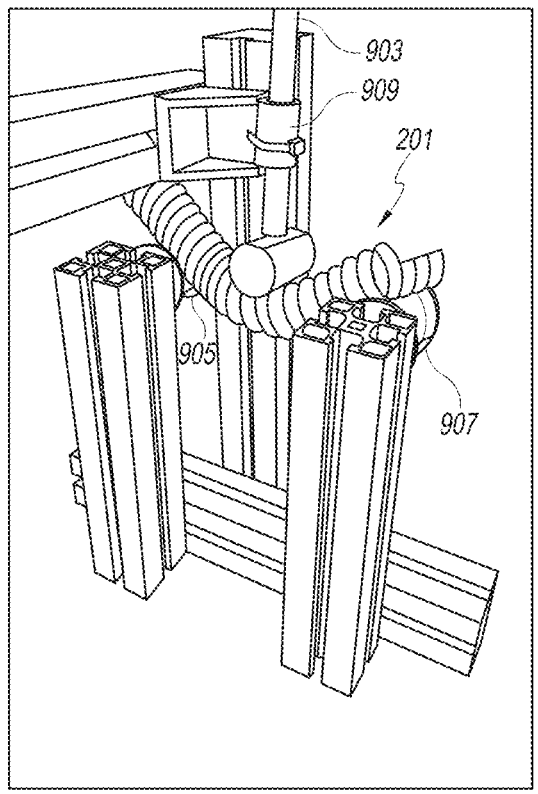
Figure 9F:
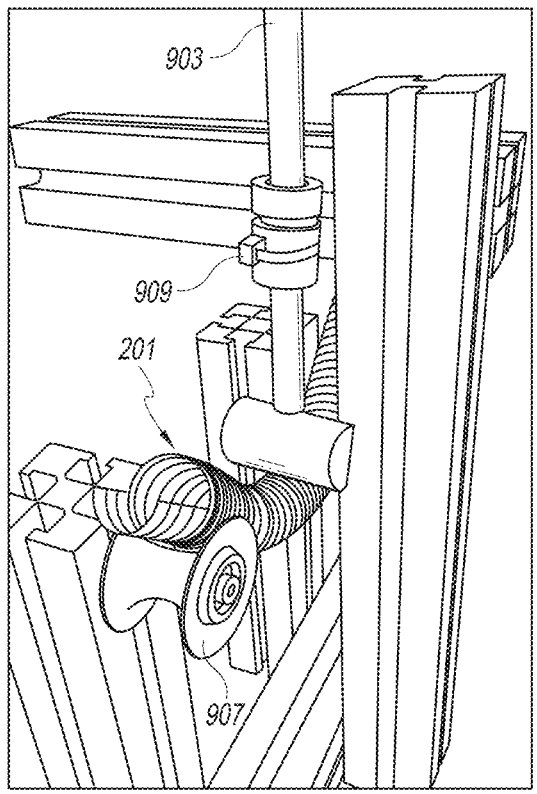

FIG. 9C shows a front-perspective view of the second sample under testing in the jig 901. FIG. 9D shows a rear-perspective view of the second sample under testing in the jig 901. FIG. 9E shows a front-perspective view of the first sample under testing in the jig 901. FIG. 9F shows a rear-perspective view of the first sample under testing in the jig 901. As shown in FIGS. 9C through 9F, the second sample shown in FIGS. 9E and 9F had substantially greater vertical deflection than the first sample shown in FIGS. 9C and 9D. Specifically, the second sample had a vertical deflection of 3 mm, while the first sample was much more flexible, having a vertical deflection of 42 mm.

Figure 10A:
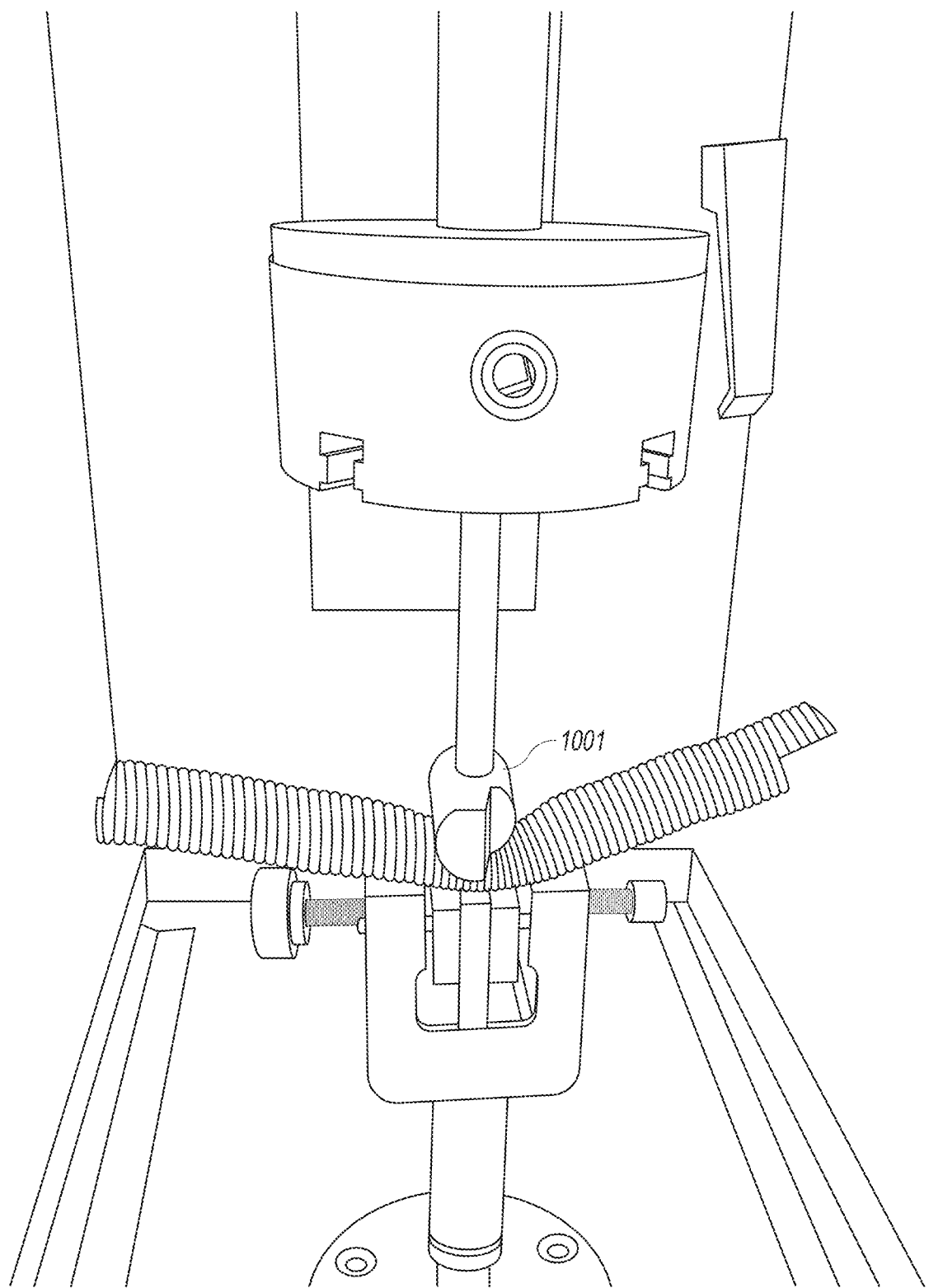
FIG. 10A shows a crush resistance testing jig.

Crush resistance testing was performed on four tube samples using an Instron machine set up as shown in the photograph in FIG. 10A. The cylinder 1001 was plunged downwards 16 mm from the top of the tube at a rate of 60 mm/min. The Instron machine has a load cell to accurately measure force exerted on a component versus extension. The load vs. extension was plotted, as shown in FIG. 10B.

Figure 10B:
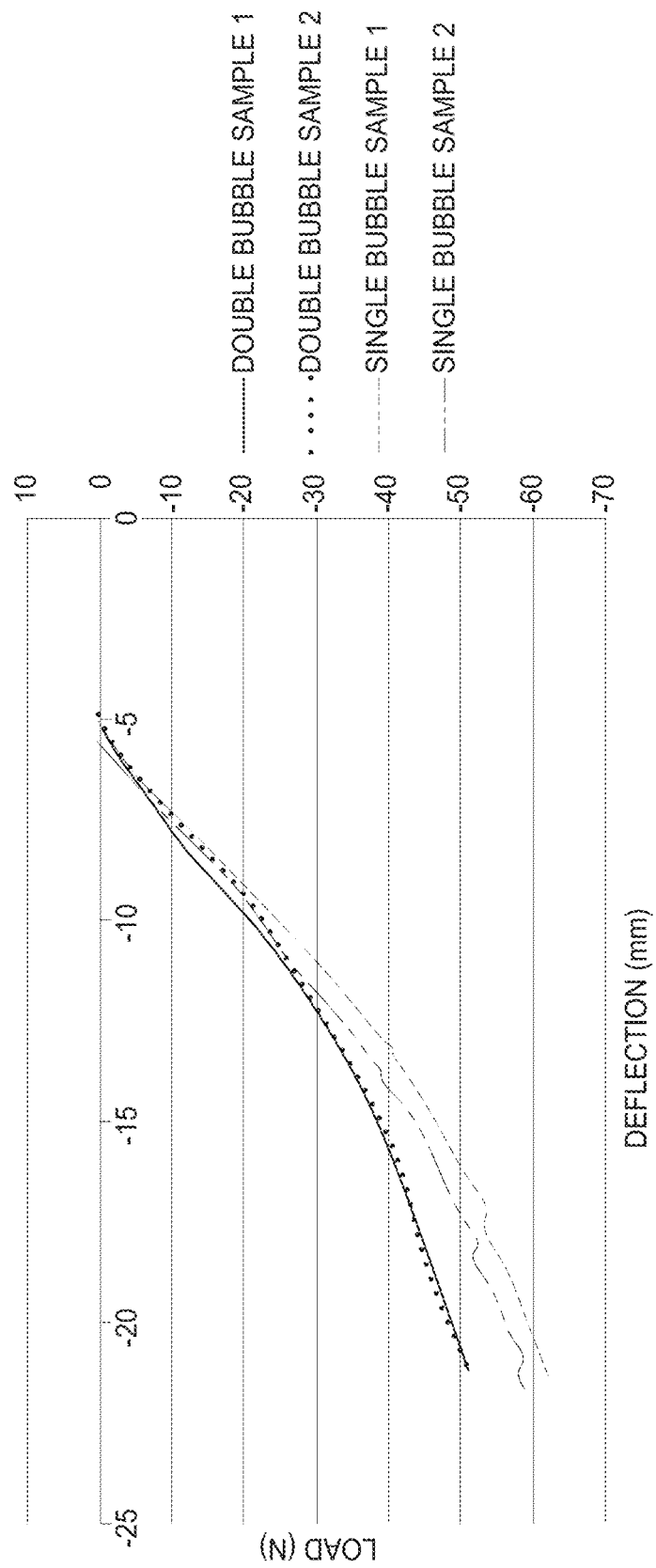
FIG. 10B shows a plot of load vs. extension, used for determining crush stiffness.

The crush stiffness for each sample was found by fitting a line of best fit to the data of FIG. 10B and calculating its gradient. The calculated crush stiffness for each sample is shown in TABLE 14A. In TABLE 14A (and elsewhere in this disclosure), the designation "double bubble" refers to a sample of tube comprising two bubbles between wraps of the second elongate member 205, when the sample is viewed in longitudinal cross section. The designation "single bubble" refers to a sample of tube comprising a single bubble between wraps of the second elongate member 205, when the sample is viewed in longitudinal cross section. The average crush stiffness (measured in N/mm) represents the average maximum force per unit width which produces no crush.

TABLE 14A

| Sample | Crush Stiffness (N/mm) | Average |
| --- | --- | --- |
| Double Bubble, Sample 1 | 3.26 | 3.21 |
| Double Bubble, Sample 2 | 3.15 | |
| Single Bubble, Sample 1 | 3.98 | 3.86 |
| Single Bubble, Sample 2 | 3.74 | |

As shown in the foregoing table, single bubble tubes had an average crush stiffness of 3.86 N/mm, while double bubble tubes had an average crush stiffness of 3.21 N/mm. In other words, the double bubble tubes had an approximately 16.8% lower resistance to crush than the single bubble tubes. Nevertheless, crush stiffness per unit thickness for the double bubble tubes was observed to be approximately 165% of the value for the single bubble tubes, as shown below in TABLE 14B.

TABLE 14B

| | Bubble Thickness (mm) | Crush Stiffness (N/mm) | Stiffness/Bubble Thickness (N/mm$^2$) |
| --- | --- | --- | --- |
| Double Bubble | 0.22 | 3.21 | 14.32 |
| Single Bubble | 0.43 | 3.86 | 8.70 |

Stated another way, when outer bubble thickness is taken into account, the double bubble tube is around 65% more resistant to crush than the single bubble tube variant. Similar to the bubbles shown in FIGS. 2F and 2G, the tested bubbles in the double bubble configuration are taller than they are wide, which results in more material in the vertical plane. Thus, it is believed that the unexpected improvement in crush resistance per unit thickness of the bubble may be attributed to the additional vertical web between beads working in the direction of crush.

Tensile testing was also performed on the single and double bubble tube samples. Both samples were 230 mm in length and were elongated by 15 mm at a rate of 10 mm/min. The force required to elongate the samples was measured. The results are shown in TABLE 14C.

TABLE 14C

| Sample | Peak Force at 15 mm extension (N) |
| --- | --- |
| Double Bubble | 17.60 |
| Single Bubble | 54.65 |

As shown in TABLE 14C, the double bubble tube was significantly more extensible in the axial (longitudinal) plane. This increase in longitudinal extensibility is believed to be due to the single bubble tube having more material between the beads working in the axial plane.

Thermal Properties

In embodiments of a composite tube 201 incorporating a heating filament 215, heat can be lost through the walls of the first elongate member 203, resulting in uneven heating. As explained above, one way to compensate for these heat losses is to apply an external heating source at the first elongate member 203 walls, which helps to regulate the temperature and counter the heat loss. Other methods for optimizing thermal properties can also be used, however.

Reference is again made to FIGS. 5A through 5C, which demonstrate example configurations for bubble height (that is, the cross-sectional height of the first elongate member 203 measured from the surface facing the inner lumen to the surface forming the maximum outer diameter) to improve thermal properties.

The dimensions of the bubble can be selected to reduce heat loss from the composite tube 201. Generally, increasing the height of the bubble increases the effective thermal resistance of the tube 201, because a larger bubble height permits the first elongate member 203 to hold more insulating air. However, it was discovered that, at a certain bubble height, changes in air density cause convection inside the tube 201, thereby increasing heat loss. Also, at a certain bubble height the surface area becomes so large that the heat lost through surface outweighs the benefits of the increased height of the bubble. Certain embodiments include these realizations.

The radius of curvature and the curvature of the bubble can be useful for determining a desirable bubble height. The curvature of an object is defined as the inverse of the radius of curvature of that object. Therefore, the larger a radius of curvature an object has, the less curved the object is. For example, a flat surface would have a radius of curvature of ∞, and therefore a curvature of 0.

FIG. 5A shows a longitudinal cross-section of a top portion of a composite tube. FIG. 5A shows an embodiment of a composite tube 201 where the bubble has a large height. In this example, the bubble has a relatively small radius of curvature and therefore a large curvature. Also, the bubble is approximately three to four times greater in height than the height of the second elongate member 205.

FIG. 5B shows a longitudinal cross-section of a top portion of another composite tube. FIG. 5B shows an embodiment of a composite tube 201 where the bubble is flattened on top. In this example, the bubble has a very large radius of curvature but a small curvature. Also, the bubble is approximately the same height as the second elongate member 205.

FIG. 5C shows a longitudinal cross-section of a top portion of another composite tube. FIG. 5C shows an embodiment of a composite tube 201 where the width of the bubble is greater than the height of the bubble. In this example, the bubble has radius of curvature and the curvature between that of FIG. 5A and FIG. 5B, and the center of the radius for the upper portion of the bubble is outside of the bubble (as compared to FIG. 5A). The inflection points on the left and right sides of the bubble are about at the middle (heightwise) of the bubble (as opposed to in the lower portion of the bubble, as in FIG. 5A). Also, the height of the bubble is approximately double that of the second elongate member 205, resulting in a bubble height between that of FIG. 5A and FIG. 5B.

The configuration of FIG. 5A resulted in the lowest heat loss from the tube. The configuration of FIG. 5B resulted in the highest heat loss from the tube. The configuration of FIG. 5C had intermediate heat loss between the configurations of FIGS. 5A and 5B. However, the large external surface area and convective heat transfer in the configuration of FIG. 5A led to inefficient heating. Thus, of the three bubble arrangements of FIGS. 5A-5C, FIG. 5C was determined to have the best overall thermal properties. The practical implication of this thermal efficiency is that, when the same thermal energy was input to the three tubes, the configuration of FIG. 5C allowed for the largest temperature rise along the length of the tube. The bubble of FIG. 5C is sufficiently large to increase the insulating air volume, but not large enough to cause a significant convective heat loss. The configuration of FIG. 5B was determined to have the poorest thermal properties, namely that the configuration of FIG. 5B allowed for the smallest temperature rise along the length of the tube. The configuration of FIG. 5A had intermediate thermal properties and allowed for a lower temperature rise than the configuration of FIG. 5C.

It should be appreciated that although the FIG. 5C configuration may be preferred in certain embodiments, other configurations, including those of FIGS. 5A, 5B and other variations, may be utilized in other embodiments as may be desired.

TABLE 15 shows the height of the bubble, the outer diameter of the tube, and the radius of curvature of the configurations shown in each of FIGS. 5A, 5B, and 5C.

TABLE 15

| Tube (Fig.) | 5A | 5B | 5C |
|---|---|---|---|
| Bubble height (mm) | 3.5 | 5.25 | 1.75 |
| Outer diameter (mm) | 21.5 | 23.25 | 19.75 |
| Radius of curvature (mm) | 5.4 | 3.3 | 24.3 |

TABLE 16A shows the height of the bubble, the outer diameter, and the radius of curvature of further configurations as shown in FIGS. 11A, 11B, and 11C.

TABLE 8A

| Tube (Fig.) | 10A | 10B | 10C |
|---|---|---|---|
| Bubble height (mm) | 6.6 | 8.4 | 9.3 |
| Outer diameter (mm) | 24.6 | 26.4 | 27.3 |
| Radius of curvature (mm) | 10 | 8.7 | 5.7 |

Figure 11D:
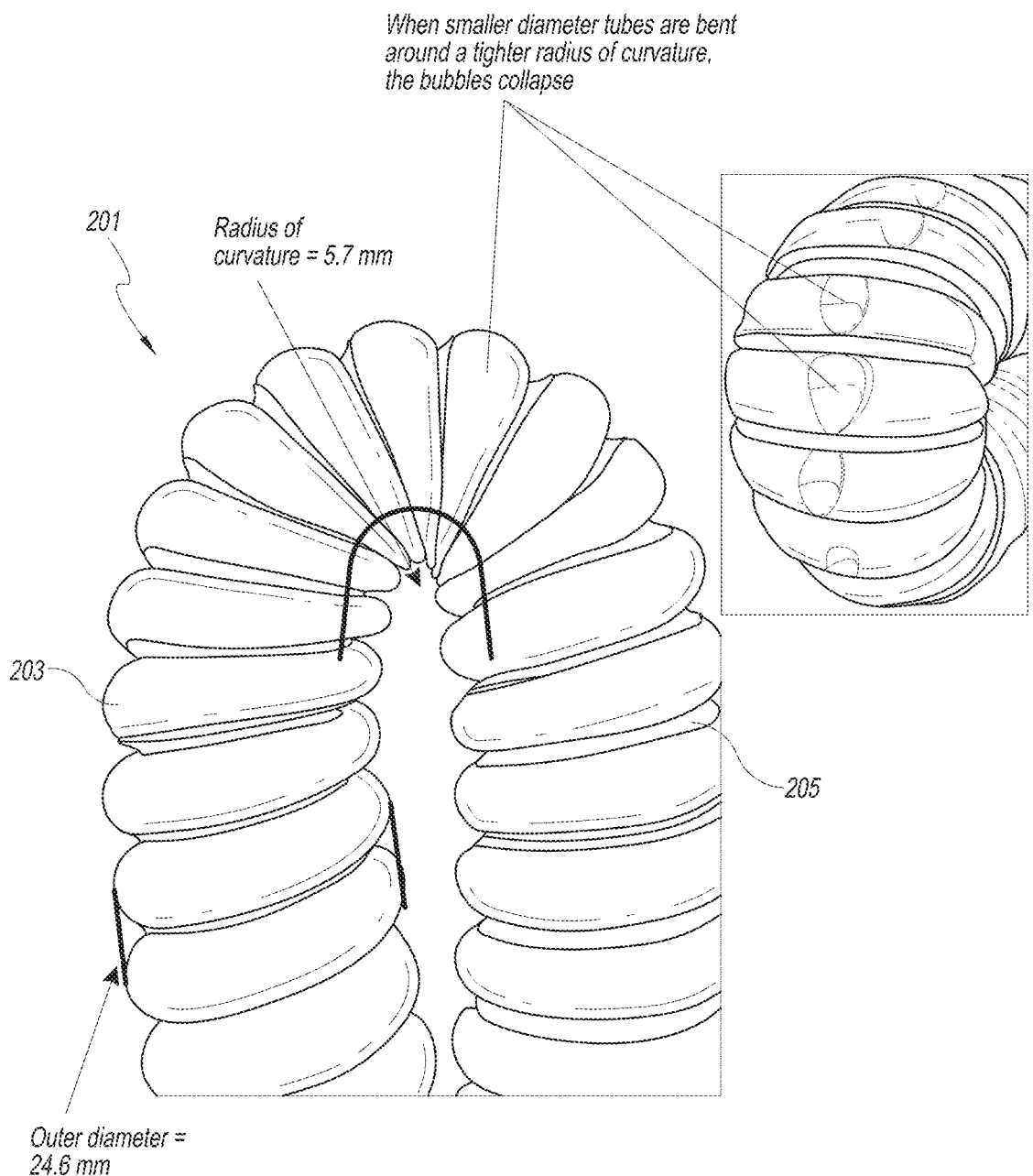

It should be noted that, in general, the smaller the radius of curvature, the tighter the tube can be bent around itself without the bubble collapsing or "kinking." For example, FIG. 11D shows a tube that has been bent beyond its radius of curvature (specifically, it shows the tube of FIG. 11A bent around a radius of curvature of 5.7 mm), thereby causing kinking in the walls of the bubble. Kinking is generally undesirable, as it can detract from the appearance of the tube, and can impair the thermal properties of the tube.

Accordingly, in some applications, the configurations with increased bending properties (such as those shown in FIG. 5A or 5B) can be desirable despite having less efficient thermal properties. In some applications, it has been found that a tube with an outer diameter of 25 mm to 26 mm (or about 25 mm to about 25 mm) provides satisfactory performance. It should be appreciated that although the configurations of FIGS. 5A and 5B may be preferred in certain embodiments, other configurations, including those of FIGS. 11A-11D and other variations, may be utilized in other embodiments as may be desired.

Reference is again made to FIGS. 5C through 5F which demonstrate example positioning of heating element 215 with similar bubble shapes to improve thermal properties. The location of the heating element 215 can change the thermal properties within the composite tube 201.

FIG. 5C shows a longitudinal cross-section of a top portion of another composite tube. FIG. 5C shows an embodiment of a composite tube 201 where the heating elements 215 are centrally located in the second elongate member 205. This example shows the heating elements 215 close to one another and not close to the bubble wall.

Figure 5D:
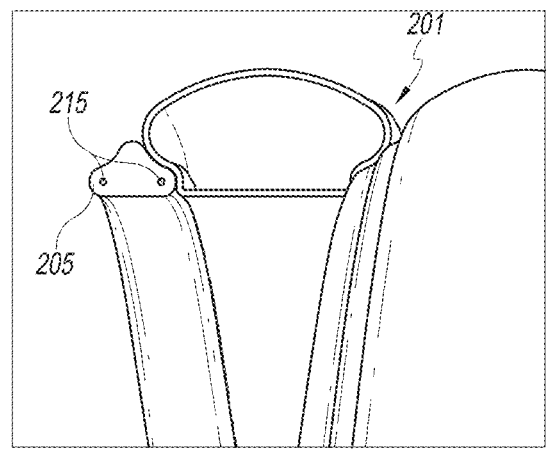
FIGS. 5D-5F show examples of filament arrangements configured to improve thermal efficiency.

FIG. 5D shows a longitudinal cross-section of a top portion of another composite tube. FIG. 5D shows an embodiment of a composite tube 201 in which the heating elements 215 are spaced farther apart, as compared to FIG. 5C, in the second elongate member 205. These heating elements are closer to the bubble wall and provide for better regulation of heat within the composite tube 201.

Figure 5E:
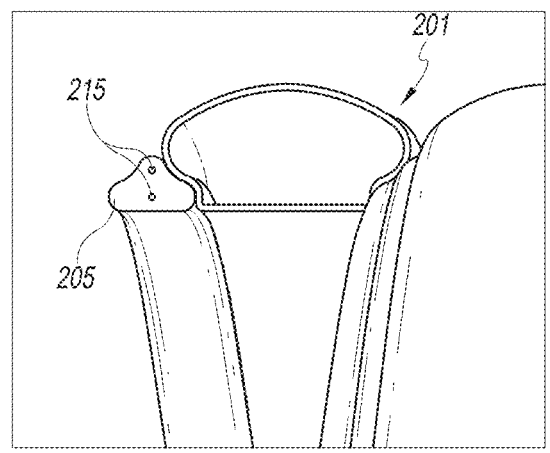

FIG. 5E shows a longitudinal cross-section of a top portion of another composite tube. FIG. 5E shows an embodiment of a composite tube 201 wherein the heating elements 215 are spaced on top of each other in the vertical axis of the second elongate member 205. In this example, the heating elements 215 are equally close to each bubble wall.

Figure 5F:
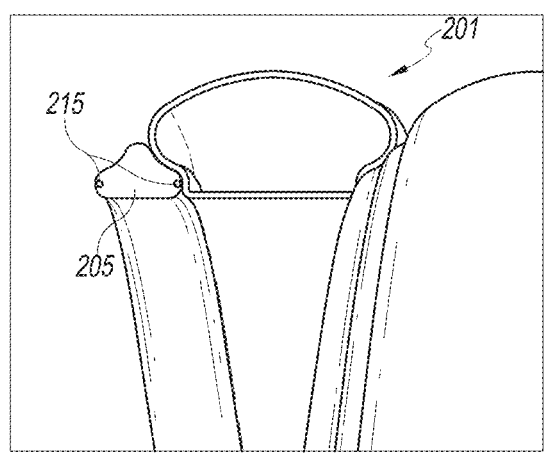

FIG. 5F shows a longitudinal cross-section of a top portion of another composite tube. FIG. 5F shows an embodiment of a composite tube 201 where the heating elements 215 are spaced at opposite ends of the second elongate member 205. The heating elements 215 are close to the bubble wall, especially as compared to FIGS. 5C-5E.

Of the four filament arrangements of FIGS. 5C-5F, FIG. 5F was determined to have the best thermal properties. Because of their similar bubble shapes, all of the configurations experienced similar heat loss from the tube. However, when the same thermal energy was input to the tubes, the filament configuration of FIG. 5F allowed for the largest temperature rise along the length of the tube, for the bulk gas temperature within the tube. The configuration of FIG. 5D was determined to have the next best thermal properties and allowed for the next largest temperature rise along the length of tube. The configuration of FIG. 5C performed next best. The configuration of FIG. 5E had the poorest performance and allowed for the smallest temperature rise along the length of the tube, when the same amount of heat was input.

It should be appreciated that although the FIG. 5F configuration may be preferred in certain embodiments, other configurations, including those of FIGS. 5C, 5D, 5E, and other variations, may be utilized in other embodiments as may be desired.

Figure 12A:
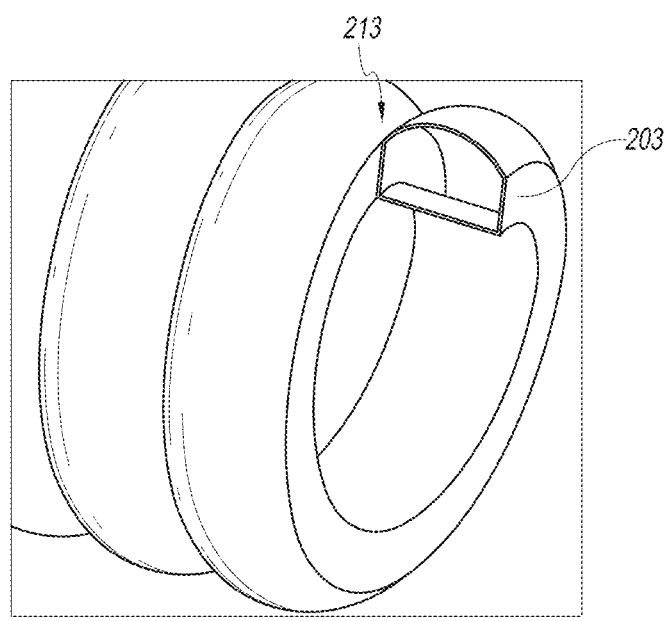
FIGS. 12A-12C show examples of first elongate member stacking.
Figure 12B:
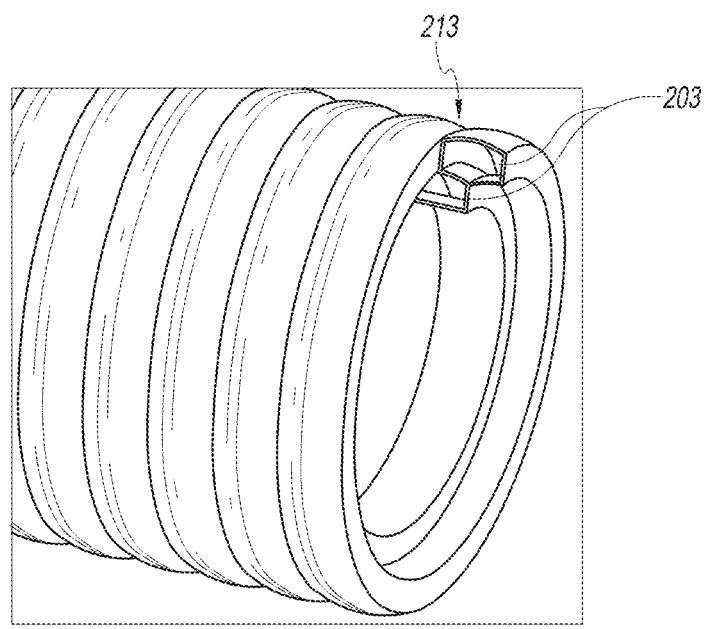
Figure 12C:
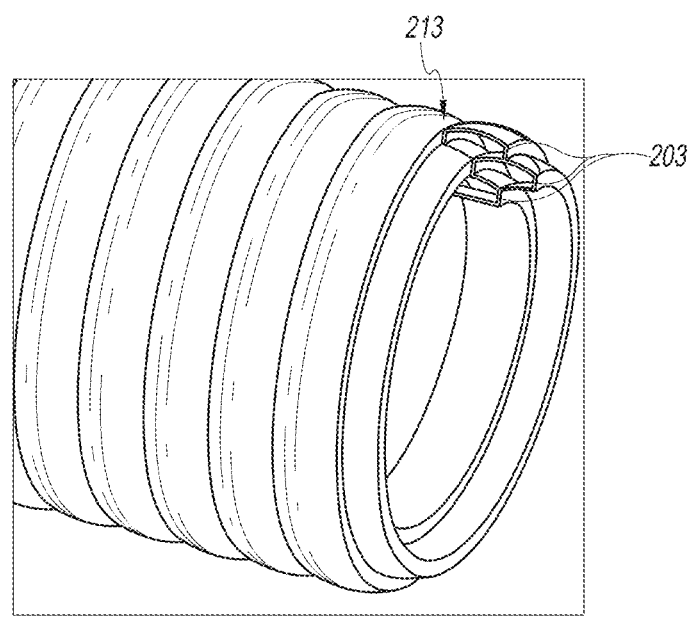

Reference is next made to FIGS. 12A through 12C, which demonstrate example configurations for stacking of the first elongate member 203. It was discovered that heat distribution can be improved in certain embodiments by stacking multiple bubbles. These embodiments can be more beneficial when using an internal heating filament 215. FIG. 12A shows a longitudinal cross-section of a top portion of another composite tube. FIG. 12A shows a cross section of a composite tube 201 without any stacking.

FIG. 12B shows a longitudinal cross-section of a top portion of another composite tube. FIG. 12B shows another example composite tube 201 with stacked bubbles. In this example, two bubbles are stacked on top of each other to form the first elongate member 203. As compared to FIG. 12A, the total bubble height is maintained, but the bubble pitch is half of FIG. 12A. Also, the embodiment in FIG. 12B has only a slight reduction in air volume. The stacking of the bubbles reduces natural convection and heat transfer in the gap between bubbles 213 and lowers the overall thermal resistance. The heat flow path increases in the stacked bubbles allowing heat to more easily distribute through the composite tube 201.

FIG. 12C shows a longitudinal cross-section of a top portion of another composite tube. FIG. 12C shows another example of a composite tube 201 with stacked bubbles. In this example, three bubbles are stacked on top of each other to form the first elongate member 203. As compared to FIG. 12A, the total bubble height is maintained, but the bubble pitch is a third of FIG. 12A. Also, the embodiment in FIG. 12B has only a slight reduction in air volume. The stacking of the bubbles reduces natural convection and heat transfer in the gap between bubbles 213.

Figure 13:
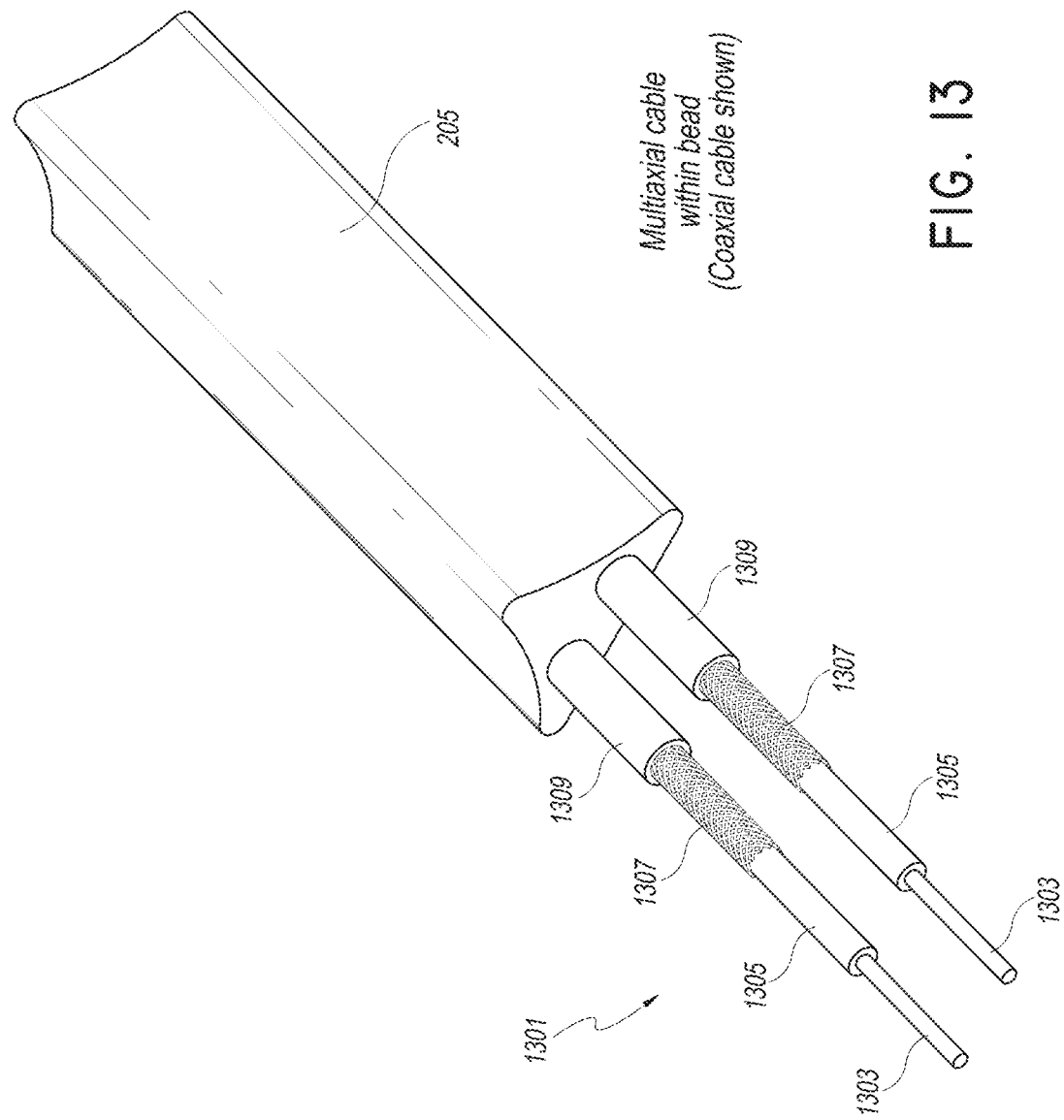
FIG. 13 shows an alternative embodiment of the second elongate member.

Referring now to FIG. 13, additional possible properties of the second elongate member 205 are shown. The second elongate member 205 comprises one or more coaxial cables 1301 having a conductor 1303 surrounded by an insulation layer 1305, a shield layer 1307, and a sheath layer 1309. In certain embodiments, one or more of cables 1301 can be a multi-axial cable, that is, have multiple conductors 1303 arranged within the insulation layer 1305. In this manner, a single assembly containing multiple wires (including heater wires and/or sensor wires) can be used in the second elongate member 205, thereby simplifying assembly and providing some shielding (via the shield layer 1307) from RF interference and the like.

In some embodiments, one or more data transmission cables can be included in the second elongate member 205. The data transmission cables can comprise fiber optic cables. In at least one embodiment, a single fiber optic cable is included in the second elongate member 205 and used in a passive mode. In a passive mode, at a first end of the cable, a light source and a light sensor are provided. At a second end, a reflector is provided. In use, the light source provides a quantity of light having certain properties towards the reflector. The reflector then reflects the light towards the light sensor, which can analyze the reflected light to determine the properties of the light. The reflector can be adapted to change the property of the reflected light depending on a property of the system. For example, the reflector can be used to monitor condensation within the interface. The reflector can comprise a material which, for example, changes color depending on the presence of condensation at the second end. The reflector can alternatively or additionally include a material which changes color or the like depending on the level of humidity (either relative humidity or absolute humidity), and/or the temperature of gas at the second end, and/or gas composition such as inhaled $O_2$ or exhaled $CO_2$.

Referring again to FIG. 2B, in some embodiments, a fluid (gas or liquid) flow can be passed along the space inside the first elongate member 203. In such embodiments, it is desirable that at least a portion of the first elongate member 203 is formed of a breathable material. Breathable is used herein to mean appreciably permeable to water vapor and substantially impermeable to liquid water and the bulk flow of gases. Suitable breathable materials include an activated perfluorinated polymer material with extreme hydrophilic properties, such as NAFION®, or a hydrophilic polyester block copolymer, such as SYMPATEX®. Other suitable materials include polymers commercially embodied in EVAQUA™ and EVAQUA 2™ conduits (Fisher & Paykel Healthcare Ltd., Auckland, New Zealand). Suitable materials are further described in PCT Publication WO 2011/077250, filed Dec. 22, 2010 and published Jun. 30, 2011, and U.S. Pat. No. 6,769,431, filed May 8, 2001 and issued Aug. 3, 2003.

The flow through the first elongate member 203 can be useful for drying or humidifying the gas flow through the tube 201 lumen 207, as desired. Conversely, the flow through the tube 201 lumen 207 can be useful for drying or humidifying the gas flow through the first elongate member 203, as desired. Exhaled respiratory gases can be carried through the first elongate member 203. As another example, a liquid such as liquid water can be carried. As yet another example, a humidified or saturated gas stream can be carried. As yet another example, a dry gas stream or a stream of compressed ambient air can be carried. In the foregoing embodiments, the first elongate member 203 can be open on both ends, to facilitate the flow of fluid through the first elongate member 203. One end of the first elongate member 203 can be connected to a suitable source, such as a source of exhaled respiratory gas, liquid water, humidified gas, dry gas, or compressed air, as desired. The other end can be connected to a suitable outlet or allowed to vent to the atmosphere.

For example, with reference to FIG. 2B, the portion 211 of the first elongate member 203 that forms the lumen 207 of the tube 201 can be formed of the breathable material, as described above. The outward-facing portion 219 (facing the ambient atmosphere and facing away from the lumen) of the first elongate member 203 can be formed of an impermeable material, that is, a material that is not appreciably permeable to water vapor, liquid water, or the bulk flow of gases, as described elsewhere in this disclosure. In use, a quantity of humidification fluid (such as water) can be passed through the space formed by the first elongate member 203. As the humidification fluid is heated (for example, by the heating filaments 215 disposed in the second elongate member 205), a portion of the humidification fluid will tend to evaporate. The water vapor can then pass through the breathable portion 211 into the bulk gas flow through the lumen 207, thereby humidifying the bulk gas flow. In such an embodiment, the combination of the humidification fluid, first elongate member 203, and heating filaments 215 can provide a means for humidifying the gas flow within the lumen 207 such that a standalone humidifier can be omitted from the system.

As another example, a gas flow can be passed along the space inside the first elongate member 203. For example, exhaled respiratory gases can be carried. Referring again to FIG. 2B, the first elongate member 203 or at least the outward-facing portion 219 of the first elongate member 203 is made of a breathable material, as described above. In this manner, as the exhaled gas travels along the length of the first elongate member 203, it will tend to dry from about 100% relative humidity at the patient-end to reduced humidity level at the opposite end.

Co-extrusion is a suitable method for forming a first elongate member 203 comprising a portion (211 or 219, depending on the desired application) formed of a breathable material and a portion (219 or 211, depending on the desired application) formed of an impermeable material.

In addition, although certain foregoing embodiments have been described with reference to a single first elongate member 203 comprising breathable and impermeable portions, it should be appreciated that desired results (such as humidification of the gas flow within the lumen 207) also can be achieved using a plurality of first elongate members 203. Suitable embodiments are shown in FIGS. 12B, 12C, 37A and 37B.

Figure 37A:
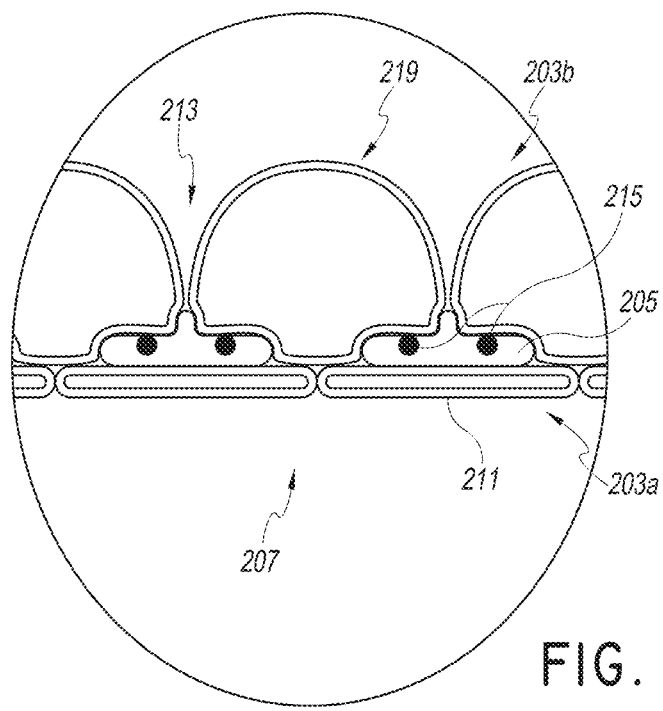
FIG. 37A shows a longitudinal cross-section of a top portion of a tube comprising two first elongate members.

FIG. 37A shows a cross section of tube comprising two first elongate members. A first first-elongate-member 203a is disposed proximal the tube lumen 207. A second first-elongate-member 203b faces the ambient atmosphere and faces away from the lumen 207. The inner portion of the first first-elongate-member 203a forms the lumen 207 wall. The first first-elongate-member 203a can define a conduit for a humidification fluid, such as liquid water. The first first-elongate-member 203a can be formed from a breathable material. As the humidification fluid is heated (for example, by the heating filaments 215 disposed in the second elongate member 205), a portion of the humidification fluid will tend to evaporate. The vapor can then pass through the walls of the first first-elongate-member 203a into the bulk gas flow through the lumen 207, thereby humidifying the bulk gas flow. In such an embodiment, the combination of the humidification fluid, first first-elongate-member 203a, and heating filaments 215 can provide a means for humidifying the gas flow within the lumen 207 such that a standalone humidifier can be omitted from the system. It should be appreciated that the dimensions shown in FIG. 37A are not necessarily to scale. For example, the first first-elongate-member 203a can be relatively larger, and the second first-elongate-member 203b can be relatively smaller as shown in FIG. 12B. It should also be appreciated that the heating filaments 215 need not necessarily be housed in the second elongate member 205. For example, as shown in FIG. 12B, the second elongate member can be omitted. The heating filaments 215 can be housed, for instance, in a portion of the second first-elongate-member 203b proximal the first first-elongate-member 203a.

Figure 37B:
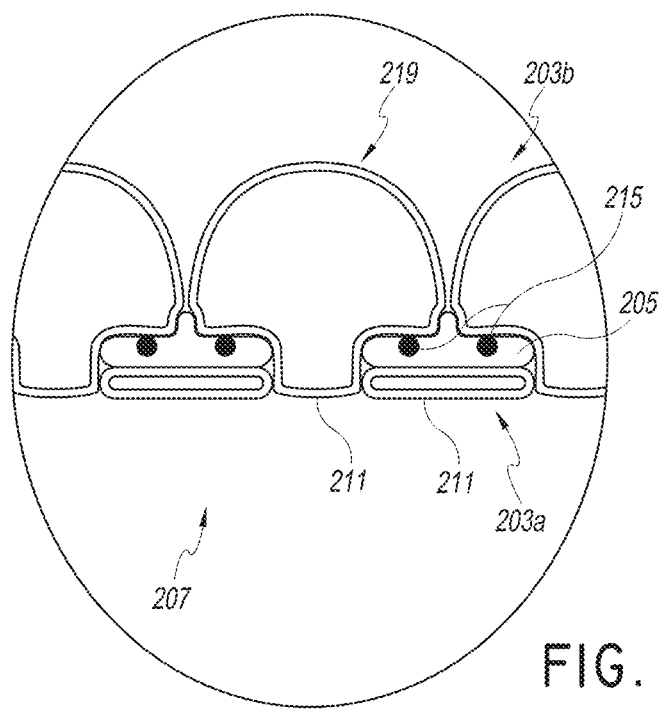
FIG. 37B shows another longitudinal cross-section of a top portion of a tube comprising two first elongate members.

FIG. 37B also shows a cross section of tube comprising two first elongate members. A first first-elongate-member 203a is disposed proximal the tube lumen 207. A second first-elongate-member 203b faces the ambient atmosphere and faces away from the lumen 207. The inner portion of the first first-elongate-member 203a forms part of the lumen 207 wall. An inner portion of the second first-elongate-member 203b also forms part of the lumen 207 wall. As discussed above with reference to FIG. 37A, the first first-elongate-member 203a can define a conduit for a humidification fluid, such as liquid water, and the combination of the humidification fluid, first first-elongate-member 203, and heating filaments 215 can provide a means for humidifying the gas flow within the lumen 207 such that a standalone humidifier can be omitted from the system. Again, it should be appreciated that the dimensions shown in FIG. 37B are not necessarily to scale. For example, the first first-elongate-member 203a can be relatively larger, and the second first-elongate-member 203b can be relatively smaller as shown in FIG. 12B. It should also be appreciated that the heating filament need not necessarily be housed in the second elongate member. For example, as shown in FIG. 12B, the second elongate member can be omitted. The heating filament can be housed, for instance, in a portion of the second first-elongate-member 203b proximal the first first-elongate-member 203a. [0235] Referring now to FIGS. 14A-14E and 15A-15E, some variations of the composite tube 201 configuration are shown which are adapted to provide increased lateral stretch in the composite tube 201. FIGS. 15A-15E show a stretched state of the composite tubes shown in FIGS. 14A-14E, respectively.

Certain embodiments include the realization that the tubes shown in FIGS. 14A, 14B, and 14E comprise a second elongate member 205 having a shape that increases stretch capability. For example, in FIG. 14A, the second elongate member 205 is substantially oblate having a profile substantially the same height as the first elongate member 203. As shown in FIG. 15A, this allows the second elongate member 205 to deform outwards to at least twice the width compared to the second elongate member 205 at rest. In FIGS. 14B and 14E, the second elongate member 205 is shaped so as to have an accordion-like shape. On stretching, the second elongate member 205 can therefore accommodate an increase amount of stretching by flattening (as shown in FIGS. 15B and 15E, respectively).

In FIGS. 14C and 14D, the first elongate member 203 is given a shape that allows it to deform outward, thereby allowing an increased lateral stretch (as shown in FIGS. 15C and 15D, respectively).

Medical Circuits

Figure 16:
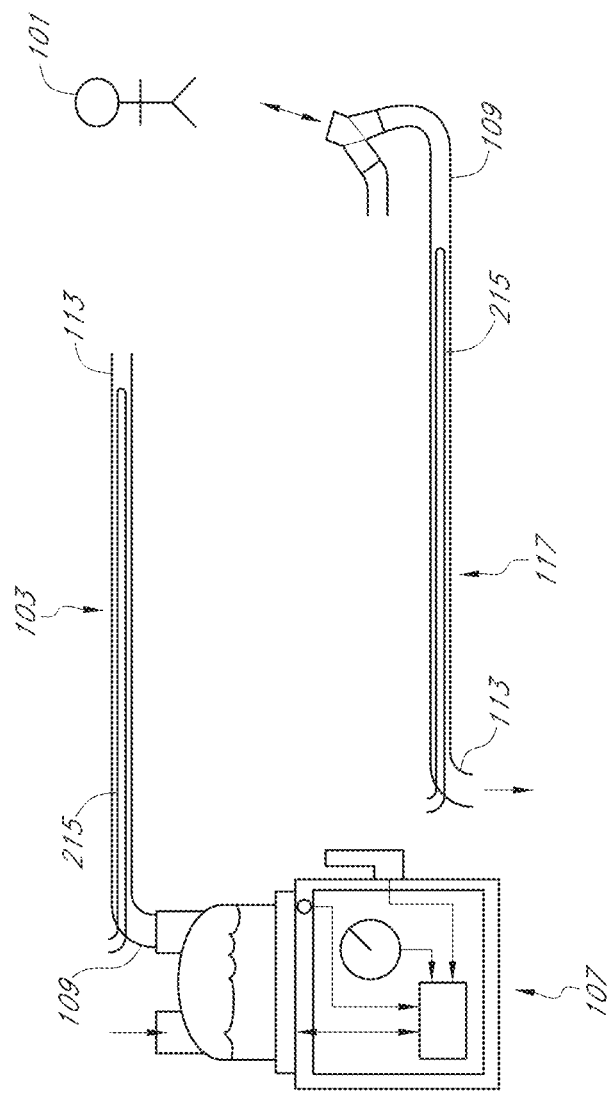
FIG. 16 shows an example medical circuit according to at least one embodiment.

Reference is next made to FIG. 16, which shows an example medical circuit according to at least one embodiment. The circuit comprises one or more composite tubes as described above, namely for the inspiratory tube 103 and/or the expiratory tube 117. The properties of the inspiratory tube 103 and the expiratory tube 117 are similar to the tubes described above with respect to FIG. 1. The inspiratory tube 103 has an inlet 109, communicating with a humidifier 107, and an outlet 113, through which humidified gases are provided to the patient 101. The expiratory tube 117 also has an inlet 109, which receives exhaled humidified gases from the patient, and an outlet 113. As described above with respect to FIG. 1, the outlet 113 of the expiratory tube 117 can vent exhaled gases to the atmosphere, to the ventilator/blower unit 105, to an air scrubber/filter (not shown), or to any other suitable location.

As described above, heating filaments 215 can be placed within the inspiratory tube 103 and/or the expiratory tube 117 to reduce the risk of rain out in the tubes by maintaining the tube wall temperature above the dew point temperature.

Component of an Insufflation System

Laparoscopic surgery, also called minimally invasive surgery (MIS), or keyhole surgery, is a modern surgical technique in which operations in the abdomen are performed through small incisions (usually 0.5 to 1.5 cm) as compared to larger incisions needed in traditional surgical procedures. Laparoscopic surgery includes operations within the abdominal or pelvic cavities. During laparoscopic surgery with insufflation, it may be desirable for the insufflation gas (commonly $CO_2$) to be humidified before being passed into the abdominal cavity. This can help prevent "drying out" of the patient's internal organs, and can decrease the amount of time needed for recovery from surgery. Insufflation systems generally comprise humidifier chambers that hold a quantity of water within them. The humidifier generally includes a heater plate that heats the water to create a water vapour that is transmitted into the incoming gases to humidify the gases. The gases are transported out of the humidifier with the water vapor.

Figure 17:
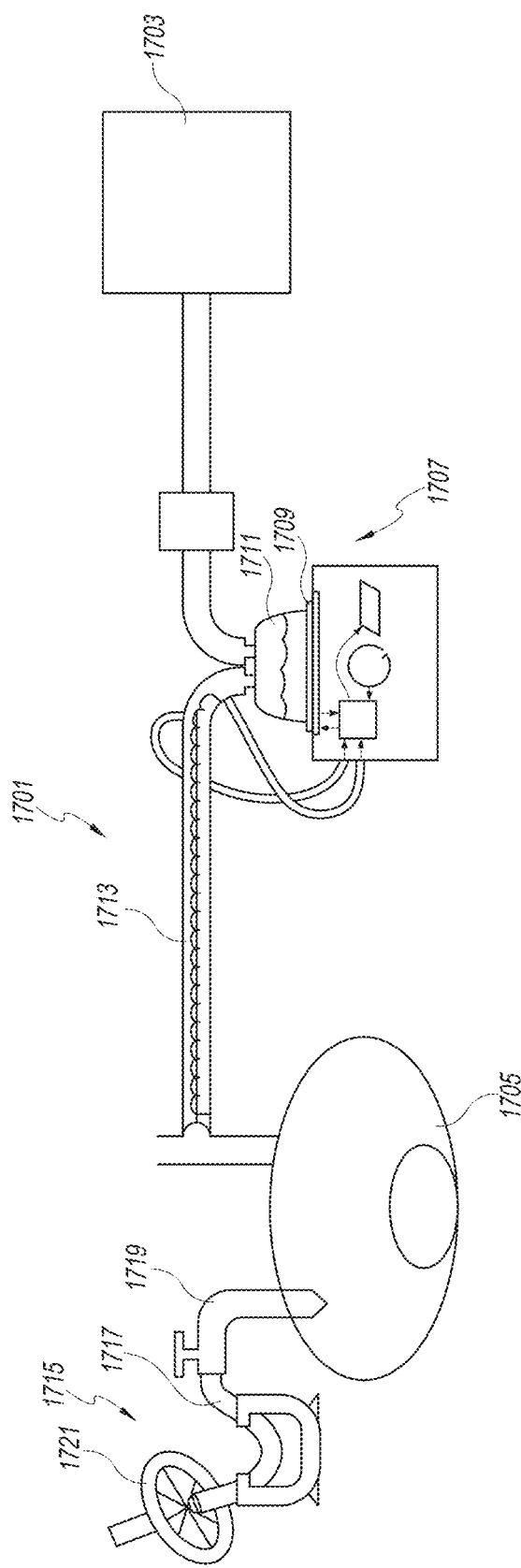
FIG. 17 shows an insufflation system according to at least one embodiment.

Reference is next made to FIG. 17, which shows an insufflation system 1701, according to at least one embodiment. The insufflation system 1701 includes an insufflator 1703 that produces a stream of insufflation gases at a pressure above atmospheric for delivery into the patient 1705 abdominal or peritoneal cavity. The gases pass into a humidifier 1707, including a heater base 1709 and humidifier chamber 1711, with the chamber 1711 in use in contact with the heater base 1709 so that the heater base 1709 provides heat to the chamber 1711. In the humidifier 1707, the insufflation gases are passed through the chamber 1711 so that they become humidified to an appropriate level of moisture.

The system 1701 includes a delivery conduit 1713 that connects between the humidifier chamber 1711 and the patient 1705 peritoneal cavity or surgical site. The conduit 1713 has a first end and second end, the first end being connected to the outlet of the humidifier chamber 1711 and receiving humidified gases from the chamber 1711. The second end of the conduit 1713 is placed in the patient 1705 surgical site or peritoneal cavity and humidified insufflation gases travel from the chamber 1711, through the conduit 1713 and into the surgical site to insufflate and expand the surgical site or peritoneal cavity. The system also includes a controller (not shown) that regulates the amount of humidity supplied to the gases by controlling the power supplied to the heater base 1709. The controller can also be used to monitor water in the humidifier chamber 1711. A smoke evacuation system 1715 is shown leading out of the body cavity of the patient 1705.

The smoke evacuation system 1715 can be used in conjunction with the insufflation system 1701 described above or may be used with other suitable insufflation systems. The smoke evacuation system 1715 comprises a discharge or exhaust limb 1717, a discharge assembly 1719, and a filter 1721. The discharge limb 1717 connects between the filter 1721 and the discharge assembly 1719, which in use is located in or adjacent to the patient 1705 surgical site or peritoneal cavity. The discharge limb 1717 is a self-supporting tube (that is, the tube is capable of supporting its own weight without collapsing) with two open ends: an operative site end and an outlet end.

At least one embodiment includes the realization that the use of a composite tube as the conduit 1713 can deliver humidified gases to the patient 1705 surgical site with minimized heat loss from the humidified gases.

Coaxial Tube

A coaxial breathing tube can also comprise a composite tube as described above. In a coaxial breathing tube, a first gas space is an inspiratory limb or an expiratory limb, and the second gas space is the other of the inspiratory limb or expiratory limb. One gas passageway is provided between the inlet of said inspiratory limb and the outlet of said inspiratory limb, and one gas passageway is provided between the inlet of said expiratory limb and the outlet of said expiratory limb. In one embodiment, the first gas space is said inspiratory limb, and the second gas space is said expiratory limb. Alternatively, the first gas space can be the expiratory limb, and the second gas space can be the inspiratory limb.

Figure 18:
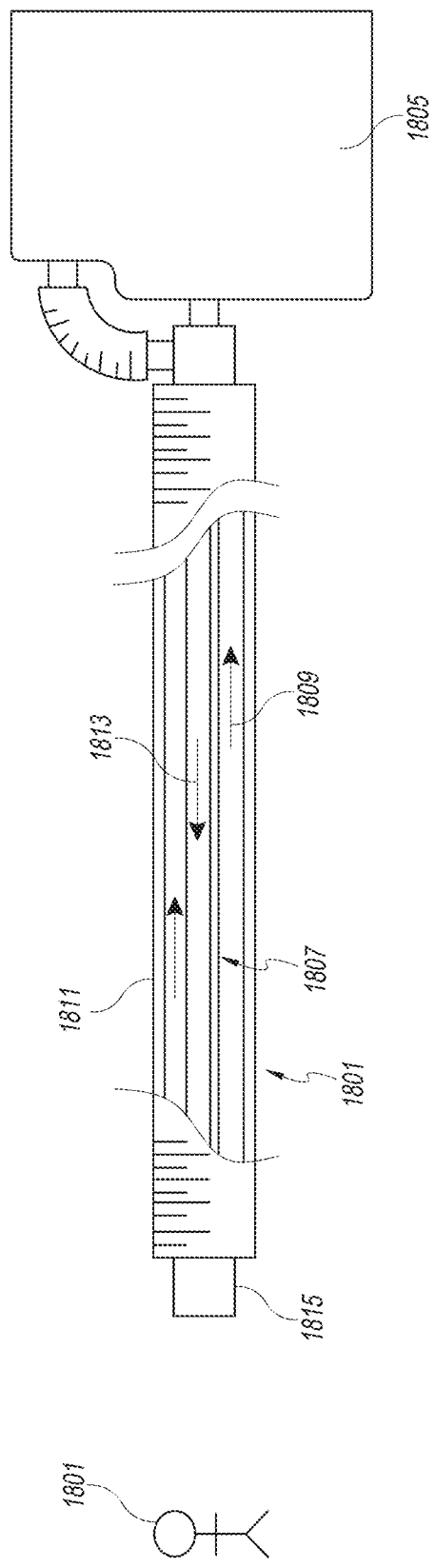
FIG. 18 is a schematic illustration of a coaxial tube, according to at least one embodiment.

Reference is next made to FIG. 18, which shows a coaxial tube 1801 according to at least one embodiment. In this example, the coaxial tube 1801 is provided between a patient 1801 and a ventilator 1805. Expiratory gases and inspiratory gases each flow in one of the inner tube 1807 or the space 1809 between the inner tube 1807 and the outer tube 1811. It will be appreciated that the outer tube 1811 may not be exactly aligned with the inner tube 1807. Rather, "coaxial" refers to a tube situated inside another tube.

For heat transfer reasons, the inner tube 1807 can carry the inspiratory gases in the space 1813 therewithin, while the expiratory gases are carried in the space 1809 between the inner tube 1807 and the outer tube 1811. This airflow configuration is indicated by arrows. However, a reverse configuration is also possible, in which the outer tube 1811 carries inspiratory gases and the inner tube 1807 carries expiratory gases.

In at least one embodiment, the inner tube 1807 is formed from a corrugated tube, such as a Fisher & Paykel model RT100 disposable tube. The outer tube 1811 can be formed from a composite tube, as described above.

With a coaxial tube 1801, the ventilator 1805 may not become aware of a leak in the inner tube 1807. Such a leak may short circuit the patient 1801, meaning that the patient 1801 will not be supplied with sufficient oxygen. Such a short circuit may be detected by placement of a sensor at the patient end of the coaxial tube 1801. This sensor may be located in the patient end connector 1815. A short circuit closer to the ventilator 1805 will lead to continued patient 1801 re-breathing of the air volume close to the patient 1801. This will lead to a rise in the concentration of carbon dioxide in the inspiratory flow space 1813 close to the patient 1801, which can be detected directly by a $CO_2$ sensor. Such a sensor may comprise any one of a number of such sensors as is currently commercially available. Alternatively, this re-breathing may be detected by monitoring the temperature of the gases at the patient end connector 1815, wherein a rise in temperature above a predetermined level indicates that re-breathing is occurring.

In addition to the above to reduce or eliminate the formation of condensation within either the inner tube 1807 or outer tube 1811, and to maintain a substantially uniform temperature in the gases flow through the coaxial tube 1801, a heater, such as a resistance heater filament, may be provided within either the inner tube 1807 or outer tube 1811, disposed within the gases spaces 1809 or 1813, or within the inner tube 1807 or outer tube 1811 walls themselves.

Nasal Cannulas and Other Patient Interfaces

Figure 19A:
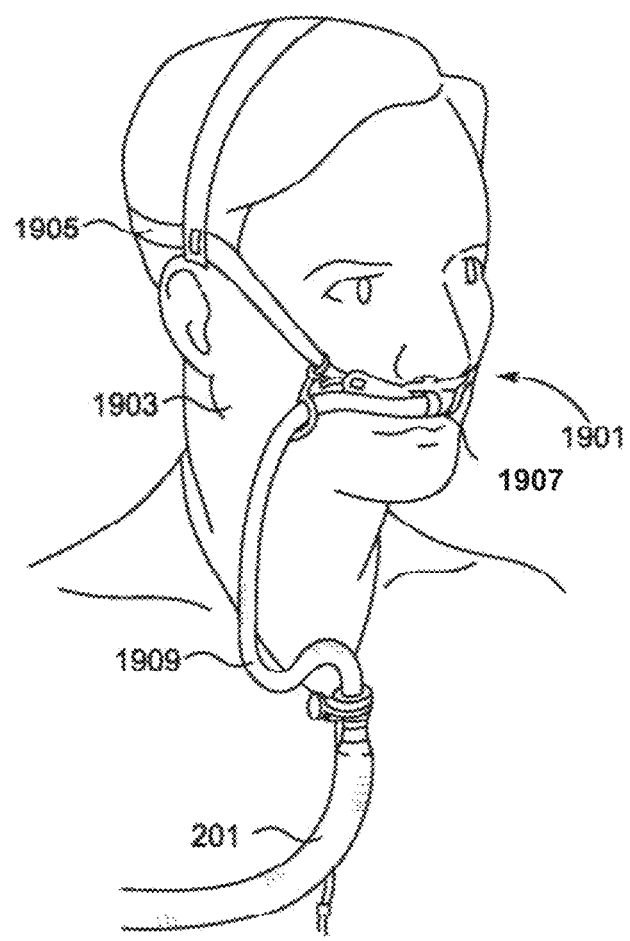
FIGS. 19A-19B show a composite tube in use with a patient interface.

Reference is next made to FIG. 19A, which shows composite tube 201 in use with a nasal cannula patient interface 1901. In this example, the patient interface 1901 is positioned on the face of the patient 1903 with headgear 1905 secured around the back of the head of the patient 1901. The patient interface includes a cannula body 1907 and a delivery tube 1909. A composite tube 201, as described, communicates with the delivery tube 1909 to supply inspiratory gases to the patient interface 1901.

In the past, the delivery tube 1909 has been used to decouple the weight of heated respiratory tubing from the patient interface 1901. Previously-used delivery tubes 1909 consisted of a length of flexible tubing. It was important that the delivery tube 1909 be lightweight so that the mass of the delivery tube 1909 did not drag the patient interface 1901 off a patient's face. Heated tubes were substantially bulkier and heavier than unheated tubes. Thus, previously-used delivery tubes 1909 were unheated. In order to achieve satisfactory flexibility, previously-used delivery tubes 1909 also had poor insulation properties. Without good insulating and heating, rainout in the delivery tubes 1909 was a problem. Thus, delivery tubes 1909 were kept as short as possible to minimize rainout. The short length did not consistently prevent the weight of heated respiratory tubing from dragging the patient interface 1901, however. Thus, previously-used delivery tubes have a number of drawbacks.

The composite tubes 201 described herein provide good insulation while maintaining good flexibility and light weight. Thus, in some embodiments, the delivery tube 1909 can be a composite tube 201. Composite tubes 201 can provide improved insulation properties over delivery tubes previously known in the art. In addition, the length of the delivery tube can be longer and provide better decoupling of tube drag. The composite-tube 201 delivery tube 201 can optionally have heating filaments (not shown) in the second elongate member (not shown). The heating filaments, if present, can provide heat input. Alternatively, the heating filaments can provide structural support for the second elongate member without being energized.

The length of the unheated composite-tube 201 delivery tube 1909 can be greater than the length of a normal unheated extension while still maintaining the same or less amount of heat loss because of the better insulation properties of the composite tube 201. An increased length of delivery tube 1909 is beneficial to keep the patient's movement from dragging on the tube connections. An increased extension length will also allow for better head movement without compromising patient comfort.

Figure 19B:
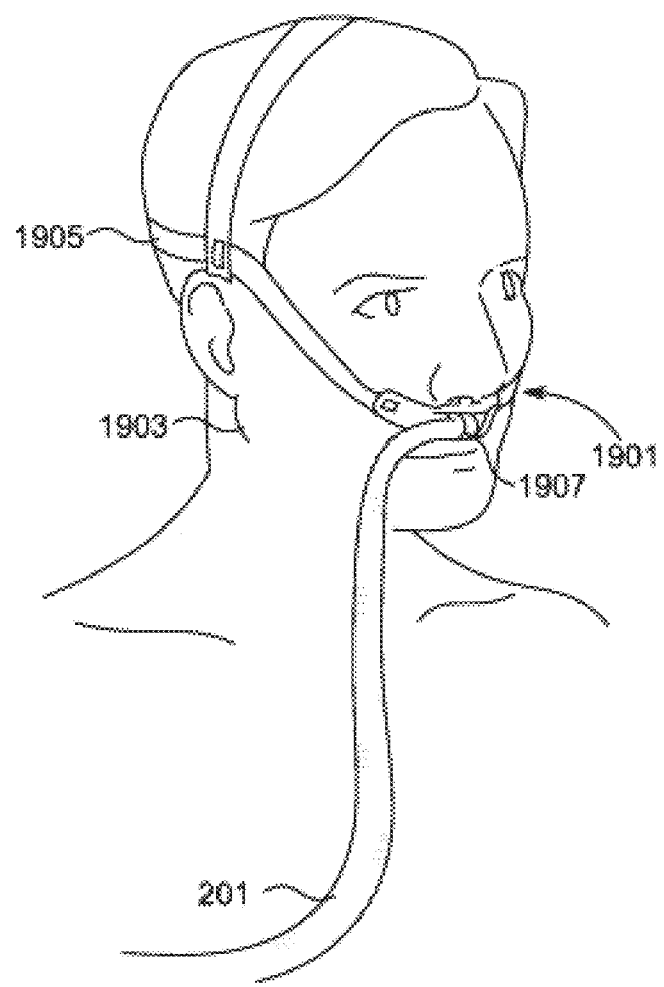

In addition, certain embodiments include the realization that eliminating a separate delivery tube 1909 can have a number of benefits, discussed below. Thus, as shown in FIG. 19B, the delivery tube 1909 and composite tube 201 can desirably be a unitary component, which extends to the cannula body 1907.

In a typical patient interface 1901, a heated tube (in place of composite tube 201 of FIG. 19A) supplies inspiratory gases to an unheated delivery tube 1909. The temperature of the inspiratory gases can experience significant thermal losses (for example, 20° C. or more or thereabout) along the length of the unheated delivery tube 1909. To compensate, the temperature at the patient end of the heated tube is held higher than the required temperature actually delivered to the patient 1901. In addition, condensation can rain out as the temperature drops in the delivery tube 1909. It was realized that extending a heated composite tube 201 to the cannula body 1907 in place of the delivery tube 1909, as shown in FIG. 19B, can reduce input energy requirements, as the patient end of the composite tube 201 can be held at a lower temperature. This configuration can also reduce rainout by eliminating the unheated delivery tube 1909 from the patient interface.

Desirably, the composite tube 201 can be tapered. In at least one embodiment, the patient-end portion of the composite tube 201 is tapered to fit the inlet of the cannula body 1907. In at least one embodiment, the diameter of a length of the composite tube 201 near the patient end is smaller than the diameter of the remainder of the composite tube 201. For example, the length of the composite tube 201 near the patient end can be in the range of 50 to 300 mm (or about 50 to 300 mm). A smaller diameter tube near the patient end can advantageously reduce tube weight near the cannula body.

The composite tube 201 can comprise a temperature sensor (not shown) near at least the patient end of the composite tube 201. In addition to, or instead of, a temperature sensor, the composite tube 201 can comprise another kind of sensor (not shown) near at least the patient end of the composite tube 201. For example, the composite tube 201 can comprise a pressure sensor (not shown) near at least the patient end of the composite tube 201. Pressure sensors can be particularly advantageous for CPAP control and nasal high-flow therapy. When the composite tube 201 and delivery tube 1909 are a unitary component, the sensor(s) are close to the patient's 1903 nostrils, which can provide more accurate information relating to the delivered gas. Example patient-end sensor configurations are described in greater detail below.

A unitary configuration is also desirable because it can reduce wiring on a patient 1901. If the cannula body 1907 is equipped with one or more sensors or other electrical components, it is necessary to provide an electrical connection to the cannula body 1907. If the composite tube 201 and the delivery tube are a unitary component, electrical lines can run along the composite tube 201, as described above, to the patient end of the composite tube 201 at the cannula body 1907. No separate electrical connection to the cannula body 1907 is required.

The unitary configuration can incorporate a variable-pitch composite tube 201, as described above. In a tube that has no or little unheated extension, the heating would continue to the cannula body 1907 where the sensing element would be located. These tubes require reduced end-of-tube temperatures to ensure the delivery of saturated gases at 37 C. This is because, ordinarily, the end of tube temperature is set to much higher than 37° C. to account for heat loss in the unheated extension. However, a configuration without an unheated extension is more likely to suffer condensation near the unit end. Redistributing the heating to a region proximal to the unit end of the tube will help to boost $T_{gas}>T_{dew}$, and hence reduce the occurrence of condensation, without delivering excessively high end of tube temperature.

It should be appreciated that, although the configurations in FIG. 19B may be preferred in certain embodiments, other configurations, including the configuration of FIG. 19A, may be utilized in other embodiments as may be desired.

The composite tubes 201 of this disclosure can also be incorporated in and/or used with other patient interfaces, such as a full face mask 2001 (FIG. 20A), a nasal mask 2003 (FIG. 20B), and a nasal/pillow mask 2005 (FIG. 20C). As discussed above, the composite tube 201 can serve as a delivery tube 1909 or eliminate the need for a delivery tube entirely.

Cleaning

Returning again to FIG. 2A, in at least one embodiment, materials for a composite tube can be selected to handle various methods of cleaning. In some embodiments, high level disinfection (around 20 cleaning cycles) can be used to clean the composite tube 201. During high level disinfection, the composite tube 201 is subject to pasteurization at about 75° C. for about 30 minutes. Next, the composite tube 201 is bathed in 2% glutaraldehyde for about 20 minutes. The composite tube 201 is removed from the glutaraldehyde and submerged in 6% hydrogen peroxide for about 30 minutes. Finally, the composite tube 201 is removed from the hydrogen peroxide and bathed in 0.55% orthophthalaldehyde (OPA) for about 10 minutes.

In other embodiments, sterilization (around 20 cycles) can be used to clean the composite tube 201. First, the composite tube 201 is placed within autoclave steam at about 121° C. for about 30 minutes. Next, the temperature of the autoclave steam is increased to about 134° C. for about 3 minutes. After autoclaving, the composite tube 201 is surrounded by 100% ethylene oxide (ETO) gas. Finally, the composite tube 201 is removed from the ETO gas and submerged in about 2.5% glutaraldehyde for about 10 hours.

The composite tube 201 may be made of materials to withstand the repeated cleaning process. In some embodiments, part or all of the composite tube 201 can be made of, but is not limited to, styrene-ethylene-butene-styrene block thermo plastic elastomers, for example Kraiburg TF6STE. In other embodiments, the composite tube 201 can be made of, but is not limited to, hytrel, urethanes, or silicones.

Methods Of Manufacture

Reference is next made to FIGS. 21A through 21F which demonstrate example methods for manufacturing composite tubes.

Figure 21A:
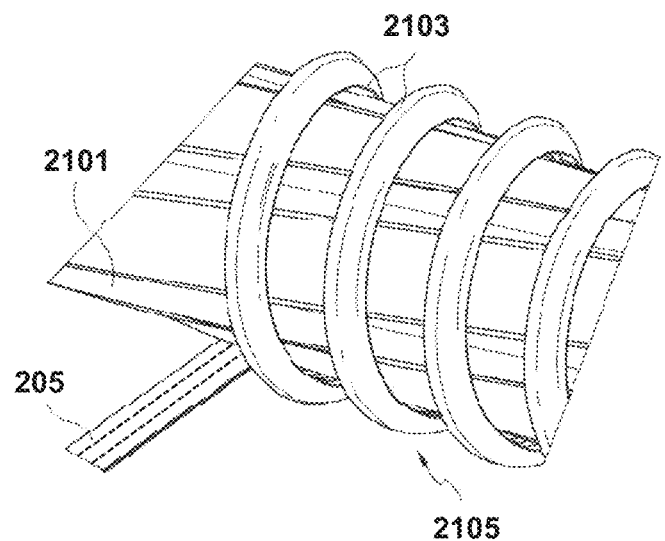
FIG. 21A shows an aspect in a method for forming the composite tube.

Turning first to FIG. 21A, in at least one embodiment, a method of manufacturing a composite tube comprises providing the second elongate member 205 and spirally wrapping the second elongate member 205 around a mandrel 2101 with opposite side edge portions 2103 of the second elongate member 205 being spaced apart on adjacent wraps, thereby forming a second-elongate-member spiral 2105. The second elongate member 205 may be directly wrapped around the mandrel in certain embodiments. In other embodiments, a sacrificial layer may be provided over the mandrel.

In at least one embodiment, the method further comprises forming the second elongate member 205. Extrusion is a suitable method for forming the second elongate member 205. The second extruder can be configured to extrude the second elongate member 205 with a specified bead height. Thus, in at least one embodiment, the method comprises extruding the second elongate member 205.

Figure 21B:
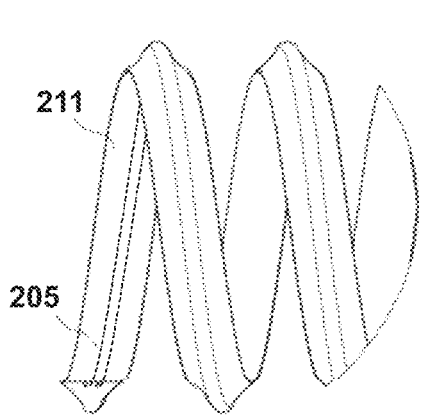
FIG. 21B shows a spiral-wound second elongate member.

As shown in FIG. 21B, extrusion can be advantageous because it can allow heating filaments 215 to be encapsulated in the second elongate member 205 as the second elongate member is formed 205, for example, using an extruder having a cross-head extrusion die. Thus, in certain embodiments, the method comprises providing one or more heating filaments 215 and encapsulated the heating filaments 215 to form the second elongate member 205. The method can also comprise providing a second elongate member 205 having one or more heating filaments 215 embedded or encapsulated in the second elongate member 205.

Figure 21C:
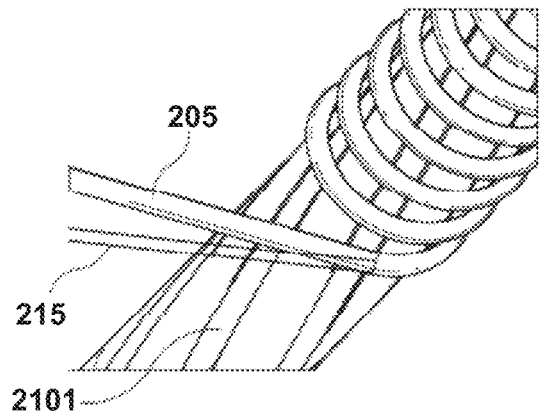
FIG. 21C shows another aspect in a method for forming the composite tube.

In at least one embodiment, the method comprises embedding one or more filaments 215 in the second elongate member 205. For example, as shown in FIG. 21C, filaments 215 can be pressed (pulled or mechanically positioned) into the second elongate member 205 to a specified depth. Alternatively, cuts can be made in the second elongate member 205 to a specified depth, and the filaments 215 can be placed into the cuts. Preferably, pressing or cutting is done shortly after the second elongate member 205 is extruded and the second elongate member 205 is soft.

Figure 21D:
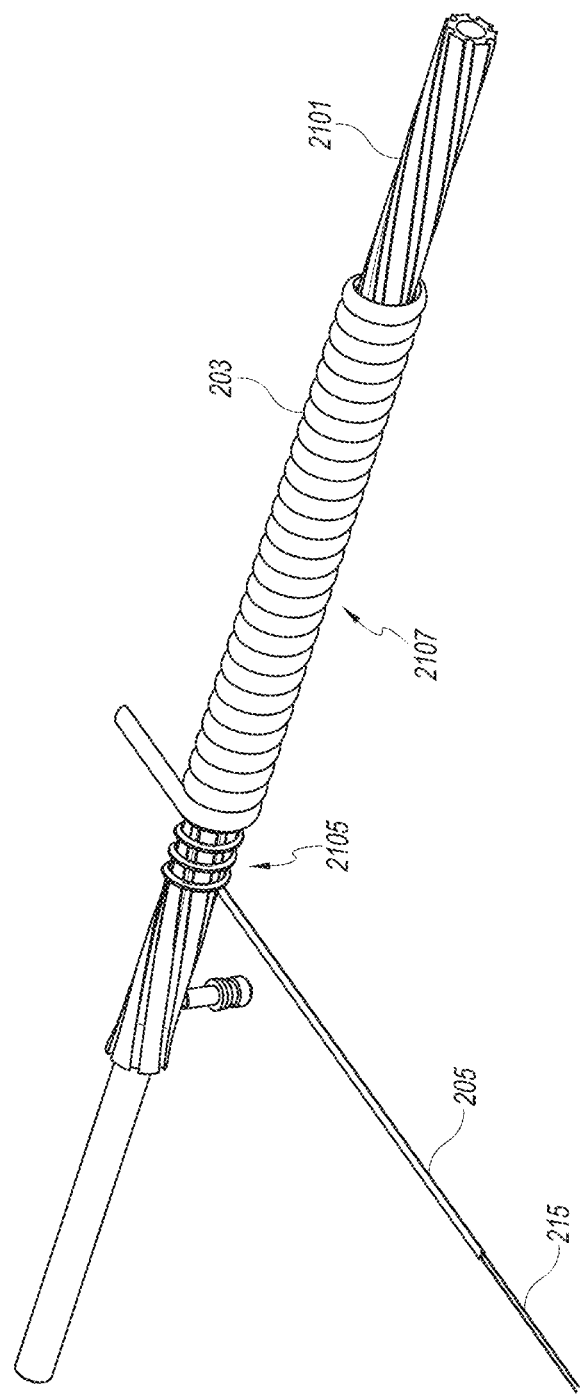
FIG. 21D shows another aspect in a method for forming the composite tube.
Figure 21E:
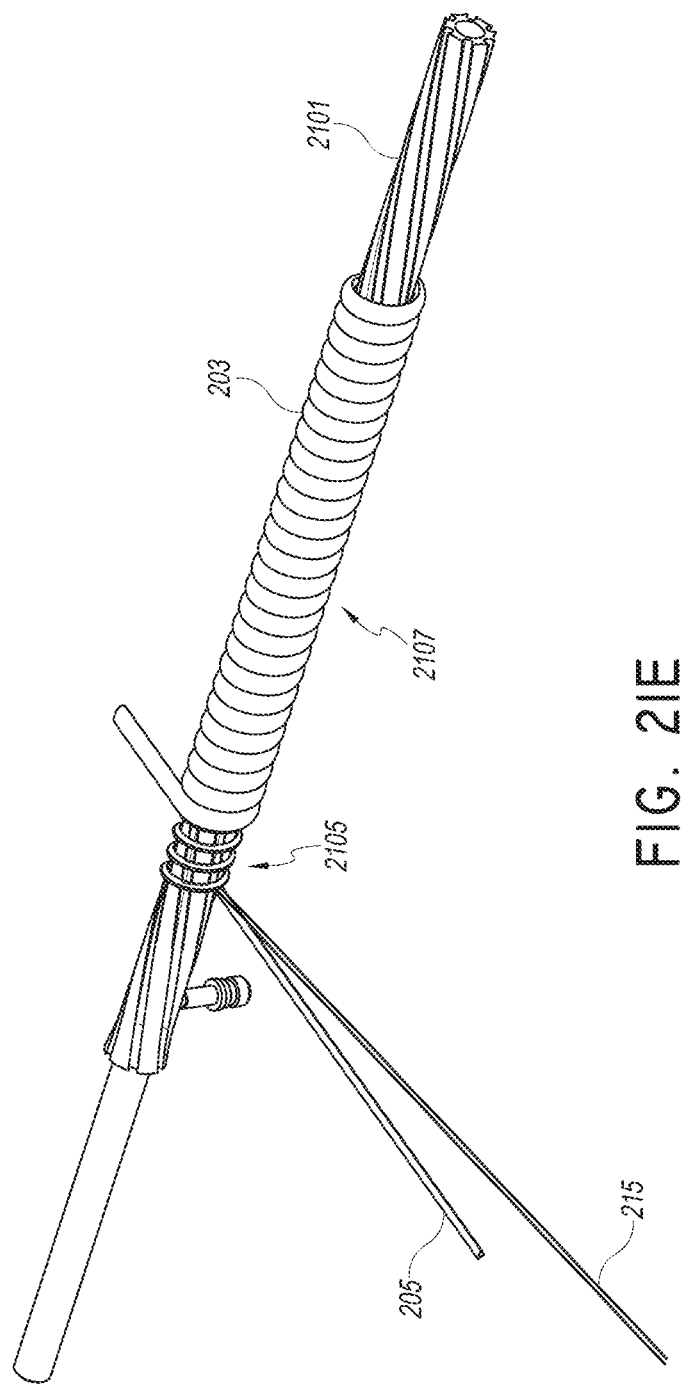
FIG. 21E shows another aspect in a method for forming the composite tube.

As shown in FIGS. 21D and 21E, in at least one embodiment, the method comprises providing the first elongate member 203 and spirally wrapping the first elongate member 203 around the second-elongate-member spiral 2105, such that portions of the first elongate member 203 overlap adjacent wraps of the second-elongate-member spiral 205 and a portion of the first elongate member 203 is disposed adjacent the mandrel 2101 in the space between the wraps of the second-elongate-member spiral 2105, thereby forming a first-elongate-member spiral 2107. FIG. 21D shows such an example method, in which heating filaments 215 are encapsulated in the second elongate member 205, prior to forming the second-elongate-member spiral. FIG. 21E shows such an example method, in which heating filaments 215 are embedded in the second elongate member 205, as the second-elongate-member spiral 2105 is formed. An alternative method of incorporating filaments 215 into the composite tube comprises encapsulating one or more filaments 215 between the first elongate member 203 and the second elongate member 205 at a region where the first elongate member 203 overlaps the second elongate member 205.

As discussed above, at least one embodiment comprises a tube having multiple wraps of the first elongate member 203 between wraps of the second elongate member 205. Accordingly, in certain embodiments, the method comprises providing the first elongate member 203 and spirally wrapping the first elongate member 203 around the second-elongate-member spiral 2105, such that a first side portion of the first elongate member 203 overlaps a wrap of the second-elongate-member spiral 2105 and a second side portion of the first elongate member 203 contacts an adjacent side portion of the first elongate member 203. A portion of the first elongate member 203 is disposed adjacent the mandrel 2101 in the space between the wraps of the second-elongate-member spiral 2105, thereby forming a first-elongate-member spiral 2107 comprising multiple wraps of the first elongate member 203 between wraps of the second elongate member 205.

Figure 22A:
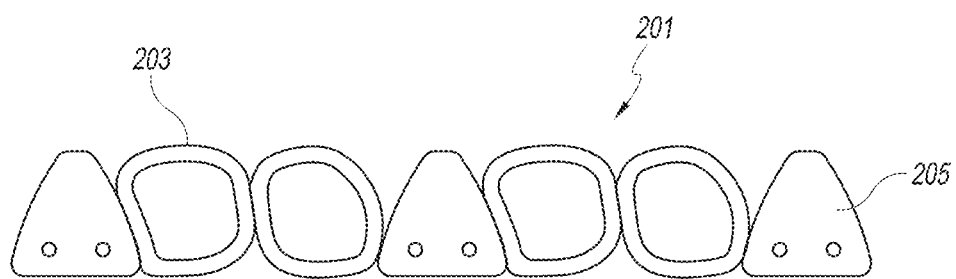
FIGS. 22A-22C show example configurations of longitudinal cross sections of tubes.

In at least one embodiment, the first elongate member 203 is wrapped multiple times between winds of the second elongate member 205. An example schematic of the resulting longitudinal cross-section is shown in FIG. 22A. Adjacent wraps of the first elongate member 203 can be fused using any suitable technique, such as heat fusing, adhesive, or other attachment mechanism. In at least one embodiment, adjacent molten or softened bubbles can be touched together and thereby bonded while hot and subsequently cooled with an air jet. Adjacent wraps of the first elongate member 203 can also be joined by winding them on the mandrel in a softened state and allowing them to cool.

Figure 22B:
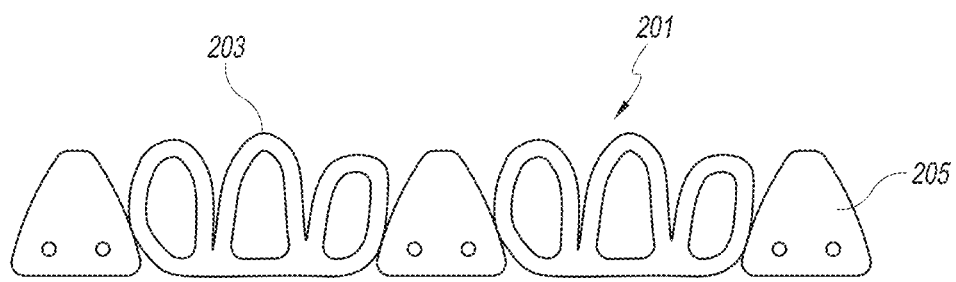
Figure 22C:
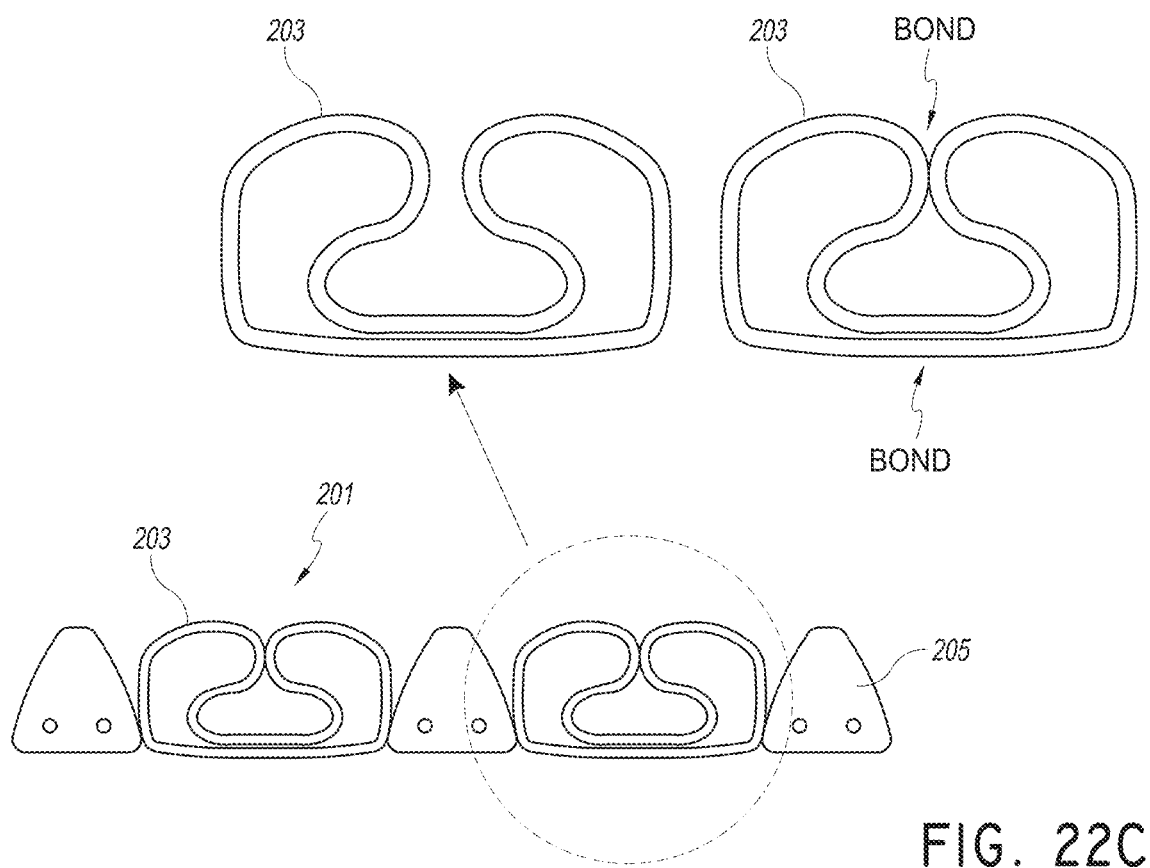

In at least one embodiment, the first elongate member 203 is wrapped a single time or multiple times between winds of the second elongate member 205, and the bubble or bubbles between winds of the second elongate member 205 are further collapsed into additional discrete bubbles using an appropriate technique such as a heat treatment. An example schematic of the resulting longitudinal cross-section is shown in FIG. 22B. As shown in FIG. 22B, one bubble of the first elongate member 203 can be collapsed into two or three or more discrete bubbles using any suitable technique, such as application of a mechanical force with an object or application of a force with a directed air jet. Another example schematic of a resulting longitudinal cross-section is shown in FIG. 22C. In this example, a center portion of a bubble is collapsed such that the top of the bubble is bonded to the bottom of the bubble to form two discrete bubbles separated by a flat bottom portion. Then, adjacent side portions of the two discrete bubbles are bonded to form a structure comprising three discrete bubbles.

The above-described alternatives for incorporating one or more heating filaments 215 into a composite tube have advantages over the alternative of having heating filaments in the gas path. Having the heating filament(s) 215 out of the gas path improves performance because the filaments heat the tube wall where the condensation is most likely to form. This configuration reduces fire risk in high oxygen environments by moving the heating filament out of the gas path. This feature also reduces performance as it reduces the heating wires effectiveness at heating the gases that are passing through the tube. Nevertheless, in certain embodiments, a composite tube 201 comprises one or more heating filaments 215 placed within the gas path. For example, heating filaments can be emplaced on the lumen wall (tube bore), for example, in a spiral configuration. An example method for disposing one or more heating filaments 215 on the lumen wall comprises bonding, embedding, or otherwise forming a heating filament on a surface of the second elongate member 205 that, when assembled, forms the lumen wall. Thus, in certain embodiments, the method comprises disposing one or more heating filaments 215 on the lumen wall.

Regardless of whether the heating filaments 215 are embedded or encapsulated on the second elongate member 205 or disposed on the second elongate member 205, or otherwise placed in or on the tube, in at least one embodiment, pairs of filaments can be formed into a connecting loop at one end of the composite tube to form a circuit.

Figure 21F:
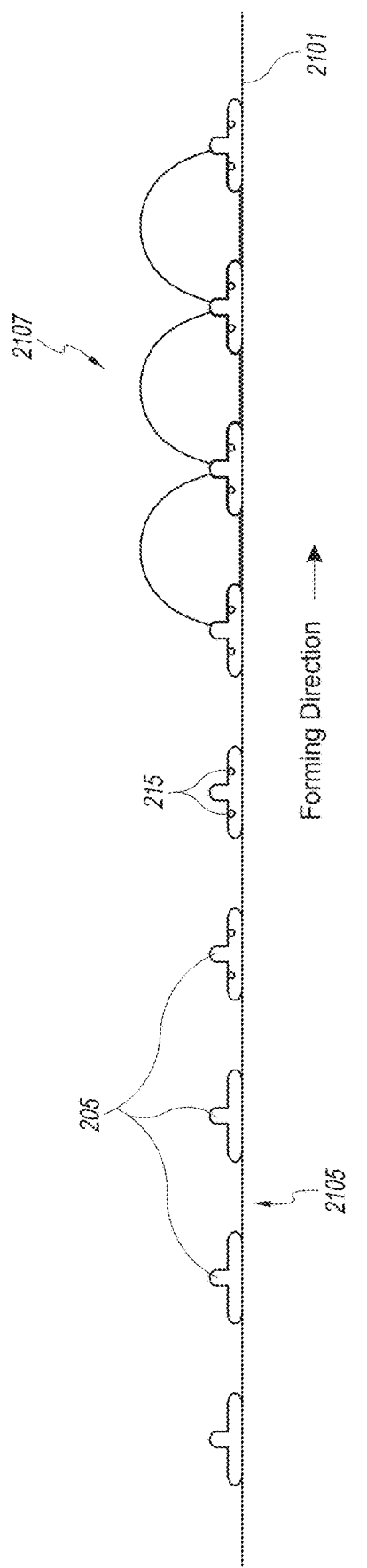
FIG. 21F shows another aspect in a method for forming the composite tube.

FIG. 21F shows a longitudinal cross-section of the assembly shown in FIG. 21E, focusing on a top portion of the mandrel 2101 and a top portion of the first-elongate-member spiral 2107 and second-elongate-member spiral 2105. This example shows the second-elongate-member spiral 2105 having a T-shaped second elongate member 205. As the second-elongate member is formed, heating filaments 215 are embedded in the second elongate member 205. The right side of FIG. 21F shows the bubble-shaped profile of the first-elongate-member spiral, as described above.

The method can also comprise forming the first elongate member 203. Extrusion is a suitable method for forming the first elongate member 203. Thus, in at least one embodiment, the method comprises extruding the first elongate member 203. The first elongate member 203 can also be manufactured by extruding two or more portions and joining them to form a single piece. As another alternative, the first elongate member 203 can also be manufactured by extruding sections that produce a hollow shape when formed or bonded adjacently on a spiral-tube forming process.

The method can also comprise supplying a gas at a pressure greater than atmospheric pressure to an end of the first elongate member 203. The gas can be air, for example. Other gases can also be used, as explained above. Supplying a gas to an end of the first elongate member 203 can help maintain an open, hollow body shape as the first elongate member 203 is wrapped around the mandrel 2101. The gas can be supplied before the first elongate member 203 is wrapped around the mandrel 2101, while the first elongate member 203 is wrapped around the mandrel 2101, or after the first elongate member 203 is wrapped around the mandrel 2101. For instance, an extruder with an extrusion die head/tip combination can supply or feed air into the hollow cavity of the first elongate member 203 as the first elongate member 203 is extruded. Thus, in at least one embodiment, the method comprises extruding the first elongate member 203 and supplying a gas at a pressure greater than atmospheric pressure to an end of the first elongate member 203 after extrusion. A pressure of 15 to 30 cm $H_2O$ (or about 15 to 30 cm $H_2O$) has been found to be suitable.

In at least one embodiment, the first elongate member 203 and the second elongate member 205 are spirally wound about the mandrel 2101. For example, the first elongate member 203 and second elongate member 205 may come out of an extrusion die at an elevated temperature of 200° C. (or about 200° C.) or more and then be applied to the mandrel after a short distance. Preferably, the mandrel is cooled using a water jacket, chiller, and/or other suitable cooling method to a temperature of 20° C. (or about 20° C.) or less, e.g., approaching 0° C. (or about 0° C.). After 5 (or about 5) spiral wraps, the first elongate member 203 and second elongate member 205 are further cooled by a cooling fluid (liquid or gas). In one embodiment, the cooling fluid is air emitted from a ring with jets encircling the mandrel. After cooling and removing the components from the mandrel, a composite tube is formed having a lumen extending along a longitudinal axis and a hollow space surrounding the lumen. In such an embodiment, no adhesive or other attachment mechanism is needed to connect the first and second elongate members. Other embodiments may utilize an adhesive or other attachment mechanism to bond or otherwise connect the two members. In another embodiment, the second elongate member 205 after extrusion and placement of the heating filaments may be cooled to freeze the location of the heating filaments. The second elongate member 205 may then be re-heated when applied to the mandrel to improve bonding. Example methods for re-heating include using spot-heating devices, heated rollers, etc.

The method can also comprise formed pairs of heating or sensing filaments into a connecting loop at one end of the composite tube. For example, end sections of two heating or sensing filaments can be extricated from the second elongate member 205 and then formed into a connecting loop e.g., by tying, bonding, soldering, adhering, fusing, etc. the two filaments together. As another example, end sections of the heating filaments can be left free from the second elongate member 205 during the manufacturing process and then formed into a connecting loop when the composite tube is assembled.

Figure 23A:
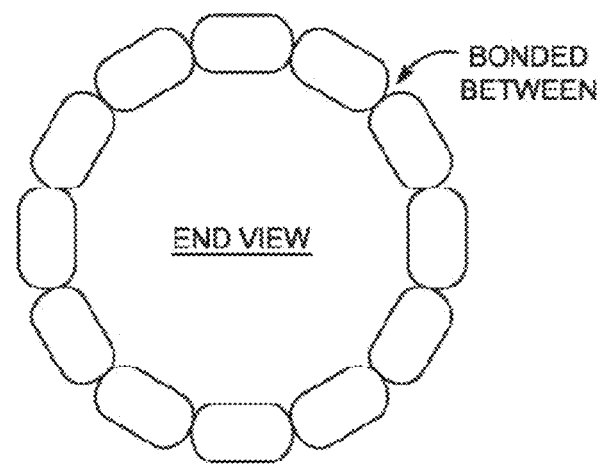
Figure 23B:
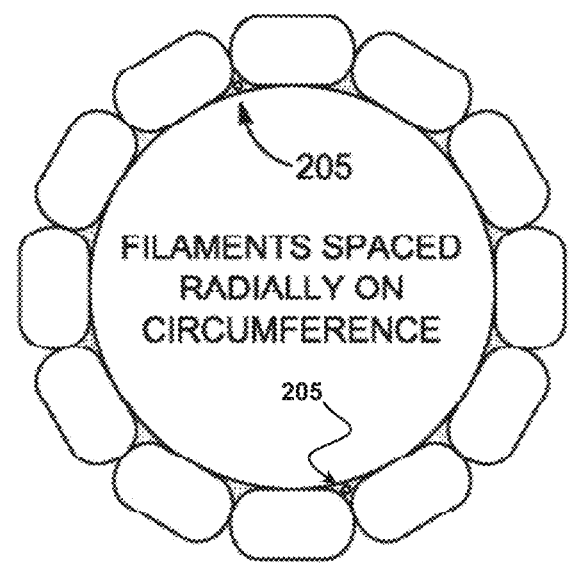
Figure 23F:
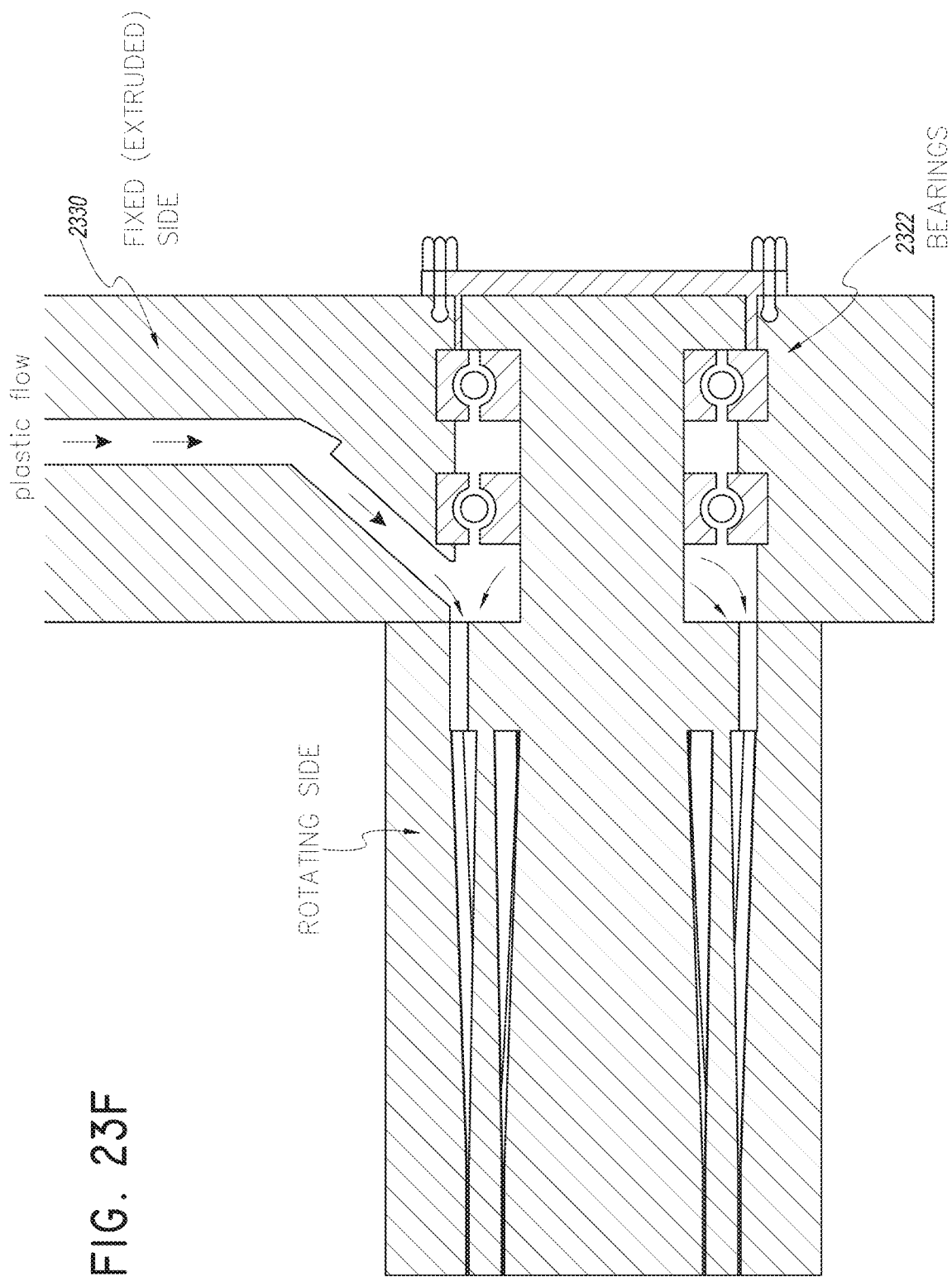
Figure 23G:
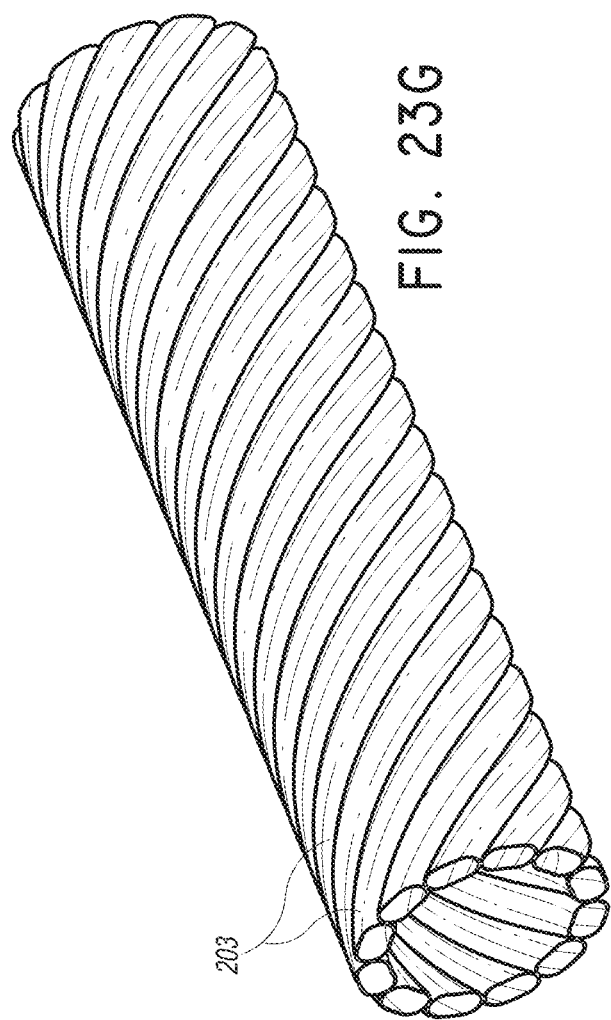
Figure 23H:
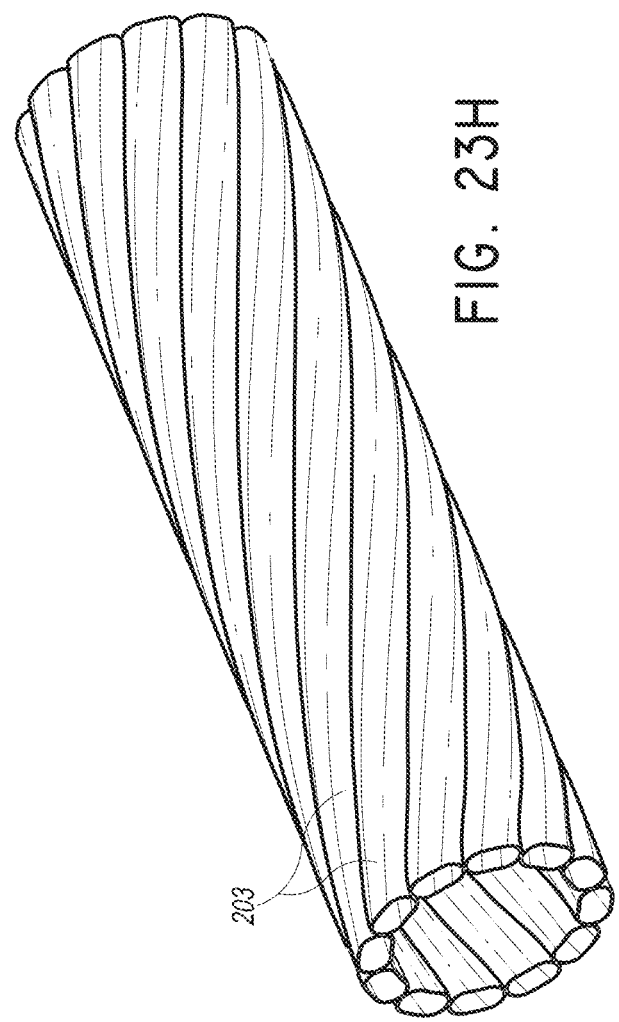

With reference now to FIGS. 23A-23H, an alternative method of forming a tube 201 involves an extrusion tool 2301 having a series of flow paths running therealong. The extrusion tool 2301 can be used to form tubes such as the example tubes shown in FIGS. 23G and 23H. As shown, tubes produced using the extrusion tool 2301 can include a plurality of first elongate members 203 extending generally along the longitudinal axis of the tube. In some embodiments, the extrusion tool 2301 includes a body 2310 and a central extension 2320. In some embodiments, the body 2310 and extension 2320 are generally cylindrical. The body 2310 can include one or more flow paths 2312 that allow for the passage of a molten plastic or another material through the body 2310 from an input end 2314 to an output or extrusion end 2316. In some embodiments, the flow paths have a substantially conical longitudinal cross-section (that is, are wider where the molten plastic first enters at the input 2314 and narrower near the extrusion end 2316). The flow paths can have various configurations to produce tubes 201 having various profiles. For example, the flow path configuration shown at the output or extrusion end 2316 in FIGS. 23C and 23D can produce a tube 201 having an end view profile as shown in FIG. 23A. FIG. 21B shows an end view of the tube of FIG. 23A including second elongate members 205, which may include heating filaments 215, disposed between adjacent bubbles or first elongate members 203. In use, the tool 2301 is adapted to rotate so as to induce the tube 201 to be helically formed. As shown in FIG. 23F, the central extension 2320 can couple the extrusion tool 2301 to an extruder 2330. Bearings 2322 disposed between the central extension 2320 and the extruder 2330 can allow the central extension 2320 and body 2310 to rotate relative to the extruder 2330. The rate of rotation of the tool 2301 can be adjusted to change the pitch or helix angle of the first elongate members 203. For example, a faster rate of rotation can produce a smaller helix angle, as shown in FIG. 23G. A slower rate of rotation can produce a larger helix angle, as shown in FIG. 23H.

As discussed above with reference to FIGS. 8A and 8B, certain embodiments can comprise a composite tube with a variable pitch. When manufacturing such embodiments, a mandrel 2101 and control system is preferably provided that can alter the effective pitch of the first elongate member 203 and second elongate member 205 (that is, the "ropes"). This can be achieved, for example, by controlling the ratio of rope speed to mandrel 2101 precession rate while maintaining a constant tangential speed at the critical dimension, that is, the pitch center diameter of the ropes. Pitch center diameter determines the pitch center going through the middle of the ropes. This value depends on speed. It is also predictable, so if the pitch center diameter is different from expected, speed can be adjusted to bring the pitch center diameter to the expected value. Altering the effective pitch can also be achieved, for example, by controlling the ratio of rope speed to mandrel 2101 precession while maintaining a constant rotational rate for the spiral composite tube 201 so formed. By controlling the rope speed, any changes in extrudate output are compensated for.

Yet another approach for manufacturing a variable-pitch composite tube 201 uses an integrated system in which extrusion rate and mandrel 2101 precession rate are altered in unison. For example, in this mode, the rope speed may stay the same, but the precession of the mandrel 2101 when enabled will require a slowdown in extrusion rate to match the extrudate output with the tangential speed of the spiral tube 201 so formed.

Still another approach for manufacturing a variable-pitch composite tube 201 moves the incident angle of the second elongate member 205 and first elongate member 203 to alter the pitch of the tube 201. In these embodiments, the extruders can be on a slide way, which will allow a change in angle, such as a rotary table where the center of rotation is where the second elongate member 205 and first elongate member 203 meet the mandrel 2101. This method can allow up to 3-5 mm (or about 3-5 mm) of variation in pitch.

Reference is next made to FIGS. 24A through 24F which show transverse cross-sections of tubes comprising a single tube-shaped element having a first elongate member or portion 203 and a second elongate member or portion 205. As illustrated, the second elongate portions 205 are integral with the first elongate portions 203, and extend along the entire length of the single tube-shaped element. In the embodiments illustrated, the single tube-shaped element is an elongate hollow body having in transverse cross-section a relatively thin wall defining in part the hollow portion 2201, with two reinforcement portions 205 with a relatively greater thickness or relatively greater rigidity on opposite sides of the elongate hollow body adjacent the relatively thin wall. These reinforcement portions form a portion of the inner wall of the lumen 207 after the elongate hollow body is spirally wound, such that these reinforcement portions are also spirally positioned between adjacent turns of the elongate hollow body.

In at least one embodiment, the method comprises forming an elongate hollow body comprising the first elongate portion 203 and the reinforcement portion 205. Extrusion is a suitable method for forming the elongate hollow body. Suitable cross-sectional shapes for the tube-shaped element are shown in FIGS. 24A through 24F.

The elongate hollow body can be formed into a medical tube, as explained above, and the foregoing discussion is incorporated by this reference. For example, in at least one embodiment, a method of manufacturing a medical tube comprises spirally wrapping or winding the elongate hollow body around a mandrel. This may be done at an elevated temperature, such that the elongate hollow body is cooled after being spirally wound to join adjacent turns together. As shown in FIG. 24B, opposite side edge portions of the reinforcement portions 205 can touch on adjacent turns. In other embodiments, opposite side edge portions of the second elongate member 205 can overlap on adjacent turns, as shown in FIGS. 24D and 24E. Heating filaments 215 can be incorporated into the second elongate member as explained above and as shown in FIGS. 24A through 24F. For example, heating filaments may be provided on opposite sides of the elongate hollow body such as shown in FIGS. 24A-24D. Alternatively, heating filaments may be provided on only one side of the elongate hollow body, such as shown in FIGS. 24E-24F. Any of these embodiments could also incorporate the presence of sensing filaments.

Placement of Chamber-End Connector with Electrical Connectivity

Figure 25A:
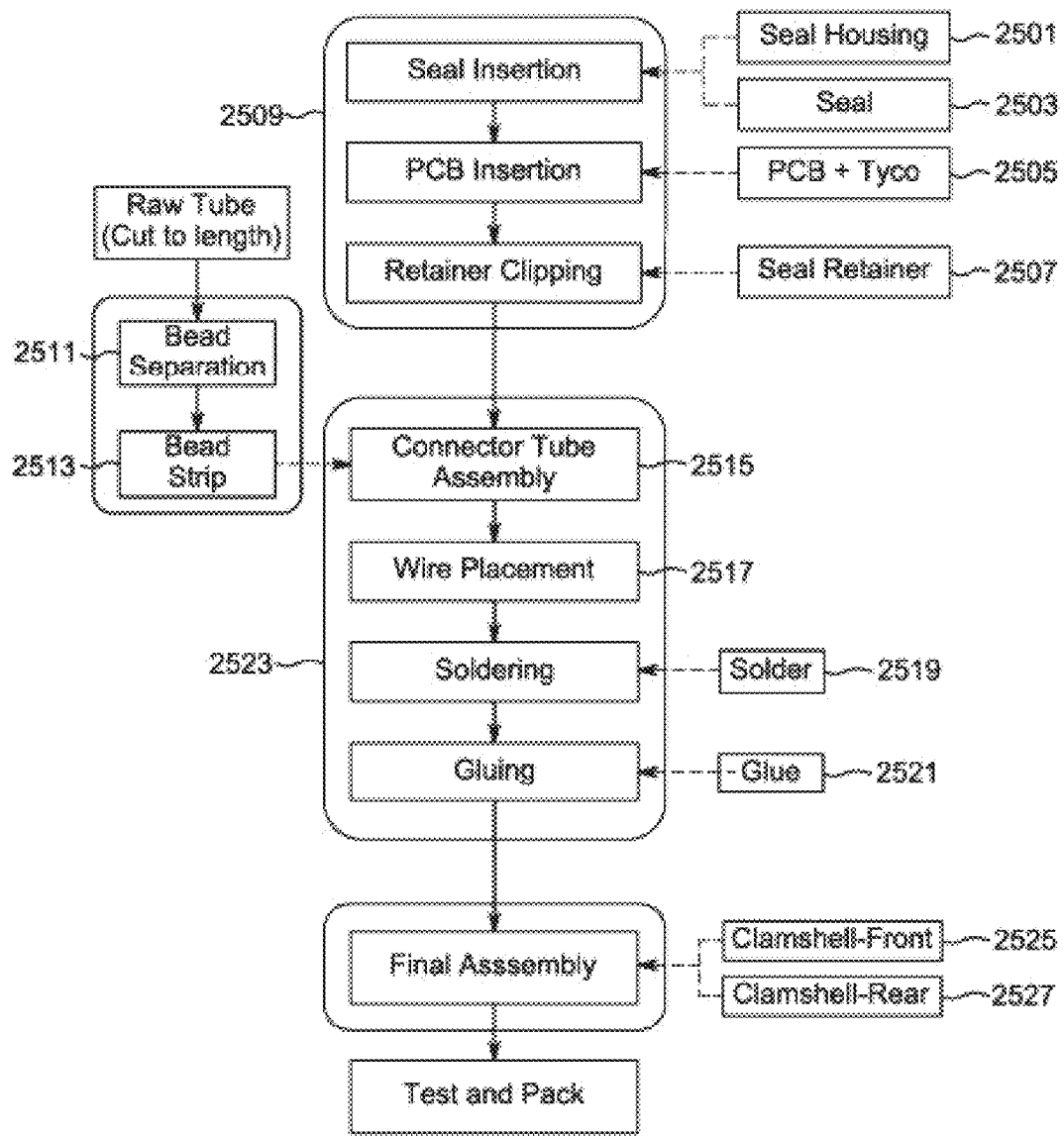

Reference is next made to FIG. 25A, which shows an example flow chart for attaching a connector to the end of the tube that is configured in use to connect to a humidifier. For example, as described above with reference to FIG. 1, inlet 109 of the inspiratory tube 103 connects to humidifier 107 via port 111. The example flow chart of FIG. 25A can make an inlet 109 capable of physically and electrically connecting to the humidifier 107.

Figure 25B:
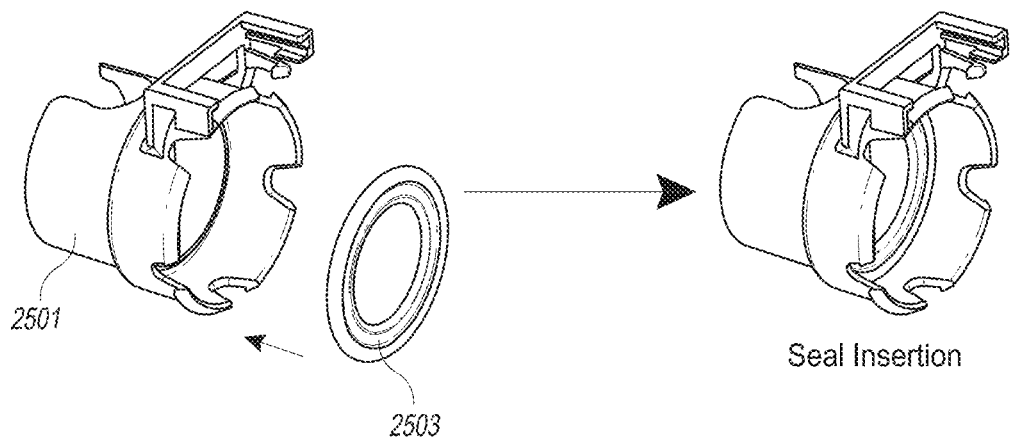

In this example, a seal 2503 is inserted into a seal housing 2501. The act of seal insertion is also shown in greater detail in FIG. 25B. The seal housing 2501 is made of a molded plastic. One open end is sized and configured for connecting to a humidifier. The seal 2503 can be an o-ring, as shown in FIG. 25B. A suitable configuration for the o-ring can be a double-toric configuration comprising thicker concentric toruses connected by a thinner web. In this example, the o-ring is molded from a single elastomeric material, such as rubber or silicone. The seal 2503 is seated in a compliant ridge in the seal housing 2501. The seal 2503 is designed to seal against an outer surface of the port of the humidifier chamber. The seal 2503 can deflect to extend along the outer surface of the port. In other words, the double o-ring configuration includes an inner O-ring and an outer O-ring connected by a flange. The outer O-ring will be sealed within the connector while the inner O-ring can deflect along the flange portion and squeeze against the outer surface of the port. In such a position, a horizontal plane extending through a center axis of the inner O-ring may be in a different plane than a horizontal plane extending through a center axis of the outer O-ring.

Figure 25C:
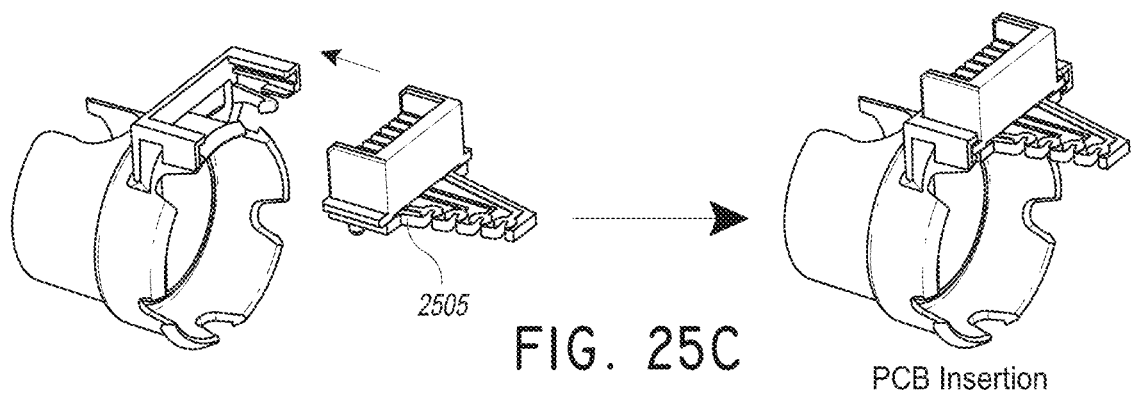

Turning again to the example of FIG. 25A, a printed circuit board (PCB) is inserted into a compliant dock on the seal housing 2501. The act of PCB insertion is shown in greater detail in FIG. 25C. In FIG. 25C, an assembly 2505 comprising a PCB and a PCB electrical connector is inserted into a compliant dock on the seal housing 2501. A variety of PCBs of suitable size and configuration can be used. A variety of PCB electrical connectors can also be used. For example, the PCB electrical connector can be a straight-through connector or a bi-directional connector. The PCB comprises four connection pads suitable for receiving four conductive filaments encased in the second elongate member of the tube. However, the PCB can be configured to receive a suitable number of conductive filaments, if the second elongate member contains more or fewer than four conductive filaments.

Figure 25D:
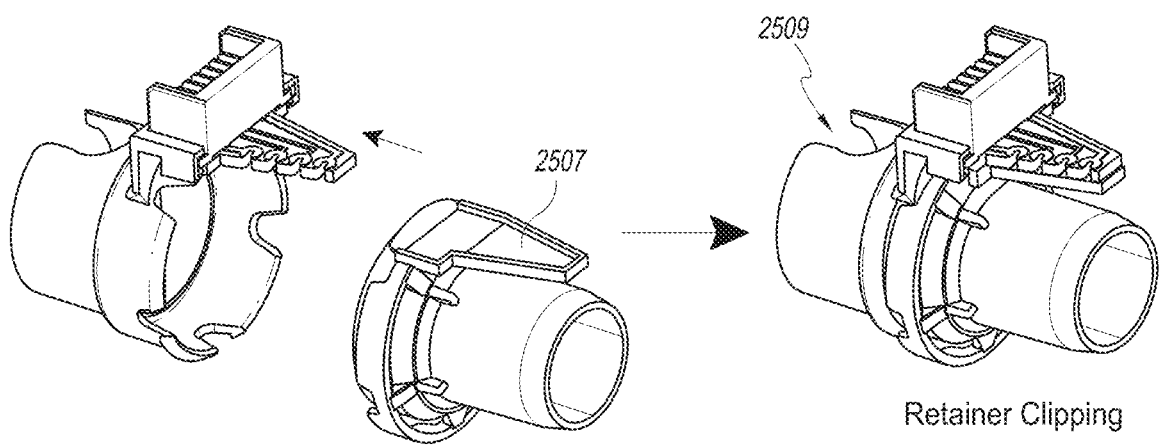

Turning again to the example of FIG. 25A, and as shown in greater detail in FIG. 25D, a seal retainer 2507 is clipped onto one open end of the seal housing 2501 with the seal 2503 seated on the compliant ridge. Clipping the seal retainer 2507 in place compresses the seal 2503 and thereby forms a liquid- and gas-resistant connection between the seal housing 2501 and the seal retainer 2507. In this example, the seal retainer 2507 is made from a molded plastic. In this example, the seal retainer 2507 also comprises a protruding portion sized and shaped to fit around the PCB. The protruding portion serves to support and protect the more flexible and fragile PCB. The protruding portion can be omitted in certain embodiments, however. The resulting assembly comprising the seal housing 2501, seal 2503, PCB and PCB connector assembly 2505, and the seal retainer 2507 is referred to herein as a connector tube assembly 2515.

Figure 25E:
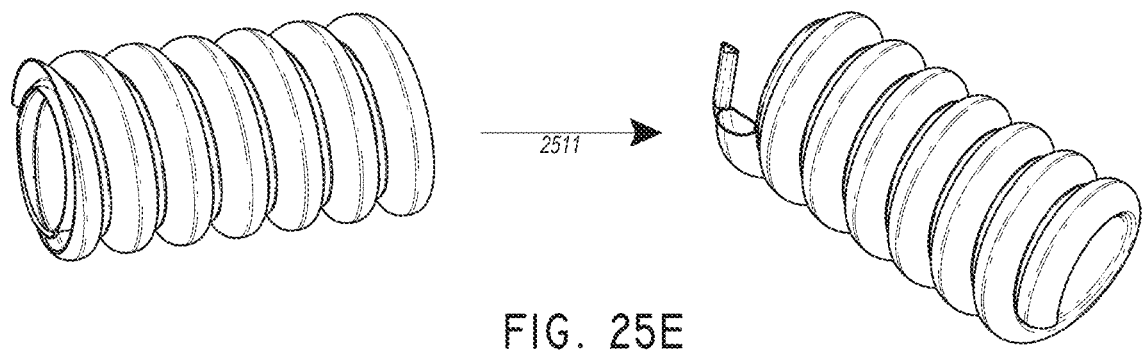
Figure 25F:
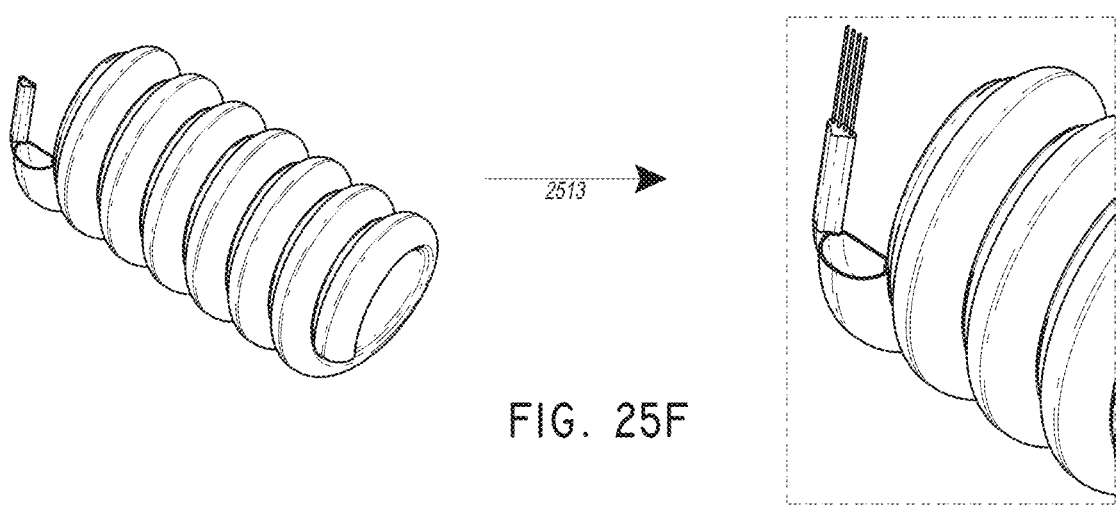
Figure 35A:
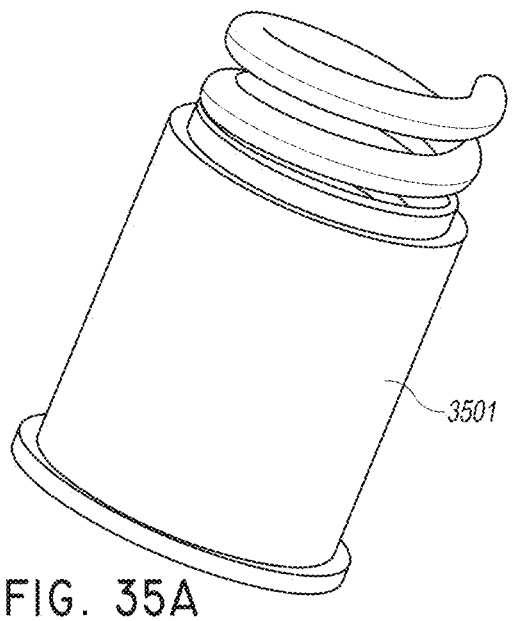
FIGS. 35A-35E show schematics relating to a connector suitable for attaching a tube to a humidifier port, patient interface, or any other suitable component.
Figure 35B:
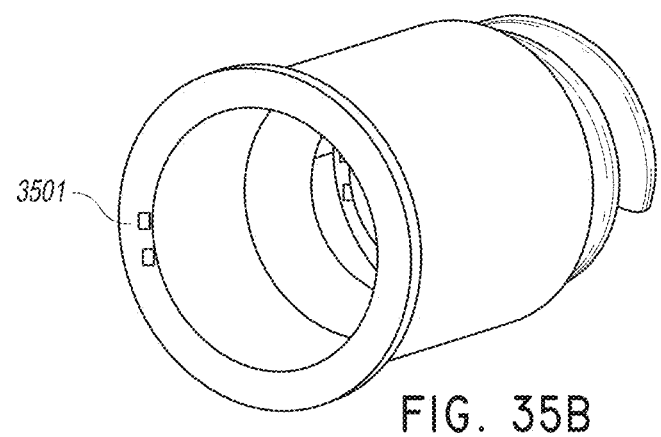

Turning again to the example of FIG. 25A, the tube is prepared for connection to the connector tube assembly 2515. As shown FIG. 25A and in greater detail in FIG. 25E, in step 2511, a portion of the second elongate member at one end of the tube is separated from the first elongate member. Then, in step 2513, a length of the separated second elongate member is stripped away to reveal four conductive filaments (or the number of conductive filaments contained in the second elongate member). Step 2513 is shown in greater detail in FIG. 35F.

Figure 25G:
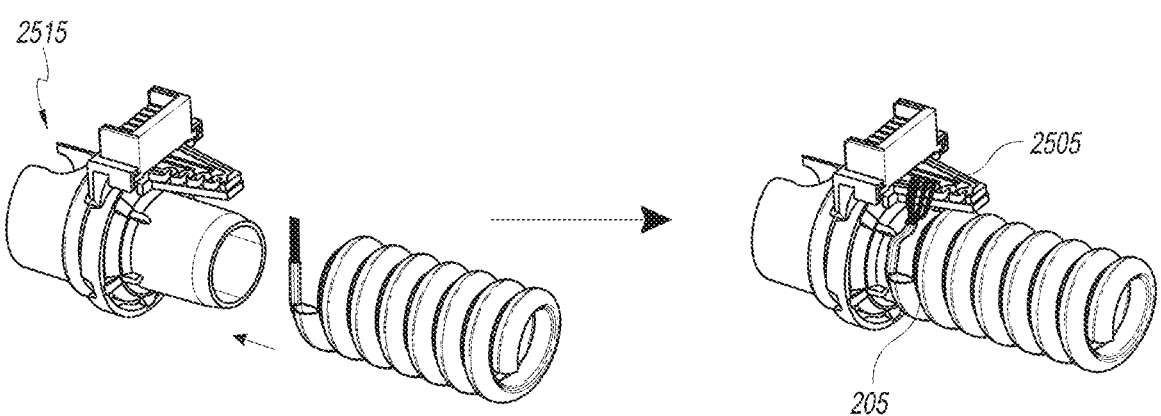

As explained in FIG. 25A and as shown in greater detail in FIG. 25G, the portion of the tube with the stripped length of the second elongate member is inserted in the connector tube assembly 2515. In FIG. 25G, the second elongate member 205 has a bent shape to accommodate the position of the PCB connector assembly 2505. The PCB connector assembly 2505 can also be sized and positioned to reduce or eliminate the bent shape, for example, by shifting the PCB connector assembly further toward the connector end. As shown in step 2517 of FIG. 25A and FIG. 25H, the four conductive filaments are inserted in the four connection pads of the PCB. Then, as shown in FIGS. 25A and 25I, a bead of solder 2519 is placed over each filament-connection pad connection to secure the filament to the connection pad and ensure a good electrical connection between each filament and its corresponding connection pad.

The foregoing step of placing the bead of solder 2519 can be omitted in certain embodiments. FIGS. 26A-26E show an example connector assembly configuration that does not require soldering to connect the filaments to the connector assembly.

FIG. 26A shows a connector assembly 2601 comprising a clip housing 2603 and a circuit connector 2605. A stripped length 2607 of the second elongate member 205 exposes the heating filaments 215 that can be inserted in the clips 2609 in the clip housing 2403. Each clip 2609 is electrically conductive. Suitable materials for a clip 2609 include, for example, aluminum, copper, and gold. A clip 2609 retains a heating filament 215 without the need for solder. An electrical lead 2611 can run between each clip 2609 and the circuit connector 2605.

FIG. 26B shows a top-down view of the connector assembly 2601 showing the clips 2609 positioned in the clip housing 2603.

FIG. 26C shows a clip 2609 in greater detail. The clip 2609 comprises a folded portion 2613, a retention tab portion 2615, a flanged portion 2617, and elongated portion 2619. A heating filament (not shown) is inserted into the flanged portion 2617 so that the folded portion 2613 accepts and retains the heating filament. The shape of the flanged portion 2617 facilitates insertion of the heating filament and guides the heating filament into place. Nevertheless, the flanged portion 2617 can have a straight shape, if desired. The flanged portion 2617 can also have another suitable shape, such as a partial flange. The folded portion has a catch portion 2621 that is compliant with the retention tab portion 2615. The retention tab portion 2615 is angled so that a heating filament is able to slide past the retention tab portion 2615 in one direction into the folded portion 2613. The retention tab portion 2615 also catches the heating filament to prevent it from inadvertently falling out of the folded portion 2613. The elongated portion 2619 is electrically conductive and transmits the electrical current from the heating filament into and/or across the clip housing 2603.

Figure 26E:
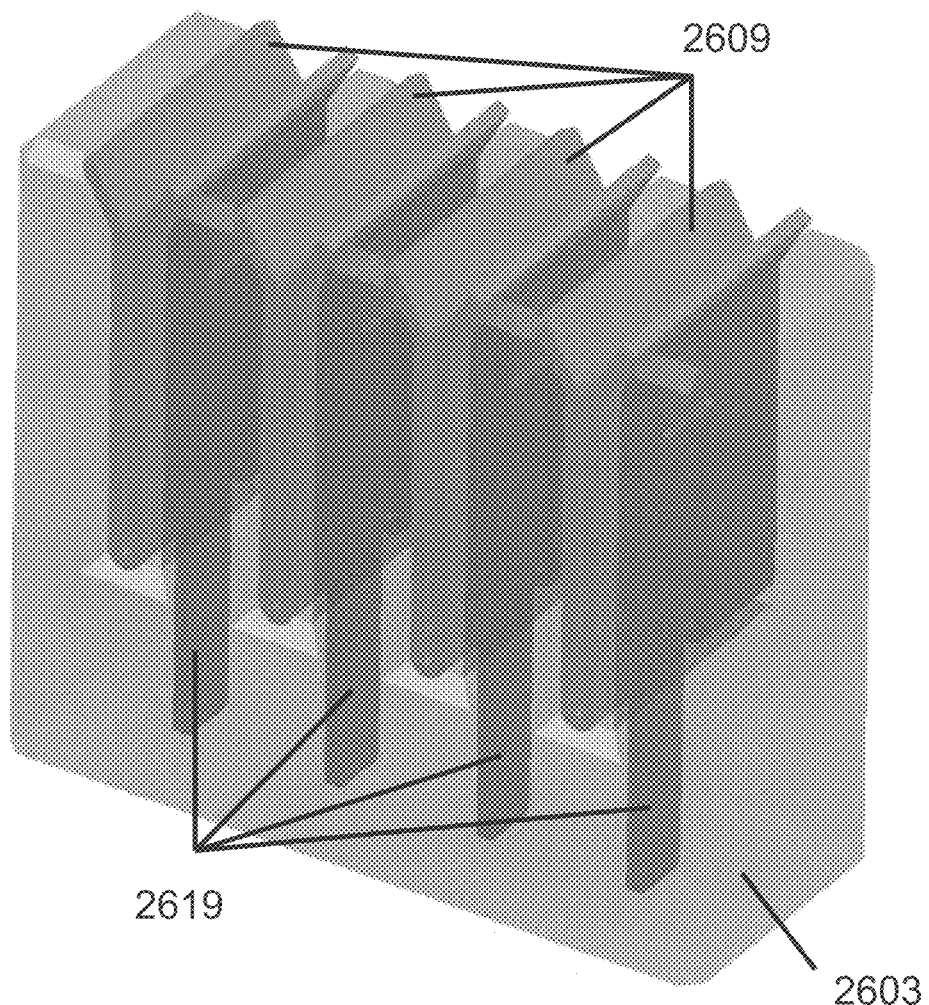
Figure 27A:
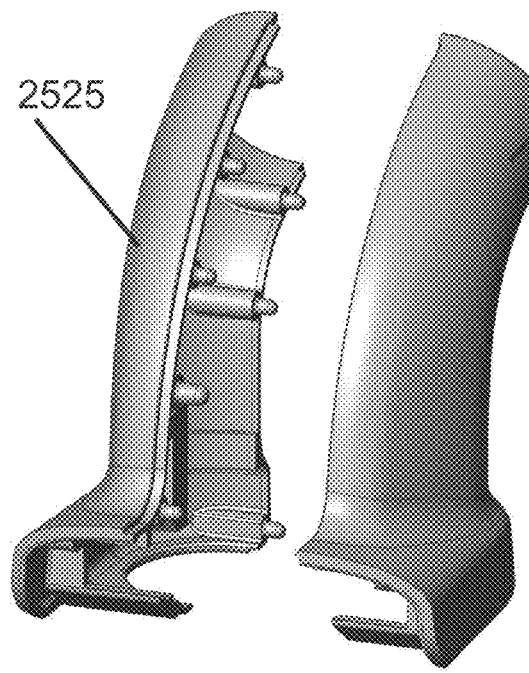
FIGS. 27A-27E show a clamshell suitable for use with the connector of FIGS. 25A-25L.
Figure 27B:
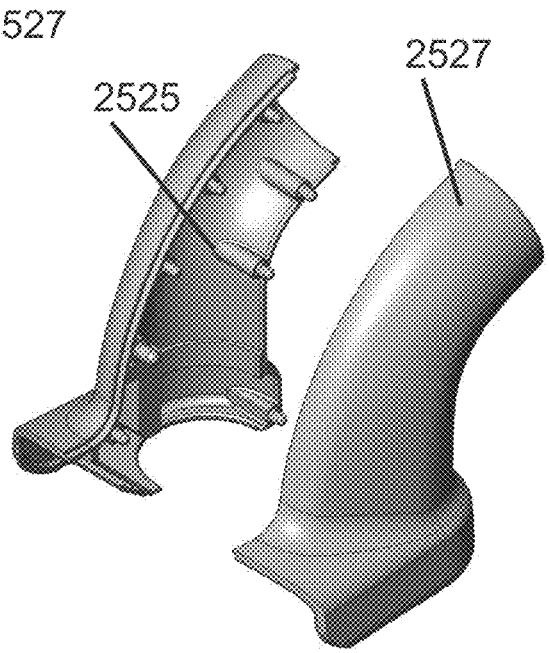
Figure 27C:
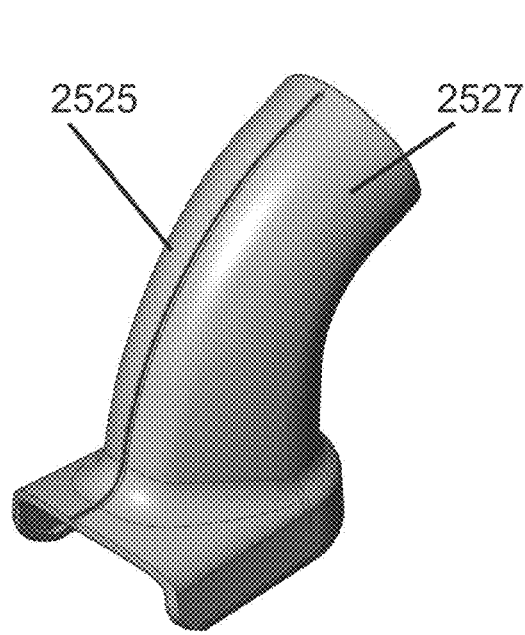
Figure 27D:
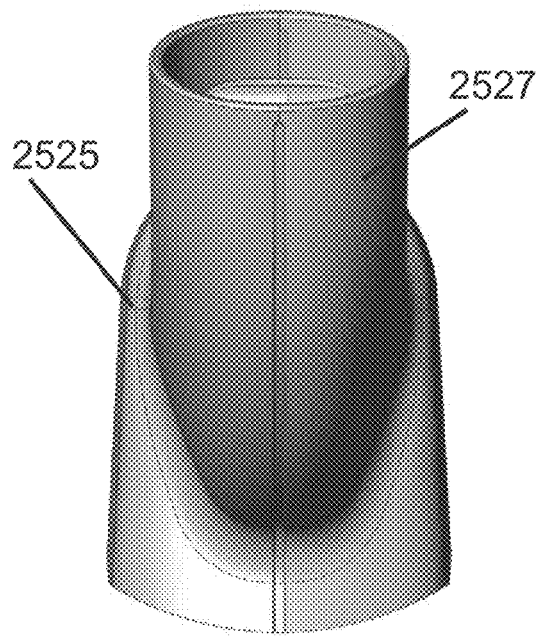
Figure 27E:
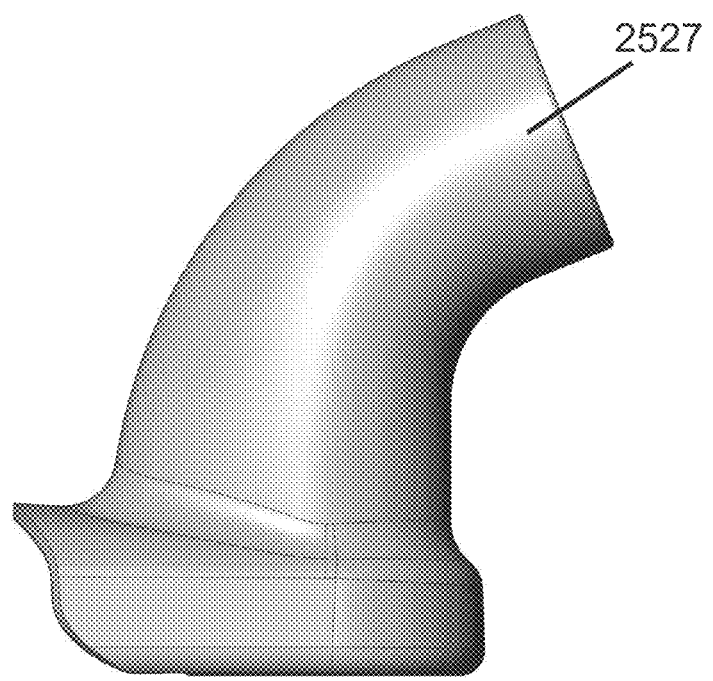
Figure 28A:
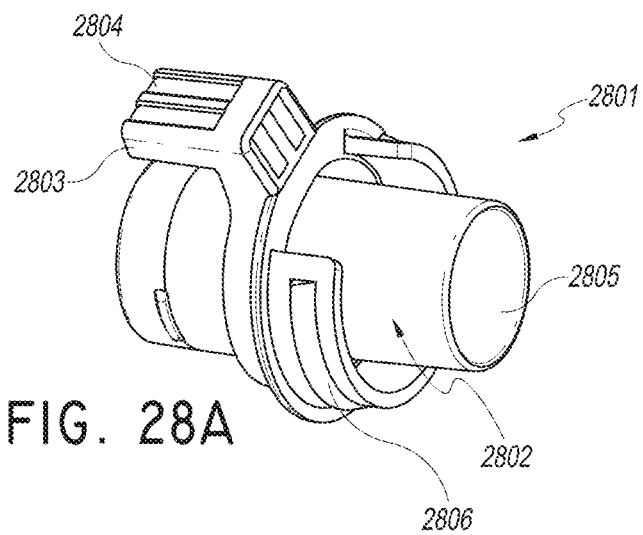
Figure 28B:
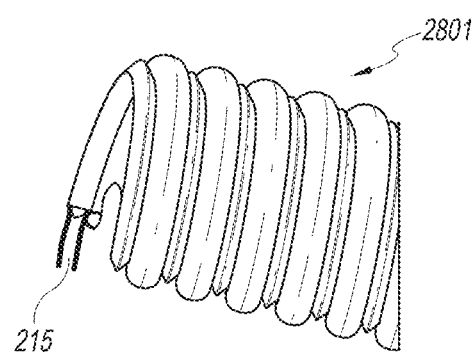
Figure 28C:
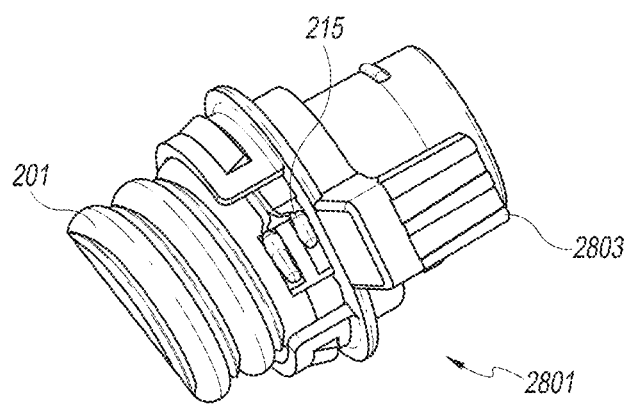
Figure 28D:
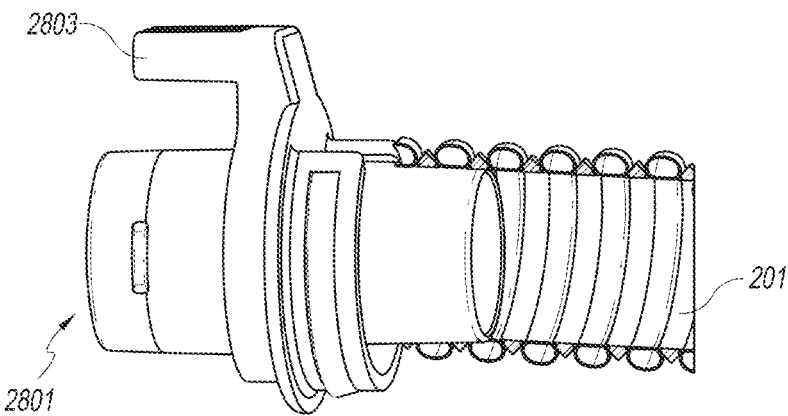
Figure 28E:
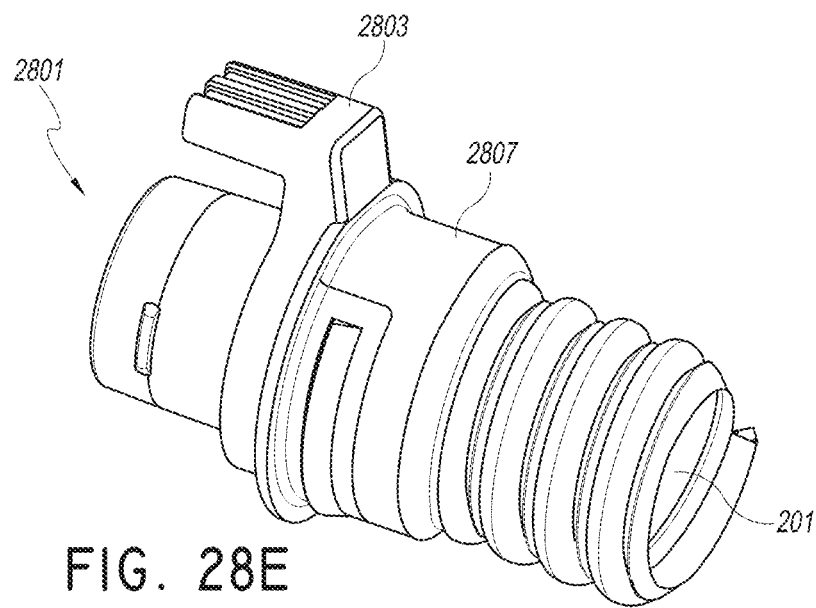
Figure 28F:
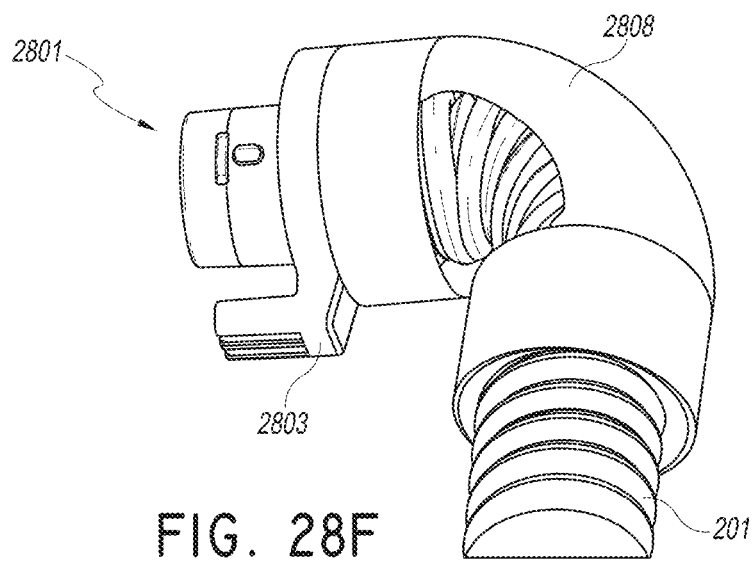

FIG. 26D is a cross section of the view of FIG. 26C and demonstrates the position of the tab portion 2615 and the catch portion 2621 in greater detail. FIG. 26E shows how the clips 2609 are positioned in the clip housing 2603. The clip housing 2603 is shown transparent to demonstrate the position of the elongated portion 2619.

Referring again to FIG. 25A, to ensure that all pieces of the connector tube assembly 2515 are securely fixed to each other, a layer of glue 2521 is then applied. Glue is a broad term and refers to a material for joining, fixing, or attaching other materials. A glue can be adhesive or sticky to the touch when it is in a liquid or semi-solid state. When the glue has dried or otherwise cured into a solid state, the glue can be adhesive or non-adhesive or non-sticky to the touch. The glue can be a resin, such as an epoxy resin, or an elastomer (thermoset or thermoplastic). Use of TPE materials can be advantageous because they are generally flexible and can accommodate twisting, bending, or pressure without shattering.

Figure 25J:
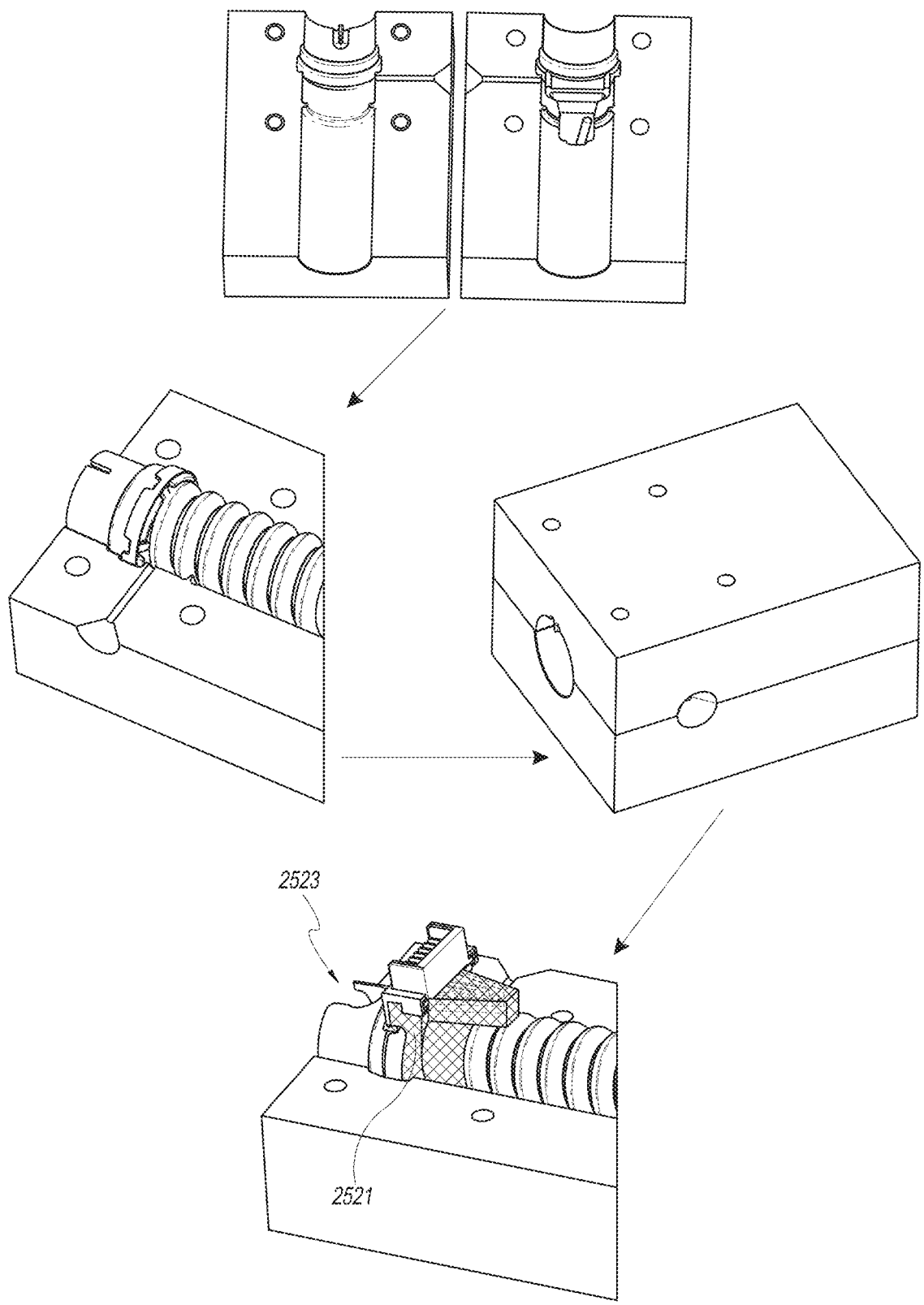

An example method for applying the glue 2521 is shown in FIG. 25J. In this method, a two-block mold is provided. In this example, the mold is made of a metal, such as aluminum or stainless steel, however any suitable material can be used. For instance, the mold can be made from Teflon® PTFE blocks. One block is configured to accommodate the protruding PCB and PCB connector assembly 2505 of the connector tube assembly 2515 and the adjacent tube, and the other block is configured to accommodate the opposite portion of the tube and connector tube assembly 2515. The tube is placed in the compliant mold portions such that the blocks stack one on top of the other. A liquid glue is introduced into an inlet hole in the mold, and the glue is allowed to harden. Then, the mold is removed to expose the glued tube-and-connector assembly 2523, which includes a layer of hardened glue 2521 covering the PCB and the joint between the tube and the connector tube assembly 2515. The glue layer can cover the PCB and all of the soldered connections on the PCB. In this manner, the layer of glue can protect the PCB and the connections from corrosion. In other words, the glue serves at least three functions: sealing the connector and the conduit, holding the PCB in place and potting the PCB; the glue layer forms a pneumatic seal, a mechanical bond and a PCB pot. In addition, the glue layer can act as an electrically insulating barrier, for example, by keeping out moisture and liquids from reaching the electrical components and creating a conductive path to a user of the device.

Figure 25K:
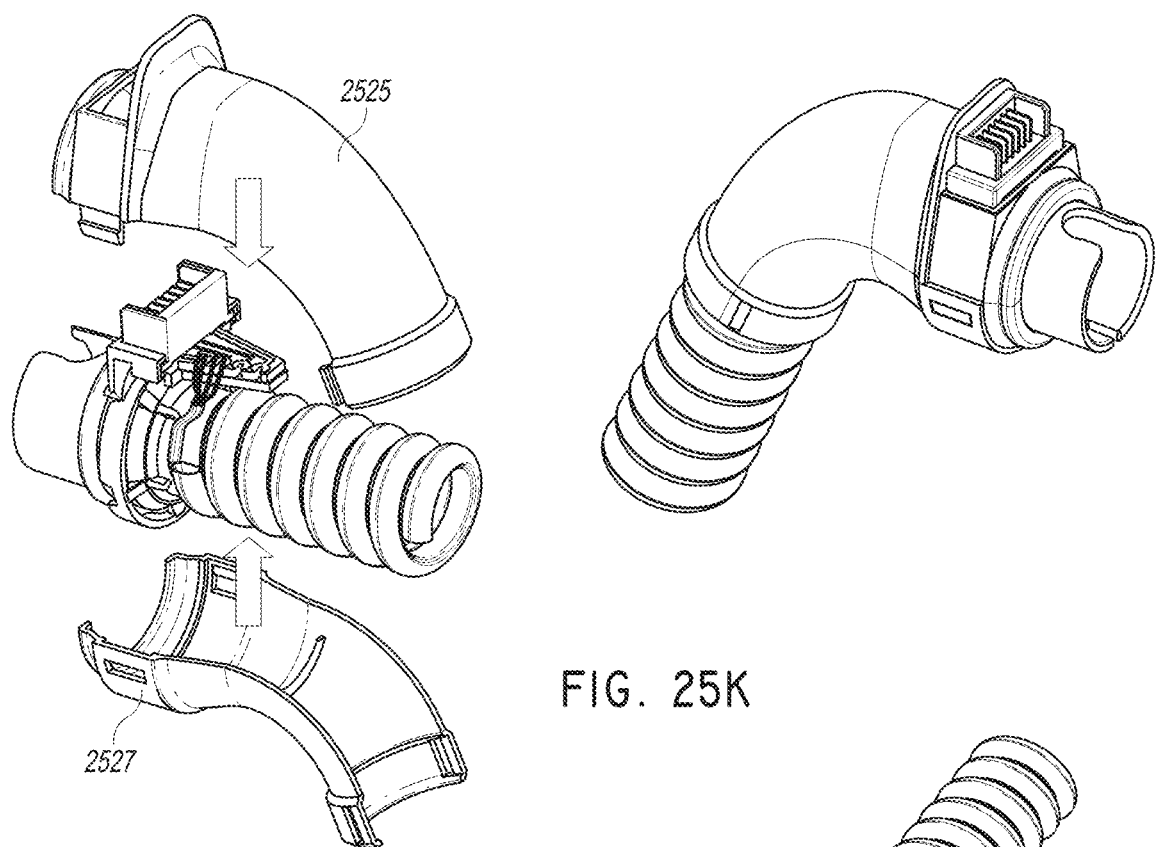

Returning again to FIG. 25A, the tube-and-connector assembly 2523 is then in condition for final assembly. As shown in greater detail in FIG. 25K, a first clamshell 2525 and a second clamshell 2527 are snapped together around the tube-and-connector assembly 2523 such that a portion of the PCB connector is left exposed. The first clamshell 2523 and second clamshell 2527 shown in FIG. 25K are top and bottom clamshells, respectively.

Figure 25L:
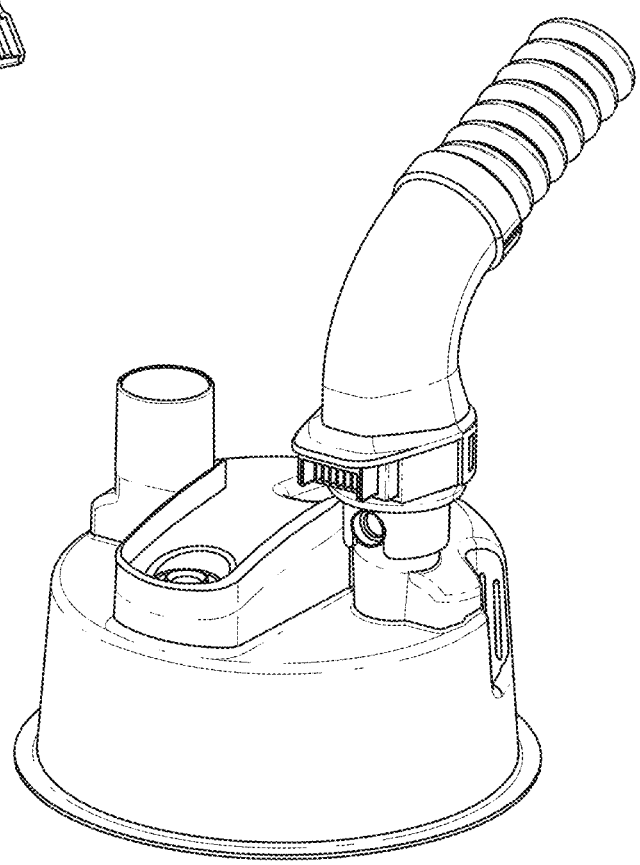

An alternative clamshell design is shown in FIGS. 27A-27E, in which the first 2525 and second 2527 clamshells are left and right clamshells, respectively. The clamshell 2525, 2527 portions (FIG. 25K or FIGS. 27A-27E) can be made of molded plastic or any other suitable material. The clamshell 2525, 2527 portions (FIG. 25K or FIGS. 27A-27E) serve to further protect the tube-and-connector assembly 2523 (FIGS. 25A and 25J) and to maintain the tube-and-connector assembly in a bent position that promotes the return of condensate to the humidifier unit when in use. As shown in FIG. 25L, the final assembly can readily snap into a humidifier with a compliant electrical connector near the connection port.

Although the foregoing manufacturing method has been described with reference to a flow chart, the flow chart merely provides an example method for attaching a connector to the end of the tube that is configured in use to connect to a humidifier. The method described herein does not imply a fixed order to the steps. Nor does it imply that any one step is required to practice the method. Embodiments may be practiced in any order and combination that is practicable.

Placement of Alternative Device-End Connectors

Reference is next made to FIGS. 28A-28F which show a connector which can be used for medical circuits having electrical wires running therethrough. The connector 2801 comprises a cut-out 2802, which in certain embodiments is 30 mm (or about 30 mm) across. In certain embodiments, on one end of the cut-out 2802 is a L-shaped arm 2803 which extends in part outward from the connector 2801 and in part parallel to the longitudinal axis of the connector 2801.

The arm 2803 can have one or more electrical conductors 2804 embedded therein. The conductors 2804 can be made of copper or brass or another suitably conductive material and can be formed as flat L-shaped pieces running substantially along the length of the arm 2803.

The connector 2801 can further comprise an inner portion 2805 adapted to sit substantially inside a portion of the tube 201 and an outer portion 2806 adapted to substantially surround a portion of the tube 201.

A portion of the second elongate member 205 is stripped away to reveal the one or more filaments 215 embedded therein. Preferably about 5 mm of the filaments 215 are revealed. The connector 2801 is then attached to the tube 215 such that the inner portion 2805 sits within tube 201 and the outer portion 2806 sits around the tube 201. Preferably the connector 2801 is oriented such that the revealed ends of the filaments 215 are located at or near the cut-out 2802.

The revealed ends of the filaments 215 are then electrically and/or physically connected to the conductors 2804. This can be done by soldering the ends to the conductors 2804, or any other method known in the art.

A member 2807 can be inserted or molded on top of at least a portion of connector 2801 and, optionally, tube 201 to promote the attachment between the connector 2801 and the tube 201. The member 2807 can be a hard material or a soft material, such as a soft rubber or elastomer.

In some embodiments, a substantially L-shaped elbow 2808 can be placed over the assembly. The elbow 2808 can provide some additional strength to the connection and can provide a predetermined bend in the tube 201 (such that the connector 2801 can tend to sit at an angle of about 90° from the body of the tube 201).

Figure 29E:
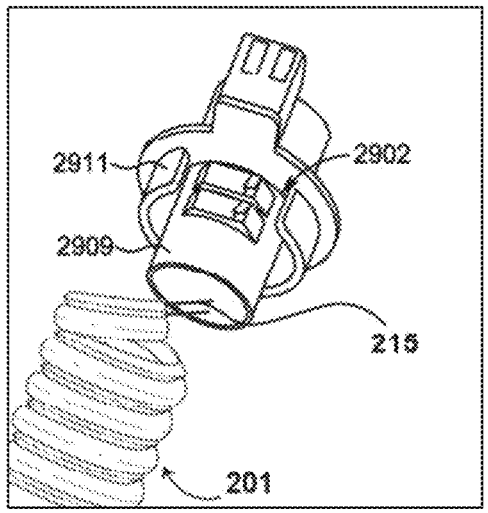

Reference is next made to FIGS. 29A-29L which shows another connector 2901 which can be used for medical circuits having electrical wires running therethrough. Referring first to FIG. 29A, the connector 2901 permits a composite tube to be connected to a device, such as a CPAP device (not shown). The connector 2901 carries an electrical terminal on an L-shaped arm 2903, which engages a complementary electrical terminal of the device to permit electrical signals or electrical energy to be transmitted between the device and a composite tube. In the illustrated arrangement, the electrical terminal of the connector 2901 is a plug 2905 that complies with a receptacle or port of the device. This arrangement could also be reversed, however, if desired. In this example, the plug electrically communicates with electrical contacts 2906 for establishing an electrical connection with a composite tube. Here, the electrical contacts 2906 are molded into the connector 2901. The connector 2901 further comprises filament holders 2907 that are also molded into the connector 2901. The connector 2901 also comprises a cut-out 2902, which in certain embodiments is 30 mm (or about 30 mm) across.

As shown in FIGS. 29B and 29C, a portion (e.g., a 10-mm portion) of the second elongate member 205 is stripped away to reveal a small length of the one or more filaments 215 embedded therein. Preferably, about 5 mm or 10 mm of the filaments 215 are revealed.

As shown in FIG. 29E, the connector 2901 is then attached to the tube 215 such that an inner portion 2909 of the connector 2901 sits within tube 201 and an outer portion 2911 of the connector 2901 sits around the tube 201. Preferably the connector 2901 and composite tube 201 are oriented such that the revealed ends of the filaments 215 are located at or near the cut-out 2902 and the filaments 215 are aligned to meet near the contacts 2906.

Figure 29F:
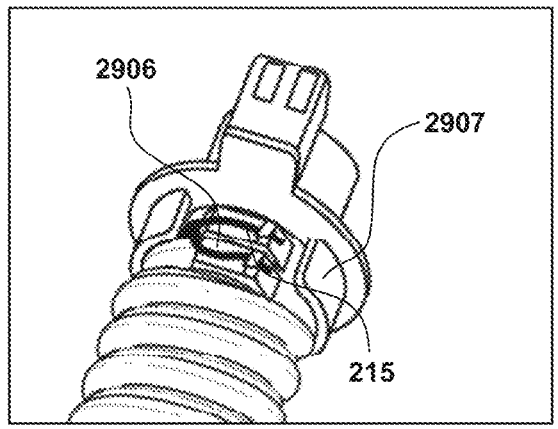

As shown in FIG. 29F, the heating filaments 215 are positioned under the wire holders 2907 so that each heating filament 215 is positioned over a contact 2906.

Figure 29G:
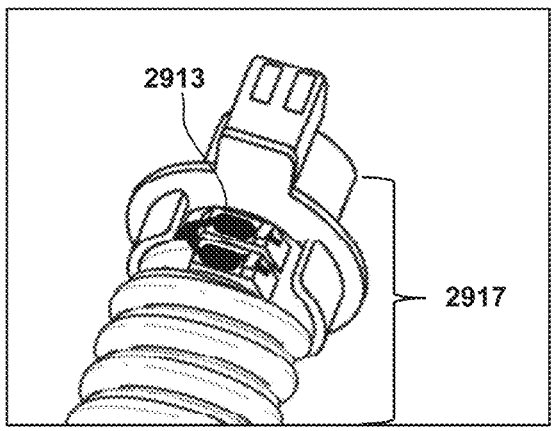
Figure 29H:
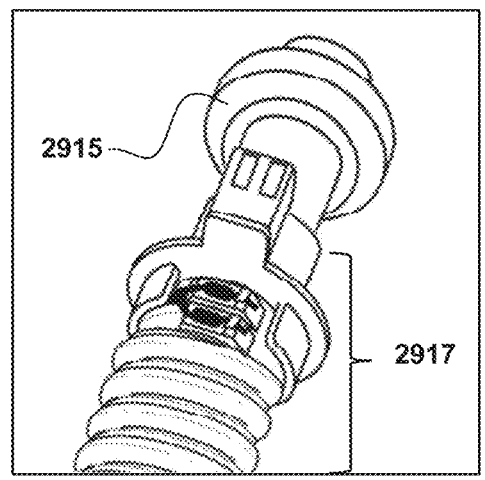
Figure 29I:
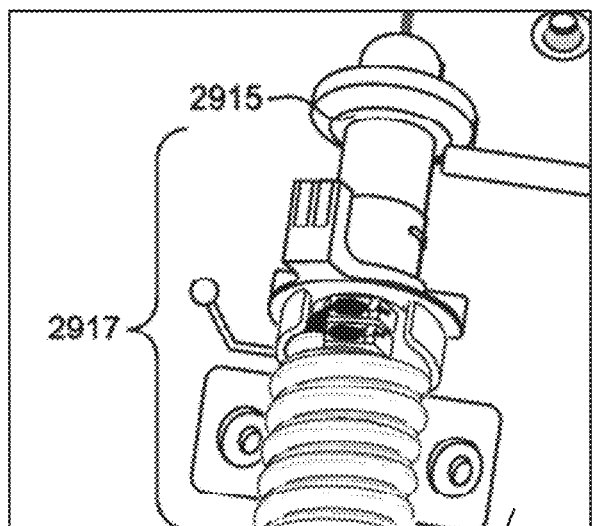
Figure 29J:
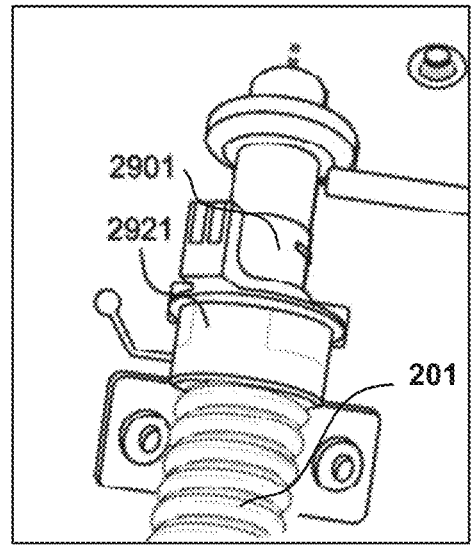
Figure 29K:
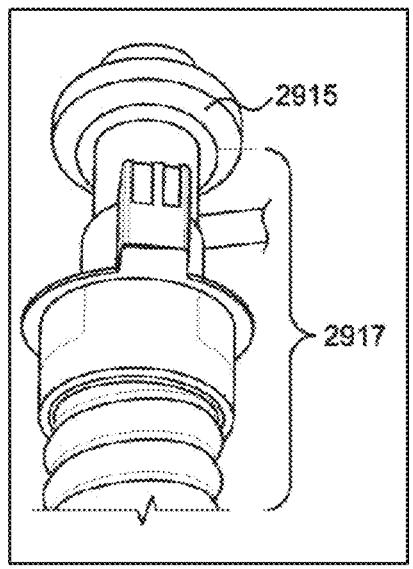

As shown in FIG. 29G, a bead of solder 2913 is placed over each heating filament 215 at the respective contact 2906. The combination of connector 2901 and composite tube 201 is designated here as a connector-tube assembly 2917. As shown in FIG. 29H, a mold tool core 2915 is inserted into the connector 2901. As shown in FIG. 29I, the connector-tube assembly 2917 and core 2915 are placed in an injection mold tool 2919. In FIG. 29J, a molded material 2921 is molded over the cut-out (not shown), thereby bonding the connector 2901 and composite tube 201. Suitable molded materials 2921 include plastic and rubber. The connector-tube assembly 2917 and core 2915 are removed from the injection mold tool (not shown), as in FIG. 29K.

Figure 29L:
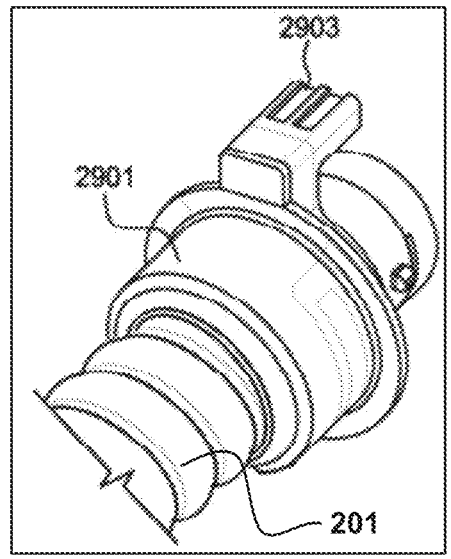

As shown in FIG. 29L, the core 2915 is removed, thereby providing a composite tube 201 with a device-end connector 2901. The method of FIGS. 29A-29J allows the plug 2903 to be electrically connected to the heating filament and/or other electrical element(s) (not shown) of the composite tube 201. Preferably, the heating circuit of the device provides electrical energy to the heating filament of the composite tube 201 so that the heating filament can provide heat energy to the flow of humidified air passing through the composite tube 201. As discussed herein, such an arrangement can prevent or limit condensation within the composite tube 201. In addition, or in the alternative, the plug 2903 and device port could provide for other electrical signals, such as data signals, to be communicated between the device and the composite tube 201. For example, a sensor at the patient interface-end of the composite tube 201 could provide data regarding one or more parameters of the flow of air (e.g., temperature, humidity level) for use by the control system of the device. Any other desirable electrical signals could also be transmitted.

The foregoing methods of attaching connectors to composite tubes are provided by way of example. The methods described do not imply a fixed order to the steps. Nor do they imply that any one step is required to practice the methods. Embodiments may be practiced in any order and combination that is practicable.

Placement of Patient-End Connector with Electrical Connectivity

Figure 30I:
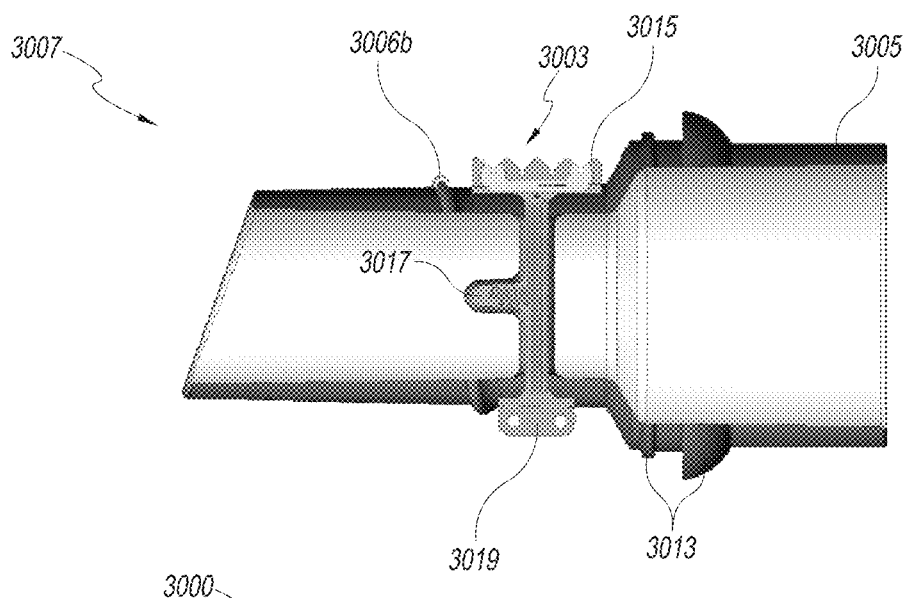
FIGS. 30A-30O show schematics relating to a connector suitable for attaching a tube to a patient interface.
Figure 30J:
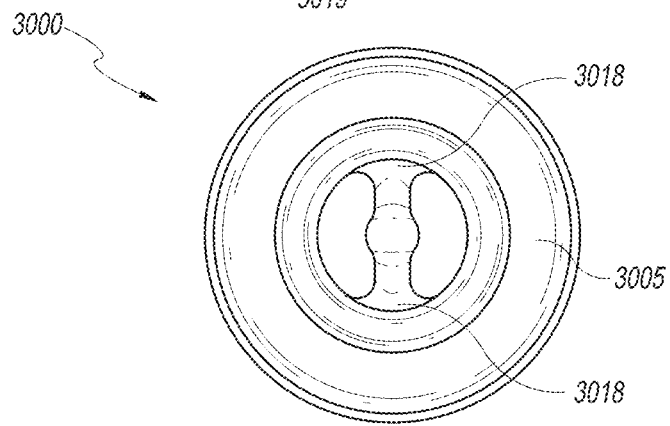
Figure 30K:
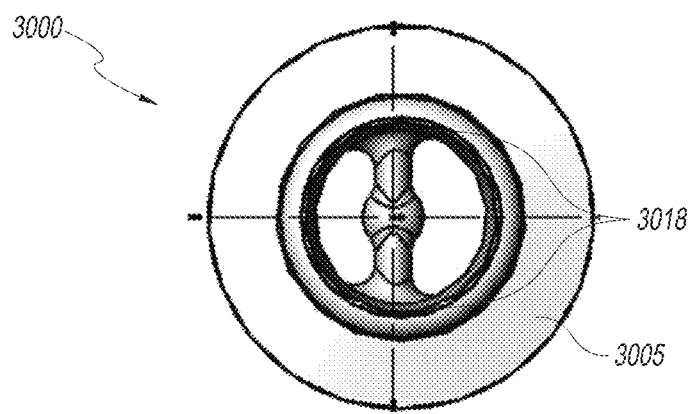
Figure 30L:
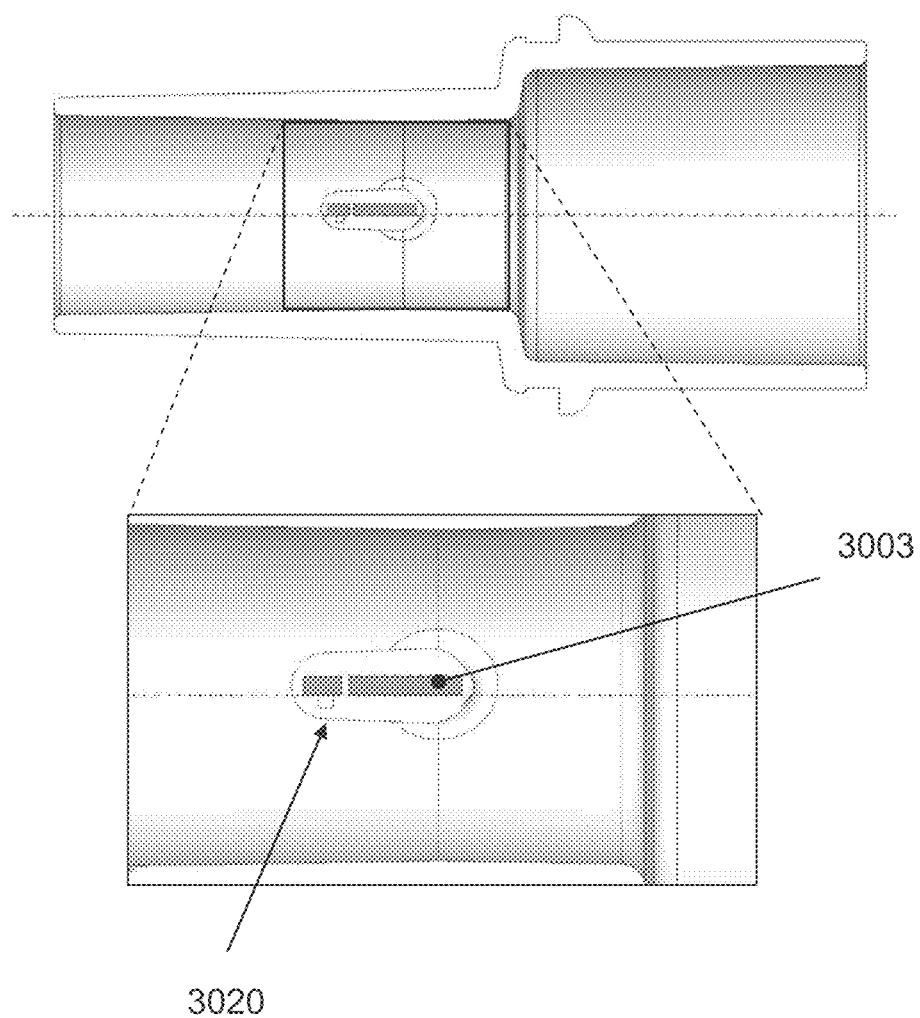
Figure 30M:
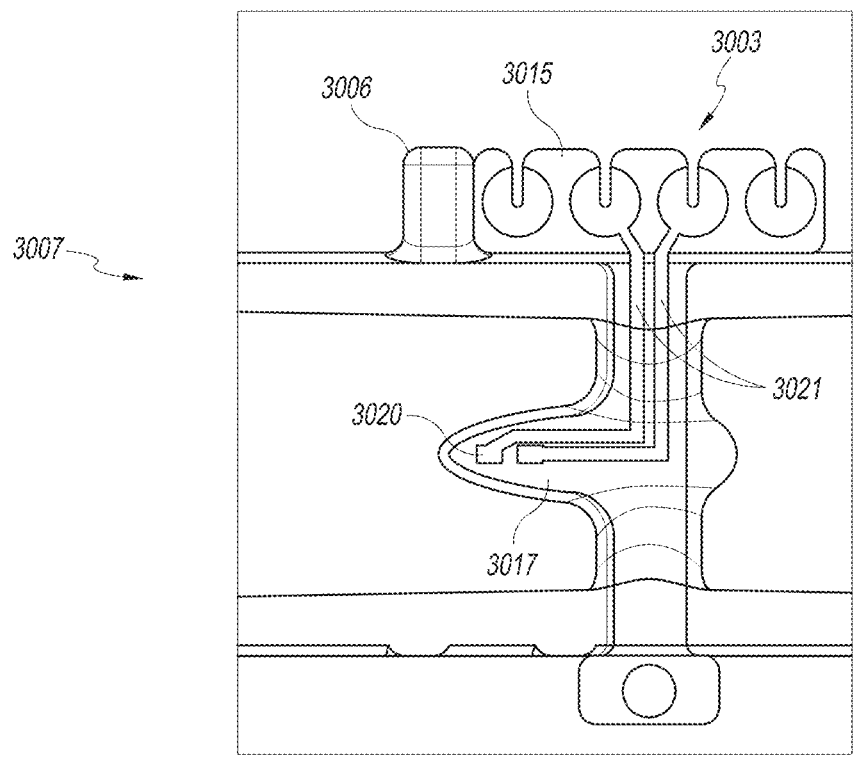
Figure 30N:
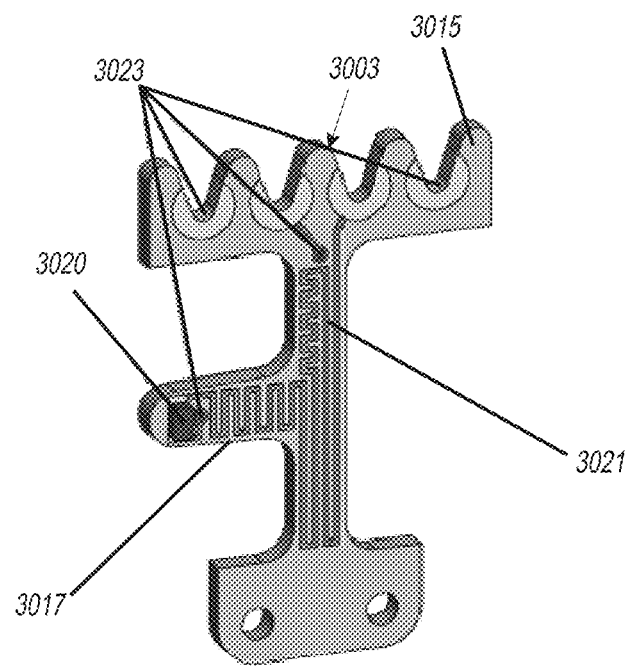
Figure 30O:
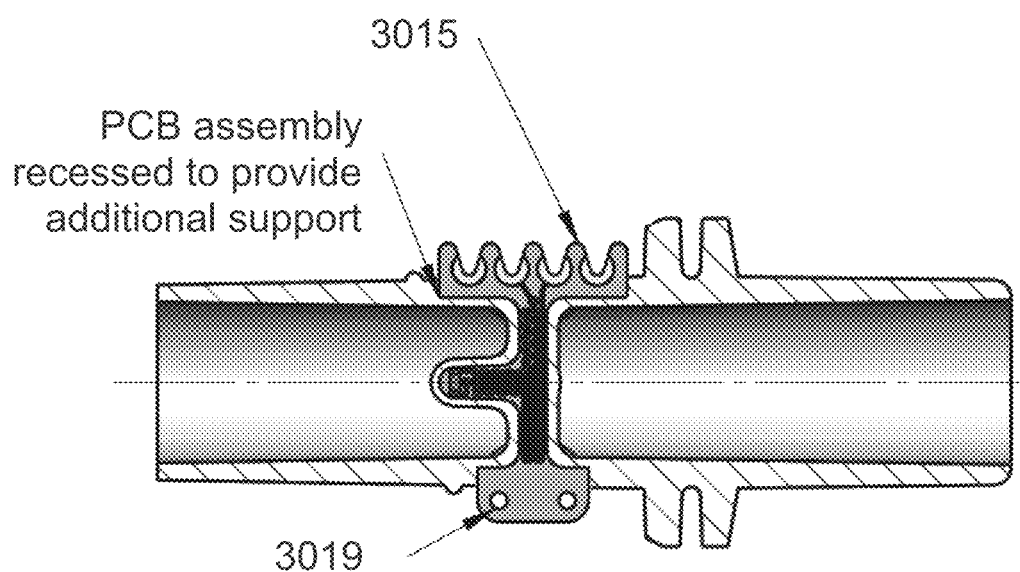

Reference is next made to FIGS. 30A-30O, which show an example connector 3000 for connecting one end of the tube 201 to a patient interface (not shown). The end of the connector 3000 that connects to the patient interface is indicated by reference 3001.

FIG. 30A shows a side perspective view of the connector 3000.

As shown in FIGS. 30B-30F, the connector 3000 comprises a PCB assembly 3003 and an insert 3005, designated together as an insert assembly 3007 when assembled together, and a cover 3009. Each of FIGS. 30B-30D and 30F shows a side-perspective view that generally corresponds with the view of FIG. 30A. FIG. 30E shows a side-plan view.

The insert 3005 and cover 3009 are preferably molded plastic components. The insert 3005 can serve one or more purposes, including providing a receptor for the tube 201, providing a suitable conduit for the gas-flow path, providing a housing for the PCB assembly 3003, and providing a housing for a sensor (not shown), such as a thermistor. The cover 3009 protects and covers the relatively fragile PCB assembly 3003 and protects the connection between the tube 201 and the insert 3005. As shown in FIGS. 30D and 30E, the end of the insert 3005 that is inserted in the tube 201 (that is, the end that is opposite end 3001) can be angled, which can aid insertion into the tube 201. In some embodiments, however, the end that is opposite end 3001 can be blunt or tapered.

As shown in FIG. 30D, the insert desirably includes a stop portion 3006a. The stop portion 3006a can promote correct placement of the tube 201 with respect to the insert 3005. The stop portion 3006a can also serve to protect the PCB assembly 3003 from directly contacting the tube 201. An alternative configuration is shown in FIG. 30E. In FIG. 30E, stop portion 3006b is formed as a spiral or helical component, such as a spiral or helical rib. This configuration is advantageous because the shape complements the spirally wound tube 201, thereby providing a secure connection between insert 3005 and tube 201.

Figure 31A:
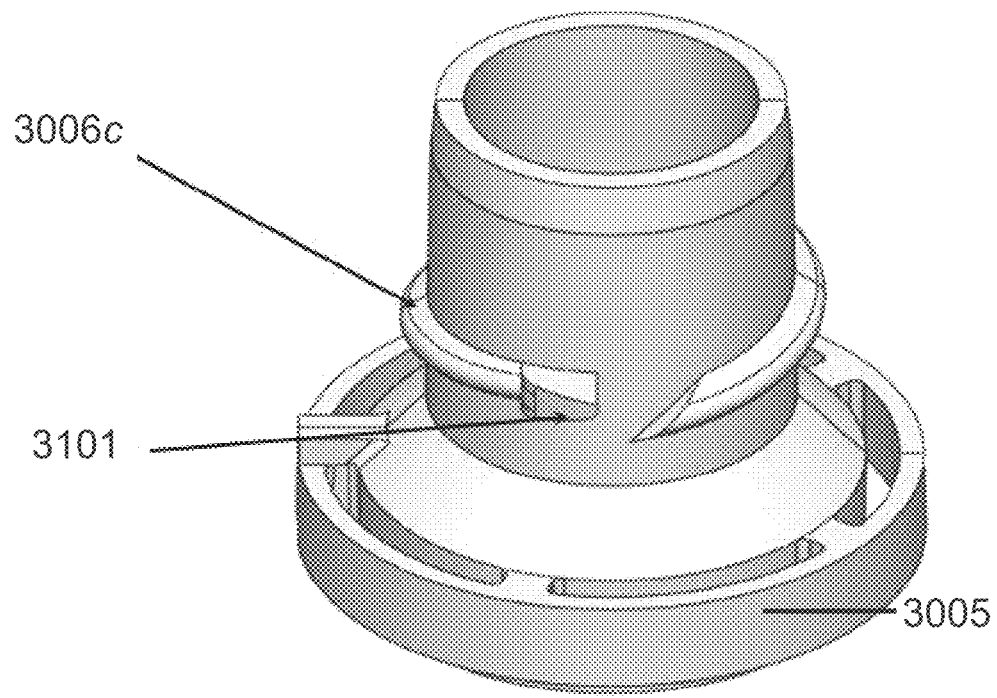
FIGS. 31A-31B show a stop portion suitable for use with the connector of FIGS. 30A-30O.
Figure 31B:
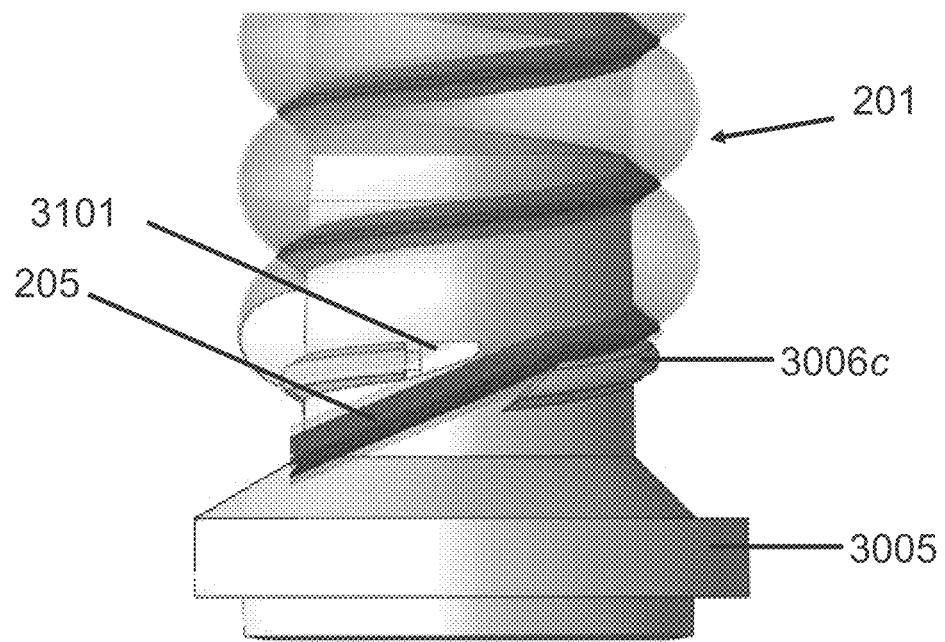

Yet another alternative configuration is shown in FIGS. 31A and 31B. In these figures, stop portion 3006c is formed as a spiral or helical component, such as a spiral or helical rib. Again, this configuration is advantageous because the shape complements the spirally wound tube 201 (FIG. 31B), thereby providing a secure connection between insert 3005 and tube 201. In this configuration, the stop portion 3006c comprises an orientational stopping feature 3101. As shown in FIG. 31B, a surface of the orientation stopping feature 3101 is tapered such that the orientational stopping feature 3101 resembles a fin The shape of the orientational stopping feature 3101 can pinch, grasp, or otherwise retain the second elongate member 205 of the tube 201. The orientational stopping feature 3101 thus can serve to better hold the tube 201 in the correct position by preventing the tube 201 from shifting and/or turning.

Returning to FIG. 30E, the patient end 3001 of the insert 3005 is larger than it is in FIG. 30D and illustrates how the size can be modified for different applications (for example, connecting to infant or adult patient interfaces).

FIG. 30G shows a cross section of the connector 3000 and generally corresponds with the same side perspective view as FIG. 30A. In certain embodiments, there is an insulating gap, such as an air gap, between the tube 201 and the insert 3005 to protect the sensor (discussed below) from heat radiating from the heating filament(s) in the tube 201, which can induce sensor error at low flows. In FIG. 30G, such a gap would appear above and below sensor portion 3017. Alternative, in certain embodiments, the insert 3005 is formed such that air bubbles are encapsulated in the insert 3005. For example, the insert 3005 can comprise a foamed plastic.

FIG. 30H shows a cross section of the insert assembly 3007 and generally corresponds with the side perspective view of FIG. 30D. FIG. 30I shows an alternative cross section of the insert assembly 3007 and generally corresponds with the side plan view of FIG. 30E. These figures show greater details regarding the relative placement of the tube 201, insert assembly 3007, and/or cover 3009.

As shown in FIGS. 30G-30I, a generally annular catch structure 3013, which comprises two molded rings extending radially outward from the body of the insert 3005. The molded rings comply with a notch 3011, which comprises a molded ring extending radially inward from the cover 3009. The notch 3011 and catch structure 3013 hold the cover 3009 on the insert 3005.

Figure 32B:
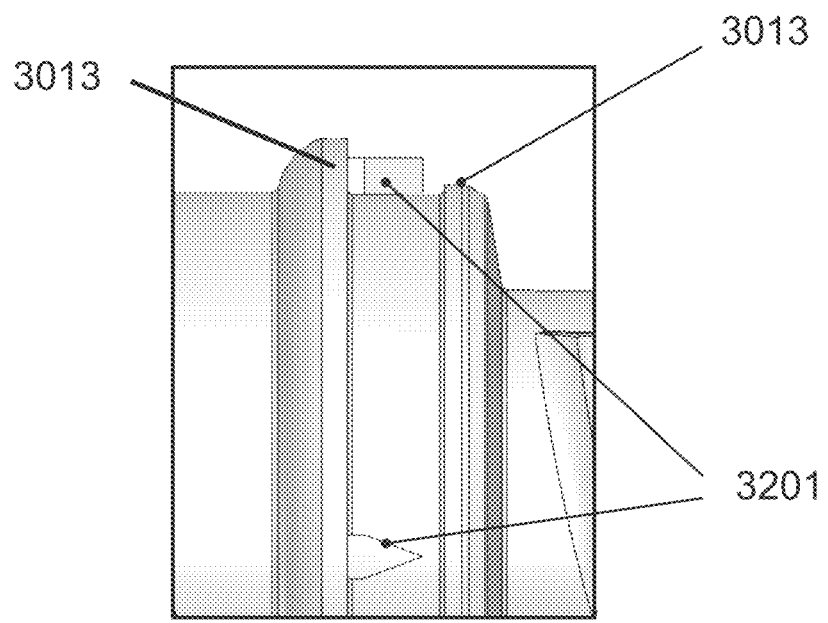
FIGS. 32A-32D show an anti-rotation feature suitable for use with the connector of FIGS. 30A-30O.
Figure 32A:
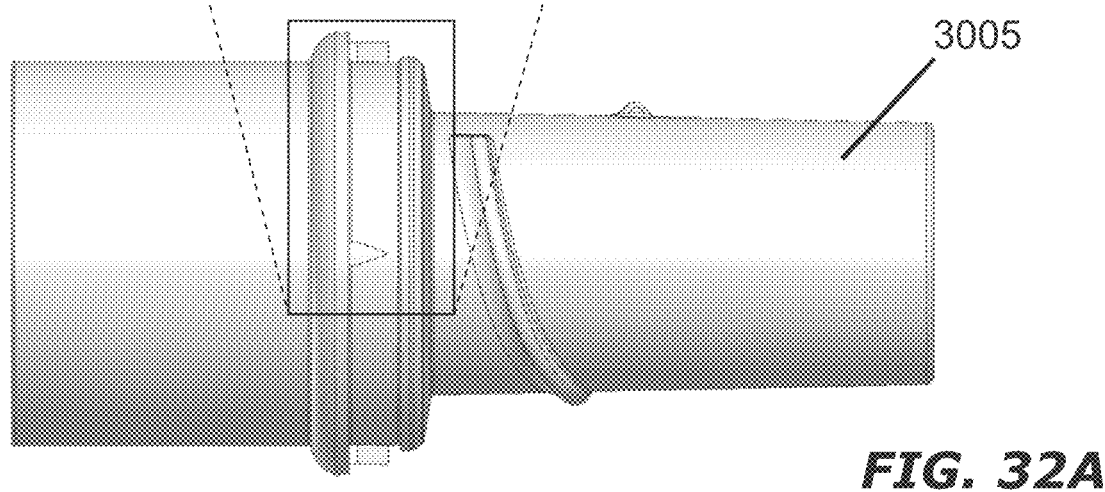
Figure 32D:
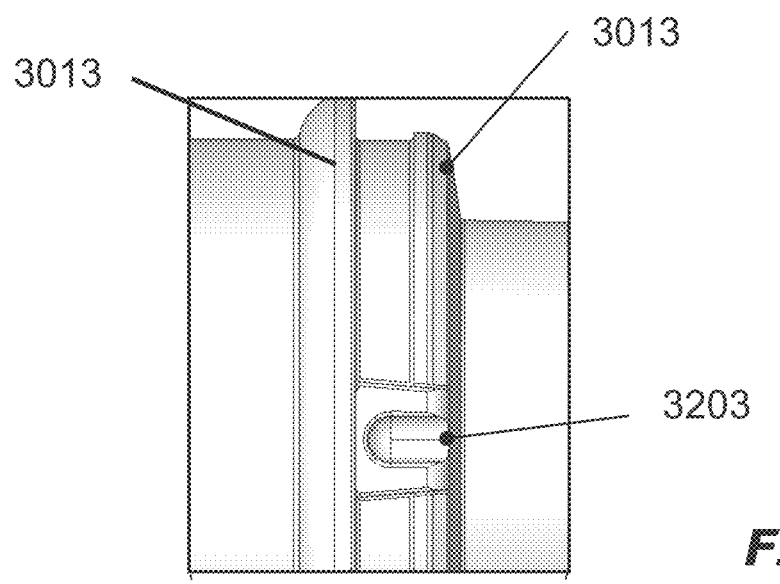
Figure 32C:
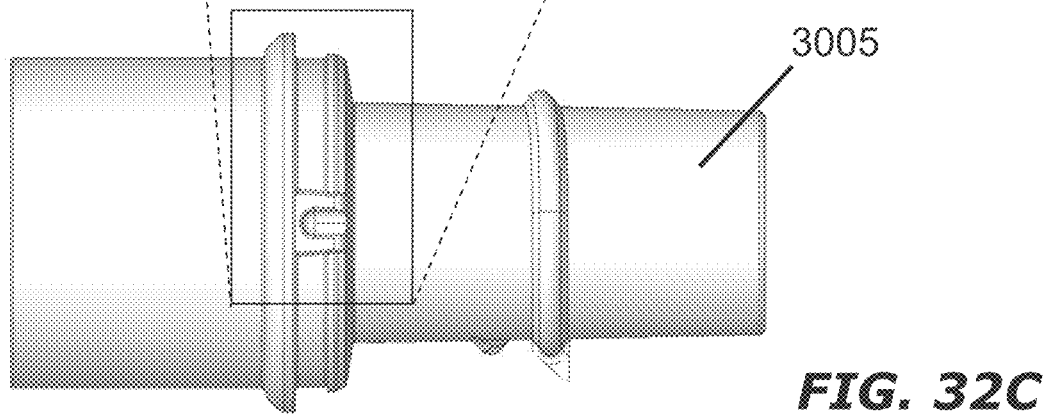

An alternative configuration for the catch structure 3013 is shown in FIGS. 32A and 32B. Again, the catch structure 3013 is generally annular and comprises two molded rings extending radially outward from the body of the insert 3005. A plurality of anti-rotation projections 3201 extends perpendicularly between the rings. In this example, there are four projections 3201 evenly spaced around the circumference of the catch structure 3013 (e.g., at 90° intervals). The projections 3201 engage compliant notches in the cover (not shown) and prevent the cover from rotating on the insert assembly. Yet another alternative configuration for the catch structure 3013 is shown in FIGS. 32C-32D. Again, the catch structure 3013 is generally annular and comprises two molded rings extending radially outward from the body of the insert 3005. Anti-rotation notches 3203 are disposed between the rings. In this example, there are four notches 3203 evenly spaced around the circumference of the catch structure 3013 (e.g., at 90° intervals). These notches 3203 engage compliant projections in the cover (not shown) and prevent the cover from rotating on the insert assembly.

FIGS. 30G-30I further illustrate that PCB assembly 3003 comprises a PCB 3015, a sensor portion 3017, and a locating portion 3019. The PCB assembly 3003 is located such that, in use, the sensor portion 3017 is within the fluid flow path through the insert 3005.

The sensor portion 3017 includes one or more sensors, such as a temperature sensor. The sensor is preferably located on the projecting portion of the sensor portion 3017. A suitable temperature sensor includes a thermistor, thermocouple, resistance temperature detector, or bi-metallic thermometer.

The PCB 3015 completes the heating and/or sensing circuit of the composite tube 201.

The locating portion 3019 improves stability and facilitates locating the PCB assembly 3003 during manufacturing. Nevertheless, the locating portion 3019 can be omitted in certain embodiments.

FIG. 30I also illustrates that the PCB assembly 3003 can be further stabilized in the insert 3005 by recessing at least part of the PCB 3015 and/or the locating portion 3019 in the outer surface of the insert 3005. The recessed configuration is also shown in FIG. 30N.

The configurations of FIGS. 30G-30I have a number of advantages. For example, certain embodiments include the realization that placing the sensor portion 3017 within the fluid flow path promotes accurate measurements, regardless of flow rate, ambient temperatures, and so forth. In addition, certain embodiments include the realization that there is less potential for fluid leak than a configuration having a separate sensor attached to a connector, due to poor user setup of the circuit.

Further, certain embodiments include the realization that, because the PCB assembly 3003 passes across the full width of the insert 3005, the PCB assembly 3003 can be used to pass connection leads across a tube 201. As discussed below, FIGS. 33A-33D illustrate a PCB assembly 3301 design capable of passing connection leads across a tube, the respective figures illustrating two sides of the PCB assembly 3301. The concept of passing connection leads across a tube 201 is further discussed below with reference to FIG. 34, in the context of an intermediate connector between two tube 201 segments.

Turning first to FIGS. 33A and 33B, the PCB assembly 3301 includes connection pads 3303, 3305 for the heating filament and/or sensor connections. The connection pads 3303, 3305 are configured to be on opposite sides of the PCB assembly 3303 to facilitate connections with spirally-wound heating filaments.

The PCB assembly 3301 includes sensor connection pads 3307 for the sensor. The sensor can be coupled to a diode through signal connection pads 3309 on the PCB assembly 3301. As illustrated, the PCB assembly 3301 includes a gap 3311 configured to thermally insulate the sensor from the other electrical components and tracks. In some embodiments, the gap 3311 can be filled with an insulating material to further thermally isolate the sensor connected to sensor connection pads 3307. In addition, the PCB assembly 3301 can be configured to position the sensor apart from the other active and/or passive electrical components, such as with the protruding feature 3313.

The PCB assembly 3301 includes power connection pad 3315 for a diode electrically coupled to the heating filaments through conductive tracks on the PCB assembly 3301. The power connection pad 3315 can be electrically and thermally coupled to heat sink 3317 to aid in dissipating heat, to reduce or minimize effects on the accuracy of the temperature reading of the thermistor coupled to the sensor connection pads 3307.

Figure 33C:
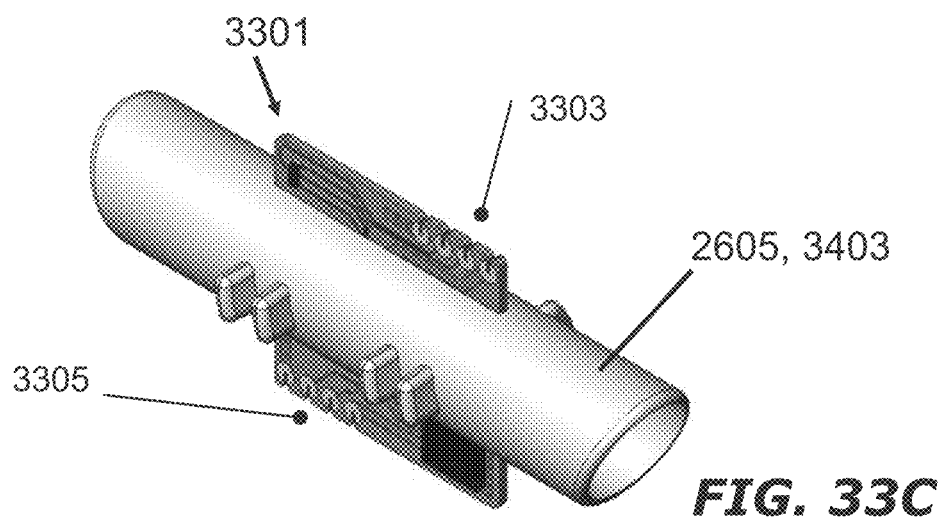
Figure 33D:
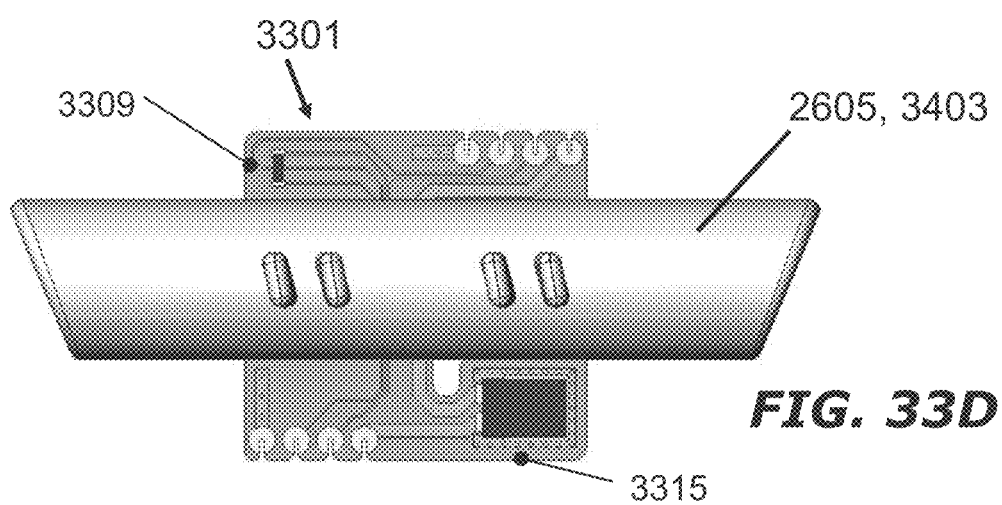

FIGS. 33C and 33D show the PCB assembly 2901 of FIGS. 33A and 33B in place across insert 2605, discussed above with respect to FIGS. 30A-30O, or an intermediate connector 3403, discussed below with respect to FIG. 34.

Thus, in at least one embodiment, a respiratory conduit segment, such as the insert 2605 or intermediate connector 3403, comprises a lumen extending along a longitudinal axis and a wall surrounding the lumen, the lumen defining a gas-flow path when in use; and a PCB assembly 3301 comprising a printed circuit board and further comprising a first portion extending across the lumen along a diameter or chord line, such that a portion of the printed circuit board assembly generally bisects at least part of the flow path, the first portion being overmolded by an overmolding composition, a second portion adjacent the first portion projecting outward from the wall in a direction away from the lumen, the second portion comprising one or more connection pads 3303 on the printed circuit board configured to receive one or more wires from a first assembly, a third portion adjacent the first portion projecting outward from the wall in a direction away from the lumen and in a direction opposite the second portion, the third portion comprising one or more connection pads 3305 on the printed circuit board configured to receive one or more wires from a second assembly that is distinct from the first assembly, and one or more conductive tracks on the printed circuit board electrically coupled to the one or more connection pads of the second portion and to the one or more connection pads of the third portion and configured to provide electrical connectivity between the first assembly and the second assembly.

The first assembly and second assembly can each be a breathing tube. Or the first assembly can be a breathing tube and the second assembly can be a patient interface, for example.

Returning again to the examples of FIGS. 30G-30I, the sensor portion 3017 is mounted or formed such that the sensor portion 3017, PCB 3015, and locating portion 3019 form a unit. For example, sensor portion 3017, PCB 3015, and locating portion 3019 can be mounted to each other using a suitable process such as soldering. Sensor portion 3017, PCB 3015, and locating portion 3019 can be unitarily formed from a suitable material, such as a circuit board substrate.

The sensor portion 3017 can be electrically connected to the PCB 3015 using a suitable technique, such as circuit printing. For example, the electrical connection can comprise conductive tracks, such as copper tracks. To electrically connect the conductive filaments in the second elongate member of the tube 201 to the connection pads of the PCB assembly 3003, a procedure similar to that shown and described above with respect to FIGS. 25E-25I can be used. Additional electrical components, such as diodes (not shown), can be located at either side of the PCB 3015 inside and/or outside of the gas path. Locating a diode outside the gas path is discussed above with reference to sensor connection pads 3307 and signal connection pads 3309 and as shown in FIGS. 33A-33B.

Returning again to the examples of FIGS. 30G-30I, the PCB assembly 3003 can be mounted within the insert 3005 using, for example, an overmolding process, as known in the art. A material having a thermal conductivity in the range of 0.03-0.6 W/m·K or thereabout, such as polypropylene (thermal conductivity 0.1-0.22 W/m·K), can be used for at least a portion of the overmolding. Use of a material with low thermal conductivity can advantageously reduce interference from the ambient environment during sensor measurements, as it poorly conducts heat from the sensor portion 3017 to the insert 3005 walls. Certain embodiments include the realization that overmolding of a unitary PCB assembly 3003 allows more consistent placement of a sensor than overmolding a sensor alone. Furthermore, certain embodiments include the realization that overmolding a sensor placed inside center of the tube may make the sensor less sensitive to radiant effects.

As shown in FIGS. 30G-30I, the PCB assembly 3003 passes through the width of the insert 3005 and is supported by opposite walls of the insert 3005. Because the PCB assembly 3003 is supported on opposite sides of the insert 3005, the PCB assembly 3003 can be relatively thin (that is, having less thickness and less width than a PCB with one support on the tube). The thin profile can promote fluid flow by providing less resistance to flow than a thicker profile.

The overmolding around the sensor portion 3017 is preferably configured to reduce the drag on fluids flowing around the sensor portion 3017. The overmolding can have an aerodynamically efficient tapered shape, such as an airfoil shape, for example, a wing shape, a fully tapered torpedo shape (as shown in FIGS. 30F and 30G), or bullet shape that is partially tapered with one blunt edge (as shown in FIG. 30H). These tapered shapes promote fluid flow. In addition, when placed within the fluid flow, these tapered shapes reduce turbulence and vortices at the trailing edge of the tapered shape, which can cause unwanted cooling of humidified gas and forming of condensation. Condensation formation can lead to inaccurate measurement, as well as unwanted temperature drop in the gas delivered to a patient. Thus, the tapered shape can promote more accurate readings. In addition, the tapered shape can reduce collection of condensate that does form and also reduce buildup of patient secretions, by promoting runoff.

The tapered shape can also be selected to reduce turbulent flow by reducing the formation of vortices in the flow and increase the likelihood that the flow remains laminar.

The distance between the tapered shape and the inner wall of the insert 3005 is preferably selected to allow for more space. In at least one embodiment, the distance between tapered shape and the inner wall of the insert 3005 is at least 10% (or about 10%) or at least 30% (or about 30%), such as 33% (or about 33%) or 40% (or about 40%) of the inner diameter. In at least one embodiment, the distance between the tapered shape and the inner wall of the insert 3005 is greater than 2 mm (or about 2 mm). Allowing for more space decreases the likelihood that condensate becomes trapped in the space.

The overmolding promotes reading a more averaged temperature. There is some temperature variation across the insert 3005, with higher temperatures toward the center of the insert 3005 and lower temperatures along the insert 3005 walls. An asymmetric temperature profile, in which the highest temperature is offset from the center line of the insert 3005, is especially prevalent with bent tubes 203. The overmolding has a larger surface area than the sensor portion 3017 of the PCB assembly 3003 and the overmolding material distributes the heat so that the sensor of the sensor portion 3017 measures a more averaged temperature across the fluid path.

FIG. 30J shows an end view of the connector 3000 taken along the width of the connector, as seen from the patient end portion 3001 of the connector 3000, and looking toward the tube (not shown). In this view, the overmolded tapered shape housing the PCB assembly 3003 (not shown) is generally centered. FIG. 30K shows an alternative configuration. In this view, the tapered shape is offset from the center line. As shown in FIGS. 30J and 30K, the junctions 3018 between the inner wall of the insert 3005 and the overmolded tapered shape housing the PCB assembly optionally can have fillets to reduce flow disturbance and reduce areas for fluid build-up. The fillets of the junctions 3018 can be 1 mm (or about 1 mm) in radius, for example.

FIG. 30L shows the offset positioning of the tapered shape of FIG. 30K in greater detail. Because the sensor 3020 projects outward from the PCB assembly 3003, the offset configuration can improve accuracy by placing the sensor 3020 closer to the center line. In addition, the offset configuration can also be desirable because the PCB assembly 3003 can be housed in one side of the mold tool during manufacturing, thereby simplifying the manufacturing process.

FIG. 30M shows a longitudinal cross section of the insert assembly 3007 showing additional details of the PCB assembly 3003. A sensor 3020 is placed into the flow path. The sensor 3020 can provide temperature and/or gas flow information to allow assessment of conditions near the patient interface. The sensor 3020 is preferably located close to the edge of the projecting part of the sensor portion 3017. The thickness of the overmolding proximal the sensor 3020 is preferably thinner than the thickness of the overmolding around the other portions of the PCB assembly 3003, as shown in FIG. 30O. Reducing the overmolding thickness increases heat transfer to promote more accurate temperature measurements.

With reference again to FIG. 30M, conductive tracks 3021 electrically connect the sensor 3020 to the PCB 3015. (Note that sensor 3020 is not specifically shown in FIG. 30M; rather the structure designated 3020 represents the general position of the sensor. The structure designated 3020 shows two conductive pads that the sensor would bridge across. The structure is designated as a sensor for sake of illustration.) Through holes 3023 allow components to make contact with the required conductive layers. FIG. 30N shows an alternative configuration of the PCB assembly 3003. In FIG. 30N, the conductive tracks 3021 have a tortuous path. It was realized that increasing the length of the conductive tracks 3021 within the fluid path allows the temperature of the conductive tracks 3021 to more closely reflect the temperature within the fluid path, thereby reducing ambient effects on the sensor 3020 through the conductive tracks 3021. Preferably, there is increased surface area of copper near the sensor 3020. The increased copper promotes accurate detection of temperature around the sensor 3020 area.

In certain embodiments, the tapered shape can extend upstream along the gas path towards the source of the gas flow. This configuration promotes more accurate measurement by ensuring the sensor 3020 projects into the fluid flow, before the fluid is cooled as it passes the overmolding. This configuration can also promote more accurate measurements by reducing the "stem effect." All contact-type temperature sensors are subject to stem effect. When a probe is immersed in a fluid flow, a thermally conductive path is created by the probe's stem. In a case where the ambient temperature is cooler than the temperature of the measured fluid stream, heat is conducted away from the probe tip via the probe's stem to the outer atmosphere. This results in the sensing tip reading a temperature that is lower than the actual surrounding fluid. And in a case where the ambient temperature is hotter than the temperature of the measured fluid stream, heat is conducted toward the probe tip via the probe's step from the outer atmosphere. This results in the sensing tip reading a temperature that is higher than the actual surrounding fluid. The tapered shape configuration reduces the stem effect by projecting the sensor 3020 away from the part of the sensor portion 3017 connecting the PCB 3015 and locating portion 3019 (that is, away from the "stem"). In certain embodiments, the tapered shape extends upstream by at least 6 mm (or about 6 mm) from the part of the sensor portion 3017 connecting the PCB 3015 and locating portion 3019.

In certain embodiments, the tapered shape can extend downstream away from the source of the gas flow. This configuration can be advantageous, for example, when the design of the overmolded PCB assembly 3003 significantly alters the average downstream fluid properties such that it is desirable to accurately measure the fluid properties leaving the tube.

Heating filaments (not shown here but described above) in the second elongate member can be connected to the PCB 3015, which can provide termination points to complete the heating filament circuit. The PCB 3015 can also be used to provide additional termination points to provide power to additional heating filaments in a secondary tube, such as in a segmented inspiratory limb configuration for use with a humidification system, the segmented inspiratory limb having a connector configured to couple heating filaments and sensors in two segments. A suitable PCB assembly configuration is discussed above with reference to FIGS. 33A-33D.

Returning again to FIG. 30M, this configuration eliminates the need to have a separate power line running to the heating filaments. This configuration further ensures that the heating filaments run along the tube 203 and terminate at approximately the same position on the tube 203 as the sensor 3020. Thus, the configuration minimizes temperature drop from the end of the heating filaments to the sensor 3020. This configuration can also reduce temperature drop from the end of the heating filaments and a second heating filament in an additional section of tube. The configuration can also be used to heat the covering connector of the sensor 3020, thereby reducing heat losses to a cold ambient, and further improving accuracy in temperature measurement.

Although the foregoing describes placing one or more sensors at the patient end of a tube 201, it should be appreciated that this sensor configuration can be applied along any part of the fluid pathway of a tube 201.

Figure 34:
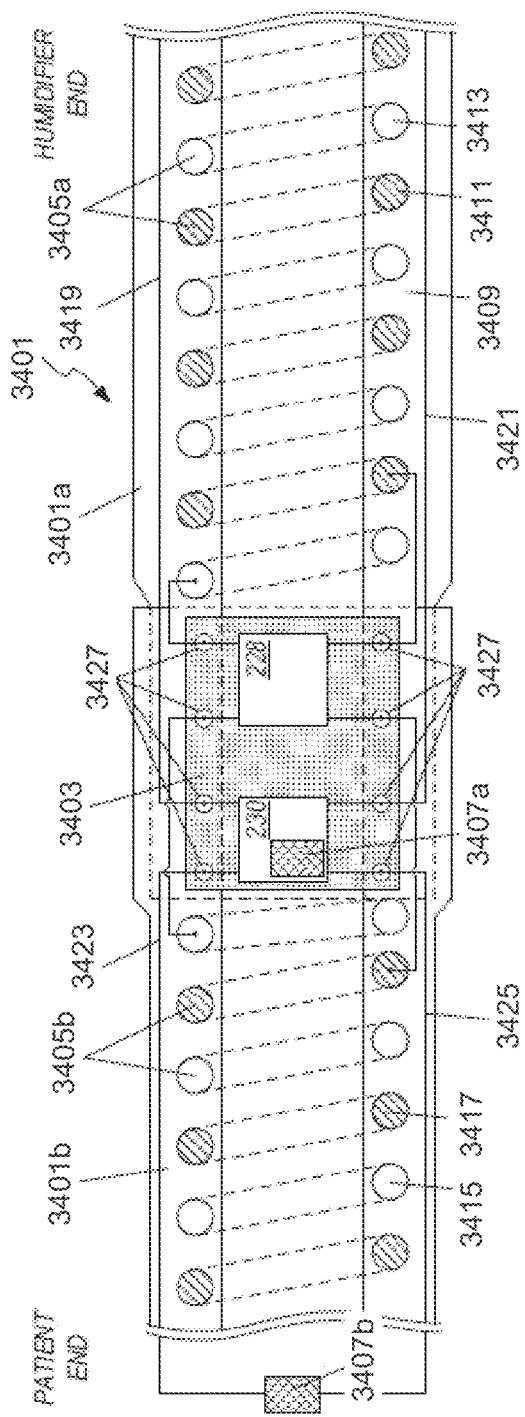
FIG. 34 illustrates a segmented inspiratory limb for use with a humidification system, the segmented inspiratory limb having an intermediate connector configured to couple heating filaments and/or temperature sensors in the two segments.

For example, FIG. 34 illustrates a portion of a segmented inspiratory limb 3401 for use with a respiratory humidification system, the segmented inspiratory limb 3401 comprising a first segment 3401a and a second segment 3401b and having an intermediate connector 3403 configured to couple first heater wires 3405a to second heater wires 3405b and a first temperature sensor 3407a to a second temperature sensor 3407b in the respective segments 3401a and 3401b. Coupling the two segments 3401a and 3401b can comprise mechanically coupling the segments to form a single can be conduit through which humidified gases can be delivered to a user wherein mechanically coupling the segments 3401a and 3401b can result in electrically coupling the respective heater wires 3405a, 3405b and the respective temperature sensors 3407a, 3407b through the intermediate connector 3403. The PCB assembly 3301 shown in FIGS. 33A and 33B is suitable for use with the intermediate connector 3403 of FIG. 34.

Returning again to FIG. 34, the segmented inspiratory limb 3401 can comprise a structure 3409 forming a lumen through which humidified gases can pass. The structure 3409 can include paths formed within walls of the structure 3409 configured to house heater wires 3405a or 3405b such that the heater wires 3405a or 3405b are shielded from the humidified gases travelling through the lumen and/or are covered by an external surface of the structure 3409 so that they are not exposed. For example, the structure 3409 can be a composite tube wherein the heater wire paths are coils molded into the tube, as discussed above. The structure 3409 can comprise any type of suitable material and can include insulating material and/or flexible material. In some embodiments, the structure 3409 and the intermediate connector 3403 can be configured such that, when the first and second segments 3401a and 3401b are mechanically coupled, the heater wires 3405a and 3405b wrap over the intermediate connector 3403 in such a way as to be electrically coupled to the intermediate connector 3403. In some embodiments, the first segment 3401a and/or the intermediate connector 3403 can exclude any flying leads for connecting to the second segment 3401b, thereby facilitating connection of the second segment 3401b to the first segment 3401a.

The structure 3409 at complementary ends of the first and second segments 3401a and 3401b can be configured to house the intermediate connector 3403. Thus, the intermediate connector 3403 can be internal to the inspiratory limb 3401. In some embodiments, the complementary ends of the first and second segments 3401a and 3401b can be configured to shield the intermediate connector 3403 from humidified gases travelling through the inspiratory limb 3401. In some embodiments, the intermediate connector 3403 is both internal to the inspiratory limb 3401 and shielded from humidified gases in the conduit, thereby reducing or eliminating exposure of electrical connections on the intermediate connector 3403.

In some embodiments, the first heater wires 3405a can comprise two wires 3411 and 3413 and the second heater wires 3405b can comprise two wires 3415 and 3417. The two wires 3411 and 3413 in the first segment 3401a can be electrically coupled to one another through electrical components 3419 wherein the electrical coupling creates an electrical path through the wire 3411, at least a portion of the electrical components 3419, and the wire 3413. Similarly, the two wires 3415 and 3417 in the second segment 3401b can be electrically coupled to one another through electrical components 3419 and/or electrically shorted together at an end of the segment 3401b opposite the intermediate connector 3401b, such as through a patient-end connector (not shown). By coupling the wires 3415 and 3417 of the second segment 3401b at the intermediate connector 3403, electrical connections at the patient-end of the inspiratory limb 3401 are reduced or eliminated which can reduce cost, system complexity, and/or risk to the patient.

The intermediate connector 3403 can be configured to allow a single controller to control power to the heater wires 3405a, 3405b, such as a humidifier controller. In some embodiments, the humidifier controller controls the heater wires 3405a, 3405b without any additional control functionality located on the intermediate connector 3403. For example, the intermediate connector 3403 can include passive components without any logic circuitry wherein the passive components direct power to heater wires 3405a and/or 3405b as selected by the controller. This can allow the intermediate connector 3403 to be designed using relatively inexpensive components and can reduce the complexity of the design.

In some embodiments, heating of the two segments 3401a and 3401b can be accomplished using a maximum of four wires in each segment 3401a, 3401b. For example, in the first segment 3401a the four wires can include a first heater wire 3411, a second heater wire 3413, a signal temperature sensor wire 3419, and a return temperature sensor wire 3421. In the second segment 3401b the four wires can include a first heater wire 3415, a second heater wire 3417, a signal temperature sensor wire 3423, and a return temperature sensor wire 3425. By coupling the second heater wires 3415, 3417 to the first heater wires 3411, 3413 at connection points 3427, and by coupling the second temperature sensor wires 3423, 3425 to the first temperature sensor wires 3419, 3421 at connection points 3427, a controller can be configured to provide power independently to the first heater wires 3405a and the second heater wires 3405b and to read temperature sensor data independently from the temperature sensors 204a and 204b without including more than four wires in either segment 3401a or 3401b. In some embodiments, control of the heater wires 3405a and 3405b and reading of the temperature sensors 3407a and 3407b can be accomplished using less than four wires in each segment (e.g., using three wires or using two wires) or more than four wires in each segment (e.g., using five wires, using six wires, using seven wires, using eight wires, or using more than eight wires).

The intermediate connector 3403 can include electrical components 3419 configured to allow a controller to selectively control heater wires 3405a, 3405b. The controller can be configured to control heating of the inspiratory limb 3401 using two modes wherein a first control mode comprises providing power to the heater wires 3405a in the first segment, and a second control mode comprises providing power to the heater wires 3405a and 3405b in the first and second segments 3401a and 3401b. Thus, the controller can be configured to independently control heater wire sections. This ability allows for the controller to control heating of the inspiratory limb 3401 when the second segment 3401b is not present by solely controlling the heating of the inspiratory limb according to the first control mode, thereby allowing for the respiratory humidification system to be used in a variety of circumstances without modifying the controller or humidification unit. In some embodiments, the control modes can include a mode where power is delivered only to the heater wires 3405*b* in the second segment 3401*b*. In some embodiments, the controller includes an electrical power source that provides electrical current. The first and second control modes can be based at least in part on the voltage supplied by the power source wherein a positive voltage or positive current can trigger the first control mode and a negative voltage or a negative current can trigger the second control mode. In some embodiments, the power source provides rectified AC or DC power to the heater wires 3405*a*, 3405*b* and a change in the rectification or polarity triggers a change in the control mode. By switching control modes, control of heating in the breathing circuit can be accomplished with any power supply that can switch the polarity of the output signal. In some embodiments, the amount of power provided to the heater wires 3405*a*, 3405*b* can be adjusted by adjusting a duty cycle of power applied to the heater wires 3405*a*, 3405*b*. For example, pulse-width modulation (PWM) can be used to power the heater wires 3405*a*, 3405*b* and the duty cycle of the PWM signal can be adjusted to control the power delivered. In another example, the amount of power provided to the heater wires 3405*a*, 3405*b* can be adjusted by controlling the amplitude of the power signal.

The intermediate connector 3403 can include electrical components 3421 configured to allow a controller to selectively read temperature sensors 3407*a*, 3407*b*. Selective reading can be accomplished through the use of a source of electrical current wherein applying a positive current across the wires 3419 to 3421 can result in the controller measuring a temperature-related signal from the first temperature sensor 3407*a* and applying a negative current across the wires 3419 and 3421 can result in the controller measuring a temperature-related signal from the second temperature sensor 3407*b* or from both the first and second temperature sensors 3407*a*, 3407*b*. The controller can use the readings from the temperature sensors 3407*a*, 3407*b* to adjust power to the heater wires 3405*a*, 3405*b*, using, for example pulse-width modulation. The first temperature sensor 3407*a* can be positioned near the connection or intersection of the first and second segments 3401*a* and 3401*b* to provide to the controller a temperature of gases entering the second segment 3401*b*, which can correspond to entering an incubator or other such region having a different ambient temperature. The second temperature sensor 3407*b* can be positioned at a patient-end of the second segment 3401*b* to provide to the controller a temperature of gases delivered to the patient or the temperature prior to the final piece before the patient, such as a wye-piece. The controller can use these temperature readings to adjust power to the heater wires 3405*a*, 3405*b* to maintain the temperature of the gas at the patient-end of the inspiratory limb 3401 at a targeted or suitable temperature. The targeted or suitable temperature can vary depending at least in part on the application and environment it is being used in, and can be about 37° C., about 40° C., at least about 37° C. and/or less than or equal to about 38° C., at least about 36.5° C. and/or less than or equal to about 38.5° C., at least about 36° C. and/or less than or equal to about 39° C., at least about 35° C. and/or less than or equal to about 40° C., at least about 37° C. and/or less than or equal to about 41° C., or at least about 39.5° C. and/or less than or equal to about 40.5° C. In some embodiments, the second temperature sensor 3407*b* can be positioned inside the incubator but not attached to the breathing circuit. By measuring the temperature inside the incubator, the temperature of the second segment 3401*b* can be calculated.

The controller can independently control the amount of power delivered in the first and second control modes, as described herein. Based at least in part on feedback from the temperature sensors 3407*a* and/or 3407*b*, the controller can independently adjust power delivered in the first and second control modes, thereby resulting in varying heater power ratios between the first and second segments 3401*a* and 3401*b*.

In some embodiments, the first temperature sensor 3407*a* is positioned within the flow of gas within the inspiratory limb 3401. In some embodiments, the intermediate connector 3403 or the first segment 3401*a* can include a mechanical component that decreases turbulence in the flow of the gas across the first temperature sensor 3407*a* which can increase accuracy in the temperature sensor's 3407*a* readings. In some embodiments, the mechanical component (e.g., a cross-member feature within the inspiratory conduit) that decreases turbulence also secures the temperature sensor 3407*a* within the flow of the gases. In some embodiments, the intermediate connector 3403 and the mechanical component are configured to thermally isolate the temperature sensor 3407*a* from the electrical components on the intermediate connector 3403.

In some embodiments, the intermediate connector 3403 includes additional connection points in addition to the connection points 3427 illustrated in FIG. 34. The additional connection points can be used to incorporate further functionality into the breathing circuit such as, for example, incorporating a memory device (PROM), a micro-controller, additional circuits, and the like.

Moreover, the composite tube 201 can be an inspiratory tube or an expiratory tube.

Placement of Spiral-Style Connector

Reference is next made to FIGS. 35A-35F which show a connector without electrical connectivity to a PCB. However, as will be appreciated by those skilled in the art, that the connector could be equally adapted to have electrical connectivity to a PCB. The connector is suitable for connecting to, for example, a patient interface or a humidifier. It is particularly suited for use as a patient-end connector and/or device-end connector in an obstructive-sleep apnea environment.

A spiral-ended molded insert 3501 is provided. The end of the insert 3501 opposite the spiral end is molded for insertion on or attachment to a humidifier port, and/or a patient interface port, and/or any other desired component. The insert 3501 can be a hard material, such as a hard plastic, for example, polypropylene.

Figure 35C:
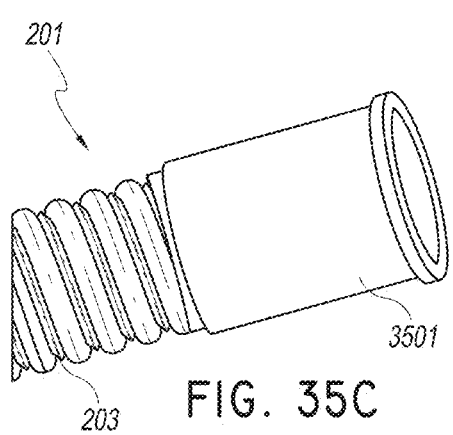
Figure 35D:
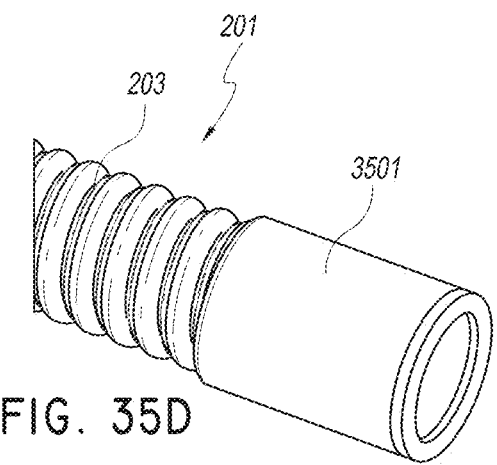
Figure 35E:
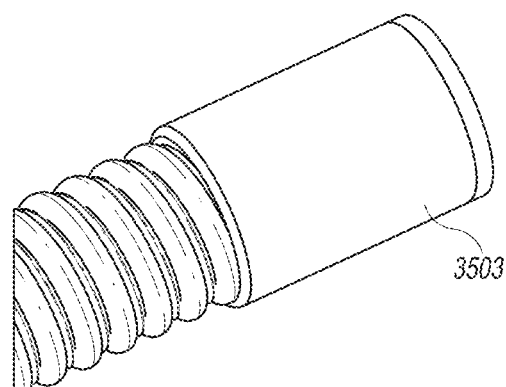

As shown in FIG. 35C, the spiral end of the insert 3501 is screwed into the compliant turns of the tube 201. In this example, the spiral turns of the insert 3501 are sized and configured to fit into the turns of the first elongate member 203 of the tube 201.

It should be noted that, in the case of a tube having one or more electrically powered wires therein, an electrical connection can be provided on at least a portion of the insert 3501. When the insert 3501 is installed, the electrical connector will preferably align with the wires, thereby facilitating electrical connection. Solder or the like can then be used to secure the connection.

A member 3503 can be inserted or molded on top of at least a portion of insert 3501 and, optionally, tube 201 to promote the attachment between the insert 3501 and the tube 201. The member 3503 can be a hard material or a soft material, such as a soft plastic, rubber, or PTFE, for example polypropylene. In some cases, the insert 3501 (or at least the spiral end of the insert 3501) provides sufficient lateral crush resistance to enable high-pressure molding techniques to be used, where the pressure can exceed the lateral crush resistance of the tube 201 without the insert 3501. Member 3503 can also advantageously provide a soft surface to grip on when inserting and removing tube from a component.

The foregoing method of attaching a connector to a spiral-wound tube is provided by way of example. The method described herein does not imply a fixed order to the steps. Nor does it imply that any one step is required to practice the method. Embodiments may be practiced in any order and combination that is practicable.

Placement of Alternative Patient-End Connector

Figure 36A:
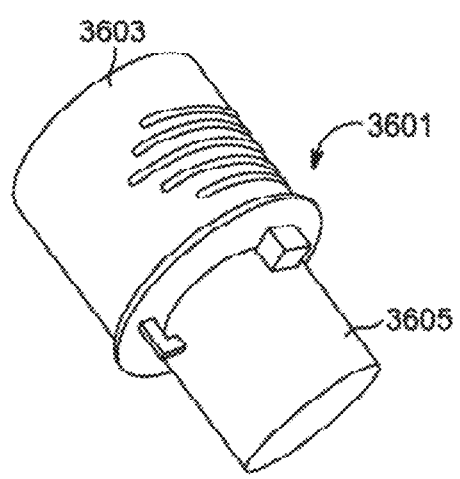
FIGS. 36A-36K show schematics relating to another connector suitable for attaching a tube to a humidifier port, patient interface, or any other suitable component.
Figure 36B:
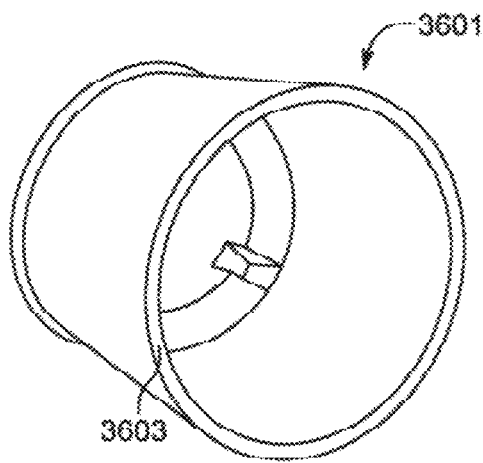

Reference is next made to FIGS. 36A-36K. FIGS. 36A and 36B show a patient-end connector 3601 without electrical connectivity. The connector 3601 has a patient end 3603 with a standard-size medical taper suitable for use with a patient interface. The tube end 3605 of the connector 3601 is suitable for connection to a composite tube 201, as described below. The connector 3601 is preferably a pre-molded component formed from a suitable material such as plastic, rubber, or PTFE.

Figure 36C:
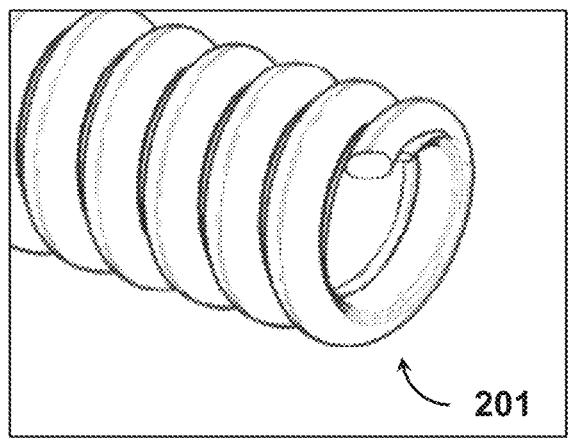
Figure 36D:
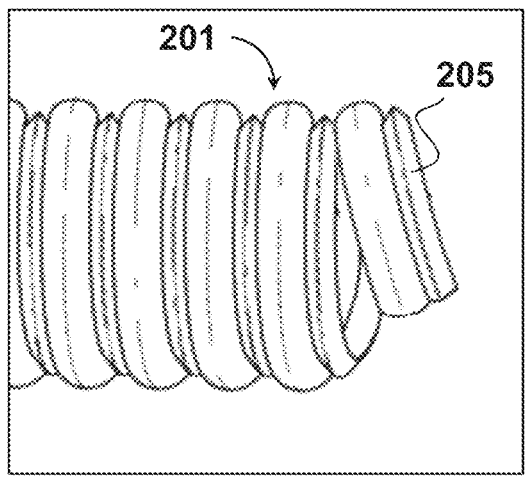
Figure 36E:
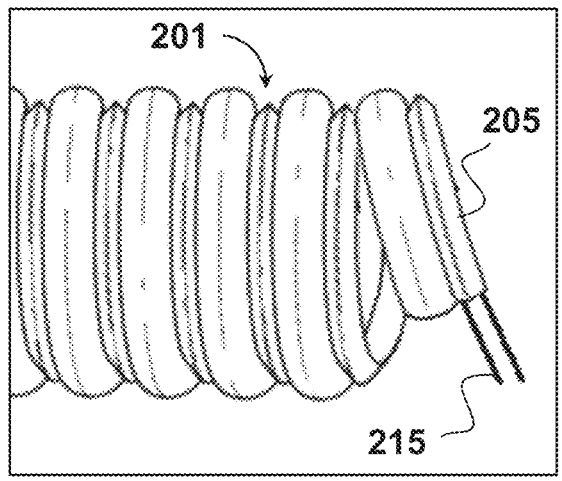
Figure 36F:
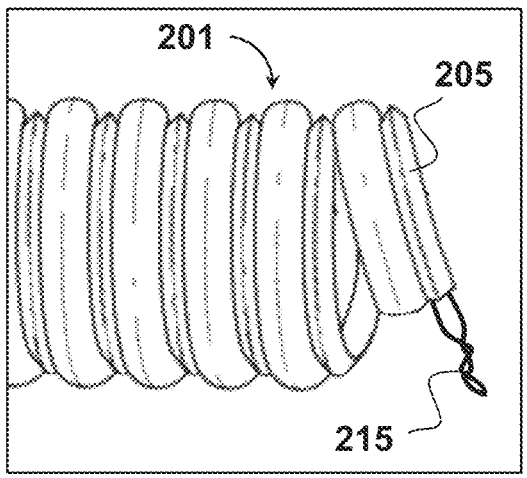

As shown in FIGS. 36C and 36D, a portion (e.g., a 10-mm portion) of the second elongate member 205 is stripped away to reveal a small length of the one or more filaments 215 embedded therein. Preferably, about 5 mm or 10 mm of the filaments 215 are revealed. As shown in FIG. 36D, the filaments 215 are twisted together and optionally secured, for example, by soldering, thereby creating a closed loop circuit.

Figure 36G:
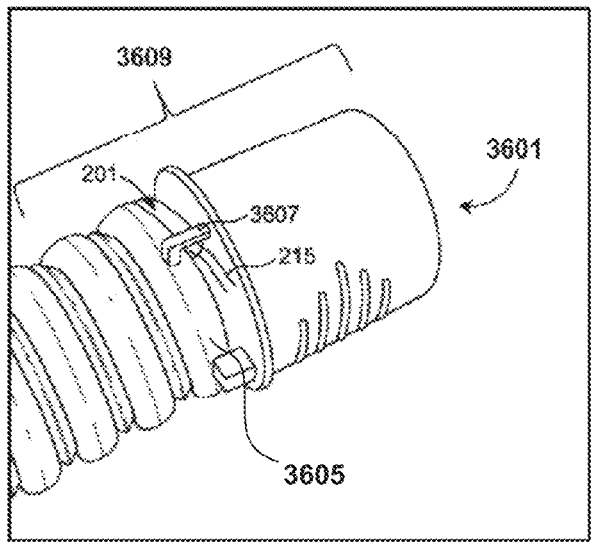

Turning next to FIG. 36G, the tube end 3605 of the connector 3601 is inserted into the tube 201 and the twisted filaments 215 are placed under a retaining loop 3607. The retaining loop 3607 diminishes movement of the filaments 215 during molding. The retaining loop 3607 also advantageously aligns the rotational pitch of the composite tube 201 to the connector 3601, which in turn promotes proper alignment of the tube 201 in the mold. The combination of connector 3601 and composite tube 201 is designated here as a connector-tube assembly 3609.

Figure 36H:
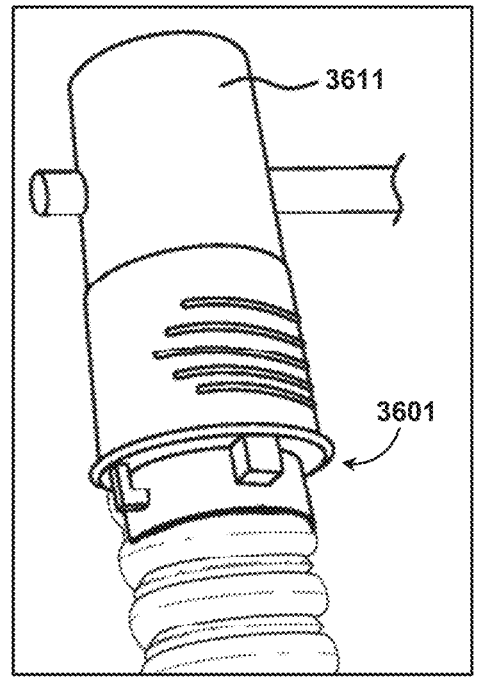
Figure 36I:
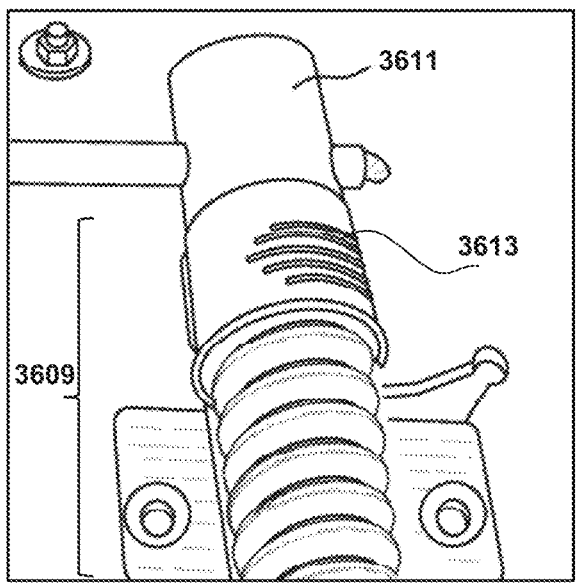
Figure 36J:
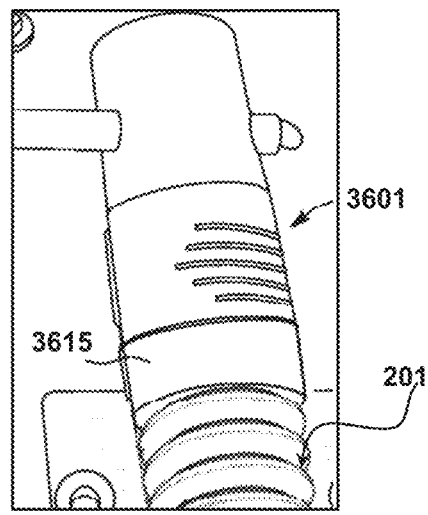
Figure 36K:
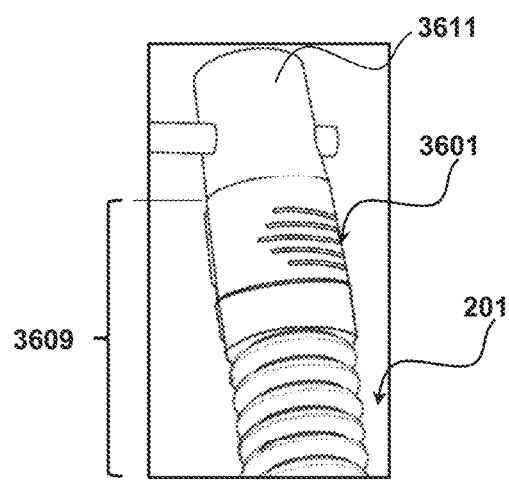

As shown in FIG. 36H, a mold tool core 3611 is inserted into the connector 3601. As shown in FIG. 36I, the connector-tube assembly 3609 and core 3611 are placed in an injection mold tool 3613. In FIG. 36J, a molded material 3615 is molded over junction region between the composite tube 201 and the connector 3601, thereby bonding composite tube 201 and the connector 3601. Suitable molded materials 3615 include plastic and rubber. The connector-tube assembly 3609 and core 3611 are removed from the injection mold tool (not shown), as in FIG. 36K. The core 3611 is removed, thereby providing a composite tube 201 with a patient-end connector 3601.

The foregoing method of attaching a connector to a composite tube is provided by way of example. The method described does not imply a fixed order to the steps. Nor does it imply that any one step is required to practice the methods. Embodiments may be practiced in any order and combination that is practicable.

The foregoing description of the invention includes preferred forms thereof. Modifications may be made thereto without departing from the scope of the invention. To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

Through the description and the claims, the terms "comprises," "comprising," and the like are to be construed in an inclusive sense, that is, in the sense of "including but not limited to," unless the context clearly requires otherwise.

Although the invention has been described by way of example and with reference to possible embodiments thereof, it is to be understood that modifications or improvements may be made thereto without departing from the spirit and scope of the invention and without diminishing its attendant advantages. Furthermore, where reference has been made to specific components or integers of the invention having known equivalents, such equivalents are herein incorporated as if individually set forth.

Any discussion of the prior art throughout the specification should in no way be considered as an admission that such prior art is widely known or forms part of the common general knowledge in the field anywhere in the world.

What is claimed is:

1. A respiratory conduit comprising:
    a lumen extending along a longitudinal axis and a wall surrounding the lumen, the lumen configured to define a gas-flow path when in use; and,
    a component securely connected to the wall and extending across a full width of the lumen such that the component is supported at each end by the wall surrounding the lumen, the component comprising:
        a printed circuit board (PCB) with a temperature sensor provided on a surface of the PCB, a sensor portion disposed in the lumen; and
        the sensor portion comprising a projecting portion wherein the projecting portion is configured to extend longitudinally upstream along the gas-flow path while the respiratory conduit is in use.

2. The respiratory conduit of claim 1, wherein the component also comprises a dividing portion, the dividing portion being embedded in the wall, the dividing portion of the component extending across the lumen along a diameter or chord line such that the dividing portion generally bisects at least part of the gas-flow path, and at least part of the dividing portion being overmolded by an overmolding composition.

3. The respiratory conduit of claim 2, wherein the component comprises a wiring portion adjacent the dividing portion and projecting outward from the wall in a direction away from the lumen, the wiring portion being configured to provide an electrical connection to the temperature sensor.

4. The respiratory conduit of claim 3, wherein the component comprises a support portion adjacent the dividing portion and projecting outward in a direction away from the lumen and in a direction opposite to the wiring portion.

5. The respiratory conduit of claim 2, wherein the dividing portion divides at least part of the gas-flow path into two unequal parts.

6. The respiratory conduit of claim 1, wherein the sensor portion is overmolded by the overmolding composition.

7. The respiratory conduit of claim 6, wherein the overmolding composition proximal the sensor portion comprises a tapered shape extending along the longitudinal axis and/or an airfoil shape, a wing shape, a torpedo shape, or a bullet shape.

8. The respiratory conduit of claim 6, wherein a thinnest part of the overmolding composition is proximal an upstream leading edge or a downstream leading edge of the sensor portion.

9. The respiratory conduit of claim 1, wherein a cross-lumen distance between the sensor portion and the wall is at least 30% of a diameter of the lumen.

10. The respiratory conduit of claim 1, wherein the component is positioned within a patient-end connector configured to connect a tube to a patient interface.

11. The respiratory conduit of claim 10, wherein the patient-end connector comprises an insert configured to be connected at one end to the tube and at another end to the patient interface, the insert forming at least a part of the lumen defining the gas-flow path and configured to provide a housing for the PCB and the temperature sensor of the component.

12. The respiratory conduit of claim 11, wherein the patient-end connector comprises a cover configured to protect and cover the PCB and a connection location of the insert to the tube.

13. The respiratory conduit of claim 1 further comprising a tube, wherein the PCB is configured to be connected to one or more conductive filaments provided in a wall of the tube.

14. The respiratory conduit of claim 1, wherein the temperature sensor is close to an edge of the projecting portion of the sensor portion.

15. The respiratory conduit of claim 14, wherein a first conductive pad connects to the temperature sensor on the projecting portion of the sensor portion.

16. The respiratory conduit of claim 15 further comprising a second conductive pad and the temperature sensor bridges across a gap between the first conductive pad and the second conductive pad.

17. A conduit for delivering humidified gases to a patient, the conduit comprising:
a connector configured to connect to a tube, the connector comprising a lumen extending along a longitudinal axis and a wall surrounding the lumen, the lumen defining a gas-flow path for the humidified gases when in use; and
a printed circuit board (PCB) assembly comprising:
a dividing portion embedded in the wall, the dividing portion extending across a full width of the lumen along a diameter or chord line such that the dividing portion generally bisects at least part of the gas-flow path, and at least part of the dividing portion being overmolded by an overmolding composition;
a wiring portion adjacent the dividing portion, the wiring portion projecting outward from the wall; and
a sensor portion disposed in the lumen of the connector and comprising at least one sensor, the sensor portion being overmolded by the overmolding composition.

18. The conduit of claim 17, wherein the tube comprises:
a first elongate member having a hollow body; and
a second elongate member spirally wound and joined between adjacent turns of the first elongate member.

19. The conduit of claim 18, wherein the first elongate member is spirally wound to form at least a portion of the tube and the hollow body of the first elongate member defining a hollow portion of the wall surrounding the lumen.

20. The conduit of claim 19, wherein the second elongate member forms at least a portion of the wall surrounding the lumen.

21. The conduit of claim 20, wherein one or more conductive filaments are embedded or encapsulated within the second elongate member.

22. The conduit of claim 21, wherein at least one of the one or more conductive filaments is a heating filament and/or a sensing filament.

23. The conduit of claim 22, wherein the wiring portion is configured to electrically connect to the one or more conductive filaments.

24. The conduit of claim 17, wherein the dividing portion divides at least part of the gas-flow path into two unequal parts.

* * * * *